US012054769B2

(12) United States Patent
Knutsen et al.

(10) Patent No.: US 12,054,769 B2
(45) Date of Patent: Aug. 6, 2024

(54) SEXUAL MATURATION IN RAINBOW TROUT

(71) Applicant: AquaGen AS, Trondheim (NO)

(72) Inventors: Tim Martin Knutsen, Ås (NO); Sven Arild Korsvoll, Etnedal (NO); Torben Fejer Nielsen, Jelling (DK)

(73) Assignee: AQUAGEN AS, Trondheim (NO)

(*) Notice: Subject to any disclaimer, the term of this patent is extended or adjusted under 35 U.S.C. 154(b) by 716 days.

(21) Appl. No.: 17/125,053

(22) Filed: Dec. 17, 2020

(65) Prior Publication Data
US 2021/0189472 A1 Jun. 24, 2021

(30) Foreign Application Priority Data

Dec. 18, 2019 (EP) .................................... 19217649

(51) Int. Cl.
C07H 21/04 (2006.01)
A01K 61/17 (2017.01)
A01K 61/95 (2017.01)
C12N 5/075 (2010.01)
C12N 5/076 (2010.01)
C12Q 1/6827 (2018.01)
G16B 20/20 (2019.01)

(52) U.S. Cl.
CPC ............ *C12Q 1/6827* (2013.01); *A01K 61/17* (2017.01); *A01K 61/95* (2017.01); *C12N 5/0609* (2013.01); *C12N 5/061* (2013.01); *G16B 20/20* (2019.02)

(58) Field of Classification Search
CPC ...................................................... G16B 20/20
See application file for complete search history.

(56) References Cited

FOREIGN PATENT DOCUMENTS

EP 0235726 A2 9/1987
WO 8911548 A1 11/1989

OTHER PUBLICATIONS

Brookes (Gene, 234, 1999, 177-186).*
Anonymous; "Axiom Trout Genotyping Array" [Datasheet]; Affymetrix, Inc.; Dec. 17, 2014; Retrieved on May 7, 2020 from https://genomics.neogen.com/pdf/prodinfo/axiom_trou_genotyping_array_datasheet.pdf; 2 pages.
Easton, A. et al.; "The genetic architecture of embryonic developmental rate and genetic covariation with age at maturation in rainbow trout *Oncorhynchus mykiss*"; Journal of Fish Biology, vol. 78, Issue No. 2; 2011; pp. 602-623.
European Search Report for European Application 19217649.3; Date of European Filing: Dec. 18, 2019; Date of Search: May 8, 2020; 11 pages.
Moghadam, H. et al.; "Quantitative trait loci for body weight, condition factor and age at sexual maturation in Arctic charr (*Salvelinus alpinus*): comparative analysis with rainbow trout (*Oncorhynchus mykiss*) and Atlantic salmon (*Salmo salar*)"; Molecular Genetics and Genomics, vol. 277, Issue No. 6; 2007; pp. 647-661.
Pedersen, et al.; "Quantitative trait loci for precocious parr maturation, early smoltification, and adult maturation in double-backcrossed trans-Atlantic Salmon (*Salmo salar*)"; Aquaculture, vols. 410-411; 2013; pp. 164-171.
Gutierrez, A. et al.; "Genome-Wide Association Study (GWAS) for Growth Rate and Age at Sexual Maturation in Atlantic Salmon (*Salmo salar*)"; PLoS One, vol. 10, Issue No. 3; e0119730; 2015; 10 pages; DOI: 10.1371/journal.pone.0119730.
Yang, J. et al.; "Advantages and pitfalls in the application of mixed model association methods"; Nature Genetics, vol. 46, Issue No. 2; 2014; pp. 100-106.
Yang, J. et al.; "GCTA: a tool for genome-wide complex trait analysis"; American Journal of Human Genetics, vol. 88, Issue No. 1; 2011; pp. 76-82.

* cited by examiner

*Primary Examiner* — Amy Rose Hudson
(74) *Attorney, Agent, or Firm* — Karen A. LeCuyer; DeWitt LLP

(57) ABSTRACT

Described herein are polymorphisms, and in particular single nucleotide polymorphisms (SNP) associated with late onset of sexual maturation in rainbow trout (*Oncorhynchus mykiss*). In particular, provided are methods for predicting late onset of sexual maturation in rainbow trout, methods for selecting a rainbow trout having late onset of sexual maturation and kit suitable for carrying out said methods. Further provided are rainbow trout cells, sperm and unfertilized eggs carrying at least one allele conferring late onset of sexual maturation in their genome.

13 Claims, 3 Drawing Sheets

Specification includes a Sequence Listing.

SEXUAL MATURATION IN RAINBOW TROUT

CROSS-REFERENCE TO RELATED APPLICATIONS

This application claims priority to European Application 19217649.3 filed on Dec. 18, 2020, which is incorporated herein by reference in its entirety.

FIELD OF THE DISCLOSURE

The present disclosure relates generally to polymorphisms, and in particular single nucleotide polymorphisms (SNP) associated with late onset of sexual maturation in rainbow trout (*Oncorhynchus mykiss*). In particular, the present disclosure provides methods for predicting late onset of sexual maturation in rainbow trout, methods for selecting a rainbow trout having late onset of sexual maturation and kit suitable for carrying out said methods. The present disclosure further provides rainbow trout cells, sperm and unfertilized eggs carrying at least one allele conferring late onset of sexual maturation in their genome.

BACKGROUND

Aquaculture has developed rapidly over the last decades in order to meet the growing demand for marine foods, a demand that cannot be met by increased harvest of wild stocks as they already are under stress from commercial fisheries. Many species, ranging from sea urchins to anadromous fish, such as salmon and trout, are now farmed effectively at a large scale. However, there are at present very few breeding programs established for cultured marine species.

Atlantic salmon (*Salmo salar*) and Rainbow Trout (*Oncorhynchus mykiss*) are two of the species where breeding programs have been successfully established. Both species have been actively bred for more than four decades, and substantial advances have been made with regard to disease resistance and growth-related traits. Among the growth-related traits, age and size at sexual maturation is one of the most important from an economically point of view.

Sexual maturation, or puberty, is the process in which a juvenile individual develops into a sexually functional adult with the ability to produce gametes and gains the somatic and behavioral competence to function as a mating partner and a parent. Gonadal development is initiated already before hatching with the initiation of germ cell formation, gonadal development and continues in stages until final sexual maturation occurs. The heavy investments in gonadal development and gamete production has several negative consequences for growth rate, welfare and product quality of farmed fish.

Growth rate is typically high at onset of puberty. However, a few months into the maturation process, feeding will cease, and somatic weight will decrease as resources are routed to gonadal development and gamete production. Early sexual maturation is therefore considered a serious drawback for aquaculture due to its undesirable impacts on growth.

Further, maturation also represents a welfare issue since the anadromous fish gradually will lose tolerance to seawater due to compromised hypo-osmoregulation ability during maturation. When the wild fish begins to mature, they typically migrate to their native rivers, an escape that is not possible for farmed fish due to their confinement in cages in seawater facilities. Without the possibility to escape seawater, the consequence of reduced sea water tolerance is dehydration, stress and possible negative effects on the immune system. Thus, early sexual maturation is therefore considered a serious drawback for aquaculture due to its undesirable impacts on fish welfare.

It has also been reported that sexual maturation causes reduction in fat- and protein content of fish filets; loss of flesh pigmentation, as the pigment is shifted to skin and gametes; and changes in smell and taste of the fish filets. Thus, early sexual maturation is therefore considered a serious drawback for aquaculture due to its undesirable impacts on product quality.

The behavior of farmed fish also changes during sexual maturation. Behavioral changes have been observed in females, but these changes seem to especially affect males that take on a dominant role during mate competition and become more aggressive toward other males.

Further, when immature salmon escape, they are likely to run out to sea where survival is low; subsequently they are less likely to survive to mate with wild fish. A mature fish is likely to seek up-river in order to mate. Thus, keeping the fish in an immature stage throughout the production cycle will not only be beneficial to the industry with regards to growth, product quality and animal welfare, but is also an effort that could benefit the wild fish strains whose gene pools are less likely to be negatively impacted by farmed fish with late maturation.

Thus, there is a need for anadromous fish that enters sexual maturation at a late stage. In particular, there is a need for anadromous fish that remain sexually immature throughout the production cycle.

Maturation seems to be controlled by several intrinsic factors such as size, growth rate and fat deposition, in addition to several extrinsic factors such as photoperiod, temperature, diet, stress exposure and competition. When these intrinsic and extrinsic factors together meet certain conditions, the brain-pituitary-gonad axis is triggered, and maturation is continued to the next step.

Based on the knowledge of how the extrinsic factors affect sexual maturation of fish, it has been common practice to expose farmed fish to continuous light to delay sexual maturation and thereby avoid the negative effects of early maturation.

However, increased water temperature is known to be associated with early maturation, and the increasing ocean temperatures caused by global warming may therefore to some extent overrun the inhibitory effect of continuous light on maturation. In the future it may therefore be necessary to use other means than continuous light to delay sexual maturation of farmed fish.

An alternative to the use of continuous light is to look at the genetic variability in the search for a genetic pattern associated with late onset of sexual maturation. However, as will be discussed further below, there are some challenges that need to be solved if fish are to be selected for late sexual maturation based on genetics.

Farmed fish has typically been selected for improved growth and is provided with optimal feeding condition. The result being that farmed anadromous fish often show a phenotypic response to their improved growth conditions where both age and size at puberty is reduced, accompanying the high growth rate and large size achieved through selective breeding. For this reason, it may be challenging for breeding programs to select for late maturity as the phenotypic response can mask the genetic variability in age and size at maturity.

There is therefore a need for improved methodologies for assessing late onset of sexual maturation in rainbow trout, particularly methodologies that allow the direct assaying and selection of individual's having late onset of sexual maturation.

Journal of fish biology, vol 78, no. 2, 11 Jan. 2011, pages 602-623 teaches correlations between quantitative trait locus (QTL) involved in developmental rate and age at maturation in rainbow trout *Oncorhynchus mykiss*.

Molecular Genetics and Genomics, springer, Berlin, De, vol. 277, no. 6, 17 Feb. 2007, pages 647-661, XP019517829 relates to putative growth and maturation timing QTL locations in Arctic charr, several of these regions showing homologies to the identified maturation timing QTL regions in Atlantic salmon and/or rainbow trout.

Aquaculture, vol. 410-411, 1 Oct. 2013, pages 164-171, XP055692262, Amsterdam, NL relates to QTL associated with smolting and maturation in rainbow trout.

Neogen provides a high-density genotyping array for high-resolution genetics research and aquaculture breeding in rainbow trout. The array includes 57,501 markers and is available in both 96 and 384 formats.

SUMMARY OF THE INVENTION

The present inventors have solved this need by having identified polymorphisms, and in particular single nucleotide polymorphisms (SNP), within the genome of rainbow trout which are associated with late onset of sexual maturation.

In a first aspect, a method for predicting late onset of sexual maturation in rainbow trout (*Oncorhynchus mykiss*) comprises determining the presence of at least one allele, such as at least two alleles, conferring late onset of sexual maturation ("late maturation allele") within the genome of said rainbow trout; wherein the at least one late maturation allele is an allele of at least one single nucleotide polymorphism (SNP), the at least one SNP being selected from the SNPs listed in Table 1.

According to certain aspects, provided is a method for predicting late onset of sexual maturation in rainbow trout, the method comprising determining the identity of a nucleotide of at least one allele, optionally of at least two alleles, of at least one single nucleotide polymorphism (SNP) associated with late onset of sexual maturation within the genome of said rainbow trout, said at least one SNP being selected from the group consisting of SNP #1 to SNP #164.

According to certain embodiments, provided is a method for predicting late onset of sexual maturation in rainbow trout (*Oncorhynchus mykiss*), the method comprising determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 1 to 164, or at a position corresponding to position 31 of a nucleotide sequence which is derived from any one of SEQ ID NOs: 1 to 164 by 1 to 5, such as 1 to 2, nucleotide substitutions; with the proviso that said nucleotide substitution(s) are not at position 31 of said derived sequences.

The rainbow trout has late onset of sexual maturation when the nucleotide of the at least one allele is a nucleotide corresponding to the late maturation allele of the respective SNP. The late maturation allele of each SNP is specified in Table 1.

In a second aspect, a method for selecting a rainbow trout having late onset of sexual maturation comprises determining the presence of at least one allele, such as at least two alleles, conferring late onset of sexual maturation ("late maturation allele") within the genome of said rainbow trout; and selecting said rainbow trout as having late onset of sexual maturation when the at least one late maturation allele is present; wherein the at least one late maturation allele is an allele of at least one SNP, the at least one SNP being selected from the SNPs listed in Table 1.

According to certain aspects, a method for selecting a rainbow trout having late onset of sexual maturation comprises determining the identity of a nucleotide of at least one allele, such as at least two alleles, of at least one SNP associated with late onset of sexual maturation within the genome of said rainbow trout; the at least one SNP being selected from the group consisting of SNP #1 to SNP #164; and selecting said rainbow trout as having late onset of sexual maturation when the nucleotide of the at least one allele is a nucleotide corresponding to the late maturation allele of the SNP.

According to certain aspects, a method for selecting a rainbow trout having late onset of sexual maturation comprises determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 1 to 164, or at a position corresponding to position 31 of a nucleotide sequence which is derived from any one of SEQ ID NOs: 1 to 164 by 1 to 5, such as 1 to 2, nucleotide substitutions; with the proviso that said nucleotide substitution(s) are not at position 31 of said derived sequences; and selecting said rainbow trout as having late onset of sexual maturation when the nucleotide of the at least one allele is a nucleotide corresponding to the late maturation allele of the SNP.

The rainbow trout has late onset of sexual maturation when the nucleotide of the at least one allele is a nucleotide corresponding to the late maturation allele of the respective SNP. The late maturation allele of each SNP is specified in Table 1.

In a further aspect, provided herein is a rainbow trout, such as an isolated rainbow trout, or a progeny thereof having late onset of sexual maturation comprising within its genome at least one allele, such as at least two alleles, conferring late onset of sexual maturation ("late maturation allele"); wherein the at least one late maturation allele is an allele of at least one single nucleotide polymorphism (SNP), the at least one SNP being selected from the SNPs listed in Table 1.

Late onset of sexual maturation will have positive impacts on growth since the fish does not need to invest energy in gonadal development and gamete production. Further, late onset of sexual maturation will also help the fish to maintain tolerance to seawater for a prolonged period of time which will have a positive effect on fish welfare. Late onset of sexual maturation may also i) improve fat- and protein content of fish filets; ii) improve flesh pigmentation; and iii) improve smell and taste of the fish filet. Late onset of sexual maturation may also reduce aggressive behavior of the fish, in particular for male fish, for a prolonged period of time. Further, gene pools of wild fish strains are less likely to be negatively impacted by farmed fish with late maturation.

Thus, the purpose of providing an (isolated) rainbow trout having late onset of sexual maturation may include:
  improving growth of the (isolated) rainbow trout;

maintaining optimal tolerance to seawater for a prolonged period of time;
improving fat- and protein content of fish filets;
improving flesh pigmentation;
improving smell and taste of the fish filet;
reducing undesirable behavior, such as aggressive behavior, commonly associated with mature fish; and/or
reducing negative impact of escaped farmed fish on gene pools of wild fish strains.

In view of the above, it is clear that the fish farming industry has a need for an (isolated) rainbow trout having late onset of sexual maturation. Thus, another purpose of providing an (isolated) rainbow trout having late onset of sexual maturation is to fulfill this need by providing a plurality of such fish. A plurality of such fish may be obtained by using the (isolated) rainbow trout for breeding purposes.

According to certain aspects, a rainbow trout, such as an isolated rainbow trout, or progeny thereof comprises within its genome at least one nucleotide sequence selected from the group consisting of a) the nucleotide sequences set forth in SEQ ID NOs: 165 to 328, and b) nucleotide sequences derived from any one of SEQ ID NOs: 165 to 328 by 1 to 5, such as 1 to 2, nucleotide substitutions, provide that said nucleotide substitutions are not at position 31 of said derived sequence.

The rainbow trout has late onset of sexual maturation when the nucleotide of the at least one allele is a nucleotide corresponding to the late maturation allele of the respective SNP. The late maturation allele of each SNP is specified in Table 1.

In another aspect, provided herein is a population of rainbow trout, such as an isolated population of rainbow trout, each individual rainbow trout within the population being a rainbow trout according to the further aspect referred to above.

In another aspect, provided is a population of rainbow trout, such as an isolated population of rainbow trout, wherein at least 50%, such as at least 60%, at least 70%, at least 80%, at least 90%, at least 95% or at least 99% of the rainbow trout within the population comprises within its genome at least one allele conferring late onset of sexual maturation ("late maturation allele"); the at least one late maturation allele being an allele of at least one single nucleotide polymorphism (SNP), the at least one SNP being selected from the SNPs listed in Table 1.

The purpose of providing an (isolated) rainbow trout having late onset of sexual maturation is discussed above. However, the fish farming industry is farming a population of fish, not single individuals, and it is common that all fish are treated in a similar manner. It is therefore an advantage if the population of fish at each facility is as homogenous as possible. By having a homogenous population of fish, the response to feeding and other treatments would be expected to be similar within this population.

Further provided is a rainbow trout or progeny thereof which comprises in its genome at least one allele, such as at least two alleles, conferring late onset of sexual maturation obtainable by a process comprising the steps of: genotyping the rainbow trout, selecting individuals having at least one allele, preferably two alleles, conferring late onset of sexual maturation ("late maturation allele"); and mating individuals in such a way that at least one individual within each mated pair has two alleles conferring late onset of sexual maturation.

In a third aspect, an isolated rainbow trout cell comprises within its genome at least one allele conferring late onset of sexual maturation ("late maturation allele"); wherein the at least one late maturation allele is an allele of at least one single nucleotide polymorphism (SNP), the at least one SNP being selected from the SNPs listed in Table 1.

According to certain embodiments, provided herein is a rainbow trout cell, such as an isolated rainbow trout cell, which comprises within its genome at least one nucleotide sequence selected from the group consisting of a) the nucleotide sequences set forth in SEQ ID NOs: 165 to 328, and b) nucleotide sequences derived from any one of SEQ ID NOs: 165 to 328 by 1 to 5, such as 1 to 2, nucleotide substitutions, provide that said nucleotide substitutions are not at position 31 of said derived sequence.

The rainbow trout has late onset of sexual maturation when the nucleotide of the at least one allele is a nucleotide corresponding to the late maturation allele of the respective SNP. The late maturation allele of each SNP is specified in Table 1.

In another aspect, a population of rainbow trout cells is provided, such as an isolated population of rainbow trout cells, each individual cell within the population being a cell according to the third aspect.

In another aspect, a population of rainbow trout cells is provided, such as an isolated population of rainbow trout cells, wherein at least 50%, such as at least 60%, at least 70%, at least 80%, at least 90%, at least 95% or at least 99% of the rainbow trout cells within the population comprises within its genome at least one allele conferring late onset of sexual maturation ("late maturation allele"); the at least one late maturation allele being an allele of at least one single nucleotide polymorphism (SNP), the at least one SNP being selected from the SNPs listed in Table 1.

In a fourth aspect, an isolated rainbow trout egg or spermatozoa comprises within its genome at least one allele conferring late onset of sexual maturation ("late maturation allele"); wherein the isolated rainbow trout egg is unfertilized; and the at least one late maturation allele is an allele of at least one single nucleotide polymorphism (SNP), the at least one SNP being selected from the SNPs listed in Table 1.

Late onset of sexual maturation will have positive impacts on growth since the fish does not need to invest energy in gonadal development and gamete production, Further, late onset of sexual maturation will also help the fish to maintain tolerance to seawater for a prolonged period of time which will have a positive effect on fish welfare. Late onset of sexual maturation may also i) improve fat- and protein content of fish filets; ii) improve flesh pigmentation; and iii) improve smell and taste of the fish filet. Late onset of sexual maturation may also reduce aggressive behavior of the fish, in particular for male fish, for a prolonged period of time. Further, gene pools of wild fish strains are less likely to be negatively impacted by farmed fish with late maturation.

Thus, the purpose of providing an (isolated) rainbow trout having late onset of sexual maturation may include:
improving growth of the (isolated) rainbow trout;
maintaining optimal tolerance to seawater for a prolonged period of time;
improving fat- and protein content of fish filets;
improving flesh pigmentation;
improving smell and taste of the fish filet;
reducing undesirable behavior, such as aggressive behavior, commonly associated with mature fish; and/or
reducing negative impact of escaped farmed fish on gene pools of wild fish strains.

In view of the above, it is clear that there is a need in the fish farming industry for an (isolated) rainbow trout having late onset of sexual maturation. This need may be fulfilled by providing a plurality of such fish. A plurality of such fish may be obtained by breeding using the isolated rainbow trout egg or spermatozoa according to the fourth aspect of the present invention.

Thus, the (isolated) rainbow trout egg or spermatozoa according to the fourth aspect is intended to be used for breeding purposes for obtaining an (isolated) rainbow trout having late onset of sexual maturation. Said in other words, the (isolated) rainbow trout egg or spermatozoa according to the fourth aspect invention will provide the genetic material necessary to obtain an (isolated) rainbow trout having late onset of sexual maturation and thereby:
- improve growth of the (isolated) rainbow trout;
- maintain optimal tolerance to seawater for a prolonged period of time;
- improve fat- and protein content of fish filets;
- improve flesh pigmentation;
- improve smell and taste of the fish filet;
- reduce undesirable behavior, such as aggressive behavior, commonly associated with mature fish; and/or
- reduce negative impact of escaped farmed fish on gene pools of wild fish strains.

According to certain aspects, provided is an isolated rainbow trout egg or spermatozoa which comprises within its genome at least one nucleotide sequence selected from the group consisting of a) the nucleotide sequences set forth in SEQ ID NOs: 165 to 328, and b) nucleotide sequences derived from any one of SEQ ID NOs: 165 to 328 by 1 to 5, such as 1 to 2, nucleotide substitutions, provide that said nucleotide substitutions are not at position 31 of said derived sequence.

The rainbow trout has late onset of sexual maturation when the nucleotide of the at least one allele is a nucleotide corresponding to the late maturation allele of the respective SNP. The late maturation allele of each SNP is specified in Table 1.

In another aspect, provided is a population of rainbow trout eggs or spermatozoa, such as an isolated population of rainbow trout egg or spermatozoa, each individual egg or spermatozoa within the population being an egg or spermatozoa according to the present disclosure.

Further provided is a population of rainbow trout eggs or spermatozoa, such as an isolated population of rainbow trout eggs or spermatozoa, wherein at least 50%, such as at least 60%, at least 70%, at least 80%, at least 90%, at least 95% or at least 99% of the rainbow trout eggs or spermatozoa within the population comprises within its genome at least one allele conferring late onset of sexual maturation ("late maturation allele"); the at least one late maturation allele being an allele of at least one single nucleotide polymorphism (SNP), the at least one SNP being selected from the SNPs listed in Table 1 and each individual rainbow trout egg within the population being unfertilized.

The purpose of providing an (isolated) rainbow trout egg or spermatozoa according to the fourth aspect is discussed above. When these eggs or spermatozoa are used for breeding purposes, they are not used individually but rather as a population of eggs or spermatozoa. By using a population of such eggs or spermatozoa, the resulting fish population will be homogenous with respect to the late maturation allele. Thus, the purpose of providing a population of (isolated) rainbow trout eggs or spermatozoa according is to provide a fish population which will be homogenous with respect to the late maturation allele.

In a fifth aspect, provided is oligonucleotide, such as an isolated oligonucleotide, comprising at least 8 contiguous nucleotides, such as at least 10 contiguous nucleotides, at least 12 contiguous nucleotides, at least 14 contiguous nucleotides, at least 16 contiguous nucleotides, at least 18 contiguous nucleotides or at least 20 contiguous nucleotides, of a nucleotide sequence set forth in any one of SEQ ID NOs: 1 to 164, or a complementary sequence thereof; or of a nucleotide sequence derived from any one of SEQ ID NOs: 1 to 164 by 1 to 5, such as 1 to 2, nucleotide substitutions, or a complementary sequence thereof, provided that said nucleotide substitutions are not at position 31 of said derived sequence, with the proviso that that the oligonucleotide includes a late maturation allele or a normal maturation allele, the late maturation allele and the normal maturation allele being alleles of single nucleotide polymorphisms (SNP), the SNP being selected from the SNPs listed in Table 1.

The purpose of obtaining an oligonucleotide according to the fifth aspect is to provide a tool to be used in the method according to the first and/or second aspect. The oligonucleotide according to the fifth aspect is suitable for determining the presence of at least one allele, such as at least two alleles, conferring late onset of sexual maturation ("late maturation allele") within a genome of a rainbow trout.

In one embodiment according to the fifth aspect, the oligonucleotide has a total length of 8 to 61 nucleotides, such as a total length of 10 to 61 nucleotides, a total length of 12 to 61 nucleotides, a total length of 14 to 61 nucleotides, a total length of 16 to 61 nucleotides, a total length of 18 to 61 nucleotides or a total length of 20 to 61 nucleotides.

In another embodiment according to the fifth aspect, the oligonucleotide has a total length of 8 to 50 nucleotides, such as a total length of 10 to 50 nucleotides, a total length of 12 to 50 nucleotides, a total length of 14 to 50 nucleotides, a total length of 16 to 50 nucleotides, a total length of 18 to 50 nucleotides or a total length of 20 to 50 nucleotides.

In another embodiment according to the fifth aspect, the oligonucleotide has a total length of 8 to 40 nucleotides, such as a total length of 10 to 40 nucleotides, a total length of 12 to 40 nucleotides, a total length of 14 to 40 nucleotides, a total length of 16 to 40 nucleotides, a total length of 18 to 40 nucleotides or a total length of 20 to 40 nucleotides.

Also provided in a sixth aspect is a kit for predicting late onset of sexual maturation in rainbow trout, the kit comprising at least one of the oligonucleotides according to the fifth aspect.

Further provided in a seventh aspect is a kit for selecting a rainbow trout having late onset of sexual maturation, the kit comprising at least one of the oligonucleotides according to the fifth aspect.

In an eighth aspect, a method for obtaining gametes from rainbow trout (*Oncorhynchus mykiss*) having late onset of sexual maturation comprises:
- providing an initial population of rainbow trout;
- obtaining a nucleic acid sample from at least one individual rainbow trout within said initial population;
- detecting in each of said nucleic acid samples the presence of at least one allele conferring late onset of sexual maturation ("late maturation allele") within the genome of said rainbow trout; wherein the at least one late maturation allele is an allele of at least one single nucleotide polymorphism (SNP), the at least one SNP being selected from the SNPs listed in Table 1;
- selecting a rainbow trout from said initial population based on the presence of the at least one late maturation allele in the nucleic acid samples; and
- isolating gametes from said selected trout.

In one embodiment according to the eight aspect, said gametes are eggs.

In one embodiment according to the eight aspect, said gametes are spermatozoa.

In a ninth aspect, a method for obtaining rainbow trout gametes comprising within their genome at least one late maturation allele comprises
  providing an initial population of rainbow trout gametes;
  obtaining a nucleic acid sample from at least one individual gamete within said initial population;
  detecting in each of said nucleic acid samples the presence of at least one allele conferring late onset of sexual maturation ("late maturation allele") within the genome of said gamete; wherein the at least one late maturation allele is an allele of at least one single nucleotide polymorphism (SNP), the at least one SNP being selected from the SNPs listed in Table 1; and
  selecting and isolating a gamete from said initial population based on the presence of the at least one late maturation allele in the nucleic acid samples; and In one embodiment according to the nineth aspect, said gametes are eggs.

In one embodiment according to the nineth aspect, said gametes are spermatozoa.

In a tenth aspect, a method for obtaining rainbow trout having late onset of sexual maturation comprises
  providing rainbow trout eggs comprising within their genome at least one late maturation allele; wherein the at least one late maturation allele is an allele of at least one single nucleotide polymorphism (SNP), the at least one SNP being selected from the SNPs listed in Table 1;
  providing rainbow trout spermatozoa; and
  utilizing the rainbow trout eggs and the rainbow trout spermatozoa to produce rainbow trout having late onset of sexual maturation.

In one embodiment according to the tenth aspect, the rainbow trout eggs are obtained by the foregoing methods.

In one embodiment according to the tenth aspect, the rainbow trout spermatozoa comprises within their genome at least one late maturation allele; wherein the at least one late maturation allele is an allele of at least one single nucleotide polymorphism (SNP), the at least one SNP being selected from the SNPs listed in Table 1.

In one embodiment according to the tenth aspect, the rainbow trout spermatozoa
  comprise within their genome at least one late maturation allele; wherein the at least one late maturation allele is an allele of at least one single nucleotide polymorphism (SNP), the at least one SNP being selected from the SNPs listed in Table 1; and
  are obtained by the method according to the eight and/or nineth aspect In an eleventh aspect, a method for obtaining rainbow trout having late onset of sexual maturation comprises
  providing rainbow trout spermatozoa comprising within their genome at least one late maturation allele; wherein the at least one late maturation allele is an allele of at least one single nucleotide polymorphism (SNP), the at least one SNP being selected from the SNPs listed in Table 1;
  providing rainbow trout eggs; and
  utilizing the rainbow trout eggs and the rainbow trout spermatozoa to produce rainbow trout having late onset of sexual maturation.

In one embodiment according to the eleventh aspect, the rainbow trout spermatozoa are obtained by the method according to the eight and/or ninth aspect.

In one embodiment according to the eleventh aspect, the rainbow trout eggs comprises within their genome at least one late maturation allele; wherein the at least one late maturation allele is an allele of at least one single nucleotide polymorphism (SNP), the at least one SNP being selected from the SNPs listed in Table 1.

In one embodiment according to the tenth aspect, the rainbow trout eggs:
  comprise within their genome at least one late maturation allele; wherein the at least one late maturation allele is an allele of at least one single nucleotide polymorphism (SNP), the at least one SNP being selected from the SNPs listed in Table 1; and
  are obtained by the method according to the eight and/or nineth aspect of the present invention.

In a twelfth aspect, a method for obtaining fertilized rainbow trout eggs which will mature into a rainbow trout having late onset of sexual maturation comprises
  providing rainbow trout eggs comprising within their genome at least one late maturation allele; wherein the at least one late maturation allele is an allele of at least one single nucleotide polymorphism (SNP), the at least one SNP being selected from the SNPs listed in Table 1;
  providing rainbow trout spermatozoa; and
  fertilizing the rainbow trout eggs using the rainbow trout spermatozoa thereby producing a fertilized rainbow trout egg which will mature into a rainbow trout having late onset of sexual maturation.

In one embodiment according to the twelfth aspect, the rainbow trout eggs are obtained by the method according to the eight and/or nineth aspect.

In one embodiment according to the twelfth aspect, the rainbow trout spermatozoa comprises within their genome at least one late maturation allele; wherein the at least one late maturation allele is an allele of at least one single nucleotide polymorphism (SNP), the at least one SNP being selected from the SNPs listed in Table 1.

In one embodiment according to the twelfth aspect, the rainbow trout spermatozoa:
  comprise within their genome at least one late maturation allele; wherein the at least one late maturation allele is an allele of at least one single nucleotide polymorphism (SNP), the at least one SNP being selected from the SNPs listed in Table 1; and
  are obtained by the method according to the eight and/or nineth aspect of the present invention.

In a thirteenth aspect, a method for obtaining fertilized rainbow trout eggs which will mature into a rainbow trout having late onset of sexual maturation comprises
  providing rainbow trout spermatozoa comprising within their genome at least one late maturation allele; wherein the at least one late maturation allele is an allele of at least one single nucleotide polymorphism (SNP), the at least one SNP being selected from the SNPs listed in Table 1;
  providing rainbow trout eggs; and
  fertilizing the rainbow trout eggs using the rainbow trout spermatozoa thereby producing a fertilized rainbow trout egg which will mature into a rainbow trout having late onset of sexual maturation.

In one embodiment according to the thirteenth aspect, the rainbow trout spermatozoa are obtained by the method according to the eight and/or nineth aspect.

In one embodiment according to the thirteenth aspect, the rainbow trout eggs comprises within their genome at least one late maturation allele; wherein the at least one late maturation allele is an allele of at least one single nucleotide polymorphism (SNP), the at least one SNP being selected from the SNPs listed in Table 1.

In one embodiment according to the thirteenth aspect, the rainbow trout eggs
comprise within their genome at least one late maturation allele; wherein the at least one late maturation allele is an allele of at least one single nucleotide polymorphism (SNP), the at least one SNP being selected from the SNPs listed in Table 1; and
are obtained by the method according to the eight and/or nineth aspect of the present invention.

In one embodiment according to the thirteenth aspect, the method further comprises a step of rinsing the fertilized rainbow trout eggs; preferably using water.

In one embodiment according to the thirteenth aspect, the method further comprising subjecting the fertilized rainbow trout eggs to disinfection treatment.

In one embodiment according to the thirteenth aspect, the method further comprising the steps of:
rinsing the fertilized rainbow trout eggs, preferably using water, to obtain rinsed fertilized rainbow trout eggs; and
subjecting the rinsed fertilized rainbow trout eggs to disinfection treatment.

In a fourteenth aspect, a method for obtaining rainbow trout having late onset of sexual maturation comprises
providing an initial population of rainbow trout;
obtaining a nucleic acid sample from at least one individual rainbow trout within said initial population;
detecting in each of said nucleic acid samples the presence of at least one allele conferring late onset of sexual maturation ("late maturation allele") within the genome of said rainbow trout; wherein the at least one late maturation allele is an allele of at least one single nucleotide polymorphism (SNP), the at least one SNP being selected from the SNPs listed in Table 1;
selecting a rainbow trout from said initial population based on the presence of the at least one late maturation allele in the nucleic acid samples; and
mating said selected rainbow trout with a second rainbow trout to produce progeny rainbow trout having late onset of sexual maturation.

In one embodiment according to the fourteenth aspect, at least one rainbow trout within said mating pair is homozygous for the late maturation allele.

In one embodiment according to the fourteenth aspect, each rainbow trout within said mating pair is homozygous for the late maturation allele.

BRIEF DESCRIPTION OF THE DRAWINGS

The present invention is described in detail by reference to the following drawings.

A distinctive and highly significant QTL for maturity is detected on chromosome 28. The most preferred SNPs are marked in light grey color (SNP #120, 127-131, 134-135, 137-138, 140, 142, 143-144, 146-147; 16 SNPs in total). All of these SNPs (16 in total) have a p-value lower than 3.12e-7 and are located within a genomic region of 1.9 megabases.

Figure 2A:
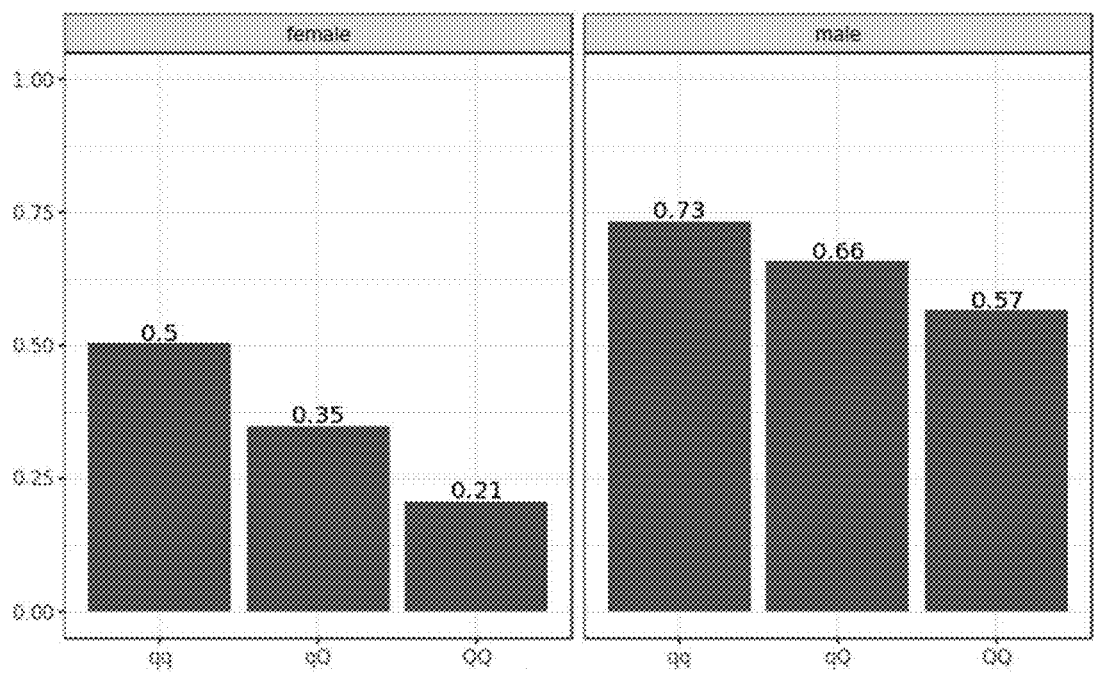

FIG. 2a illustrates the effect of SNP #140 on sexual maturation in male and female rainbow trout. X-axis indicates the allelic variants of SNP #140. Y-axis indicates the fraction of fish that are sexually mature.

| Genotype | Allelic variants |
| --- | --- |
| qq | homozygous for normal maturation allele |
| qQ | heterozygous for late maturation allele |
| QQ | homozygous for late maturation allele |

The figure shows how the genotype correlate with maturation without correcting for polygenic effect (effect of all other genes, i.e. family effect) and other potential co-factors. The effect size of the allele is adjusted for the polygenic effect and sex; hence it is a more accurate measure. The effect is significant in both male and female Trout; but seems to be somewhat larger in female Trout.

Figure 2B:
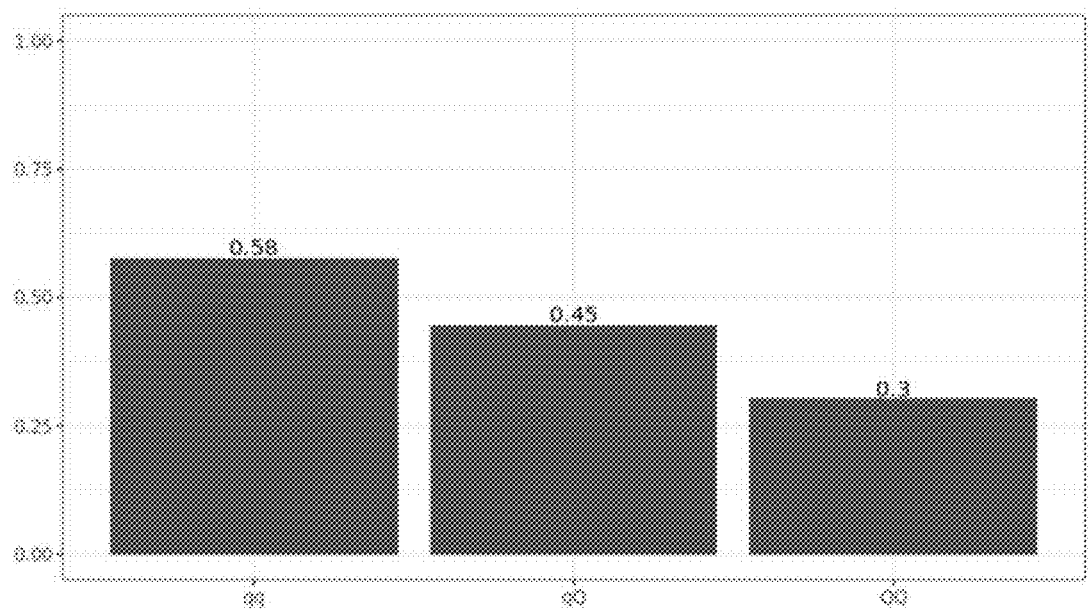

FIG. 2b shows unadjusted effect of SNP #140 on sexual maturation in both sexes combined. X-axis indicates the allelic variants of SNP #140. Y-axis indicates the fraction of fish that are sexually mature.

| Genotype | Allelic variants |
| --- | --- |
| qq | homozygous for normal maturation allele |
| qQ | heterozygous for late maturation allele |
| QQ | homozygous for late maturation allele |

Figure 3:
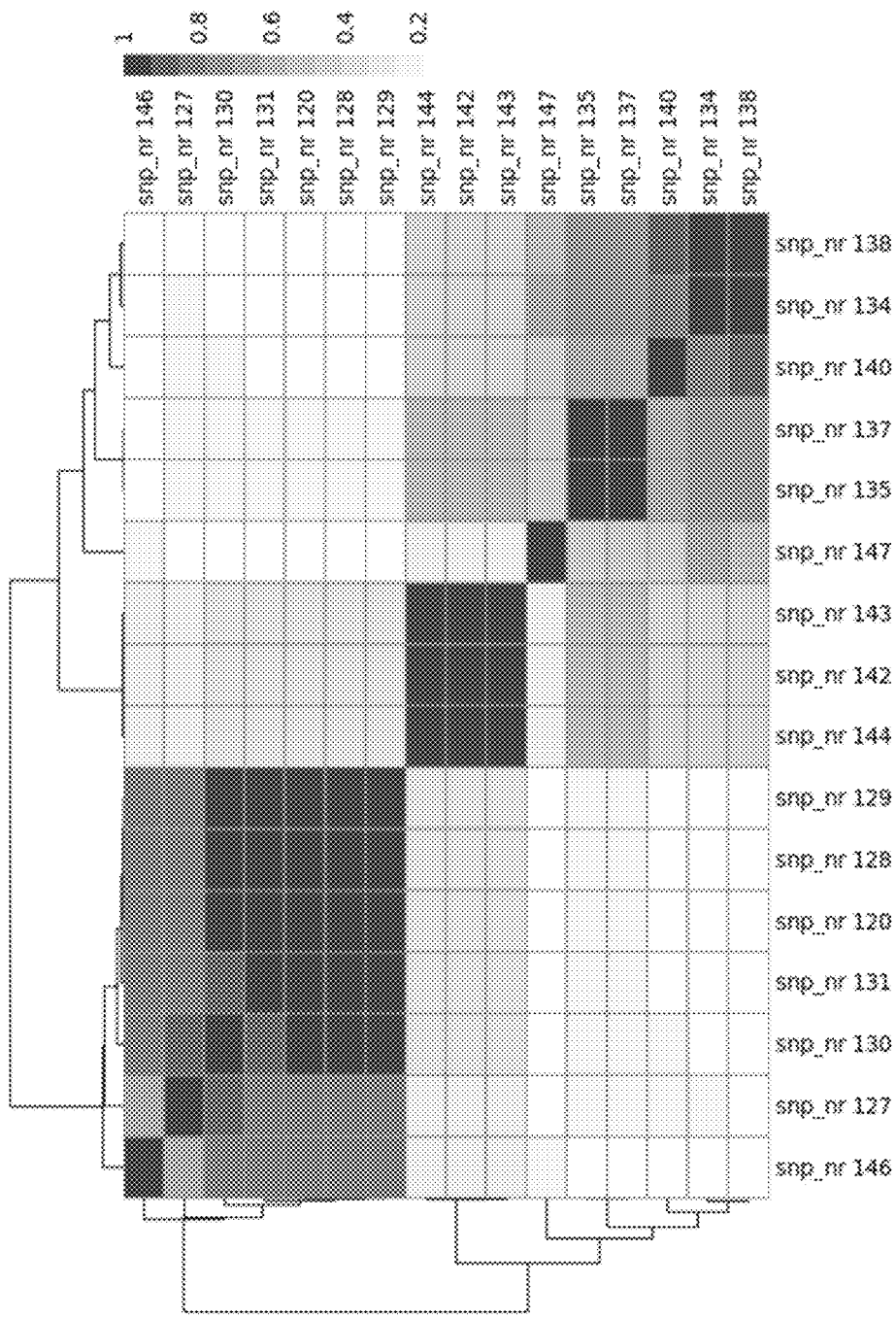

FIG. 3 shows a squared correlation (R2) matrix between the most preferred SNPs on chromosome 28 (SNP #120, 127-131, 134-135, 137-138, 140, 142, 143-144, 146-147; 16 SNPs in total). The SNPs are clustered together based on R2 and all show varying degree of elevated squared correlations to each other.

DETAILED DESCRIPTION

Unless specifically defined herein, all technical and scientific terms used have the same meaning as commonly understood by a skilled artisan in the fields of genetics, biochemistry, and molecular biology.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will prevail.

Where a numerical limit or range is stated herein, the endpoints are included. Also, all values and sub ranges within a numerical limit or range are specifically included as if explicitly written out.

Definitions

As used herein, late onset of sexual maturation means that an individual having late onset of sexual maturation has a higher probability of maturing later than a random individual (under the same conditions, i.e. under same intrinsic and extrinsic factors) with whom it is comparable. Two individuals are comparable if they are, with regards to all discriminating factors except the genotype at the SNP which is used for predicting late onset of sexual maturation, random representatives of one and the same population of rainbow trout.

As used herein, a "late maturation allele" is an allele conferring late onset of sexual maturation. This means that a rainbow trout having such allele at the position of a polymorphism detailed herein shows late onset of sexual maturation. The "late maturation allele" may identify a single nucleotide polymorphism that can be used to detect or determine the degree of late sexual maturation.

As used herein, a "polymorphism" is a variation in a genomic sequence. In particular, a polymorphism is a position on the genome where different allelic variants are generally found between individuals of a population, or between individuals from different populations. The polymorphism may be a single nucleotide difference present at a locus or may be an insertion or deletion of one or a few nucleotides at a position of a gene.

As used herein, a "single nucleotide polymorphism" or "SNP" refers to a single base (nucleotide) polymorphism in a DNA sequence among individuals in a population. As such, a single nucleotide polymorphism is characterized by the presence in a population of one or two, three or four different nucleotides (i.e. adenine, cytosine, guanine or thymine), typically less than all four nucleotides, at a particular locus in a genome, such as the genome of rainbow trout.

As used herein, "polymorphic sequence" refers to a nucleotide sequence including a polymorphic site at which a SNP or another type of polymorphism occurs.

As used herein, a "polymorphic site" is the locus or position within a given sequence at which divergence occurs. Preferred polymorphic sites have at least two alleles, each occurring at frequency greater than 1%, and more preferably greater than 10%. Those skilled in the art will recognize that nucleic acid molecules may be double-stranded molecules and that reference to a particular site on one strand refers, as well, to the corresponding site on a complementary strand. In defining a polymorphic site or allele reference to an adenine, a thymine, a cytosine, or a guanine at a particular site on one strand of a nucleic acid molecule also defines the thymine, adenine, guanine, or cytosine (respectively) at the corresponding site on a complementary strand of the nucleic acid.

Herein, when a polymorphism is specified as having a particular allele, then it is understood that that particular allele goes together with the sequence given for the polymorphism. For example, when it is said that thymine is the late maturation allele of Affx-88940276, then it is understood that the late maturation allele of Affx-88940276 harbors a thymine nucleotide in the polymorphic site defined in Table 2 when the DNA is read in the direction defined in Table 2. In other words, as stated in Table 2, the late maturation form of the DNA sequence of Affx-88940276 (with flanking sequences) is CCGCCAGTGTCGATGC-CAAACCCTTGAAAATAGGT[C/T]GG-GAAAGGAAATCC TTTCCCTCTAAATATCTGTCG (SEQ ID NO: 329; polymorphic site in brackets) when read in the direction defined in Table 2. When read in the opposite direction, the sequence of Affx-88940276 (with flanking sequence) is GCTGTC-TATAAATCTCCCTTTCCTAAAGGAAAGGG[T/C]TG-GATAAAAGTTCCC AAACCGTAGCTGTGACCGCC (SEQ ID NO: 330; polymorphic site in brackets). Although only one direction is used when late maturation alleles and normal maturation alleles are defined herein, the two read directions are equivalent.

As used herein, a "sample", such as a biological sample that includes nucleic acid molecules, is a sample obtained from a rainbow trout, including, but not limited to, cells, tissue, and bodily fluids.

As used herein, an "oligonucleotide" is a plurality of joined nucleotides joined by native phosphodiester bonds, typically from 8 to 300 nucleotides in length.

As used herein, "probes" and "primer" are isolated oligonucleotides of at least 8 nucleotides, such as at least 10 nucleotides, capable of hybridizing to a target nucleic acid.

As used herein, "isolated" means that an organism or a biological component, such as a cell, population of cells or a nucleic acid molecule, has been separated from its natural environment.

As used herein, "genetic linkage" refers to the tendency of polymorphisms that are located close to each other on a chromosome to be inherited together during meiosis. Thus, polymorphisms located close to each other on the same chromosome are said to be genetically linked. Alleles at two such genetically linked loci are co-inherited (from parents to offspring) more often than they are not. Assume, for example, two polymorphisms; polymorphism A having alleles A1 and A2, and polymorphism B having alleles B1 and B2. Assume further that a given rainbow trout carries all of the alleles A1, A2, B1, and B2 (in other words, this rainbow trout is heterozygous at both marker and marker B). If alleles A1 and B1 are, in this particular rainbow trout, located on the same chromosome copy, then alleles A1 and B1 are co-inherited, to the offspring of the rainbow trout, more often than not.

As used herein, "genetic linkage analysis" refers to a statistical procedure where genotype data, coming from sets of animals comprising parents and their offspring, are investigated in order to test for the presence of genetic linkage between polymorphisms. Genetic linkage analysis can be used in order to assign polymorphisms to chromosomes, provided that the analysis incorporates polymorphisms that have already been assigned to chromosome using, for example, Fluorescence In Situ Hybridization.

As used herein "Fluorescence In Situ Hybridization" or "FISH" refers to a technique that detect the presence or absence of specific DNA sequences on chromosomes. FISH can be used in order to assign known DNA polymorphisms to chromosomes.

"Centi-Morgen" is a unit of measurement, used to describe genetic distances, where genetic distance is a measure of the extent to which two polymorphisms are genetically linked.

Linkage disequilibrium (LD) or, more precisely, gametic phase linkage disequilibrium, is used in order to describe the co-inheritance of alleles at genetically linked polymorphisms, at the population level. Assume, for example, two polymorphisms located on the same chromosome; polymorphism A having alleles A1 and A2, and polymorphism B having alleles B1 and B2. All copies of the chromosome in question will harbor a combination of alleles at the two loci (i.e. a haplotype), and there are four possible haplotypes: A1-B1, A1-B2, A2-B1, and A2-B2. The two loci are in said to be LD with each other if the number of A1-B1 and A2-B2 haplotypes within the population are significantly larger or significantly smaller than the number of A1-B2 and A2-B1 haplotypes.

Polymorphisms and Late Maturation Allele(s) of the Invention

The present inventors have identified several quantitative trait locus (QTL) responsible for a significant fraction of the genetic variation related to sexual maturation in rainbow trout. More specifically, the present inventors have identified polymorphisms, and in particular single nucleotide polymorphisms (SNP), within the genome, more particularly on chromosome 1 to 29, of rainbow trout which are associated with late onset of sexual maturation. Specific details of single nucleotide polymorphisms of the invention are provided in Table 1 below. The respective nucleotide sequences including the SNP (at position 31) are shown in Table 2.

The polymorphisms of the invention can be present in either of two forms, i.e., the polymorphisms have two alleles.

One allele can be characterized as being an allele conferring late onset of sexual maturation. This means that a rainbow trout having such allele at the position of a polymorphism detailed herein shows late onset of sexual maturation. This allele is herein denoted "late maturation allele". The respective late maturation allele for each of the single nucleotide polymorphism of the invention is specified in Table 1 below. A late maturation allele according to the present invention may therefore be used to predict late onset of sexual maturation in a rainbow trout. A late maturation allele according to the present invention may also be used to select a rainbow trout having late onset of sexual maturation.

The other allele can be characterized as being an allele that does not confer late onset of sexual maturation. Such allele is herein denoted "normal maturation allele".

Rainbow trout are diploid, in some case triploid organisms, and thus possess at least two copies of the polymorphisms of the invention (one copy to be found on each copy of the chromosome).

As demonstrated herein, if at least one allele of a polymorphism, and more particularly of a SNP, is the respective late maturation allele, then the rainbow trout has late onset of sexual maturation as compared to a rainbow trout wherein both alleles are normal maturation alleles (i.e. such rainbow trout being homozygous for the normal maturation allele). In a great number of cases the onset of sexual maturation is even further delayed if both alleles of a polymorphism, and more particularly of a SNP, are the respective late maturation alleles (such rainbow trout being homozygous for the late maturation allele). Such further increase is, for example, seen for SNP #140 (FIGS. 2a and 2b) which is the most statistically significant SNP associated with late onset of sexual maturation (see table 3).

A polymorphism of the invention may be any of several polymorphisms associated with late onset of sexual maturation of a rainbow trout. Particularly, a polymorphism of the invention is a polymorphism located on any one of chromosome 1 to 29 of rainbow trout (following the nomenclature of Palti et al. (2011)), i.e. a polymorphism found to be located on any one of chromosome 1 to 29 on the basis of genetic linkage analysis, Fluorescence In Situ Hybridization (FISH) or any other method that assigns DNA polymorphisms to their respective chromosomes.

A polymorphism of the invention may be any polymorphism, including single nucleotide polymorphism, located within any of the rainbow trout genomic sequences listed in the column titled "GenBank contig" in Table 1.

A polymorphism of the invention may be any polymorphism, including single nucleotide polymorphism, which is in strong linkage disequilibrium (LD) with any one of the SNPs listed in table 1. Here, two polymorphisms are defined to be in strong LD if the square of the correlation coefficient between the two loci (r2, the most commonly used measure of LD) is equal to or larger than 0.5, more preferably equal to or larger than 0.7, even more preferably equal to or larger than 0.8 and most preferably equal to or larger than 0.9. A person who is skilled in the art will know how to estimate r2, as well as what data is required for this estimation.

A polymorphism of the invention may be at least one of the single nucleotide polymorphisms listed in Table 1. Therefore, according to certain embodiments, the at least one SNP of the invention is selected from the SNPs listed in Table 1. Each of the SNPs listed in Table 1 is contemplated as being disclosed individually as part of the present invention.

TABLE 1

SNPs associated with sexual maturation in Rainbow trout.

| SNP# | Affymetrix ID | Chromosome | GenBank contig | Position in Genbank contig | Late maturation allele | Normal maturation allele |
|---|---|---|---|---|---|---|
| 1 | Affx-88904935 | chr1 | CM007935.1 | 63783597 | T | C |
| 2 | Affx-88955402 | chr1 | CM007935.1 | 64700514 | A | C |
| 3 | Affx-88936832 | chr1 | CM007935.1 | 65578255 | G | A |
| 4 | Affx-88950378 | chr1 | CM007935.1 | 65615419 | A | G |
| 5 | Affx-88925365 | chr2 | CM007936.1 | 54285214 | A | G |
| 6 | Affx-88946858 | chr2 | CM007936.1 | 56918053 | C | T |
| 7 | Affx-88954034 | chr2 | CM007936.1 | 57044148 | C | T |
| 8 | Affx-88936668 | chr2 | CM007936.1 | 59081958 | A | C |
| 9 | Affx-88953569 | chr2 | CM007936.1 | 62341749 | A | G |
| 10 | Affx-88961158 | chr2 | CM007936.1 | 62572758 | C | T |
| 11 | Affx-88934762 | chr2 | CM007936.1 | 63306724 | G | A |
| 12 | Affx-88923797 | chr2 | CM007936.1 | 63685704 | T | C |
| 13 | Affx-88905095 | chr3 | CM007937.1 | 19524784 | A | G |
| 14 | Affx-88915123 | chr3 | CM007937.1 | 19535483 | A | G |
| 15 | Affx-88954577 | chr3 | CM007937.1 | 19603901 | G | T |
| 16 | Affx-88938133 | chr3 | CM007937.1 | 30879389 | A | C |
| 17 | Affx-88915067 | chr4 | CM007938.1 | 8909969 | C | T |
| 18 | Affx-88941840 | chr4 | CM007938.1 | 11240214 | G | A |
| 19 | Affx-88904592 | chr4 | CM007938.1 | 12590767 | T | G |
| 20 | Affx-88958567 | chr4 | CM007938.1 | 71235287 | C | T |
| 21 | Affx-88920423 | chr5 | CM007939.1 | 51055810 | A | G |
| 22 | Affx-88951600 | chr5 | CM007939.1 | 71720042 | A | G |

TABLE 1-continued

SNPs associated with sexual maturation in Rainbow trout.

| SNP# | Affymetrix ID | Chromosome | GenBank contig | Position in Genbank contig | Late maturation allele | Normal maturation allele |
|---|---|---|---|---|---|---|
| 23 | Affx-88958428 | chr5 | CM007939.1 | 81401808 | A | G |
| 24 | Affx-88921734 | chr5 | CM007939.1 | 82479766 | G | T |
| 25 | Affx-88952785 | chr6 | CM007940.1 | 6340153 | G | A |
| 26 | Affx-88954186 | chr6 | CM007940.1 | 18411308 | G | A |
| 27 | Affx-88940319 | chr6 | CM007940.1 | 29053396 | A | C |
| 28 | Affx-88936711 | chr6 | CM007940.1 | 32381726 | A | G |
| 29 | Affx-88909681 | chr7 | CM007941.1 | 18849968 | C | A |
| 30 | Affx-88920716 | chr7 | CM007941.1 | 33271630 | T | C |
| 31 | Affx-88936725 | chr7 | CM007941.1 | 34065749 | C | A |
| 32 | Affx-88930546 | chr7 | CM007941.1 | 35811286 | G | T |
| 33 | Affx-88932380 | chr8 | CM007942.1 | 69313777 | T | C |
| 34 | Affx-88919018 | chr8 | CM007942.1 | 70769104 | A | G |
| 35 | Affx-88948691 | chr8 | CM007942.1 | 70793135 | T | C |
| 36 | Affx-88916802 | chr8 | CM007942.1 | 77412834 | G | A |
| 37 | Affx-88916833 | chr9 | CM007943.1 | 22487940 | A | G |
| 38 | Affx-88929636 | chr9 | CM007943.1 | 22627473 | A | G |
| 39 | Affx-88926137 | chr9 | CM007943.1 | 22675057 | A | G |
| 40 | Affx-88926394 | chr9 | CM007943.1 | 31913561 | A | G |
| 41 | Affx-88934825 | chr10 | CM007944.1 | 31683283 | G | A |
| 42 | Affx-88904537 | chr10 | CM007944.1 | 33539443 | T | C |
| 43 | Affx-88959739 | chr10 | CM007944.1 | 39056184 | T | G |
| 44 | Affx-88956881 | chr11 | CM007945.1 | 3987284 | G | T |
| 45 | Affx-88951001 | chr11 | CM007945.1 | 49414158 | G | T |
| 46 | Affx-88954986 | chr11 | CM007945.1 | 57541195 | T | C |
| 47 | Affx-88916907 | chr11 | CM007945.1 | 67172627 | C | T |
| 48 | Affx-88947853 | chr12 | CM007946.1 | 27799868 | C | A |
| 49 | Affx-88939958 | chr12 | CM007946.1 | 57549580 | G | A |
| 50 | Affx-88911641 | chr12 | CM007946.1 | 86816745 | T | C |
| 51 | Affx-88957555 | chr13 | CM007947.1 | 12693726 | G | T |
| 52 | Affx-88942222 | chr13 | CM007947.1 | 32421268 | G | A |
| 53 | Affx-88904308 | chr13 | CM007947.1 | 45827883 | C | T |
| 54 | Affx-88931117 | chr14 | CM007948.1 | 19467149 | C | T |
| 55 | Affx-88959989 | chr14 | CM007948.1 | 21894963 | C | T |
| 56 | Affx-88918911 | chr14 | CM007948.1 | 24115228 | T | G |
| 57 | Affx-88922027 | chr14 | CM007948.1 | 24920208 | G | A |
| 58 | Affx-88921698 | chr15 | CM007949.1 | 24569160 | T | C |
| 59 | Affx-88925753 | chr15 | CM007949.1 | 27726385 | T | C |
| 60 | Affx-88956336 | chr15 | CM007949.1 | 27801757 | C | A |
| 61 | Affx-88961133 | chr15 | CM007949.1 | 54519499 | G | T |
| 62 | Affx-88921645 | chr16 | CM007950.1 | 36765420 | T | G |
| 63 | Affx-88949977 | chr16 | CM007950.1 | 48753210 | A | G |
| 64 | Affx-88957804 | chr16 | CM007950.1 | 49749575 | A | G |
| 65 | Affx-88913266 | chr17 | CM007951.1 | 38785093 | A | G |
| 66 | Affx-88939862 | chr17 | CM007951.1 | 38831122 | G | T |
| 67 | Affx-88915748 | chr18 | CM007952.1 | 21596568 | T | C |
| 68 | Affx-88922933 | chr18 | CM007952.1 | 22420190 | G | A |
| 69 | Affx-88915837 | chr18 | CM007952.1 | 27494999 | C | T |
| 70 | Affx-88929378 | chr19 | CM007953.1 | 30636790 | C | A |
| 71 | Affx-88961378 | chr19 | CM007953.1 | 34580702 | A | C |
| 72 | Affx-88953889 | chr19 | CM007953.1 | 36847192 | C | T |
| 73 | Affx-88922131 | chr19 | CM007953.1 | 36901034 | G | A |
| 74 | Affx-88958970 | chr20 | CM007954.1 | 2000433 | G | T |
| 75 | Affx-88910072 | chr20 | CM007954.1 | 10825499 | T | G |
| 76 | Affx-88933134 | chr20 | CM007954.1 | 15246572 | A | C |
| 77 | Affx-88939049 | chr21 | CM007955.1 | 12015696 | T | G |
| 78 | Affx-88950195 | chr21 | CM007955.1 | 14532693 | T | C |
| 79 | Affx-88933377 | chr21 | CM007955.1 | 14717955 | G | A |
| 80 | Affx-88909724 | chr21 | CM007955.1 | 34227983 | A | G |
| 81 | Affx-88917486 | chr22 | CM007956.1 | 4433427 | A | G |
| 82 | Affx-88941752 | chr22 | CM007956.1 | 23757569 | G | T |
| 83 | Affx-88942920 | chr22 | CM007956.1 | 24124923 | A | T |
| 84 | Affx-88945639 | chr23 | CM007957.1 | 46442301 | A | G |
| 85 | Affx-88905397 | chr23 | CM007957.1 | 46444905 | T | G |
| 86 | Affx-88949049 | chr23 | CM007957.1 | 47383604 | A | G |
| 87 | Affx-88923532 | chr23 | CM007957.1 | 48284540 | C | T |
| 88 | Affx-88924387 | chr23 | CM007957.1 | 48657925 | G | T |
| 89 | Affx-88905064 | chr23 | CM007957.1 | 48711098 | A | G |
| 90 | Affx-88957818 | chr24 | CM007958.1 | 20952836 | A | G |
| 91 | Affx-88945529 | chr24 | CM007958.1 | 25019945 | T | C |
| 92 | Affx-88940262 | chr24 | CM007958.1 | 25020252 | T | C |
| 93 | Affx-88928194 | chr25 | CM007959.1 | 10849854 | C | A |
| 94 | Affx-88944575 | chr25 | CM007959.1 | 14555851 | T | C |
| 95 | Affx-88911550 | chr25 | CM007959.1 | 14574366 | A | G |
| 96 | Affx-88940618 | chr25 | CM007959.1 | 15498993 | C | T |

TABLE 1-continued

SNPs associated with sexual maturation in Rainbow trout.

| SNP# | Affymetrix ID | Chromosome | GenBank contig | Position in Genbank contig | Late maturation allele | Normal maturation allele |
|---|---|---|---|---|---|---|
| 97 | Affx-88918400 | chr25 | CM007959.1 | 47014119 | T | G |
| 98 | Affx-88926265 | chr25 | CM007959.1 | 47014758 | G | A |
| 99 | Affx-88945363 | chr25 | CM007959.1 | 47015074 | A | G |
| 100 | Affx-88914956 | chr25 | CM007959.1 | 48229209 | G | A |
| 101 | Affx-88959143 | chr25 | CM007959.1 | 48397292 | C | T |
| 102 | Affx-88907320 | chr26 | CM007960.1 | 10225818 | T | G |
| 103 | Affx-88950639 | chr26 | CM007960.1 | 10495031 | A | C |
| 104 | Affx-88951915 | chr26 | CM007960.1 | 12901743 | G | A |
| 105 | Affx-88939677 | chr26 | CM007960.1 | 26154364 | C | T |
| 106 | Affx-88921625 | chr27 | CM007961.1 | 7278740 | G | A |
| 107 | Affx-88918503 | chr27 | CM007961.1 | 7764626 | C | T |
| 108 | Affx-88958017 | chr27 | CM007961.1 | 7820269 | C | A |
| 109 | Affx-88911327 | chr27 | CM007961.1 | 10784017 | C | T |
| 110 | Affx-88950248 | chr28 | CM007962.1 | 9037911 | C | A |
| 111 | Affx-88932371 | chr28 | CM007962.1 | 9072612 | C | T |
| 112 | Affx-88923416 | chr28 | CM007962.1 | 9082601 | C | T |
| 113 | Affx-88955399 | chr28 | CM007962.1 | 9102905 | T | C |
| 114 | Affx-88908191 | chr28 | CM007962.1 | 9446099 | T | C |
| 115 | Affx-88923808 | chr28 | CM007962.1 | 9632653 | A | G |
| 116 | Affx-88908821 | chr28 | CM007962.1 | 9909392 | G | A |
| 117 | Affx-88955530 | chr28 | CM007962.1 | 10202248 | A | G |
| 118 | Affx-88941807 | chr28 | CM007962.1 | 10237515 | A | G |
| 119 | Affx-88904869 | chr28 | CM007962.1 | 10252908 | T | G |
| 120 | Affx-88912748 | chr28 | CM007962.1 | 10378833 | C | A |
| 121 | Affx-88924717 | chr28 | CM007962.1 | 10406672 | A | C |
| 122 | Affx-88946195 | chr28 | CM007962.1 | 10407234 | C | A |
| 123 | Affx-88931804 | chr28 | CM007962.1 | 10500800 | G | A |
| 124 | Affx-88929559 | chr28 | CM007962.1 | 10502719 | T | G |
| 125 | Affx-88905073 | chr28 | CM007962.1 | 10564775 | G | T |
| 126 | Affx-88947012 | chr28 | CM007962.1 | 10593406 | G | A |
| 127 | Affx-88939287 | chr28 | CM007962.1 | 10605800 | A | G |
| 128 | Affx-88947787 | chr28 | CM007962.1 | 11093692 | C | T |
| 129 | Affx-88932913 | chr28 | CM007962.1 | 11096202 | C | T |
| 130 | Affx-88952141 | chr28 | CM007962.1 | 11139401 | G | T |
| 131 | Affx-88913454 | chr28 | CM007962.1 | 11148320 | T | C |
| 132 | Affx-88959734 | chr28 | CM007962.1 | 11200364 | T | G |
| 133 | Affx-88915384 | chr28 | CM007962.1 | 11251982 | T | G |
| 134 | Affx-88927547 | chr28 | CM007962.1 | 11382381 | A | C |
| 135 | Affx-88946147 | chr28 | CM007962.1 | 11414120 | G | A |
| 136 | Affx-88938817 | chr28 | CM007962.1 | 11414342 | C | T |
| 137 | Affx-88953900 | chr28 | CM007962.1 | 11414399 | A | G |
| 138 | Affx-88947402 | chr28 | CM007962.1 | 11487704 | C | T |
| 139 | Affx-88918233 | chr28 | CM007962.1 | 11523747 | C | T |
| 140 | Affx-88940276 | chr28 | CM007962.1 | 11537736 | T | C |
| 141 | Affx-88913684 | chr28 | CM007962.1 | 11575843 | G | T |
| 142 | Affx-88921970 | chr28 | CM007962.1 | 11667915 | A | G |
| 143 | Affx-88945246 | chr28 | CM007962.1 | 11704242 | A | G |
| 144 | Affx-88958541 | chr28 | CM007962.1 | 11745469 | T | C |
| 145 | Affx-88949728 | chr28 | CM007962.1 | 11771654 | A | G |
| 146 | Affx-88961021 | chr28 | CM007962.1 | 12063041 | T | C |
| 147 | Affx-88907679 | chr28 | CM007962.1 | 12252318 | A | G |
| 148 | Affx-88951316 | chr28 | CM007962.1 | 12259307 | G | T |
| 149 | Affx-88930743 | chr28 | CM007962.1 | 12593967 | G | T |
| 150 | Affx-88941593 | chr28 | CM007962.1 | 12700154 | T | C |
| 151 | Affx-88948678 | chr28 | CM007962.1 | 12735308 | C | T |
| 152 | Affx-88912846 | chr28 | CM007962.1 | 12847942 | A | C |
| 153 | Affx-88915764 | chr28 | CM007962.1 | 12982469 | C | T |
| 154 | Affx-88905807 | chr28 | CM007962.1 | 13010185 | C | A |
| 155 | Affx-88948195 | chr28 | CM007962.1 | 13365774 | A | C |
| 156 | Affx-88937868 | chr28 | CM007962.1 | 13877922 | A | G |
| 157 | Affx-88929314 | chr28 | CM007962.1 | 13927035 | A | G |
| 158 | Affx-88919686 | chr28 | CM007962.1 | 14120232 | G | T |
| 159 | Affx-88948530 | chr28 | CM007962.1 | 14551487 | C | T |

TABLE 1-continued

SNPs associated with sexual maturation in Rainbow trout.

| SNP# | Affymetrix ID | Chromosome | GenBank contig | Position in Genbank contig | Late maturation allele | Normal maturation allele |
|---|---|---|---|---|---|---|
| 160 | Affx-88911474 | chr28 | CM007962.1 | 14570553 | C | T |
| 161 | Affx-88944645 | chr28 | CM007962.1 | 18046487 | C | T |
| 162 | Affx-88952966 | chr29 | CM007963.1 | 12570007 | C | T |
| 163 | Affx-88904400 | chr29 | CM007963.1 | 17738627 | T | G |
| 164 | Affx-88914995 | chr29 | CM007963.1 | 38728561 | T | C |

A = Adenine, G = Guanine; C = Cytosine, T = Thymine.

Affymetrix ID is a unique identifier given to each SNP by Affymetrix, the provider of a commercial genotyping assay which incorporates many of the SNPs listed in the table; the Affymetrix ID serves as a link to further details pertaining to the SNPs, provided in a file which can be downloaded from http://www.affymetrix.com/estore/.

Chromosome indicates on which chromosome the SNPs are situated.

GenBank contig is the name of a GenBank DNA contig (a genome sequence from rainbow trout) wherein the SNP resides, and the position is the position of the SNP within this contig.

Figure 1A:
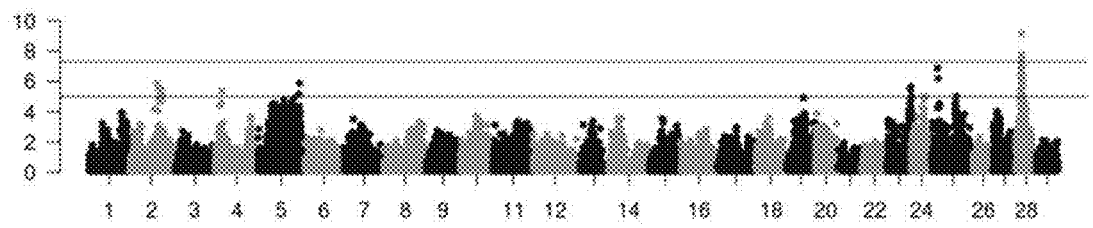
FIG. 1a shows Genome Wide Association Study on maturity for A17 Nucleus eggs from 2017 (AquaGen). X-axis=Chromosome number. Y-axis −log 10(P). A number of chromosomes have distinct peaks, but the most distinctive and highly significant QTL was detected on chromosome 28 (see FIG. 1b).
Figure 1B:
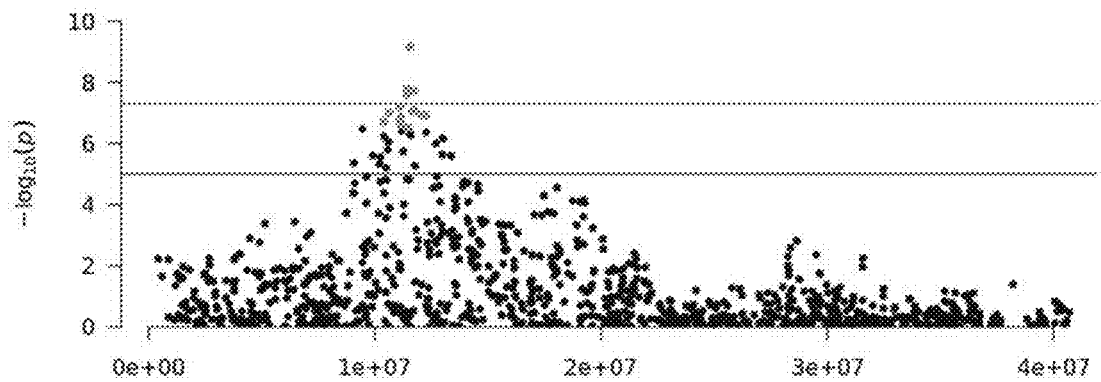
FIG. 1b is a regional Manhattan plot showing the QTL on chromosome 28 and thus represents an extract of the information related to chromosome 28 presented in FIG. 1a. X-axis=position on chromosome 28. Y-axis −log 10(P).

SNPs in bold are of particular interest. All of these SNPs are located within a genomic region of 1.9 megabases on chromosome 28 (FIG. 1b), have a p-value lower than 3.12e−7 (FIG. 1b) and show varying degree of elevated squared correlations to each other (FIG. 3).

TABLE 2

Nucleotide sequence for each SNP including the polymorphic site. The polymorphic site and the corresponding allelic variants are indicated in brackets. The column labeled "Nucleotide sequence including SNP site" provides a reference nucleotide sequence for identification of the SNP within the genome of a rainbow trout. The sequences SEQ ID NO: 1 to 164 are each polymorphic sequences including a polymorphic site. SNPs in bold are of particular interest. All of these SNPs are located within a genomic region of 1.9 megabases on chromosome 28 (FIG. 1b), have a p-value lower than 3.12e-7 (FIG. 1b) and show varying degree of elevated squared correlations to each other (FIG. 3).

| SNP# | SEQ ID NO | Nucleotide sequence including SNP site | Late maturation allele | Normal maturation allele |
|---|---|---|---|---|
| 1 | 1 | AGTATATGATGATTCAATGAGATACAGTAC[C/T]TTACACTTTATTGCCCATTTCCATGAAAAT | T | C |
| 2 | 2 | TCAGTCCATAAGTAATGCAAAGATCAAAGT[A/C]ATTCTACAGAAACCGATTGGGCAGACTAAC | A | C |
| 3 | 3 | AGTACAAACAGAGATGTGTTATGTTAGACA[A/G]CTGAAGTGAACCGCTACACCTGCTTGGTGC | G | A |
| 4 | 4 | GAGTGCAGTGGATAGAGACAGCTCCTCAGT[A/G]CATAAAGGCCCACCTGTCCTGGGGGAAGAT | A | G |
| 5 | 5 | TACTATAATCGGGGACAGTGACATGCATCG[A/G]CCCACAAAGTTTTTAAGACTGCAGTTATGT | A | G |
| 6 | 6 | GGAACCAGTCACTGTCTCACTACATTTTCA[C/T]GTGGCAGTTTTGTCTTCCACCGTGCAAGCC | C | T |
| 7 | 7 | TTGGTTCTTGCAACTCTATAGCTCTGGGTC[C/T]TTCCCTTACCTCGGCACGGCAGCCAGTCAG | C | T |
| 8 | 8 | CTGTATAAAGTTGTTACTGCAGGTACAGGC[A/C]GTGATGCTGAGACTCTTCTGCCAAGACACC | A | C |
| 9 | 9 | ATCGTACTGAGCTTGTTGTCATTGCAGGCA[A/G]TCTCAACTCTGTGCATTACACTGAAGACTT | A | G |
| 10 | 10 | AGACAGATCATCAAAAGCTTTTATTCTGAT[C/T]AAGTTCAGTAGTTTGTTTAGGACACTGAAA | C | T |
| 11 | 11 | TGACCTGCAGCTATGCACCATAATCTAGCA[A/G]GTTCATTTGAACACCCTTTGAAAAGGTAAT | G | A |
| 12 | 12 | TCTATACTACGGTCTATTGCCTATTTTTAA[C/T]GTATCTTTAATTTCGTATCCCAGTTATTAG | T | C |
| 13 | 13 | TTACCATACTAACTTGTAGGGCTGAGCAAT[A/G]TATTTTGAATACAGGCACAGAGCCACATAC | A | G |
| 14 | 14 | CTACACTAAAATGCAATTTGATCTGGACAG[A/G]TTGTCTGTTATGCTATTGCAGTGTTATGAC | A | G |
| 15 | 15 | CACTACCTGATGCAGTCCCAGTTTGTGATT[G/T]TTATCTGCAGAAACTCAAATATAAATTCCA | G | T |
| 16 | 16 | GACGCTGCTGTTCCTGCTGCTGCCACCACA[A/C]CCATTTCCTCTCGTCATGAGCAAAAGCTAT | A | C |
| 17 | 17 | AGGTACCCTGCACTACATTCCTAGCGCGAC[C/T]AGAGGATGGTATAGAAAATGTAATGGTATA | C | T |
| 18 | 18 | TCTCTGAGTGAGATCAAGAACGGTTCGGTT[A/G]TCTACGACTGTTGGGGCCACTTCATAGAAC | G | A |
| 19 | 19 | TGCAGATATGAACAGCTTGAGTAAAAAGAT[G/T]ATGTTACCCACTGAACATCAATGAACAAAT | T | G |
| 20 | 20 | CAAAGGGACTTATCTTCTCCCAAAAGACAA[C/T]GGGCCGATCATTTAACGAATCTTCTCTTGA | C | T |
| 21 | 21 | CTGCGACATGTTTTGAGTTAGCGTAATTTC[A/G]TACTAAAGATTGGAGAAGTGTGCCTAATTA | A | G |

TABLE 2-continued

Nucleotide sequence for each SNP including the polymorphic site. The polymorphic site and the corresponding allelic variants are indicated in brackets. The column labeled "Nucleotide sequence including SNP site" provides a reference nucleotide sequence for identification of the SNP within the genome of a rainbow trout. The sequences SEQ ID NO: 1 to 164 are each polymorphic sequences including a polymorphic site. SNPs in bold are of particular interest. All of these SNPs are located within a genomic region of 1.9 megabases on chromosome 28 (FIG. 1b), have a p-value lower than 3.12e-7 (FIG. 1b) and show varying degree of elevated squared correlations to each other (FIG. 3).

| SNP# | SEQ ID NO | Nucleotide sequence including SNP site | Late maturation allele | Normal maturation allele |
|---|---|---|---|---|
| 22 | 22 | TTCGCCTTCACCCTGAGTTAGGACGGCTCC[A/G]AGCCCCATATTTGAGGCGTCTACCTGCACA | A | G |
| 23 | 23 | AATTGACTAACAATATTGTCTAACAAGTGC[A/G]GTATAAATAAATCCATCCTTCTCATCCTCC | A | G |
| 24 | 24 | GTATGGTTTTGAAGAGTACAACTGTGTGAG[G/T]GTGGATTGAACAAAATAGTATCTTAAACAC | G | T |
| 25 | 25 | TAAACAGCAGTTGAACGAGCTGGGCAGCGA[A/G]TCGGCCAAGATCAAGGCCATGGGCATCACC | G | A |
| 26 | 26 | GATGCGTCCCTCCAACACAGTGCATCTGCT[A/G]GTTTTGTGTGAGGACCACAGAGCCGGCATG | G | A |
| 27 | 27 | GTGCGGCAGGCGGCAGTGGTGGACAACTTC[A/C]TGTCCCAGCAAGAGAAGAAGCAGAAACACC | A | C |
| 28 | 28 | GCCTGCAGATGTTCCTCACGTGATGTGATG[A/G]CCTTTTAACTGGGCGTCCTTTGAATATAAG | A | G |
| 29 | 29 | ACGTGCCTTTTGATGGTTATTACTAGACCG[A/C]TTATTGTACCTGCCCTATTGATCAACCGGA | C | A |
| 30 | 30 | GACATAGGGACGTTTCCACATGAAGTGAAT[C/T]GGAAAAGCATACACTTACATGACTTTCAAT | T | C |
| 31 | 31 | ATCAGATTCTCCAAAAAGGTCCAGGGGAAA[A/C]AGTTTGCTGCTTTTGTTGGATATTTTTACA | C | A |
| 32 | 32 | ATGAGTGATATTACAGTTTGTCCTTCAGAT[G/T]AAACAATTGAGGAGCCAACTATGTGTAATC | G | T |
| 33 | 33 | GCATAAAGTTGATACAATTCACACAAAGTC[C/T]TTGTCGGGGGACTCCAATCCTCTGTGTTTC | T | C |
| 34 | 34 | ACACACTGCAGAGTAAACAGCAAACACTGA[A/G]AAAGCTGCACCCAGACTGGCATTCACACAC | A | G |
| 35 | 35 | TGCTCTGAGAAGGGGGTTCTGATTTCTGTC[C/T]ACAGGGGGCTCCCTCCTGCCTATCCAACGA | T | C |
| 36 | 36 | CTGTAGTATCTGGAAGCCTAGGCCCAGTAG[A/G]ATAGTGTTCTTATTCCCTATGGAGCGCATC | G | A |
| 37 | 37 | ATGAGATATGAATTAGACCTAAAGGCCTCA[A/G]CATGCTTCAGTTTTGCTGGTGCCTAGCTTG | A | G |
| 38 | 38 | CTTGAGTATGTGTGTTCCATTAGAGTGTAT[A/G]CAGAGTGTGTCGCTCGCACAGACAGATTGG | A | G |
| 39 | 39 | TGTGATTCGATTTTGTAGCTACAACAAGCG[A/G]TGGCTCAAAACCAACCTACACATTTTCAGT | A | G |
| 40 | 40 | ACAAATACAACGGGATGGAGTGCTCGTCTC[A/G]TCACATAATGTTCCCTGGCAGTGCTTCGTT | A | G |
| 41 | 41 | GTTGACCTTCTTGTTGGTGGTGAAATCGCA[A/G]TCTGTGCACTGGTACTTCTTCTTGAAGATG | G | A |
| 42 | 42 | GTCTTAACTGCAAATGTGAGCTTAAATCGG[C/T]TTTCAGCTCCCATGTATTACGGTATTCAAA | T | C |
| 43 | 43 | GGGAATGGATTGTAGCAGTGAAGGAGGAGA[G/T]TTATTGGTTTAGAGCTACACCAAGGAGCAC | T | G |
| 44 | 44 | AACAGTAAATAGAGCCTGAGATGACTCAAA[G/T]GTCTGATACATGGAGGCAGACTCCTTTCCA | G | T |
| 45 | 45 | AAGAACTGTCTGACCGGAACCACTCACACA[G/T]AAAACAGAGAGGCCCGAAGAGATACTGTTG | G | T |
| 46 | 46 | TCGTAGCATGTCTGTGTTCCTGGTGAAGAA[C/T]CTTCCAGCGGGAGTGACGGTGGAGAACCTG | T | C |
| 47 | 47 | TCACAAAATATGTATACAAGTGTAACCATG[C/T]TGGTTTTGTGGTAATATGTCATGTGTATCT | C | T |
| 48 | 48 | CGGTAAAGCCAATGGGAGCGTCCTTAACCT[A/C]AATCAGCCGGGCTACAATCACCACAACCTC | C | A |
| 49 | 49 | ATATTAGTAATCTCAAGCCATATTCATACA[A/G]TTTTGTTGAATAGGAAATACGTCATATAAT | G | A |
| 50 | 50 | GAATGGACAATGAAGTGGTATTCATTTCTA[C/T]GGGGATATTCACGGTTCTAAAAATAATGAC | T | C |
| 51 | 51 | TCTGTCAACGGTCTTCCAAAACAGTATGAC[G/T]GAATCAACAGCAGGGCTGAAACTGACTAAC | G | T |
| 52 | 52 | AAAGAAACACGTCACATTTCTAATGATCCA[A/G]CAATCACACTTGGAGGTGTCCATATCCCAC | G | A |
| 53 | 53 | TTTCATGGCAATAAATAGAAGTTGGAGAAC[C/T]CTGAGAATGTTGGAGAACCCTGAGAATGCT | C | T |
| 54 | 54 | AAAGCCATAGATAGGATATAGGCCTACCTC[C/T]GACACAGAACTGACTGAGTGTCAGTCAACT | C | T |
| 55 | 55 | CTTTAAAGTCCCTTGTCCTACATATAGTCT[C/T]TAGCTTGTAAAAAGCCCACAATACAGAGTT | C | T |

TABLE 2-continued

Nucleotide sequence for each SNP including the polymorphic site. The polymorphic site and the corresponding allelic variants are indicated in brackets. The column labeled "Nucleotide sequence including SNP site" provides a reference nucleotide sequence for identification of the SNP within the genome of a rainbow trout. The sequences SEQ ID NO: 1 to 164 are each polymorphic sequences including a polymorphic site. SNPs in bold are of particular interest. All of these SNPs are located within a genomic region of 1.9 megabases on chromosome 28 (FIG. 1b), have a p-value lower than 3.12e-7 (FIG. 1b) and show varying degree of elevated squared correlations to each other (FIG. 3).

| SNP# | SEQ ID NO | Nucleotide sequence including SNP site | Late maturation allele | Normal maturation allele |
|---|---|---|---|---|
| 56 | 56 | ATTGCAGTCTCCATTCTGGCTCTGTATCCT[G/T]TTCTCACGGAAGCCACGGTGATTTTTATAG | T | G |
| 57 | 57 | GCATGGCTTTCTGTGGCTATATTTGGGGTT[A/G]TCTCAGTCTCCAAAAATCTCTCTGAAATAA | G | A |
| 58 | 58 | CATAGTTTATTGTTGCGGACAATAACTTGC[C/T]CTCACATTAAAACTATAGTCTCTCTTACGT | T | C |
| 59 | 59 | CATTTTGGATGCATCTGAAGTCATCAGTCG[C/T]CGTATCAACAAAGGGCTTTTTATTGACTGT | T | C |
| 60 | 60 | AACTCGGTATTAGGGAAGCAAGCAGGACAA[A/C]ATGGGTTTGGATGCGGGTGAACTAACGTGA | C | A |
| 61 | 61 | ACAATGATTACCTTCAAAAAATAATGAATA[G/T]ATTATGTTTTTGCATTTGTAACTGAGCTCA | G | T |
| 62 | 62 | TCTCATTGACACCCACTGTGCTCTGTAAAT[G/T]ACTTGATTGTTTGAAGTAAGGCATACTAGG | T | G |
| 63 | 63 | GAGAGTGGTAATATCAGCAGCAGAAGCAAC[A/G]CGGTTTCCTGCTGTCCTTACTGTCGAGAGA | A | G |
| 64 | 64 | CACCACAAACCCTAGACGTATTATGAATAG[A/G]ATAAAATTTAGAGTAGGTCTCAAATTTAGG | A | G |
| 65 | 65 | ACAGGTGGTGGTAACAGAATATTCATTAAG[A/G]TTGCTACTGGCTTTTCAACTAATTCTTAGT | A | G |
| 66 | 66 | GGAGCATAGAGCAGATGATGAGAAAGGAGA[G/T]GATGTTCTGATTGAACCAACCCCTTTTGAC | G | T |
| 67 | 67 | TTTGCTGCCAATGTCATGATTGATTCAATG[C/T]ATTCGGTGCCAGTTTAGAGCTTCGTTACTC | T | C |
| 68 | 68 | ATCTCAGGGTTATAAAGGTAGAAAGGCACT[A/G]TGGGTTCAATTTTGGAAAACAAAGGAGAG | G | A |
| 69 | 69 | TTGTTCCACATGCCTGGATGCCACACAGCA[C/T]TAGATTTTCACTGCTGCAGATACCGGTATG | C | T |
| 70 | 70 | GACTGAATTGAAATGGTATTGACCCCAAAC[A/C]TGAGAGGGAAGCATCAATACAAAAGGCACA | C | A |
| 71 | 71 | CGACACAGCTGCCGTTTGGACTGCAGCCTT[A/C]AACAGTTTGACAGTTTTTGGTGTTTCTCGT | A | C |
| 72 | 72 | TGCGGTGGGTGTCTTTGTGGTGTTTCTGGC[C/T]GTCCTCTTCCTCTTCATCAATAAGAAGCTG | C | T |
| 73 | 73 | TTGTGATTAAGTAGAGGGTCACTCTGAGTA[A/G]AACAGTGCTTCATTAGACTCAAGCCTAAAA | G | A |
| 74 | 74 | TGGATCAACCATTTGTTCCAAATTCCACTT[G/T]AATGATGTAAAAGGTGTCCGCCTGCCTGCG | G | T |
| 75 | 75 | ATGTAGCATTATGTCAGACTTTCGTCAAAA[G/T]CAGTTCAAAAGGAATGGGTGCAGTGACCCT | T | G |
| 76 | 76 | GTTCCAATGGTACATTTGAGTAAATAACTT[A/C]GTTTTTACAATATTGTTTATCATTTAGTCT | A | C |
| 77 | 77 | AGAAAACACTGCCAGTTGGTTACCAACCCG[G/T]CCCATGTCCAGCTCAAAAATATGTTTTGTC | T | G |
| 78 | 78 | TGTTGTCATCCTCGTCAGAGCTGTGGACTT[C/T]CTCCTCAGAGTGAGCATCATCCAATCCATG | T | C |
| 79 | 79 | CATATACTGTTTTTATAAACTCACTGTGAT[A/G]TCCAGCTTCTGCAGAGCAAAAAGCTGGTGA | G | A |
| 80 | 80 | AAACCGTCTTTTAAGTGTTGATGACATCAG[A/G]GAGAGAATTCATTAATGATCAGAGGTACTT | A | G |
| 81 | 81 | AAGTCATTTTGGCTGTCCTGACAAGCTTTG[A/G]GTTTTAATTTTGAGGATGCCTTGGAGGACT | A | G |
| 82 | 82 | GGAATGATATTAAAGGAATTGTTGTGAGTT[G/T]TAAATGTGTTTCTTAATATGTGTATGTGTC | G | T |
| 83 | 83 | CACCTACGGATGGTACACACAATTATGACA[A/T]ACTTCTCAACTATCATTACCTCAGCCGCTA | A | T |
| 84 | 84 | CTTTCTAGCATAGCGTCGCCCACCTGCAGC[A/G]AAGCCGTCAAATATCCTGTTCTTCCTCAGG | A | G |
| 85 | 85 | AAAAGATTAATTGAGAAATAGCCATGGTAT[G/T]CTGATTTATTACTGACGTAACGGTCTCCTC | T | G |
| 86 | 86 | TAAGGCGTAGTGGTGCACTAATGGGGAAC[A/G]CGCACTACATCTTGGACCAGAGATAGAGGG | A | G |
| 87 | 87 | AGGTGTGACTGACTGACTGAAGTGTAGGTG[C/T]GAGTGAGTAACTGAATAAGAAGGTACTGTA | C | T |
| 88 | 88 | CTGTTGTGAAGGTAACTCACACGTATGTAT[G/T]TATGTAGACAAAATACTGTCATGAGTTACA | G | T |

TABLE 2-continued

Nucleotide sequence for each SNP including the polymorphic site. The polymorphic site and the corresponding allelic variants are indicated in brackets. The column labeled "Nucleotide sequence including SNP site" provides a reference nucleotide sequence for identification of the SNP within the genome of a rainbow trout. The sequences SEQ ID NO: 1 to 164 are each polymorphic sequences including a polymorphic site. SNPs in bold are of particular interest. All of these SNPs are located within a genomic region of 1.9 megabases on chromosome 28 (FIG. 1b), have a p-value lower than 3.12e-7 (FIG. 1b) and show varying degree of elevated squared correlations to each other (FIG. 3).

| SNP# | SEQ ID NO | Nucleotide sequence including SNP site | Late maturation allele | Normal maturation allele |
|---|---|---|---|---|
| 89 | 89 | ACTAAAAAATACAACAGAACATCTTCCTTT[A/G]GATTCTTAAAACCAACAAACTGGGCTTTAG | A | G |
| 90 | 90 | CACATGCTACAATGAGTTACTCTATGAACC[A/G]AACACATTACTGTCAAGTAAATTGTCTCCC | A | G |
| 91 | 91 | ACTGGACTATTTGACATGAACCTATTACCT[C/T]ACTCTCTCTCTCCCCTGACCTCCCTACCTC | T | C |
| 92 | 92 | GTGTGTGCTATACGACGTCCTCAGCGTAGT[C/T]AAGGAGAAGAAGTACATGGCCCTGGACCCA | T | C |
| 93 | 93 | ACAAATCCACGTTGATTTGACTCGCACGGC[A/C]AGGAGTATGACGCTGATAGTAAGATTATTT | C | A |
| 94 | 94 | AAGACGGTAAATCACATCAAGTTTAGATGT[C/T]GAGTGTCTGAATACTGAGGAAGTATGTCTT | T | C |
| 95 | 95 | GCATCGCTGCAGGTAAAATGAGAACCTTCA[A/G]GTTGTTTTTCATTGGGCTCATCTTCATCAT | A | G |
| 96 | 96 | CCTTCCTCACTTTCTACTTCGACTATCGCT[C/T]TCTGTCACACGCTCGTGCACACAGAATGCA | C | T |
| 97 | 97 | CATTCAAATAGGCCAAAAGTTTACATACAC[G/T]TTTTTCTCTTTTTGCAAAGCTAATCGCTAA | T | G |
| 98 | 98 | GCCTAGAATAAGCATAGATGAGATATCTTC[A/G]TCGTCTCATCAAAACATTTTGGTATTGTGC | G | A |
| 99 | 99 | CAGGTTGTCTTTGTTGAGCTTGATGAGGGC[A/G]GAGTAGAGCTCTGAGGCTCGGCCCATGCCC | A | G |
| 100 | 100 | TTGATGTAGTCTATTCCTGAAATACAAGGG[A/G]GATGACAATATAAATCATGCAGTTATGTTT | G | A |
| 101 | 101 | CAGTACAGACAAGATTTATCGATAGCATTT[C/T]ATGTATGTAACAGGAGACTGTTTATATTTC | C | T |
| 102 | 102 | CTGTGCTCGAAGCTAGCAATCACTGATAAA[G/T]CAAATAACAAGCTTTTTCTGAAAACCTTTA | T | G |
| 103 | 103 | CATTAAACCACTGATGACAACAAATATGCT[A/C]ATTTCCCCATGTCTCTGTAATGTCATCCTC | A | C |
| 104 | 104 | AACATGCAAGGCTATAACTCCCCAGCAGGA[A/G]AGAGAGGGGCTTTTACCACTCCATCAAGTC | G | A |
| 105 | 105 | AAGTATGATTCCAAATTGAACTGCAGGTGA[C/T]GCAATGCAACTCATTTCAAGCCTGCACTCA | C | T |
| 106 | 106 | GACAGTTGAATTTAACAGGTGAACATTACA[A/G]TTGATATTTTACATTGCATCATGTATGCAA | G | A |
| 107 | 107 | ATATCTATACTCCTATTAGTGAAATTGGAA[C/T]ATTATCTAGGCCTACCTACAATCATGGATT | C | T |
| 108 | 108 | AGGCCCAATACATTCTGAGATACAGGGTCC[A/C]AAGGTCTAAAACTAATAGTTCAAAACTTTC | C | A |
| 109 | 109 | CTCATTATTTCACTTGAAAGGTTTTTCCCC[C/T]GTATCACCTTTCAGTGCACAATTTAAAGGA | C | T |
| 110 | 110 | TGTATGTGTGTCTTGAAAGGTCAGGAGCTT[A/C]ACAGAGGGACTGACATTCACTGAGACCAAC | C | A |
| 111 | 111 | TTCATTTCAACACCAAGCAGCAGATCAGCT[C/T]AGAACATAAACATAAAACACCACAGTGACC | C | T |
| 112 | 112 | CATTTGCAAATGCACACTAGAAAATTTGAG[C/T]CTGGTCTGACCTAGCCCGAGCCCTACCCGA | C | T |
| 113 | 113 | ATAGCTACCATTTTGGCCCCATTACGGAAA[C/T]GTTAAGGTTTATGATATCTCCTCTAGTAAT | T | C |
| 114 | 114 | GGAGAAAGAACTTAAAAGATCAAGAACAG[C/T]ACCAATAATGCTGGGACTCCCACCAAAACA | T | C |
| 115 | 115 | CTGAGACTGTTAAGGAAGAGGAGGTGAAAA[A/G]GGAAGAAAAGCCCCTACAGTTGATTAGGGG | A | G |
| 116 | 116 | TACTCGGTATTCTCTTTAAACTACTTCCCT[A/G]TATCCCCTTCTGGTGAGCTTGGGACAGAAA | G | A |
| 117 | 117 | AAATCATCTAAAAAGCAAGATATGAAATTG[A/G]AAATGCATTCACATTTCACAGATCGTCGTC | A | G |
| 118 | 118 | GTTCATCAAAGCTCGAATTTTCCTAGTAGC[A/G]AGCCGGGACTTGGAGGTAAAACTGCAGTCT | A | G |
| 119 | 119 | CAATTAACAGAAACTGAGTCAATTCAAAAC[G/T]TTAGTTAGAGAAATTGCACATAAAAACACA | T | G |
| 120 | 120 | CCTCAACTCTCTCCCAACACAATCTTTTCC[A/C]CACTTTTTCAAATTGGATTTATTCCCAAGT | C | A |
| 121 | 121 | CACCAATACTTGGTCACCTGGCTGTAGTGG[A/C]CAAGAAAAGCCTGTTTATCATTGTGTCTT | A | C |
| 122 | 122 | GTTGTCCAGCCCAAATTACAGTTTTGTATT[A/C]TCTGTGTGACGAAAAGTATACAATTTCGAT | C | A |

TABLE 2-continued

Nucleotide sequence for each SNP including the polymorphic site. The polymorphic site and the corresponding allelic variants are indicated in brackets. The column labeled "Nucleotide sequence including SNP site" provides a reference nucleotide sequence for identification of the SNP within the genome of a rainbow trout. The sequences SEQ ID NO: 1 to 164 are each polymorphic sequences including a polymorphic site. SNPs in bold are of particular interest. All of these SNPs are located within a genomic region of 1.9 megabases on chromosome 28 (FIG. 1b), have a p-value lower than 3.12e-7 (FIG. 1b) and show varying degree of elevated squared correlations to each other (FIG. 3).

| SNP# | SEQ ID NO | Nucleotide sequence including SNP site | Late maturation allele | Normal maturation allele |
|---|---|---|---|---|
| 123 | 123 | TTCTCAGGGTCCATCATGGCGATCTCTGCA[A/G]TGGGTACTCAGTGGGTCCAGCTGCATGGTG | G | A |
| 124 | 124 | CATCAATTCCCCTGCAAGACCACAGAAAGT[G/T]ATTTGCCTTGTATTTTGCAAAGACCAAACT | T | G |
| 125 | 125 | CTGTTTGTACTGGAGAGCCATGTAATCCTA[G/T]ATCCTGTACTATCTATCCTCTTATTGTTTA | G | T |
| 126 | 126 | GGAGGTGTTCTTTACAGGGGACGAGGAGGA[A/G]GAGCTGTCTGAGAGAAAGTCCCAGAGAAAT | G | A |
| 127 | 127 | GCCCGAACGTCCTGTCCTCTATCCGCGTCA[A/G]GGTGTTGAAGGACAAATCCAGGTAAGCAAG | A | G |
| 128 | 128 | AGGCGAATGGCAGCGTCAGTAAAGTTATGT[C/T]TCTCCCTCTCAAAGTTCCTCCTCTGCTCGT | C | T |
| 129 | 129 | GTCTAATGAACACTGCCGTGGATTGTCATC[C/T]GAGTTGTCTGTTGAGTCCACAGTAACACAA | C | T |
| 130 | 130 | ATACTCTGCTAAAATTAGAACTGACCAGTT[G/T]ATTTTTTTTACATGATACATGATAATAATG | G | T |
| 131 | 131 | GTTGAATTTGGTCATATAAGGAAATGTGCC[C/T]TACTGCCTTTCGAATTTTGTGAAACTTAAA | T | C |
| 132 | 132 | GATACAGTCTGCATTTCAACAGGCTGCATT[G/T]TATTGCACCACACCCTGCTGTTATCAGATA | T | G |
| 133 | 133 | GGAAAATGTAACAACCAAACAGGACAGCAC[G/T]CGGTCTGTTGATGTTACAGGCAGCTCAGCT | T | G |
| 134 | 134 | CCATATTTCTTTGTTGTTGTTTGGAATAGT[A/C]TCCTACTCGAAAAAATATGCATTTGTATTT | A | C |
| 135 | 135 | GCCAGCGGGTCGGCACAGCCTAGTCATGCG[A/G]TCACAAGCCATTCAGTCTGGTCGCAGTCTA | G | A |
| 136 | 136 | AACAAACTAATCATCTCTAGTGGAGCGCAC[C/T]CGCACCACAAGGGGGCCTTATCGTCGACC | C | T |
| 137 | 137 | AACACTGCCCTGCCCACCACAGAGGACATC[A/G]CGCTGTTCACGGATTTAGACCAGGGCAACA | A | G |
| 138 | 138 | AACTTTGTGTGCGTTCTATCCTTGTTTCCC[C/T]CCTACAGCCAGCGGTAACATCCCGGCCATG | C | T |
| 139 | 139 | TCAACTGAACAGACAGCAACTTTCCCTCCT[C/T]GTTCATTTCATCTTCACCTGCTTCTTCTTT | C | T |
| 140 | 140 | AGTGTCGATGCCAAACCCTTGAAAATAGGT[C/T]GGGAAAGGAAATCCTTTCCCTCTAAATATC | T | C |
| 141 | 141 | ACTAGTGGAGATGAAGGGGACTGGTAATGA[G/T]AATACAGTGACAGTAGGCAGTGTTGTAAAT | G | T |
| 142 | 142 | TGTACTTGTTTTATTAAAACACAATGCAAG[A/G]CTTAAAACGAACTGTACTGTAGATATAACC | A | G |
| 143 | 143 | CCGGGTTCTGAACGAATAGGCCTACATAAC[A/G]GGACATGGATTACGATGGGACCGTTACGAA | A | G |
| 144 | 144 | CATCTCTTTCCTCCACAATGCATACTTGGG[C/T]TTATGCCTTGGGTTGGTGTATCTGAAGACA | T | C |
| 145 | 145 | AATGGCCTTTGCAACGTGTTCCCAGCACAC[A/G]CTCAGCTCGGGGAGCTTTCTGTGGTCCTCC | A | G |
| 146 | 146 | TCATTAATGTGTAGTAGCAGTTATTTAGTT[C/T]ATAATAGTGATACAACAATAATACTTCATT | T | C |
| 147 | 147 | CATTTCCTCGTATCACTAGGAGTTCCTAAC[A/G]TAACAGATGTAAGCTAGTGAGCTGTATGCT | A | G |
| 148 | 148 | AAATAGGACACCATACCTGGTTGATTTCGT[G/T]TCGGTTGTGTGAAGTCAATGTTGTAAATGT | G | T |
| 149 | 149 | GAGATTCTAATTATATATTTTTTAGAGAT[G/T]AATTATTTTGGAGGTTTATATACTCACATA | G | T |
| 150 | 150 | CATGAATAGTGGCAAAATGTCCTTCAATTT[C/T]GGTAGCTAGATCATAAAATACATTTGTACT | T | C |
| 151 | 151 | TGGTCACCAGCTGCATTAAGTACTGCAGTG[C/T]ATCTCCTCAGACTGCACCAGATATGTTCTT | C | T |
| 152 | 152 | AGTTTATTGGCGTAAACATAATCTAGAAGT[A/C]ATTTTCATAATATGCAACAATTGGCATGTA | A | C |
| 153 | 153 | ACTCTTGAGATTCGGATCAGCCTAGATGGA[C/T]GATTGAAGCTCCAGTCGATGATGAATCAAT | C | T |
| 154 | 154 | ATTTTCCCTATAATTTTGAAGAAATTGTTT[A/C]TTTAGCTCCTAATTATACACCCAGGTGTAG | C | A |
| 155 | 155 | GCCGATGGAAACAAGGTTATGGTTAGTGAC[A/C]ATACACAGCGTACCCAGTCTAATCCAAAGA | A | C |

TABLE 2-continued

Nucleotide sequence for each SNP including the polymorphic site. The polymorphic site and the corresponding allelic variants are indicated in brackets. The column labeled "Nucleotide sequence including SNP site" provides a reference nucleotide sequence for identification of the SNP within the genome of a rainbow trout. The sequences SEQ ID NO: 1 to 164 are each polymorphic sequences including a polymorphic site. SNPs in bold are of particular interest. All of these SNPs are located within a genomic region of 1.9 megabases on chromosome 28 (FIG. 1b), have a p-value lower than 3.12e-7 (FIG. 1b) and show varying degree of elevated squared correlations to each other (FIG. 3).

| SNP# | SEQ ID NO | Nucleotide sequence including SNP site | Late maturation allele | Normal maturation allele |
|---|---|---|---|---|
| 156 | 156 | GAACGGCCTGAACACCATGGACCTCAACAC[A/G]GAGTTCACTGTGGCTCGCCTGGAAGCAATA | A | G |
| 157 | 157 | CTAAGGAGGAAATGGAGCTTGTCTTGCTAA[A/G]GTCAATGGTGATGTCAATGTCTCCCTCTCA | A | G |
| 158 | 158 | GATCTTGTACGCTGTCTGTGGGCTCCCTGA[G/T]AAATAATTGTAAGAAGCCTACTGATGCCAT | G | T |
| 159 | 159 | TCTGCGTCATTCCATCCCTGCCATCACACT[C/T]CTGCTACACTGCATTCTGCGTGTGGTGTAT | C | T |
| 160 | 160 | AAAAACTGCGTGTTTATCAAATTAGAAATT[C/T]ACAACCATAAAGTTTTGCGTTGACAAAAAA | C | T |
| 161 | 161 | CTTTGAGCTGGATCCAGTCAAGAAGAAGGC[C/T]AAAGAGAGGATGGTGAAGTCCACCAGCAGC | C | T |
| 162 | 162 | AAAGCTGCTTCCAGCTGATGGTGTAGTCTA[C/T]GGACAGGTTCGTTACCCATCCACATCTCTC | C | T |
| 163 | 163 | AGAATAAATGCAATCTTAATGTGAATTTAT[G/T]TATGTTTAGAAACTGCTTACTAATAGGTAA | T | G |
| 164 | 164 | CTGAATCAAATGCTCTCACTTGCCAGACTT[C/T]GAGGTTGACAGTGCAGCAATGACAAATACA | T | C |

SEQ ID NOs: 1 to 164 has an "n" at the polymorphic site (position 31; indicated in brackets in table 2), wherein "n" is either the late maturation allele or the normal maturation allele. SEQ ID NOs: 165 to 328 are identical to SEQ ID NOs: 1 to 164 except that the "n" at the polymorphic site is the late maturation allele.

According to particular embodiments, the at least one SNP of the invention is selected from the group consisting of SNP #1 to SNP #164 listed in table 1.

According to particular embodiments, the at least one SNP of the invention is located on chromosome 1 and is selected from the group consisting of SNP #1 to SNP #4 listed in table 1.

According to particular embodiments, the at least one SNP of the invention is located on chromosome 2 and is selected from the group consisting of SNP #5 to SNP #12 listed in table 1.

According to particular embodiments, the at least one SNP of the invention is located on chromosome 3 and is selected from the group consisting of SNP #13 to SNP #16 listed in table 1.

According to particular embodiments, the at least one SNP of the invention is located on chromosome 4 and is selected from the group consisting of SNP #17 to SNP #20 listed in table 1.

According to particular embodiments, the at least one SNP of the invention is located on chromosome 5 and is selected from the group consisting of SNP #21 to SNP #24 listed in table 1.

According to particular embodiments, the at least one SNP of the invention is located on chromosome 6 and is selected from the group consisting of SNP #25 to SNP #28 listed in table 1.

According to particular embodiments, the at least one SNP of the invention is located on chromosome 7 and is selected from the group consisting of SNP #29 to SNP #32 listed in table 1.

According to particular embodiments, the at least one SNP of the invention is located on chromosome 8 and is selected from the group consisting of SNP #33 to SNP #36 listed in table 1.

According to particular embodiments, the at least one SNP of the invention is located on chromosome 9 and is selected from the group consisting of SNP #37 to SNP #40 listed in table 1.

According to particular embodiments, the at least one SNP of the invention is located on chromosome 10 and is selected from the group consisting of SNP #41 to SNP #43 listed in table 1.

According to particular embodiments, the at least one SNP of the invention is located on chromosome 11 and is selected from the group consisting of SNP #44 to SNP #47 listed in table 1.

According to particular embodiments, the at least one SNP of the invention is located on chromosome 12 and is selected from the group consisting of SNP #48 to SNP #50 listed in table 1.

According to particular embodiments, the at least one SNP of the invention is located on chromosome 13 and is selected from the group consisting of SNP #51 to SNP #53 listed in table 1.

According to particular embodiments, the at least one SNP of the invention is located on chromosome 14 and is selected from the group consisting of SNP #54 to SNP #57 listed in table 1.

According to particular embodiments, the at least one SNP of the invention is located on chromosome 16 and is selected from the group consisting of SNP #62 to SNP #64 listed in table 1.

According to particular embodiments, the at least one SNP of the invention is located on chromosome 17 and is selected from the group consisting of SNP #65 to SNP #66 listed in table 1.

According to particular embodiments, the at least one SNP of the invention is located on chromosome 18 and is selected from the group consisting of SNP #67 to SNP #69 listed in table 1.

According to particular embodiments, the at least one SNP of the invention is located on chromosome 19 and is selected from the group consisting of SNP #70 to SNP #73 listed in table 1.

According to particular embodiments, the at least one SNP of the invention is located on chromosome 20 and is selected from the group consisting of SNP #74 to SNP #76 listed in table 1.

According to particular embodiments, the at least one SNP of the invention is located on chromosome 21 and is selected from the group consisting of SNP #77 to SNP #80 listed in table 1.

According to particular embodiments, the at least one SNP of the invention is located on chromosome 22 and is selected from the group consisting of SNP #81 to SNP #83 listed in table 1.

According to particular embodiments, the at least one SNP of the invention is located on chromosome 23 and is selected from the group consisting of SNP #84 to SNP #89 listed in table 1.

According to particular embodiments, the at least one SNP of the invention is located on chromosome 24 and is selected from the group consisting of SNP #90 to SNP #92 listed in table 1.

According to particular embodiments, the at least one SNP of the invention is located on chromosome 25 and is selected from the group consisting of SNP #93 to SNP #101 listed in table 1.

According to particular embodiments, the at least one SNP of the invention is located on chromosome 26 and is selected from the group consisting of SNP #102 to SNP #105 listed in table 1.

According to particular embodiments, the at least one SNP of the invention is located on chromosome 27 and is selected from the group consisting of SNP #106 to SNP #109 listed in table 1.

According to particular preferred embodiments, the at least one SNP of the invention is located on chromosome 28 and is selected from the group consisting of SNP #110 to SNP #161 listed in table 1.

According to particular preferred embodiments, the at least one SNP of the invention is located on chromosome 28 and is selected from the group consisting of SNP #120, SNP #127 to SNP #131, SNP #134, SNP #135, SNP #137, SNP #138, SNP #140, SNP #142 to SNP #144, SNP #146 and SNP #147 listed in table 1.

According to particular preferred embodiments, the at least one SNP of the invention is located on chromosome 28 and is selected from the group consisting of SNP #140, SNP #135, SNP #143 and SNP #137 listed in table 1.

According to particular preferred embodiments, the at least one SNP of the invention is located on chromosome 28 and is selected from the group consisting of SNP #140, SNP #135, SNP #143, SNP #137 and SNP #128 listed in table 1.

According to particular preferred embodiments, the at least one SNP of the invention is located on chromosome 28 and is selected from the group consisting of SNP #140, SNP #135, SNP #143, SNP #137, SNP #128 and SNP #144 listed in table 1.

According to particular preferred embodiments, the at least one SNP of the invention is located on chromosome 28 and is selected from the group consisting of SNP #140, SNP #135, SNP #143, SNP #137, SNP #128, SNP #144 and SNP #142 listed in table 1.

According to particular preferred embodiments, the at least one SNP of the invention is located on chromosome 28 and is selected from the group consisting of SNP #140, SNP #135, SNP #143, SNP #137, SNP #128, SNP #144, SNP #142, and SNP #127 listed in table 1.

According to particular preferred embodiments, the at least one SNP of the invention is located on chromosome 28 and is selected from the group consisting of SNP #140, SNP #135, SNP #143, SNP #137, SNP #128, SNP #144, SNP #142, SNP #127 and SNP #146 listed in table 1.

According to particular preferred embodiments, the at least one SNP of the invention is located on chromosome 28 and is selected from the group consisting of SNP #140, SNP #135, SNP #143, SNP #137, SNP #128, SNP #144, SNP #142, SNP #127, SNP #146 and SNP #147 listed in table 1.

According to particular preferred embodiments, the at least one SNP of the invention is located on chromosome 28 and is selected from the group consisting of SNP #140, SNP #135, SNP #143, SNP #137, SNP #128, SNP #144, SNP #142, SNP #127, SNP #146, SNP #147 and SNP #131 listed in table 1.

According to particular preferred embodiments, the at least one SNP of the invention is located on chromosome 28 and is selected from the group consisting of SNP #140, SNP #135, SNP #143, SNP #137, SNP #128, SNP #144, SNP #142, SNP #127, SNP #146, SNP #147, SNP #131 and SNP #129 listed in table 1.

According to particular preferred embodiments, the at least one SNP of the invention is located on chromosome 28 and is selected from the group consisting of SNP #140, SNP #135, SNP #143, SNP #137, SNP #128, SNP #144, SNP #142, SNP #127, SNP #146, SNP #147, SNP #131, SNP #129 and SNP #120 listed in table 1.

According to particular preferred embodiments, the at least one SNP of the invention is located on chromosome 28 and is selected from the group consisting of SNP #140, SNP #135, SNP #143, SNP #137, SNP #128, SNP #144, SNP #142, SNP #127, SNP #146, SNP #147, SNP #131, SNP #129, SNP #120 and SNP #130 listed in table 1.

According to particular preferred embodiments, the at least one SNP of the invention is located on chromosome 28 and is selected from the group consisting of SNP #140, SNP #135, SNP #143, SNP #137, SNP #128, SNP #144, SNP #142, SNP #127, SNP #146, SNP #147, SNP #131, SNP #129, SNP #120, SNP #130 and SNP #138 listed in table 1.

According to particular preferred embodiments, the at least one SNP of the invention is located on chromosome 28 and is selected from the group consisting of SNP #140, SNP #135, SNP #143 and SNP #137 listed in table 1.

According to particular preferred embodiments, the at least one SNP of the invention is located on chromosome 28 and is selected from the group consisting of SNP #135, SNP #137, SNP #138, SNP #140, SNP #142 and SNP #143 listed in table 1.

According to particular preferred embodiments, the at least one SNP of the invention is located on chromosome 28 and is selected from the group consisting of SNP #134, SNP #135, SNP #137, SNP #138, SNP #140, SNP #142, SNP #143 and SNP #144 listed in table 1.

According to particular preferred embodiments, the at least one SNP of the invention is located on chromosome 28 and is selected from the group consisting of SNP #131, SNP #134, SNP #135, SNP #137, SNP #138, SNP #140, SNP #142, SNP #143, SNP #144 and SNP #146 listed in table 1.

According to particular preferred embodiments, the at least one SNP of the invention is located on chromosome 28 and is selected from the group consisting of SNP #130, SNP #131, SNP #134, SNP #135, SNP #137, SNP #138, SNP #140, SNP #142, SNP #143, SNP #144, SNP #146 and SNP #147 listed in table 1.

According to particular embodiments, the at least one SNP of the invention is located on chromosome 29 and is selected from the group consisting of SNP #162 to SNP #164 listed in table 1.

According to particular embodiments, the at least one SNP of the invention is selected from the group consisting of SNP #127, SNP #128, SNP #135, SNP #137, SNP #140, SNP #142, SNP #143, SNP #144, SNP #146 and SNP #147.

According to particular embodiments, the at least one SNP of the invention is selected from the group consisting of SNP #93, SNP #114, SNP #120, SNP #129, SNP #130, SNP #131, SNP #132, SNP #134, SNP #138 and SNP #148.

According to particular embodiments, the at least one SNP of the invention is selected from the group consisting of SNP #5, SNP #24, SNP #86, SNP #121, SNP #125, SNP #126, SNP #133, SNP #141, SNP #150 and SNP #154.

According to particular embodiments, the at least one SNP of the invention is selected from the group consisting of SNP #7, SNP #9, SNP #19, SNP #85, SNP #111, SNP #116, SNP #117, SNP #119, SNP #153 and SNP #155.

According to particular embodiments, the at least one SNP of the invention is selected from the group consisting of SNP #10, SNP #11, SNP #23, SNP #88, SNP #89, SNP #91, SNP #101, SNP #124, SNP #145 and SNP #151.

It is understood that the foregoing disclosure regarding the polymorphisms of the invention, and in particular regarding SNPs and late maturation allele(s), is applicable to the following aspects.

Methods for Predicting

The present invention provides in a first aspect, a method for predicting late onset of sexual maturation in rainbow trout (*Oncorhynchus mykiss*), the method comprising determining the presence of at least one allele conferring late onset of sexual maturation ("late maturation allele") within the genome of said rainbow trout; wherein the at least one late maturation allele is an allele of at least one single nucleotide polymorphism (SNP), the at least one SNP being selected from the SNPs listed in Table 1.

According to certain embodiments, the at least one late maturation allele is an allele of at least one single nucleotide polymorphism (SNP), the at least one SNP being located on chromosome 1 and being selected from SNP #1 to SNP #4 listed in table 1.

According to certain embodiments, the at least one late maturation allele is an allele of at least one single nucleotide polymorphism (SNP), the at least one SNP being located on chromosome 2 and being selected from SNP #5 to SNP #12 listed in table 1.

According to certain embodiments, the at least one late maturation allele is an allele of at least one single nucleotide polymorphism (SNP), the at least one SNP being located on chromosome 3 and being selected from SNP #13 to SNP #16 listed in table 1.

According to certain embodiments, the at least one late maturation allele is an allele of at least one single nucleotide polymorphism (SNP), the at least one SNP being located on chromosome 4 and being selected from SNP #17 to SNP #20 listed in table 1.

According to certain embodiments, the at least one late maturation allele is an allele of at least one single nucleotide polymorphism (SNP), the at least one SNP being located on chromosome 5 and being selected from SNP #21 to SNP #24 listed in table 1.

According to certain embodiments, the at least one late maturation allele is an allele of at least one single nucleotide polymorphism (SNP), the at least one SNP being located on chromosome 6 and being selected from SNP #25 to SNP #28 listed in table 1.

According to certain embodiments, the at least one late maturation allele is an allele of at least one single nucleotide polymorphism (SNP), the at least one SNP being located on chromosome 7 and being selected from SNP #29 to SNP #32 listed in table 1.

According to certain embodiments, the at least one late maturation allele is an allele of at least one single nucleotide polymorphism (SNP), the at least one SNP being located on chromosome 8 and being selected from SNP #33 to SNP #36 listed in table 1.

According to certain embodiments, the at least one late maturation allele is an allele of at least one single nucleotide polymorphism (SNP), the at least one SNP being located on chromosome 9 and being selected from SNP #37 to SNP #40 listed in table 1.

According to certain embodiments, the at least one late maturation allele is an allele of at least one single nucleotide polymorphism (SNP), the at least one SNP being located on chromosome 10 and being selected from SNP #41 to SNP #43 listed in table 1.

According to certain embodiments, the at least one late maturation allele is an allele of at least one single nucleotide polymorphism (SNP), the at least one SNP being located on chromosome 11 and being selected from SNP #44 to SNP #47 listed in table 1.

According to certain embodiments, the at least one late maturation allele is an allele of at least one single nucleotide polymorphism (SNP), the at least one SNP being located on chromosome 12 and being selected from SNP #48 to SNP #50 listed in table 1.

According to certain embodiments, the at least one late maturation allele is an allele of at least one single nucleotide polymorphism (SNP), the at least one SNP being located on chromosome 13 and being selected from SNP #51 to SNP #53 listed in table 1.

According to certain embodiments, the at least one late maturation allele is an allele of at least one single nucleotide polymorphism (SNP), the at least one SNP being located on chromosome 14 and being selected from SNP #54 to SNP #57 listed in table 1.

According to certain embodiments, the at least one late maturation allele is an allele of at least one single nucleotide polymorphism (SNP), the at least one SNP being located on chromosome 15 and being selected from SNP #58 to SNP #61 listed in table 1.

According to certain embodiments, the at least one late maturation allele is an allele of at least one single nucleotide polymorphism (SNP), the at least one SNP being located on chromosome 16 and being selected from SNP #62 to SNP #64 listed in table 1.

According to certain embodiments, the at least one late maturation allele is an allele of at least one single nucleotide polymorphism (SNP), the at least one SNP being located on chromosome 17 and being selected from SNP #65 to SNP #66 listed in table 1.

According to certain embodiments, the at least one late maturation allele is an allele of at least one single nucleotide polymorphism (SNP), the at least one SNP being located on chromosome 18 and being selected from SNP #67 to SNP #69 listed in table 1.

According to certain embodiments, the at least one late maturation allele is an allele of at least one single nucleotide polymorphism (SNP), the at least one SNP being located on chromosome 19 and being selected from SNP #70 to SNP #73 listed in table 1.

According to certain embodiments, the at least one late maturation allele is an allele of at least one single nucleotide polymorphism (SNP), the at least one SNP being located on chromosome 20 and being selected from SNP #74 to SNP #76 listed in table 1.

According to certain embodiments, the at least one late maturation allele is an allele of at least one single nucleotide polymorphism (SNP), the at least one SNP being located on chromosome 21 and being selected from SNP #77 to SNP #80 listed in table 1.

According to certain embodiments, the at least one late maturation allele is an allele of at least one single nucleotide polymorphism (SNP), the at least one SNP being located on chromosome 22 and being selected from SNP #81 to SNP #83 listed in table 1.

According to certain embodiments, the at least one late maturation allele is an allele of at least one single nucleotide polymorphism (SNP), the at least one SNP being located on chromosome 23 and being selected from SNP #84 to SNP #89 listed in table 1.

According to certain embodiments, the at least one late maturation allele is an allele of at least one single nucleotide polymorphism (SNP), the at least one SNP being located on chromosome 24 and being selected from SNP #90 to SNP #92 listed in table 1.

According to certain embodiments, the at least one late maturation allele is an allele of at least one single nucleotide polymorphism (SNP), the at least one SNP being located on chromosome 25 and being selected from SNP #93 to SNP #101 listed in table 1.

According to certain embodiments, the at least one late maturation allele is an allele of at least one single nucleotide polymorphism (SNP), the at least one SNP being located on chromosome 26 and being selected from SNP #102 to SNP #105 listed in table 1.

According to certain embodiments, the at least one late maturation allele is an allele of at least one single nucleotide polymorphism (SNP), the at least one SNP being located on chromosome 27 and being selected from SNP #106 to SNP #109 listed in table 1.

According to certain particularly preferred embodiments, the at least one late maturation allele is an allele of at least one single nucleotide polymorphism (SNP), the at least one SNP being located on chromosome 28 and being selected from SNP #110 to SNP #161 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #120, SNP #127 to SNP #131, SNP #134, SNP #135, SNP #137, SNP #138, SNP #140, SNP #142 to SNP #144, SNP #146 and SNP #147 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP #143 and SNP #137 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP #143, SNP #137 and SNP #128 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP #143, SNP #137, SNP #128 and SNP #144 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP #143, SNP #137, SNP #128, SNP #144 and SNP #142 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP #143, SNP #137, SNP #128, SNP #144, SNP #142, and SNP #127 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP #143, SNP #137, SNP #128, SNP #144, SNP #142, SNP #127 and SNP #146 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP #143, SNP #137, SNP #128, SNP #144, SNP #142, SNP #127, SNP #146 and SNP #147 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP #143, SNP #137, SNP #128, SNP #144, SNP #142, SNP #127, SNP #146, SNP #147 and SNP #131 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP #143, SNP #137, SNP #128, SNP #144, SNP #142, SNP #127, SNP #146, SNP #147, SNP #131 and SNP #129 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP #143, SNP #137, SNP #128, SNP #144, SNP #142, SNP #127, SNP #146, SNP #147, SNP #131, SNP #129 and SNP #120 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP #143, SNP #137, SNP #128, SNP #144, SNP #142, SNP #127, SNP #146, SNP #147, SNP #131, SNP #129, SNP #120 and SNP #130 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP #143, SNP #137, SNP #128, SNP #144, SNP #142, SNP #127, SNP #146, SNP #147, SNP #131, SNP #129, SNP #120, SNP #130 and SNP #138 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP #143 and SNP #137 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #135, SNP #137, SNP #138, SNP #140, SNP #142 and SNP #143 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #134, SNP #135, SNP #137, SNP #138, SNP #140, SNP #142, SNP #143 and SNP #144 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #131, SNP #134, SNP #135, SNP #137, SNP #138, SNP #140, SNP #142, SNP #143, SNP #144 and SNP #146 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #130, SNP #131, SNP #134, SNP #135, SNP #137, SNP #138, SNP #140, SNP #142, SNP #143, SNP #144, SNP #146 and SNP #147 listed in table 1.

According to certain embodiments, the at least one late maturation allele is an allele of at least one single nucleotide polymorphism (SNP), the at least one SNP being located on chromosome 29 and being selected from SNP #162 to SNP #164 listed in table 1.

According to certain embodiments, the at least one late maturation allele is an allele of at least one single nucleotide polymorphism (SNP), the at least one SNP being selected from the group consisting of SNP #127, SNP #128, SNP #135, SNP #137, SNP #140, SNP #142, SNP #143, SNP #144, SNP #146 and SNP #147 listed in table 1.

According to certain embodiments, the at least one late maturation allele is an allele of at least one single nucleotide polymorphism (SNP), the at least one SNP being selected from the group consisting of SNP #127, SNP #128, SNP #135, SNP #137, SNP #140, SNP #142, SNP #143, SNP #144, SNP #146 and SNP #148 listed in table 1.

According to certain embodiments, the at least one late maturation allele is an allele of at least one single nucleotide polymorphism (SNP), the at least one SNP being selected from the group consisting of SNP #5, SNP #24, SNP #86, SNP #121, SNP #125, SNP #126, SNP #133, SNP #141, SNP #150 and SNP #154 listed in table 1.

According to certain embodiments, the at least one late maturation allele is an allele of at least one single nucleotide polymorphism (SNP), the at least one SNP being selected from the group consisting of SNP #7, SNP #9, SNP #19, SNP #85, SNP #111, SNP #116, SNP #117, SNP #119, SNP #153 and SNP #155 listed in table 1.

According to certain embodiments, the at least one late maturation allele is an allele of at least one single nucleotide polymorphism (SNP), the at least one SNP being selected from the group consisting of SNP #10, SNP #11, SNP #23, SNP #88, SNP #89, SNP #91, SNP #101, SNP #124, SNP #145 and SNP #151 listed in table 1.

A preferred embodiment according to the first aspect of the present invention relates to a method for predicting late onset of sexual maturation in rainbow trout (*Oncorhynchus mykiss*), the method comprising: determining the presence of at least one allele conferring late onset of sexual maturation ("late maturation allele") within the genome of said rainbow trout; wherein the at least one late maturation allele is an allele of at least one single nucleotide polymorphism (SNP), the at least one SNP being SNP #140 listed in table 1 wherein the presence of a thymine at the position corresponding to position 31 of SEQ ID NO. 140 indicates that the rainbow trout has late onset of sexual maturation.

According to certain embodiments, the present invention provides a method of predicting late onset of sexual maturation in rainbow trout (*Oncorhynchus mykiss*), the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 1 to 164, or at a position corresponding to position 31 of a nucleotide sequence which is derived from any one of SEQ ID NOs: 1 to 164 by 1 to 5, such as 1 to 2, nucleotide substitutions; with the proviso that said nucleotide substitution(s) are not at position 31 of said derived sequences.

According to certain embodiments, the present invention provides a method of predicting late onset of sexual maturation in rainbow trout (*Oncorhynchus mykiss*), the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 1 to 4, or at a position corresponding to position 31 of a nucleotide sequence which is derived from any one of SEQ ID NOs: 1 to 4 by 1 to 5, such as 1 to 2, nucleotide substitutions; with the proviso that said nucleotide substitution(s) are not at position 31 of said derived sequences.

According to certain embodiments, the present invention provides a method of predicting late onset of sexual maturation in rainbow trout (*Oncorhynchus mykiss*), the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 5 to 12, or at a position corresponding to position 31 of a nucleotide sequence which is derived from any one of SEQ ID NOs: 5 to 12 by 1 to 5, such as 1 to 2, nucleotide substitutions; with the proviso that said nucleotide substitution(s) are not at position 31 of said derived sequences.

According to certain embodiments, the present invention provides a method of predicting late onset of sexual maturation in rainbow trout (*Oncorhynchus mykiss*), the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 13 to 16, or at a position corresponding to position 31 of a nucleotide sequence which is derived from any one of SEQ ID NOs: 13 to 16 by 1 to 5, such as 1 to 2, nucleotide substitutions; with the proviso that said nucleotide substitution(s) are not at position 31 of said derived sequences.

According to certain embodiments, the present invention provides a method of predicting late onset of sexual maturation in rainbow trout (Oncorhynchus mykiss), the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 17 to 20, or at a position corresponding to position 31 of a nucleotide sequence which is derived from any one of SEQ ID NOs: 17 to 20 by 1 to 5, such as 1 to 2, nucleotide substitutions; with the proviso that said nucleotide substitution(s) are not at position 31 of said derived sequences.

According to certain embodiments, the present invention provides a method of predicting late onset of sexual maturation in rainbow trout (Oncorhynchus mykiss), the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 21 to 24, or at a position corresponding to position 31 of a nucleotide sequence which is derived from any one of SEQ ID NOs: 21 to 24 by 1 to 5, such as 1 to 2, nucleotide substitutions; with the proviso that said nucleotide substitution(s) are not at position 31 of said derived sequences.

According to certain embodiments, the present invention provides a method of predicting late onset of sexual maturation in rainbow trout (Oncorhynchus mykiss), the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 25 to 28, or at a position corresponding to position 31 of a nucleotide sequence which is derived from any one of SEQ ID NOs: 25 to 28 by 1 to 5, such as 1 to 2, nucleotide substitutions; with the proviso that said nucleotide substitution(s) are not at position 31 of said derived sequences.

According to certain embodiments, the present invention provides a method of predicting late onset of sexual maturation in rainbow trout (Oncorhynchus mykiss), the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 29 to 32, or at a position corresponding to position 31 of a nucleotide sequence which is derived from any one of SEQ ID NOs: 29 to 32 by 1 to 5, such as 1 to 2, nucleotide substitutions; with the proviso that said nucleotide substitution(s) are not at position 31 of said derived sequences.

According to certain embodiments, the present invention provides a method of predicting late onset of sexual maturation in rainbow trout (Oncorhynchus mykiss), the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 33 to 36, or at a position corresponding to position 31 of a nucleotide sequence which is derived from any one of SEQ ID NOs: 33 to 36 by 1 to 5, such as 1 to 2, nucleotide substitutions; with the proviso that said nucleotide substitution(s) are not at position 31 of said derived sequences.

According to certain embodiments, the present invention provides a method of predicting late onset of sexual maturation in rainbow trout (Oncorhynchus mykiss), the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 37 to 40, or at a position corresponding to position 31 of a nucleotide sequence which is derived from any one of SEQ ID NOs: 37 to 40 by 1 to 5, such as 1 to 2, nucleotide substitutions; with the proviso that said nucleotide substitution(s) are not at position 31 of said derived sequences.

According to certain embodiments, the present invention provides a method of predicting late onset of sexual maturation in rainbow trout (Oncorhynchus mykiss), the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 41 to 43, or at a position corresponding to position 31 of a nucleotide sequence which is derived from any one of SEQ ID NOs: 41 to 43 by 1 to 5, such as 1 to 2, nucleotide substitutions; with the proviso that said nucleotide substitution(s) are not at position 31 of said derived sequences.

According to certain embodiments, the present invention provides a method of predicting late onset of sexual maturation in rainbow trout (Oncorhynchus mykiss), the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 44 to 47, or at a position corresponding to position 31 of a nucleotide sequence which is derived from any one of SEQ ID NOs: 44 to 47 by 1 to 5, such as 1 to 2, nucleotide substitutions; with the proviso that said nucleotide substitution(s) are not at position 31 of said derived sequences.

According to certain embodiments, the present invention provides a method of predicting late onset of sexual maturation in rainbow trout (Oncorhynchus mykiss), the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 48 to 50, or at a position corresponding to position 31 of a nucleotide sequence which is derived from any one of SEQ ID NOs: 48 to 50 by 1 to 5, such as 1 to 2, nucleotide substitutions; with the proviso that said nucleotide substitution(s) are not at position 31 of said derived sequences.

According to certain embodiments, the present invention provides a method of predicting late onset of sexual maturation in rainbow trout (*Oncorhynchus mykiss*), the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 51 to 53, or at a position corresponding to position 31 of a nucleotide sequence which is derived from any one of SEQ ID NOs: 51 to 53 by 1 to 5, such as 1 to 2, nucleotide substitutions; with the proviso that said nucleotide substitution(s) are not at position 31 of said derived sequences.

According to certain embodiments, the present invention provides a method of predicting late onset of sexual maturation in rainbow trout (*Oncorhynchus mykiss*), the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 54 to 57, or at a position corresponding to position 31 of a nucleotide sequence which is derived from any one of SEQ ID NOs: 54 to 57 by 1 to 5, such as 1 to 2, nucleotide substitutions; with the proviso that said nucleotide substitution(s) are not at position 31 of said derived sequences.

According to certain embodiments, the present invention provides a method of predicting late onset of sexual maturation in rainbow trout (*Oncorhynchus mykiss*), the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 58 to 61, or at a position corresponding to position 31 of a nucleotide sequence which is derived from any one of SEQ ID NOs: 58 to 61 by 1 to 5, such as 1 to 2, nucleotide substitutions; with the proviso that said nucleotide substitution(s) are not at position 31 of said derived sequences.

According to certain embodiments, the present invention provides a method of predicting late onset of sexual maturation in rainbow trout (*Oncorhynchus mykiss*), the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 62 to 64, or at a position corresponding to position 31 of a nucleotide sequence which is derived from any one of SEQ ID NOs: 62 to 64 by 1 to 5, such as 1 to 2, nucleotide substitutions; with the proviso that said nucleotide substitution(s) are not at position 31 of said derived sequences.

According to certain embodiments, the present invention provides a method of predicting late onset of sexual maturation in rainbow trout (*Oncorhynchus mykiss*), the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 65 to 66, or at a position corresponding to position 31 of a nucleotide sequence which is derived from any one of SEQ ID NOs: 65 to 66 by 1 to 5, such as 1 to 2, nucleotide substitutions; with the proviso that said nucleotide substitution(s) are not at position 31 of said derived sequences.

According to certain embodiments, the present invention provides a method of predicting late onset of sexual maturation in rainbow trout (*Oncorhynchus mykiss*), the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 67 to 69, or at a position corresponding to position 31 of a nucleotide sequence which is derived from any one of SEQ ID NOs: 67 to 69 by 1 to 5, such as 1 to 2, nucleotide substitutions; with the proviso that said nucleotide substitution(s) are not at position 31 of said derived sequences.

According to certain embodiments, the present invention provides a method of predicting late onset of sexual maturation in rainbow trout (*Oncorhynchus mykiss*), the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 70 to 73, or at a position corresponding to position 31 of a nucleotide sequence which is derived from any one of SEQ ID NOs: 70 to 73 by 1 to 5, such as 1 to 2, nucleotide substitutions; with the proviso that said nucleotide substitution(s) are not at position 31 of said derived sequences.

According to certain embodiments, the present invention provides a method of predicting late onset of sexual maturation in rainbow trout (*Oncorhynchus mykiss*), the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 74 to 76, or at a position corresponding to position 31 of a nucleotide sequence which is derived from any one of SEQ ID NOs: 74 to 76 by 1 to 5, such as 1 to 2, nucleotide substitutions; with the proviso that said nucleotide substitution(s) are not at position 31 of said derived sequences.

According to certain embodiments, the present invention provides a method of predicting late onset of sexual maturation in rainbow trout (*Oncorhynchus mykiss*), the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 77 to 80, or at a position corresponding to position 31 of a nucleotide sequence which is derived from any one of SEQ ID NOs: 77 to 80 by 1 to 5, such as 1 to 2, nucleotide substitutions; with the proviso that said nucleotide substitution(s) are not at position 31 of said derived sequences.

According to certain embodiments, the present invention provides a method of predicting late onset of sexual maturation in rainbow trout (*Oncorhynchus mykiss*), the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 81 to 83, or at a position corresponding to position 31 of a nucleotide sequence which is derived from any one of SEQ ID NOs: 81 to 83 by 1 to 5, such as 1 to 2, nucleotide substitutions; with the proviso that said nucleotide substitution(s) are not at position 31 of said derived sequences.

According to certain embodiments, the present invention provides a method of predicting late onset of sexual maturation in rainbow trout (*Oncorhynchus mykiss*), the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 84 to 89, or at a position corresponding to position 31 of a nucleotide sequence which is derived from any one of SEQ ID NOs: 84 to 89 by 1 to 5, such as 1 to 2, nucleotide substitutions; with the proviso that said nucleotide substitution(s) are not at position 31 of said derived sequences.

According to certain embodiments, the present invention provides a method of predicting late onset of sexual maturation in rainbow trout (*Oncorhynchus mykiss*), the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 90 to 92, or at a position corresponding to position 31 of a nucleotide sequence which is derived from any one of SEQ ID NOs: 90 to 92 by 1 to 5, such as 1 to 2, nucleotide substitutions; with the proviso that said nucleotide substitution(s) are not at position 31 of said derived sequences.

According to certain embodiments, the present invention provides a method of predicting late onset of sexual maturation in rainbow trout (*Oncorhynchus mykiss*), the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 93 to 101, or at a position corresponding to position 31 of a nucleotide sequence which is derived from any one of SEQ ID NOs: 93 to 101 by 1 to 5, such as 1 to 2, nucleotide substitutions; with the proviso that said nucleotide substitution(s) are not at position 31 of said derived sequences.

According to certain embodiments, the present invention provides a method of predicting late onset of sexual maturation in rainbow trout (*Oncorhynchus mykiss*), the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 102 to 105, or at a position corresponding to position 31 of a nucleotide sequence which is derived from any one of SEQ ID NOs: 102 to 105 by 1 to 5, such as 1 to 2, nucleotide substitutions; with the proviso that said nucleotide substitution(s) are not at position 31 of said derived sequences.

According to certain embodiments, the present invention provides a method of predicting late onset of sexual maturation in rainbow trout (*Oncorhynchus mykiss*), the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 106 to 109, or at a position corresponding to position 31 of a nucleotide sequence which is derived from any one of SEQ ID NOs: 106 to 109 by 1 to 5, such as 1 to 2, nucleotide substitutions; with the proviso that said nucleotide substitution(s) are not at position 31 of said derived sequences.

According to certain particularly preferred embodiments, the present invention provides a method of predicting late onset of sexual maturation in rainbow trout (*Oncorhynchus mykiss*), the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 110 to 161, or at a position corresponding to position 31 of a nucleotide sequence which is derived from any one of SEQ ID NOs: 110 to 161 by 1 to 5, such as 1 to 2, nucleotide substitutions; with the proviso that said nucleotide substitution(s) are not at position 31 of said derived sequences.

According to certain embodiments, the present invention provides a method of predicting late onset of sexual maturation in rainbow trout (*Oncorhynchus mykiss*), the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 162 to 164, or at a position corresponding to position 31 of a nucleotide sequence which is derived from any one of SEQ ID NOs: 162 to 164 by 1 to 5, such as 1 to 2, nucleotide substitutions; with the proviso that said nucleotide substitution(s) are not at position 31 of said derived sequences.

According to certain embodiments, the present invention provides a method of predicting late onset of sexual maturation in rainbow trout (*Oncorhynchus mykiss*), the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs:127, 128, 135, 137, 140, 142, 143, 144, 146 and 147, or at a position corresponding to position 31 of a nucleotide sequence which is derived from any one of SEQ ID NOs: 127, 128, 135, 137, 140, 142, 143, 144, 146 and 147 by 1 to 5, such as 1 to 2, nucleotide substitutions; with the proviso that said nucleotide substitution(s) are not at position 31 of said derived sequences.

According to certain embodiments, the present invention provides a method of predicting late onset of sexual maturation in rainbow trout (*Oncorhynchus mykiss*), the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 93, 114, 120, 129, 130, 131, 132, 134, 138 and 148, or at a position corresponding to position 31 of a nucleotide sequence which is derived from any one of SEQ ID NOs: 93, 114, 120, 129, 130, 131, 132, 134, 138 and 148 by 1 to 5, such as 1 to 2, nucleotide substitutions; with the proviso that said nucleotide substitution(s) are not at position 31 of said derived sequences.

According to certain embodiments, the present invention provides a method of predicting late onset of sexual maturation in rainbow trout (*Oncorhynchus mykiss*), the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 5, 24, 86, 121, 125, 126, 133, 141, 150 and 154, or at a position corresponding to position 31 of a nucleotide sequence which is derived from any one of SEQ ID NOs: 5, 24, 86, 121, 125, 126, 133, 141, 150 and 154 by 1 to 5, such as 1 to 2, nucleotide substitutions; with the proviso that said nucleotide substitution(s) are not at position 31 of said derived sequences.

According to certain embodiments, the present invention provides a method of predicting late onset of sexual maturation in rainbow trout (*Oncorhynchus mykiss*), the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 7, 9, 19, 85, 111, 116, 117, 119, 153 and 155 or at a position corresponding to position 31 of a nucleotide sequence which is derived from any one of SEQ ID NOs: 7, 9, 19, 85, 111, 116, 117, 119, 153 and 155 by 1 to 5, such as 1 to 2, nucleotide substitutions; with the proviso that said nucleotide substitution(s) are not at position 31 of said derived sequences.

According to certain embodiments, the present invention provides a method of predicting late onset of sexual maturation in rainbow trout (*Oncorhynchus mykiss*), the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 10, 11, 23, 88, 89, 91, 101, 124, 145 and 151, or at a position corresponding to position 31 of a nucleotide sequence which is derived from any one of SEQ ID NOs: 10, 11, 23, 88, 89, 91, 101, 124, 145 and 151 by 1 to 5, such as 1 to 2, nucleotide substitutions; with the proviso that said nucleotide substitution(s) are not at position 31 of said derived sequences.

According to certain embodiments, the present invention provides a method of predicting late onset of sexual maturation in rainbow trout (*Oncorhynchus mykiss*), the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 120, 127 to 131, 134, 135, 137, 138, 140, 142 to 144, 146 and 147, or at a position corresponding to position 31 of a nucleotide sequence which is derived from any one of SEQ ID NOs: 120, 127 to 131, 134, 135, 137, 138, 140, 142 to 144, 146 and 147 by 1 to 5, such as 1 to 2, nucleotide substitutions; with the proviso that said nucleotide substitution(s) are not at position 31 of said derived sequences.

According to certain embodiments, the present invention provides a method of predicting late onset of sexual maturation in rainbow trout (*Oncorhynchus mykiss*), the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 140, 135, 143 and 137, or at a position corresponding to position 31 of a nucleotide sequence which is derived from any one of SEQ ID NOs: 140, 135, 143 and 137 by 1 to 5, such as 1 to 2, nucleotide substitutions; with the proviso that said nucleotide substitution(s) are not at position 31 of said derived sequences.

According to certain embodiments, the present invention provides a method of predicting late onset of sexual maturation in rainbow trout (*Oncorhynchus mykiss*), the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 140, 135, 143, 137 and 128 or at a position corresponding to position 31 of a nucleotide sequence which is derived from any one of SEQ ID NOs: 140, 135, 143 and 128 by 1 to 5, such as 1 to 2, nucleotide substitutions; with the proviso that said nucleotide substitution(s) are not at position 31 of said derived sequences.

According to certain embodiments, the present invention provides a method of predicting late onset of sexual maturation in rainbow trout (*Oncorhynchus mykiss*), the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 140, 135, 143, 137, 128 and 144 or at a position corresponding to position 31 of a nucleotide sequence which is derived from any one of SEQ ID NOs: 140, 135, 143, 128 and 144 by 1 to 5, such as 1 to 2, nucleotide substitutions; with the proviso that said nucleotide substitution(s) are not at position 31 of said derived sequences.

According to certain embodiments, the present invention provides a method of predicting late onset of sexual maturation in rainbow trout (*Oncorhynchus mykiss*), the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 140, 135, 143, 137, 128, 144 and 142 or at a position corresponding to position 31 of a nucleotide sequence which is derived from any one of SEQ ID NOs: 140, 135, 143, 137, 128, 144 and 142 by 1 to 5, such as 1 to 2, nucleotide substitutions; with the proviso that said nucleotide substitution(s) are not at position 31 of said derived sequences.

According to certain embodiments, the present invention provides a method of predicting late onset of sexual maturation in rainbow trout (*Oncorhynchus mykiss*), the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 140, 135, 143, 137, 128, 144, 142 and 127 or at a position corresponding to position 31 of a nucleotide sequence which is derived from any one of SEQ ID NOs: 140, 135, 143, 137, 128, 144, 142 and 127 by 1 to 5, such as 1 to 2, nucleotide substitutions; with the proviso that said nucleotide substitution(s) are not at position 31 of said derived sequences.

According to certain embodiments, the present invention provides a method of predicting late onset of sexual maturation in rainbow trout (*Oncorhynchus mykiss*), the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 140, 135, 143, 137, 128, 144, 142, 127 and 146 or at a position corresponding to position 31 of a nucleotide sequence which is derived from any one of SEQ ID NOs: 140, 135, 143, 137, 128, 144, 142, 127 and 146 by 1 to 5, such as 1 to 2, nucleotide substitutions; with the proviso that said nucleotide substitution(s) are not at position 31 of said derived sequences.

According to certain embodiments, the present invention provides a method of predicting late onset of sexual maturation in rainbow trout (*Oncorhynchus mykiss*), the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 140, 135, 143, 137, 128, 144, 142, 127, 146 and 147 or at a position corresponding to position 31 of a nucleotide sequence which is derived from any one of SEQ ID NOs: 140, 135, 143, 137, 128, 144, 142, 127, 146 and 147 by 1 to 5, such as 1 to 2, nucleotide substitutions; with the proviso that said nucleotide substitution(s) are not at position 31 of said derived sequences.

According to certain embodiments, the present invention provides a method of predicting late onset of sexual maturation in rainbow trout (*Oncorhynchus mykiss*), the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 140, 135, 143, 137, 128, 144, 142, 127, 146, 147 and 131 or at a position corresponding to position 31 of a nucleotide sequence which is derived from any one of SEQ ID NOs: 140, 135, 143, 137, 128, 144, 142, 127, 146, 147 and 131 by 1 to 5, such as 1 to 2, nucleotide substitutions; with the proviso that said nucleotide substitution(s) are not at position 31 of said derived sequences.

According to certain embodiments, the present invention provides a method of predicting late onset of sexual maturation in rainbow trout (*Oncorhynchus mykiss*), the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 140, 135, 143, 137, 128, 144, 142, 127, 146, 147, 131 and 129 or at a position corresponding to position 31 of a nucleotide sequence which is derived from any one of SEQ ID NOs: 140, 135, 143, 137, 128, 144, 142, 127, 146, 147, 131 and 129 by 1 to 5, such as 1 to 2, nucleotide substitutions; with the proviso that said nucleotide substitution(s) are not at position 31 of said derived sequences.

According to certain embodiments, the present invention provides a method of predicting late onset of sexual maturation in rainbow trout (*Oncorhynchus mykiss*), the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 140, 135, 143, 137, 128, 144, 142, 127, 146, 147, 131, 129 and 120 or at a position corresponding to position 31 of a nucleotide sequence which is derived from any one of SEQ ID NOs: 140, 135, 143, 137, 128, 144, 142, 127, 146, 147, 131, 129 and 120 by 1 to 5, such as 1 to 2, nucleotide substitutions; with the proviso that said nucleotide substitution(s) are not at position 31 of said derived sequences.

According to certain embodiments, the present invention provides a method of predicting late onset of sexual maturation in rainbow trout (*Oncorhynchus mykiss*), the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 140, 135, 143, 137, 128, 144, 142, 127, 146, 147, 131, 129, 120 and 130 or at a position corresponding to position 31 of a nucleotide sequence which is derived from any one of SEQ ID NOs: 140, 135, 143, 137, 128, 144, 142, 127, 146, 147, 131, 129, 120 and 130 by 1 to 5, such as 1 to 2, nucleotide substitutions; with the proviso that said nucleotide substitution(s) are not at position 31 of said derived sequences.

According to certain embodiments, the present invention provides a method of predicting late onset of sexual maturation in rainbow trout (*Oncorhynchus mykiss*), the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 140, 135, 143, 137, 128, 144, 142, 127, 146, 147, 131, 129, 120, 130 and 138 or at a position corresponding to position 31 of a nucleotide sequence which is derived from any one of SEQ ID NOs: 140, 135, 143, 137, 128, 144, 142, 127, 146, 147, 131, 129, 120, 130 and 138 by 1 to 5, such as 1 to 2, nucleotide substitutions; with the proviso that said nucleotide substitution(s) are not at position 31 of said derived sequences.

According to certain embodiments, the present invention provides a method of predicting late onset of sexual maturation in rainbow trout (*Oncorhynchus mykiss*), the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 140, 135, 143 and 137 or at a position corresponding to position 31 of a nucleotide sequence which is derived from any one of SEQ ID NOs: 140, 135, 143 and 137 by 1 to 5, such as 1 to 2, nucleotide substitutions; with the proviso that said nucleotide substitution(s) are not at position 31 of said derived sequences.

According to certain embodiments, the present invention provides a method of predicting late onset of sexual maturation in rainbow trout (*Oncorhynchus mykiss*), the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 135, 137, 138, 140, 142 and 143 or at a position corresponding to position 31 of a nucleotide sequence which is derived from any one of SEQ ID NOs: 135, 137, 138, 140, 142 and 143 by 1 to 5, such as 1 to 2, nucleotide substitutions; with the proviso that said nucleotide substitution(s) are not at position 31 of said derived sequences.

According to certain embodiments, the present invention provides a method of predicting late onset of sexual maturation in rainbow trout (*Oncorhynchus mykiss*), the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 134, 135, 137, 138, 140, 142, 143 and 144 or at a position corresponding to position 31 of a nucleotide sequence which is derived from any one of SEQ ID NOs: 134, 135, 137, 138, 140, 142, 143 and 144 by 1 to 5, such as 1 to 2, nucleotide substitutions; with the proviso that said nucleotide substitution(s) are not at position 31 of said derived sequences.

According to certain embodiments, the present invention provides a method of predicting late onset of sexual maturation in rainbow trout (*Oncorhynchus mykiss*), the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 131, 134, 135, 137, 138, 140, 142, 143, 144 and 146 or at a position corresponding to position 31 of a nucleotide sequence which is derived from any one of SEQ ID NOs: 131, 134, 135, 137, 138, 140, 142, 143, 144 and 146 by 1 to 5, such as 1 to 2, nucleotide substitutions; with the proviso that said nucleotide substitution(s) are not at position 31 of said derived sequences.

According to certain embodiments, the present invention provides a method of predicting late onset of sexual maturation in rainbow trout (*Oncorhynchus mykiss*), the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 130, 131, 134, 135, 137, 138, 140, 142, 143, 144, 146 and 147 or at a position corresponding to position 31 of a nucleotide sequence which is derived from any one of SEQ ID NOs: 131, 134, 135, 137, 138, 140, 142, 143, 144 and 146 by 1 to 5, such as 1 to 2, nucleotide substitutions; with the proviso that said nucleotide substitution(s) are not at position 31 of said derived sequences.

The rainbow trout has late onset of sexual maturation when the nucleotide of the at least one allele is a nucleotide corresponding to the late maturation allele of the respective SNP. The late maturation allele of each SNP is specified in Table 1.

Methods for Selecting

The present invention provides in a second aspect, a method for selecting a rainbow trout having late onset of sexual maturation, the method comprising determining the presence of at least one allele conferring late onset of sexual maturation ("late maturation allele") within the genome of said rainbow trout; and selecting said rainbow trout as having late onset of sexual maturation when the at least one late maturation allele is present; wherein the at least one late maturation allele is an allele of at least one SNP, the at least one SNP being selected from the SNPs listed in Table 1.

According to certain embodiments, the at least one late maturation allele is an allele of at least one single nucleotide polymorphism (SNP), the at least one SNP being located on chromosome 1 and being selected from SNP #1 to SNP #4 listed in table 1.

According to certain embodiments, the at least one late maturation allele is an allele of at least one single nucleotide polymorphism (SNP), the at least one SNP being located on chromosome 2 and being selected from SNP #5 to SNP #12 listed in table 1.

According to certain embodiments, the at least one late maturation allele is an allele of at least one single nucleotide polymorphism (SNP), the at least one SNP being located on chromosome 3 and being selected from SNP #13 to SNP #16 listed in table 1.

According to certain embodiments, the at least one late maturation allele is an allele of at least one single nucleotide polymorphism (SNP), the at least one SNP being located on chromosome 4 and being selected from SNP #17 to SNP #20 listed in table 1.

According to certain embodiments, the at least one late maturation allele is an allele of at least one single nucleotide polymorphism (SNP), the at least one SNP being located on chromosome 5 and being selected from SNP #21 to SNP #24 listed in table 1.

According to certain embodiments, the at least one late maturation allele is an allele of at least one single nucleotide polymorphism (SNP), the at least one SNP being located on chromosome 6 and being selected from SNP #25 to SNP #28 listed in table 1.

According to certain embodiments, the at least one late maturation allele is an allele of at least one single nucleotide polymorphism (SNP), the at least one SNP being located on chromosome 7 and being selected from SNP #29 to SNP #32 listed in table 1.

According to certain embodiments, the at least one late maturation allele is an allele of at least one single nucleotide polymorphism (SNP), the at least one SNP being located on chromosome 8 and being selected from SNP #33 to SNP #36 listed in table 1.

According to certain embodiments, the at least one late maturation allele is an allele of at least one single nucleotide polymorphism (SNP), the at least one SNP being located on chromosome 9 and being selected from SNP #37 to SNP #40 listed in table 1.

According to certain embodiments, the at least one late maturation allele is an allele of at least one single nucleotide polymorphism (SNP), the at least one SNP being located on chromosome 10 and being selected from SNP #41 to SNP #43 listed in table 1.

According to certain embodiments, the at least one late maturation allele is an allele of at least one single nucleotide polymorphism (SNP), the at least one SNP being located on chromosome 11 and being selected from SNP #44 to SNP #47 listed in table 1.

According to certain embodiments, the at least one late maturation allele is an allele of at least one single nucleotide polymorphism (SNP), the at least one SNP being located on chromosome 12 and being selected from SNP #48 to SNP #50 listed in table 1.

According to certain embodiments, the at least one late maturation allele is an allele of at least one single nucleotide polymorphism (SNP), the at least one SNP being located on chromosome 13 and being selected from SNP #51 to SNP #53 listed in table 1.

According to certain embodiments, the at least one late maturation allele is an allele of at least one single nucleotide polymorphism (SNP), the at least one SNP being located on chromosome 14 and being selected from SNP #54 to SNP #57 listed in table 1.

According to certain embodiments, the at least one late maturation allele is an allele of at least one single nucleotide polymorphism (SNP), the at least one SNP being located on chromosome 15 and being selected from SNP #58 to SNP #61 listed in table 1.

According to certain embodiments, the at least one late maturation allele is an allele of at least one single nucleotide polymorphism (SNP), the at least one SNP being located on chromosome 16 and being selected from SNP #62 to SNP #64 listed in table 1.

According to certain embodiments, the at least one late maturation allele is an allele of at least one single nucleotide polymorphism (SNP), the at least one SNP being located on chromosome 17 and being selected from SNP #65 to SNP #66 listed in table 1.

According to certain embodiments, the at least one late maturation allele is an allele of at least one single nucleotide polymorphism (SNP), the at least one SNP being located on chromosome 18 and being selected from SNP #67 to SNP #69 listed in table 1.

According to certain embodiments, the at least one late maturation allele is an allele of at least one single nucleotide polymorphism (SNP), the at least one SNP being located on chromosome 19 and being selected from SNP #70 to SNP #73 listed in table 1.

According to certain embodiments, the at least one late maturation allele is an allele of at least one single nucleotide polymorphism (SNP), the at least one SNP being located on chromosome 20 and being selected from SNP #74 to SNP #76 listed in table 1.

According to certain embodiments, the at least one late maturation allele is an allele of at least one single nucleotide polymorphism (SNP), the at least one SNP being located on chromosome 21 and being selected from SNP #77 to SNP #80 listed in table 1.

According to certain embodiments, the at least one late maturation allele is an allele of at least one single nucleotide polymorphism (SNP), the at least one SNP being located on chromosome 22 and being selected from SNP #81 to SNP #83 listed in table 1.

According to certain embodiments, the at least one late maturation allele is an allele of at least one single nucleotide polymorphism (SNP), the at least one SNP being located on chromosome 23 and being selected from SNP #84 to SNP #89 listed in table 1.

According to certain embodiments, the at least one late maturation allele is an allele of at least one single nucleotide polymorphism (SNP), the at least one SNP being located on chromosome 24 and being selected from SNP #90 to SNP #92 listed in table 1.

According to certain embodiments, the at least one late maturation allele is an allele of at least one single nucleotide polymorphism (SNP), the at least one SNP being located on chromosome 25 and being selected from SNP #93 to SNP #101 listed in table 1.

According to certain embodiments, the at least one late maturation allele is an allele of at least one single nucleotide polymorphism (SNP), the at least one SNP being located on chromosome 26 and being selected from SNP #102 to SNP #105 listed in table 1.

According to certain embodiments, the at least one late maturation allele is an allele of at least one single nucleotide polymorphism (SNP), the at least one SNP being located on chromosome 27 and being selected from SNP #106 to SNP #109 listed in table 1.

According to certain particularly preferred embodiments, the at least one late maturation allele is an allele of at least one single nucleotide polymorphism (SNP), the at least one SNP being located on chromosome 28 and being selected from SNP #110 to SNP #161 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #120, SNP #127 to SNP #131, SNP #134, SNP #135, SNP #137, SNP #138, SNP #140, SNP #142 to SNP #144, SNP #146 and SNP #147 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP #143 and SNP #137 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP #143, SNP #137 and SNP #128 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP #143, SNP #137, SNP #128 and SNP #144 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP #143, SNP #137, SNP #128, SNP #144 and SNP #142 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP #143, SNP #137, SNP #128, SNP #144, SNP #142, and SNP #127 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP #143, SNP #137, SNP #128, SNP #144, SNP #142, SNP #127 and SNP #146 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP #143, SNP #137, SNP #128, SNP #144, SNP #142, SNP #127, SNP #146 and SNP #147 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP #143, SNP #137, SNP #128, SNP #144, SNP #142, SNP #127, SNP #146, SNP #147 and SNP #131 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP #143, SNP #137, SNP #128, SNP #144, SNP #142, SNP #127, SNP #146, SNP #147, SNP #131 and SNP #129 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP #143, SNP #137, SNP #128, SNP #144, SNP #142, SNP #127, SNP #146, SNP #147, SNP #131, SNP #129 and SNP #120 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP #143, SNP #137, SNP #128, SNP #144, SNP #142, SNP #127, SNP #146, SNP #147, SNP #131, SNP #129, SNP #120 and SNP #130 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP #143, SNP #137, SNP #128, SNP #144, SNP #142, SNP #127, SNP #146, SNP #147, SNP #131, SNP #129, SNP #120, SNP #130 and SNP #138 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP #143 and SNP #137 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #135, SNP #137, SNP #138, SNP #140, SNP #142 and SNP #143 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #134, SNP #135, SNP #137, SNP #138, SNP #140, SNP #142, SNP #143 and SNP #144 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #131, SNP #134, SNP #135, SNP #137, SNP #138, SNP #140, SNP #142, SNP #143, SNP #144 and SNP #146 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #130, SNP #131, SNP #134, SNP #135, SNP #137, SNP #138, SNP #140, SNP #142, SNP #143, SNP #144, SNP #146 and SNP #147 listed in table 1.

According to certain embodiments, the at least one late maturation allele is an allele of at least one single nucleotide polymorphism (SNP), the at least one SNP being located on chromosome 29 and being selected from SNP #162 to SNP #164 listed in table 1.

According to certain embodiments, the at least one late maturation allele is an allele of at least one single nucleotide polymorphism (SNP), the at least one SNP being selected from the group consisting of SNP #127, SNP #128, SNP #135, SNP #137, SNP #140, SNP #142, SNP #143, SNP #144, SNP #146 and SNP #147 listed in table 1.

According to certain embodiments, the at least one late maturation allele is an allele of at least one single nucleotide polymorphism (SNP), the at least one SNP being selected from the group consisting of SNP #127, SNP #128, SNP #135, SNP #137, SNP #140, SNP #142, SNP #143, SNP #144, SNP #146 and SNP #148 listed in table 1.

According to certain embodiments, the at least one late maturation allele is an allele of at least one single nucleotide polymorphism (SNP), the at least one SNP being selected from the group consisting of SNP #5, SNP #24, SNP #86, SNP #121, SNP #125, SNP #126, SNP #133, SNP #141, SNP #150 and SNP #154 listed in table 1.

According to certain embodiments, the at least one late maturation allele is an allele of at least one single nucleotide polymorphism (SNP), the at least one SNP being selected from the group consisting of SNP #7, SNP #9, SNP #19, SNP #85, SNP #111, SNP #116, SNP #117, SNP #119, SNP #153 and SNP #155 listed in table 1.

According to certain embodiments, the at least one late maturation allele is an allele of at least one single nucleotide polymorphism (SNP), the at least one SNP being selected from the group consisting of SNP #10, SNP #11, SNP #23, SNP #88, SNP #89, SNP #91, SNP #101, SNP #124, SNP #145 and SNP #151 listed in table 1.

A preferred embodiment according to the first aspect of the present invention relates to a method for selecting a rainbow trout having late onset of sexual maturation, the method comprising: determining the presence of at least one allele conferring late onset of sexual maturation ("late maturation allele") within the genome of said rainbow trout; and selecting said rainbow trout as having late onset of sexual maturation when the at least one late maturation allele is present; wherein the at least one late maturation allele is an allele of at least one SNP, the at least one SNP being SNP #140 listed in table 1 wherein the presence of a thymine at the position corresponding to position 31 of SEQ ID NO. 140 indicates that the rainbow trout has late onset of sexual maturation.

According to certain embodiments, the present invention provides a method for selecting a rainbow trout having late onset of sexual maturation, the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 1 to 164, or at a position corresponding to position 31 of a nucleotide sequence which is derived from any one of SEQ ID NOs: 1 to 164 by 1 to 5, such as 1 to 2, nucleotide substitutions; with the proviso that said nucleotide substitution(s) are not at position 31 of said derived sequences; and selecting said rainbow trout as having late onset of sexual maturation when the nucleotide of the at least one allele is a nucleotide corresponding to the late maturation allele of the SNP.

According to certain embodiments, the present invention provides a method for selecting a rainbow trout having late onset of sexual maturation, the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 1 to 4, or at a position corresponding to position 31 of a nucleotide sequence which is derived from any one of SEQ ID NOs: 1 to 4 by 1 to 5, such as 1 to 2, nucleotide substitutions; with the proviso that said nucleotide substitution(s) are not at position 31 of said derived sequences; and selecting said rainbow trout as having late onset of sexual maturation when the nucleotide of the at least one allele is a nucleotide corresponding to the late maturation allele of the SNP.

According to certain embodiments, the present invention provides a method for selecting a rainbow trout having late onset of sexual maturation, the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 5 to 12, or at a position corresponding to position 31 of a nucleotide sequence which is derived from any one of SEQ ID NOs: 5 to 12 by 1 to 5, such as 1 to 2, nucleotide substitutions; with the proviso that said nucleotide substitution(s) are not at position 31 of said derived sequences; and selecting said rainbow trout as having late onset of sexual maturation when the nucleotide of the at least one allele is a nucleotide corresponding to the late maturation allele of the SNP.

According to certain embodiments, the present invention provides a method for selecting a rainbow trout having late onset of sexual maturation, the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 13 to 16, or at a position corresponding to position 31 of a nucleotide sequence which is derived from any one of SEQ ID NOs: 13 to 16 by 1 to 5, such as 1 to 2, nucleotide substitutions; with the proviso that said nucleotide substitution(s) are not at position 31 of said derived sequences; and selecting said rainbow trout as having late onset of sexual maturation when the nucleotide of the at least one allele is a nucleotide corresponding to the late maturation allele of the SNP.

According to certain embodiments, the present invention provides a method for selecting a rainbow trout having late onset of sexual maturation, the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 17 to 20, or at a position corresponding to position 31 of a nucleotide sequence which is derived from any one of SEQ ID NOs: 17 to 20 by 1 to 5, such as 1 to 2, nucleotide substitutions; with the proviso that said nucleotide substitution(s) are not at position 31 of said derived sequences; and selecting said rainbow trout as having late onset of sexual maturation when the nucleotide of the at least one allele is a nucleotide corresponding to the late maturation allele of the SNP.

According to certain embodiments, the present invention provides a method for selecting a rainbow trout having late onset of sexual maturation, the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 21 to 24, or at a position corresponding to position 31 of a nucleotide sequence which is derived from any one of SEQ ID NOs: 21 to 24 by 1 to 5, such as 1 to 2, nucleotide substitutions; with the proviso that said nucleotide substitution(s) are not at position 31 of said derived sequences; and selecting said rainbow trout as having late onset of sexual maturation when the nucleotide of the at least one allele is a nucleotide corresponding to the late maturation allele of the SNP.

According to certain embodiments, the present invention provides a method for selecting a rainbow trout having late onset of sexual maturation, the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 25 to 28, or at a position corresponding to position 31 of a nucleotide sequence which is derived from any one of SEQ ID NOs: 25 to 28 by 1 to 5, such as 1 to 2, nucleotide substitutions; with the proviso that said nucleotide substitution(s) are not at position 31 of said derived sequences; and selecting said rainbow trout as having late onset of sexual maturation when the nucleotide of the at least one allele is a nucleotide corresponding to the late maturation allele of the SNP.

According to certain embodiments, the present invention provides a method for selecting a rainbow trout having late onset of sexual maturation, the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 29 to 32, or at a position corresponding to position 31 of a nucleotide sequence which is derived from any one of SEQ ID NOs: 29 to 32 by 1 to 5, such as 1 to 2, nucleotide substitutions; with the proviso that said nucleotide substitution(s) are not at position 31 of said derived sequences; and selecting said rainbow trout as having late onset of sexual maturation when the nucleotide of the at least one allele is a nucleotide corresponding to the late maturation allele of the SNP.

According to certain embodiments, the present invention provides a method for selecting a rainbow trout having late onset of sexual maturation, the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 33 to 36, or at a position corresponding to position 31 of a nucleotide sequence which is derived from any one of SEQ ID NOs: 33 to 36 by 1 to 5, such as 1 to 2, nucleotide substitutions; with the proviso that said nucleotide substitution(s) are not at position 31 of said derived sequences; and selecting said rainbow trout as having late onset of sexual maturation when the nucleotide of the at least one allele is a nucleotide corresponding to the late maturation allele of the SNP.

According to certain embodiments, the present invention provides a method for selecting a rainbow trout having late onset of sexual maturation, the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 37 to 40, or at a position corresponding to position 31 of a nucleotide sequence which is derived from any one of SEQ ID NOs: 37 to 40 by 1 to 5, such as 1 to 2, nucleotide substitutions; with the proviso that said nucleotide substitution(s) are not at position 31 of said derived sequences; and selecting said rainbow trout as having late onset of sexual maturation when the nucleotide of the at least one allele is a nucleotide corresponding to the late maturation allele of the SNP.

According to certain embodiments, the present invention provides a method for selecting a rainbow trout having late onset of sexual maturation, the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 41 to 43, or at a position corresponding to position 31 of a nucleotide sequence which is derived from any one of SEQ ID NOs: 41 to 43 by 1 to 5, such as 1 to 2, nucleotide substitutions; with the proviso that said nucleotide substitution(s) are not at position 31 of said derived sequences; and selecting said rainbow trout as having late onset of sexual maturation when the nucleotide of the at least one allele is a nucleotide corresponding to the late maturation allele of the SNP.

According to certain embodiments, the present invention provides a method for selecting a rainbow trout having late onset of sexual maturation, the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 44 to 47, or at a position corresponding to position 31 of a nucleotide sequence which is derived from any one of SEQ ID NOs: 44 to 47 by 1 to 5, such as 1 to 2, nucleotide substitutions; with the proviso that said nucleotide substitution(s) are not at position 31 of said derived sequences; and selecting said rainbow trout as having late onset of sexual maturation when the nucleotide of the at least one allele is a nucleotide corresponding to the late maturation allele of the SNP.

According to certain embodiments, the present invention provides a method for selecting a rainbow trout having late onset of sexual maturation, the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 48 to 50, or at a position corresponding to position 31 of a nucleotide sequence which is derived from any one of SEQ ID NOs: 48 to 50 by 1 to 5, such as 1 to 2, nucleotide substitutions; with the proviso that said nucleotide substitution(s) are not at position 31 of said derived sequences; and selecting said rainbow trout as having late onset of sexual maturation when the nucleotide of the at least one allele is a nucleotide corresponding to the late maturation allele of the SNP.

According to certain embodiments, the present invention provides a method for selecting a rainbow trout having late onset of sexual maturation, the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 51 to 53, or at a position corresponding to position 31 of a nucleotide sequence which is derived from any one of SEQ ID NOs: 51 to 53 by 1 to 5, such as 1 to 2, nucleotide substitutions; with the proviso that said nucleotide substitution(s) are not at position 31 of said derived sequences; and selecting said rainbow trout as having late onset of sexual maturation when the nucleotide of the at least one allele is a nucleotide corresponding to the late maturation allele of the SNP.

According to certain embodiments, the present invention provides a method for selecting a rainbow trout having late onset of sexual maturation, the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 54 to 57, or at a position corresponding to position 31 of a nucleotide sequence which is derived from any one of SEQ ID NOs: 54 to 57 by 1 to 5, such as 1 to 2, nucleotide substitutions; with the proviso that said nucleotide substitution(s) are not at position 31 of said derived sequences; and selecting said rainbow trout as having late onset of sexual maturation when the nucleotide of the at least one allele is a nucleotide corresponding to the late maturation allele of the SNP.

According to certain embodiments, the present invention provides a method for selecting a rainbow trout having late onset of sexual maturation, the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 58 to 61, or at a position corresponding to position 31 of a nucleotide sequence which is derived from any one of SEQ ID NOs: 58 to 61 by 1 to 5, such as 1 to 2, nucleotide substitutions; with the proviso that said nucleotide substitution(s) are not at position 31 of said derived sequences; and selecting said rainbow trout as having late onset of sexual maturation when the nucleotide of the at least one allele is a nucleotide corresponding to the late maturation allele of the SNP.

According to certain embodiments, the present invention provides a method for selecting a rainbow trout having late onset of sexual maturation, the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 62 to 64, or at a position corresponding to position 31 of a nucleotide sequence which is derived from any one of SEQ ID NOs: 62 to 64 by 1 to 5, such as 1 to 2, nucleotide substitutions; with the proviso that said nucleotide substitution(s) are not at position 31 of said derived sequences; and selecting said rainbow trout as having late onset of sexual maturation when the nucleotide of the at least one allele is a nucleotide corresponding to the late maturation allele of the SNP.

According to certain embodiments, the present invention provides a method for selecting a rainbow trout having late onset of sexual maturation, the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 65 to 66, or at a position corresponding to position 31 of a nucleotide sequence which is derived from any one of SEQ ID NOs: 65 to 66 by 1 to 5, such as 1 to 2, nucleotide substitutions; with the proviso that said nucleotide substitution(s) are not at position 31 of said derived sequences; and selecting said rainbow trout as having late onset of sexual maturation when the nucleotide of the at least one allele is a nucleotide corresponding to the late maturation allele of the SNP.

According to certain embodiments, the present invention provides a method for selecting a rainbow trout having late onset of sexual maturation, the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 67 to 69, or at a position corresponding to position 31 of a nucleotide sequence which is derived from any one of SEQ ID NOs: 67 to 69 by 1 to 5, such as 1 to 2, nucleotide substitutions; with the proviso that said nucleotide substitution(s) are not at position 31 of said derived sequences; and selecting said rainbow trout as having late onset of sexual maturation when the nucleotide of the at least one allele is a nucleotide corresponding to the late maturation allele of the SNP.

According to certain embodiments, the present invention provides a method for selecting a rainbow trout having late onset of sexual maturation, the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 70 to 73, or at a position corresponding to position 31 of a nucleotide sequence which is derived from any one of SEQ ID NOs: 70 to 73 by 1 to 5, such as 1 to 2, nucleotide substitutions; with the proviso that said nucleotide substitution(s) are not at position 31 of said derived sequences; and selecting said rainbow trout as having late onset of sexual maturation when the nucleotide of the at least one allele is a nucleotide corresponding to the late maturation allele of the SNP.

According to certain embodiments, the present invention provides a method for selecting a rainbow trout having late onset of sexual maturation, the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 74 to 76, or at a position corresponding to position 31 of a nucleotide sequence which is derived from any one of SEQ ID NOs: 74 to 76 by 1 to 5, such as 1 to 2, nucleotide substitutions; with the proviso that said nucleotide substitution(s) are not at position 31 of said derived sequences; and selecting said rainbow trout as having late onset of sexual maturation when the nucleotide of the at least one allele is a nucleotide corresponding to the late maturation allele of the SNP.

According to certain embodiments, the present invention provides a method for selecting a rainbow trout having late onset of sexual maturation, the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 77 to 80, or at a position corresponding to position 31 of a nucleotide sequence which is derived from any one of SEQ ID NOs: 77 to 80 by 1 to 5, such as 1 to 2, nucleotide substitutions; with the proviso that said nucleotide substitution(s) are not at position 31 of said derived sequences; and selecting said rainbow trout as having late onset of sexual maturation when the nucleotide of the at least one allele is a nucleotide corresponding to the late maturation allele of the SNP.

According to certain embodiments, the present invention provides a method for selecting a rainbow trout having late onset of sexual maturation, the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 81 to 83, or at a position corresponding to position 31 of a nucleotide sequence which is derived from any one of SEQ ID NOs: 81 to 83 by 1 to 5, such as 1 to 2, nucleotide substitutions; with the proviso that said nucleotide substitution(s) are not at position 31 of said derived sequences; and selecting said rainbow trout as having late onset of sexual maturation when the nucleotide of the at least one allele is a nucleotide corresponding to the late maturation allele of the SNP.

According to certain embodiments, the present invention provides a method for selecting a rainbow trout having late onset of sexual maturation, the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 84 to 89, or at a position corresponding to position 31 of a nucleotide sequence which is derived from any one of SEQ ID NOs: 84 to 89 by 1 to 5, such as 1 to 2, nucleotide substitutions; with the proviso that said nucleotide substitution(s) are not at position 31 of said derived sequences; and selecting said rainbow trout as having late onset of sexual maturation when the nucleotide of the at least one allele is a nucleotide corresponding to the late maturation allele of the SNP.

According to certain embodiments, the present invention provides a method for selecting a rainbow trout having late onset of sexual maturation, the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 90 to 92, or at a position corresponding to position 31 of a nucleotide sequence which is derived from any one of SEQ ID NOs: 90 to 92 by 1 to 5, such as 1 to 2, nucleotide substitutions; with the proviso that said nucleotide substitution(s) are not at position 31 of said derived sequences; and selecting said rainbow trout as having late onset of sexual maturation when the nucleotide of the at least one allele is a nucleotide corresponding to the late maturation allele of the SNP.

According to certain embodiments, the present invention provides a method for selecting a rainbow trout having late onset of sexual maturation, the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 93 to 101, or at a position corresponding to position 31 of a nucleotide sequence which is derived from any one of SEQ ID NOs: 93 to 101 by 1 to 5, such as 1 to 2, nucleotide substitutions; with the proviso that said nucleotide substitution(s) are not at position 31 of said derived sequences; and selecting said rainbow trout as having late onset of sexual maturation when the nucleotide of the at least one allele is a nucleotide corresponding to the late maturation allele of the SNP.

According to certain embodiments, the present invention provides a method for selecting a rainbow trout having late onset of sexual maturation, the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 102 to 105, or at a position corresponding to position 31 of a nucleotide sequence which is derived from any one of SEQ ID NOs: 102 to 105 by 1 to 5, such as 1 to 2, nucleotide substitutions; with the proviso that said nucleotide substitution(s) are not at position 31 of said derived sequences; and selecting said rainbow trout as having late onset of sexual maturation when the nucleotide of the at least one allele is a nucleotide corresponding to the late maturation allele of the SNP.

According to certain embodiments, the present invention provides a method for selecting a rainbow trout having late onset of sexual maturation, the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 106 to 109, or at a position corresponding to position 31 of a nucleotide sequence which is derived from any one of SEQ ID NOs: 106 to 109 by 1 to 5, such as 1 to 2, nucleotide substitutions; with the proviso that said nucleotide substitution(s) are not at position 31 of said derived sequences; and selecting said rainbow trout as having late onset of sexual maturation when the nucleotide of the at least one allele is a nucleotide corresponding to the late maturation allele of the SNP.

According to certain particularly preferred embodiments, the present invention provides a method for selecting a rainbow trout having late onset of sexual maturation, the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 110 to 161, or at a position corresponding to position 31 of a nucleotide sequence which is derived from any one of SEQ ID NOs: 110 to 161 by 1 to 5, such as 1 to 2, nucleotide substitutions; with the proviso that said nucleotide substitution(s) are not at position 31 of said derived sequences; and selecting said rainbow trout as having late onset of sexual maturation when the nucleotide of the at least one allele is a nucleotide corresponding to the late maturation allele of the SNP.

According to certain embodiments, the present invention provides a method for selecting a rainbow trout having late onset of sexual maturation, the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 162 to 164, or at a position corresponding to position 31 of a nucleotide sequence which is derived from any one of SEQ ID NOs: 162 to 164 by 1 to 5, such as 1 to 2, nucleotide substitutions; with the proviso that said nucleotide substitution(s) are not at position 31 of said derived sequences; and selecting said rainbow trout as having late onset of sexual maturation when the nucleotide of the at least one allele is a nucleotide corresponding to the late maturation allele of the SNP.

According to certain particularly preferred embodiments, the present invention provides a method for selecting a rainbow trout having late onset of sexual maturation, the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 127, 128, 135, 137, 140, 142, 143, 144, 146 and 147, or at a position corresponding to position 31 of a nucleotide sequence which is derived from any one of SEQ ID NOs: 127, 128, 135, 137, 140, 142, 143, 144, 146 and 147 by 1 to 5, such as 1 to 2, nucleotide substitutions; with the proviso that said nucleotide substitution(s) are not at position 31 of said derived sequences; and selecting said rainbow trout as having late onset of sexual maturation when the nucleotide of the at least one allele is a nucleotide corresponding to the late maturation allele of the SNP.

According to certain particularly preferred embodiments, the present invention provides a method for selecting a rainbow trout having late onset of sexual maturation, the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 93, 114, 120, 129, 130, 131, 132, 134, 138 and 148, or at a position corresponding to position 31 of a nucleotide sequence which is derived from any one of SEQ ID NOs: 93, 114, 120, 129, 130, 131, 132, 134, 138 and 148 by 1 to 5, such as 1 to 2, nucleotide substitutions; with the proviso that said nucleotide substitution(s) are not at position 31 of said derived sequences; and selecting said rainbow trout as having late onset of sexual maturation when the nucleotide of the at least one allele is a nucleotide corresponding to the late maturation allele of the SNP.

According to certain particularly preferred embodiments, the present invention provides a method for selecting a rainbow trout having late onset of sexual maturation, the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 5, 24, 86, 121, 125, 126, 133, 141, 150 and 154, or at a position corresponding to position 31 of a nucleotide sequence which is derived from any one of SEQ ID NOs: 5, 24, 86, 121, 125, 126, 133, 141, 150 and 154 by 1 to 5, such as 1 to 2, nucleotide substitutions; with the proviso that said nucleotide substitution(s) are not at position 31 of said derived sequences; and selecting said rainbow trout as having late onset of sexual maturation when the nucleotide of the at least one allele is a nucleotide corresponding to the late maturation allele of the SNP.

According to certain particularly preferred embodiments, the present invention provides a method for selecting a rainbow trout having late onset of sexual maturation, the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 7, 9, 19, 85, 111, 116, 117, 119, 153 and 155, or at a position corresponding to position 31 of a nucleotide sequence which is derived from any one of SEQ ID NOs: 7, 9, 19, 85, 111, 116, 117, 119, 153 and 155 by 1 to 5, such as 1 to 2, nucleotide substitutions; with the proviso that said nucleotide substitution(s) are not at position 31 of said derived sequences; and selecting said rainbow trout as having late onset of sexual maturation when the nucleotide of the at least one allele is a nucleotide corresponding to the late maturation allele of the SNP.

According to certain particularly preferred embodiments, the present invention provides a method for selecting a rainbow trout having late onset of sexual maturation, the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 10, 11, 23, 88, 89, 91, 101, 124, 145 and 151, or at a position corresponding to position 31 of a nucleotide sequence which is derived from any one of SEQ ID NOs: 10, 11, 23, 88, 89, 91, 101, 124, 145 and 151 by 1 to 5, such as 1 to 2, nucleotide substitutions; with the proviso that said nucleotide substitution(s) are not at position 31 of said derived sequences; and selecting said rainbow trout as having late onset of sexual maturation when the nucleotide of the at least one allele is a nucleotide corresponding to the late maturation allele of the SNP.

According to certain particularly preferred embodiments, the present invention provides a method for selecting a rainbow trout having late onset of sexual maturation, the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 120, 127 to 131, 134, 135, 137, 138, 140, 142 to 144, 146 and 147, or at a position corresponding to position 31 of a nucleotide sequence which is derived from any one of SEQ ID NOs: 120, 127 to 131, 134, 135, 137, 138, 140, 142 to 144, 146 and 147 by 1 to 5, such as 1 to 2, nucleotide substitutions; with the proviso that said nucleotide substitution(s) are not at position 31 of said derived sequences; and selecting said rainbow trout as having late onset of sexual maturation when the nucleotide of the at least one allele is a nucleotide corresponding to the late maturation allele of the SNP.

According to certain particularly preferred embodiments, the present invention provides a method for selecting a rainbow trout having late onset of sexual maturation, the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 140, 135, 143 and 137, or at a position corresponding to position 31 of a nucleotide sequence which is derived from any one of SEQ ID NOs: 140, 135, 143 and 137 by 1 to 5, such as 1 to 2, nucleotide substitutions; with the proviso that said nucleotide substitution(s) are not at position 31 of said derived sequences; and selecting said rainbow trout as having late onset of sexual maturation when the nucleotide of the at least one allele is a nucleotide corresponding to the late maturation allele of the SNP.

According to certain particularly preferred embodiments, the present invention provides a method for selecting a rainbow trout having late onset of sexual maturation, the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 140, 135, 143, 137 and 128 or at a position corresponding to position 31 of a nucleotide sequence which is derived from any one of SEQ ID NOs: 140, 135, 143 and 128 by 1 to 5, such as 1 to 2, nucleotide substitutions; with the proviso that said nucleotide substitution(s) are not at position 31 of said derived sequences; and selecting said rainbow trout as having late onset of sexual maturation when the nucleotide of the at least one allele is a nucleotide corresponding to the late maturation allele of the SNP.

According to certain particularly preferred embodiments, the present invention provides a method for selecting a rainbow trout having late onset of sexual maturation, the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 140, 135, 143, 137, 128 and 144 or at a position corresponding to position 31 of a nucleotide sequence which is derived from any one of SEQ ID NOs: 140, 135, 143, 128 and 144 by 1 to 5, such as 1 to 2, nucleotide substitutions; with the proviso that said nucleotide substitution(s) are not at position 31 of said derived sequences; and selecting said rainbow trout as having late onset of sexual maturation when the nucleotide of the at least one allele is a nucleotide corresponding to the late maturation allele of the SNP.

According to certain particularly preferred embodiments, the present invention provides a method for selecting a rainbow trout having late onset of sexual maturation, the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 140, 135, 143, 137, 128, 144 and 142 or at a position corresponding to position 31 of a nucleotide sequence which is derived from any one of SEQ ID NOs: 140, 135, 143, 137, 128, 144 and 142 by 1 to 5, such as 1 to 2, nucleotide substitutions; with the proviso that said nucleotide substitution(s) are not at position 31 of said derived sequences; and selecting said rainbow trout as having late onset of sexual maturation when the nucleotide of the at least one allele is a nucleotide corresponding to the late maturation allele of the SNP.

According to certain particularly preferred embodiments, the present invention provides a method for selecting a rainbow trout having late onset of sexual maturation, the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 140, 135, 143, 137, 128, 144, 142 and 127 or at a position corresponding to position 31 of a nucleotide sequence which is derived from any one of SEQ ID NOs: 140, 135, 143, 137, 128, 144, 142 and 127 by 1 to 5, such as 1 to 2, nucleotide substitutions; with the proviso that said nucleotide substitution(s) are not at position 31 of said derived sequences; and selecting said rainbow trout as having late onset of sexual maturation when the nucleotide of the at least one allele is a nucleotide corresponding to the late maturation allele of the SNP.

According to certain particularly preferred embodiments, the present invention provides a method for selecting a rainbow trout having late onset of sexual maturation, the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 140, 135, 143, 137, 128, 144, 142, 127 and 146 or at a position corresponding to position 31 of a nucleotide sequence which is derived from any one of SEQ ID NOs: 140, 135, 143, 137, 128, 144, 142, 127 and 146 by 1 to 5, such as 1 to 2, nucleotide substitutions; with the proviso that said nucleotide substitution(s) are not at position 31 of said derived sequences; and selecting said rainbow trout as having late onset of sexual maturation when the nucleotide of the at least one allele is a nucleotide corresponding to the late maturation allele of the SNP.

According to certain particularly preferred embodiments, the present invention provides a method for selecting a rainbow trout having late onset of sexual maturation, the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 140, 135, 143, 137, 128, 144, 142, 127, 146 and 147 or at a position corresponding to position 31 of a nucleotide sequence which is derived from any one of SEQ ID NOs: 140, 135, 143, 137, 128, 144, 142, 127, 146 and 147 by 1 to 5, such as 1 to 2, nucleotide substitutions; with the proviso that said nucleotide substitution(s) are not at position 31 of said derived sequences; and selecting said rainbow trout as having late onset of sexual maturation when the nucleotide of the at least one allele is a nucleotide corresponding to the late maturation allele of the SNP.

According to certain particularly preferred embodiments, the present invention provides a method for selecting a rainbow trout having late onset of sexual maturation, the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 140, 135, 143, 137, 128, 144, 142, 127, 146, 147 and 131 or at a position corresponding to position 31 of a nucleotide sequence which is derived from any one of SEQ ID NOs: 140, 135, 143, 137, 128, 144, 142, 127, 146, 147 and 131 by 1 to 5, such as 1 to 2, nucleotide substitutions; with the proviso that said nucleotide substitution(s) are not at position 31 of said derived sequences; and selecting said rainbow trout as having late onset of sexual maturation when the nucleotide of the at least one allele is a nucleotide corresponding to the late maturation allele of the SNP.

According to certain particularly preferred embodiments, the present invention provides a method for selecting a rainbow trout having late onset of sexual maturation, the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 140, 135, 143, 137, 128, 144, 142, 127, 146, 147, 131 and 129 or at a position corresponding to position 31 of a nucleotide sequence which is derived from any one of SEQ ID NOs: 140, 135, 143, 137, 128, 144, 142, 127, 146, 147, 131 and 129 by 1 to 5, such as 1 to 2, nucleotide substitutions; with the proviso that said nucleotide substitution(s) are not at position 31 of said derived sequences; and selecting said rainbow trout as having late onset of sexual maturation when the nucleotide of the at least one allele is a nucleotide corresponding to the late maturation allele of the SNP.

According to certain particularly preferred embodiments, the present invention provides a method for selecting a rainbow trout having late onset of sexual maturation, the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 140, 135, 143, 137, 128, 144, 142, 127, 146, 147, 131, 129 and 120 or at a position corresponding to position 31 of a nucleotide sequence which is derived from any one of SEQ ID NOs: 140, 135, 143, 137, 128, 144, 142, 127, 146, 147, 131, 129 and 120 by 1 to 5, such as 1 to 2, nucleotide substitutions; with the proviso that said nucleotide substitution(s) are not at position 31 of said derived sequences; and selecting said rainbow trout as having late onset of sexual maturation when the nucleotide of the at least one allele is a nucleotide corresponding to the late maturation allele of the SNP.

According to certain particularly preferred embodiments, the present invention provides a method for selecting a rainbow trout having late onset of sexual maturation, the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 140, 135, 143, 137, 128, 144, 142, 127, 146, 147, 131, 129, 120 and 130 or at a position corresponding to position 31 of a nucleotide sequence which is derived from any one of SEQ ID NOs: 140, 135, 143, 137, 128, 144, 142, 127, 146, 147, 131, 129, 120 and 130 by 1 to 5, such as 1 to 2, nucleotide substitutions; with the proviso that said nucleotide substitution(s) are not at position 31 of said derived sequences; and selecting said rainbow trout as having late onset of sexual maturation when the nucleotide of the at least one allele is a nucleotide corresponding to the late maturation allele of the SNP.

According to certain particularly preferred embodiments, the present invention provides a method for selecting a rainbow trout having late onset of sexual maturation, the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 140, 135, 143, 137, 128, 144, 142, 127, 146, 147, 131, 129, 120, 130 and 138 or at a position corresponding to position 31 of a nucleotide sequence which is derived from any one of SEQ ID NOs: 140, 135, 143, 137, 128, 144, 142, 127, 146, 147, 131, 129, 120, 130 and 138 by 1 to 5, such as 1 to 2, nucleotide substitutions; with the proviso that said nucleotide substitution(s) are not at position 31 of said derived sequences; and selecting said rainbow trout as having late onset of sexual maturation when the nucleotide of the at least one allele is a nucleotide corresponding to the late maturation allele of the SNP.

According to certain particularly preferred embodiments, the present invention provides a method for selecting a rainbow trout having late onset of sexual maturation, the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 140, 135, 143 and 137 or at a position corresponding to position 31 of a nucleotide sequence which is derived from any one of SEQ ID NOs: 140, 135, 143 and 137 by 1 to 5, such as 1 to 2, nucleotide substitutions; with the proviso that said nucleotide substitution(s) are not at position 31 of said derived sequences; and selecting said rainbow trout as having late onset of sexual maturation when the nucleotide of the at least one allele is a nucleotide corresponding to the late maturation allele of the SNP.

According to certain particularly preferred embodiments, the present invention provides a method for selecting a rainbow trout having late onset of sexual maturation, the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 135, 137, 138, 140, 142 and 143 or at a position corresponding to position 31 of a nucleotide sequence which is derived from any one of SEQ ID NOs: 135, 137, 138, 140, 142 and 143 by 1 to 5, such as 1 to 2, nucleotide substitutions; with the proviso that said nucleotide substitution(s) are not at position 31 of said derived sequences; and selecting said rainbow trout as having late onset of sexual maturation when the nucleotide of the at least one allele is a nucleotide corresponding to the late maturation allele of the SNP.

According to certain particularly preferred embodiments, the present invention provides a method for selecting a rainbow trout having late onset of sexual maturation, the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 134, 135, 137, 138, 140, 142, 143 and 144 or at a position corresponding to position 31 of a nucleotide sequence which is derived from any one of SEQ ID NOs: 134, 135, 137, 138, 140, 142, 143 and 144 by 1 to 5, such as 1 to 2, nucleotide substitutions; with the proviso that said nucleotide substitution(s) are not at position 31 of said derived sequences; and selecting said rainbow trout as having late onset of sexual maturation when the nucleotide of the at least one allele is a nucleotide corresponding to the late maturation allele of the SNP.

According to certain particularly preferred embodiments, the present invention provides a method for selecting a rainbow trout having late onset of sexual maturation, the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 131, 134, 135, 137, 138, 140, 142, 143, 144 and 146 or at a position corresponding to position 31 of a nucleotide sequence which is derived from any one of SEQ ID NOs: 131, 134, 135, 137, 138, 140, 142, 143, 144 and 146 by 1 to 5, such as 1 to 2, nucleotide substitutions; with the proviso that said nucleotide substitution(s) are not at position 31 of said derived sequences; and selecting said rainbow trout as having late onset of sexual maturation when the nucleotide of the at least one allele is a nucleotide corresponding to the late maturation allele of the SNP.

According to certain particularly preferred embodiments, the present invention provides a method for selecting a rainbow trout having late onset of sexual maturation, the method comprising: determining the identity of a nucleotide of at least one allele of at least one SNP associated with late onset of sexual maturation within the genome of said rainbow trout; the at least one SNP being located within said genome at a position corresponding to position 31 of the nucleotide sequence set forth in any one of SEQ ID NOs: 130, 131, 134, 135, 137, 138, 140, 142, 143, 144, 146 and 147 or at a position corresponding to position 31 of a nucleotide sequence which is derived from any one of SEQ ID NOs: 131, 134, 135, 137, 138, 140, 142, 143, 144 and 146 by 1 to 5, such as 1 to 2, nucleotide substitutions; with the proviso that said nucleotide substitution(s) are not at position 31 of said derived sequences; and selecting said rainbow trout as having late onset of sexual maturation when the nucleotide of the at least one allele is a nucleotide corresponding to the late maturation allele of the SNP.

The rainbow trout has late onset of sexual maturation when the nucleotide of the at least one allele is a nucleotide corresponding to the late maturation allele of the respective SNP. The late maturation allele of each SNP is specified in Table 1.

Numerous techniques are known in the art for determining the identity of a nucleotide of an allele present at a polymorphic site. For example, the determination may involve sequence analysis of the rainbow trout to be tested using, e.g., traditional sequence methodologies (e.g., the "dideoxy-mediated chain termination method," also known as the "Sanger Method" (Sanger, F., et al., J. Molec. Biol. 94: 441 (1975); Prober et al. Science 238: 336-340 (1987)) and the "chemical degradation method" also known as the "Maxam-Gilbert method" (Maxam, A. M., et al., Proc. Natl. Acad. Sci. (U.S.A.) 74: 560 (1977). Alternatively, the determination may involve single base extension of DNA oligonucleotides terminating at the polymorphic site (e.g. iPLEX assays from Sequenom (San Diego, USA) and Infinium assays from Illumina (San Diego, USA), allele-specific ligation assays (e.g. Axiom technology from Affymetrix (San Diego, USA), allele-specific PCR (e.g. SNPtype assays from Fluidigm (San Francisco) or KASP assays from LGC Genomics (Teddington, UK)), or competitive hybridization of probes complementary to the different alleles (e.g. the TaqMan assay from Applied Biosystems (Foster City, USA)).

Methods for the detection of allelic variation are also reviewed by Nollau et al., Clin. Chem. 43, 1114-1120, 1997; and in standard textbooks, for example "Laboratory Protocols for Mutation Detection", Ed. by U. Landegren, Oxford University Press, 1996 and "PCR", 2nd Edition by Newton & Graham, BIOS Scientific Publishers Limited, 1997.

For analyzing SNPs, it may for example be appropriate to use oligonucleotides specific for alternative SNP alleles. Such oligonucleotides which detect single nucleotide variations in target sequences may be referred to by such terms as "allele-specific oligonucleotides", "allele-specific probes", or "allele-specific primers". The design and use of allele-specific probes for analyzing polymorphisms is described in, e.g., Mutation Detection A Practical Approach, ed. Cotton et al. Oxford University Press, 1998; Saiki et al., Nature 324, 163-166 (1986); Dattagupta, EP235726; and Saiki, WO 89/11548.

Rainbow Trout

The present invention provides in a further aspect, a rainbow trout, such as an isolated rainbow trout, or a progeny thereof having late onset of sexual maturation comprising within its genome at least one allele, such as at least two alleles, conferring late onset of sexual maturation ("late maturation allele"); wherein the at least one late maturation allele is an allele of at least one single nucleotide polymorphism (SNP), the at least one SNP being selected from the SNPs listed in Table 1.

According to certain embodiments, the at least one late maturation allele is an allele of at least one single nucleotide polymorphism (SNP), the at least one SNP being located on chromosome 1 and being selected from SNP #1 to SNP #4 listed in table 1.

According to certain embodiments, the at least one late maturation allele is an allele of at least one single nucleotide polymorphism (SNP), the at least one SNP being located on chromosome 2 and being selected from SNP #5 to SNP #12 listed in table 1.

According to certain embodiments, the at least one late maturation allele is an allele of at least one single nucleotide polymorphism (SNP), the at least one SNP being located on chromosome 3 and being selected from SNP #13 to SNP #16 listed in table 1.

According to certain embodiments, the at least one late maturation allele is an allele of at least one single nucleotide polymorphism (SNP), the at least one SNP being located on chromosome 4 and being selected from SNP #17 to SNP #20 listed in table 1.

According to certain embodiments, the at least one late maturation allele is an allele of at least one single nucleotide polymorphism (SNP), the at least one SNP being located on chromosome 5 and being selected from SNP #21 to SNP #24 listed in table 1.

According to certain embodiments, the at least one late maturation allele is an allele of at least one single nucleotide polymorphism (SNP), the at least one SNP being located on chromosome 6 and being selected from SNP #25 to SNP #28 listed in table 1.

According to certain embodiments, the at least one late maturation allele is an allele of at least one single nucleotide polymorphism (SNP), the at least one SNP being located on chromosome 7 and being selected from SNP #29 to SNP #32 listed in table 1.

According to certain embodiments, the at least one late maturation allele is an allele of at least one single nucleotide polymorphism (SNP), the at least one SNP being located on chromosome 8 and being selected from SNP #33 to SNP #36 listed in table 1.

According to certain embodiments, the at least one late maturation allele is an allele of at least one single nucleotide polymorphism (SNP), the at least one SNP being located on chromosome 9 and being selected from SNP #37 to SNP #40 listed in table 1.

According to certain embodiments, the at least one late maturation allele is an allele of at least one single nucleotide polymorphism (SNP), the at least one SNP being located on chromosome 10 and being selected from SNP #41 to SNP #43 listed in table 1.

According to certain embodiments, the at least one late maturation allele is an allele of at least one single nucleotide polymorphism (SNP), the at least one SNP being located on chromosome 11 and being selected from SNP #44 to SNP #47 listed in table 1.

According to certain embodiments, the at least one late maturation allele is an allele of at least one single nucleotide polymorphism (SNP), the at least one SNP being located on chromosome 12 and being selected from SNP #48 to SNP #50 listed in table 1.

According to certain embodiments, the at least one late maturation allele is an allele of at least one single nucleotide polymorphism (SNP), the at least one SNP being located on chromosome 13 and being selected from SNP #51 to SNP #53 listed in table 1.

According to certain embodiments, the at least one late maturation allele is an allele of at least one single nucleotide polymorphism (SNP), the at least one SNP being located on chromosome 14 and being selected from SNP #54 to SNP #57 listed in table 1.

According to certain embodiments, the at least one late maturation allele is an allele of at least one single nucleotide polymorphism (SNP), the at least one SNP being located on chromosome 15 and being selected from SNP #58 to SNP #61 listed in table 1.

According to certain embodiments, the at least one late maturation allele is an allele of at least one single nucleotide polymorphism (SNP), the at least one SNP being located on chromosome 16 and being selected from SNP #62 to SNP #64 listed in table 1.

According to certain embodiments, the at least one late maturation allele is an allele of at least one single nucleotide polymorphism (SNP), the at least one SNP being located on chromosome 17 and being selected from SNP #65 to SNP #66 listed in table 1.

According to certain embodiments, the at least one late maturation allele is an allele of at least one single nucleotide polymorphism (SNP), the at least one SNP being located on chromosome 18 and being selected from SNP #67 to SNP #69 listed in table 1.

According to certain embodiments, the at least one late maturation allele is an allele of at least one single nucleotide polymorphism (SNP), the at least one SNP being located on chromosome 19 and being selected from SNP #70 to SNP #73 listed in table 1.

According to certain embodiments, the at least one late maturation allele is an allele of at least one single nucleotide polymorphism (SNP), the at least one SNP being located on chromosome 20 and being selected from SNP #74 to SNP #76 listed in table 1.

According to certain embodiments, the at least one late maturation allele is an allele of at least one single nucleotide polymorphism (SNP), the at least one SNP being located on chromosome 21 and being selected from SNP #77 to SNP #80 listed in table 1.

According to certain embodiments, the at least one late maturation allele is an allele of at least one single nucleotide polymorphism (SNP), the at least one SNP being located on chromosome 22 and being selected from SNP #81 to SNP #83 listed in table 1.

According to certain embodiments, the at least one late maturation allele is an allele of at least one single nucleotide polymorphism (SNP), the at least one SNP being located on chromosome 23 and being selected from SNP #84 to SNP #89 listed in table 1.

According to certain embodiments, the at least one late maturation allele is an allele of at least one single nucleotide polymorphism (SNP), the at least one SNP being located on chromosome 24 and being selected from SNP #90 to SNP #92 listed in table 1.

According to certain embodiments, the at least one late maturation allele is an allele of at least one single nucleotide polymorphism (SNP), the at least one SNP being located on chromosome 25 and being selected from SNP #93 to SNP #101 listed in table 1.

According to certain embodiments, the at least one late maturation allele is an allele of at least one single nucleotide polymorphism (SNP), the at least one SNP being located on chromosome 26 and being selected from SNP #102 to SNP #105 listed in table 1.

According to certain embodiments, the at least one late maturation allele is an allele of at least one single nucleotide polymorphism (SNP), the at least one SNP being located on chromosome 27 and being selected from SNP #106 to SNP #109 listed in table 1.

According to certain particularly preferred embodiments, the at least one late maturation allele is an allele of at least one single nucleotide polymorphism (SNP), the at least one SNP being located on chromosome 28 and being selected from SNP #110 to SNP #161 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #120, SNP #127 to SNP #131, SNP #134, SNP #135, SNP #137, SNP #138, SNP #140, SNP #142 to SNP #144, SNP #146 and SNP #147 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP #143 and SNP #137 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP #143, SNP #137 and SNP #128 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP #143, SNP #137, SNP #128 and SNP #144 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP #143, SNP #137, SNP #128, SNP #144 and SNP #142 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP #143, SNP #137, SNP #128, SNP #144, SNP #142, and SNP #127 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP #143, SNP #137, SNP #128, SNP #144, SNP #142, SNP #127 and SNP #146 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP #143, SNP #137, SNP #128, SNP #144, SNP #142, SNP #127, SNP #146 and SNP #147 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP

143, SNP #137, SNP #128, SNP #144, SNP #142, SNP #127, SNP #146, SNP #147 and SNP #131 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP #143, SNP #137, SNP #128, SNP #144, SNP #142, SNP #127, SNP #146, SNP #147, SNP #131 and SNP #129 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP #143, SNP #137, SNP #128, SNP #144, SNP #142, SNP #127, SNP #146, SNP #147, SNP #131, SNP #129 and SNP #120 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP #143, SNP #137, SNP #128, SNP #144, SNP #142, SNP #127, SNP #146, SNP #147, SNP #131, SNP #129, SNP #120 and SNP #130 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP #143, SNP #137, SNP #128, SNP #144, SNP #142, SNP #127, SNP #146, SNP #147, SNP #131, SNP #129, SNP #120, SNP #130 and SNP #138 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP #143 and SNP #137 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #135, SNP #137, SNP #138, SNP #140, SNP #142 and SNP #143 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #134, SNP #135, SNP #137, SNP #138, SNP #140, SNP #142, SNP #143 and SNP #144 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #131, SNP #134, SNP #135, SNP #137, SNP #138, SNP #140, SNP #142, SNP #143, SNP #144 and SNP #146 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #130, SNP #131, SNP #134, SNP #135, SNP #137, SNP #138, SNP #140, SNP #142, SNP #143, SNP #144, SNP #146 and SNP #147 listed in table 1.

According to certain embodiments, the at least one late maturation allele is an allele of at least one single nucleotide polymorphism (SNP), the at least one SNP being located on chromosome 29 and being selected from SNP #162 to SNP #164 listed in table 1.

According to certain embodiments, the at least one late maturation allele is an allele of at least one single nucleotide polymorphism (SNP), the at least one SNP being selected from the group consisting of SNP #127, SNP #128, SNP #135, SNP #137, SNP #140, SNP #142, SNP #143, SNP #144, SNP #146 and SNP #147 listed in table 1.

According to certain embodiments, the at least one late maturation allele is an allele of at least one single nucleotide polymorphism (SNP), the at least one SNP being selected from the group consisting of SNP #93, SNP #114, SNP #120, SNP #129, SNP #130, SNP #131, SNP #132, SNP #134, SNP #138 and SNP #148 listed in table 1.

According to certain embodiments, the at least one late maturation allele is an allele of at least one single nucleotide polymorphism (SNP), the at least one SNP being selected from the group consisting of SNP #5, SNP #24, SNP #86, SNP #121, SNP #125, SNP #126, SNP #133, SNP #141, SNP #150 and SNP #154 listed in table 1.

According to certain embodiments, the at least one late maturation allele is an allele of at least one single nucleotide polymorphism (SNP), the at least one SNP being selected from the group consisting of SNP #7, SNP #9, SNP #19, SNP #85, SNP #111, SNP #116, SNP #117, SNP #119, SNP #153 and SNP #155 listed in table 1.

According to certain embodiments, the at least one late maturation allele is an allele of at least one single nucleotide polymorphism (SNP), the at least one SNP being selected from the group consisting of SNP #10, SNP #11, SNP #23, SNP #88, SNP #89, SNP #91, SNP #101, SNP #124, SNP #145 and SNP #151 listed in table 1.

According to certain embodiments, the present invention provides a rainbow trout, such as an isolated rainbow trout, or a progeny thereof which comprises within its genome at least one nucleotide sequence selected from the group consisting of a) the nucleotide sequences set forth in SEQ ID NOs: 165 to 328, and b) nucleotide sequences derived from any one of SEQ ID NOs: 165 to 328 by 1 to 5, such as 1 to 2, nucleotide substitutions, provide that said nucleotide substitutions are not at position 31 of said derived sequence.

According to certain embodiments, the present invention provides a rainbow trout, such as an isolated rainbow trout, or a progeny thereof which comprises within its genome at least one nucleotide sequence selected from the group consisting of a) the nucleotide sequences set forth in SEQ ID NOs: 165 to 168, and b) nucleotide sequences derived from any one of SEQ ID NOs: 165 to 168 by 1 to 5, such as 1 to 2, nucleotide substitutions, provide that said nucleotide substitutions are not at position 31 of said derived sequence.

According to certain embodiments, the present invention provides a rainbow trout, such as an isolated rainbow trout, or a progeny thereof which comprises within its genome at least one nucleotide sequence selected from the group consisting of a) the nucleotide sequences set forth in SEQ ID NOs: 169 to 176, and b) nucleotide sequences derived from any one of SEQ ID NOs: 169 to 176 by 1 to 5, such as 1 to 2, nucleotide substitutions, provide that said nucleotide substitutions are not at position 31 of said derived sequence.

According to certain embodiments, the present invention provides a rainbow trout, such as an isolated rainbow trout, or a progeny thereof which comprises within its genome at least one nucleotide sequence selected from the group consisting of a) the nucleotide sequences set forth in SEQ ID NOs: 177 to 180, and b) nucleotide sequences derived from any one of SEQ ID NOs: 177 to 180 by 1 to 5, such as 1 to 2, nucleotide substitutions, provide that said nucleotide substitutions are not at position 31 of said derived sequence.

According to certain embodiments, the present invention provides a rainbow trout, such as an isolated rainbow trout, or a progeny thereof which comprises within its genome at least one nucleotide sequence selected from the group consisting of a) the nucleotide sequences set forth in SEQ ID NOs: 181 to 184, and b) nucleotide sequences derived from any one of SEQ ID NOs: 181 to 184 by 1 to 5, such as 1 to 2, nucleotide substitutions, provide that said nucleotide substitutions are not at position 31 of said derived sequence.

According to certain embodiments, the present invention provides a rainbow trout, such as an isolated rainbow trout, or a progeny thereof which comprises within its genome at least one nucleotide sequence selected from the group consisting of a) the nucleotide sequences set forth in SEQ ID NOs: 185 to 188, and b) nucleotide sequences derived from any one of SEQ ID NOs: 185 to 188 by 1 to 5, such as 1 to 2, nucleotide substitutions, provide that said nucleotide substitutions are not at position 31 of said derived sequence.

According to certain embodiments, the present invention provides a rainbow trout, such as an isolated rainbow trout, or a progeny thereof which comprises within its genome at least one nucleotide sequence selected from the group consisting of a) the nucleotide sequences set forth in SEQ ID NOs: 189 to 192, and b) nucleotide sequences derived from any one of SEQ ID NOs: 189 to 192 by 1 to 5, such as 1 to 2, nucleotide substitutions, provide that said nucleotide substitutions are not at position 31 of said derived sequence.

According to certain embodiments, the present invention provides a rainbow trout, such as an isolated rainbow trout, or a progeny thereof which comprises within its genome at least one nucleotide sequence selected from the group consisting of a) the nucleotide sequences set forth in SEQ ID NOs: 193 to 196, and b) nucleotide sequences derived from any one of SEQ ID NOs: 193 to 196 by 1 to 5, such as 1 to 2, nucleotide substitutions, provide that said nucleotide substitutions are not at position 31 of said derived sequence.

According to certain embodiments, the present invention provides a rainbow trout, such as an isolated rainbow trout, or a progeny thereof which comprises within its genome at least one nucleotide sequence selected from the group consisting of a) the nucleotide sequences set forth in SEQ ID NOs: 197 to 200, and b) nucleotide sequences derived from any one of SEQ ID NOs: 197 to 200 by 1 to 5, such as 1 to 2, nucleotide substitutions, provide that said nucleotide substitutions are not at position 31 of said derived sequence.

According to certain embodiments, the present invention provides a rainbow trout, such as an isolated rainbow trout, or a progeny thereof which comprises within its genome at least one nucleotide sequence selected from the group consisting of a) the nucleotide sequences set forth in SEQ ID NOs: 201 to 204, and b) nucleotide sequences derived from any one of SEQ ID NOs: 201 to 204 by 1 to 5, such as 1 to 2, nucleotide substitutions, provide that said nucleotide substitutions are not at position 31 of said derived sequence.

According to certain embodiments, the present invention provides a rainbow trout, such as an isolated rainbow trout, or a progeny thereof which comprises within its genome at least one nucleotide sequence selected from the group consisting of a) the nucleotide sequences set forth in SEQ ID NOs: 205 to 207, and b) nucleotide sequences derived from any one of SEQ ID NOs: 205 to 207 by 1 to 5, such as 1 to 2, nucleotide substitutions, provide that said nucleotide substitutions are not at position 31 of said derived sequence.

According to certain embodiments, the present invention provides a rainbow trout, such as an isolated rainbow trout, or a progeny thereof which comprises within its genome at least one nucleotide sequence selected from the group consisting of a) the nucleotide sequences set forth in SEQ ID NOs: 208 to 211, and b) nucleotide sequences derived from any one of SEQ ID NOs: 208 to 211 by 1 to 5, such as 1 to 2, nucleotide substitutions, provide that said nucleotide substitutions are not at position 31 of said derived sequence.

According to certain embodiments, the present invention provides a rainbow trout, such as an isolated rainbow trout, or a progeny thereof which comprises within its genome at least one nucleotide sequence selected from the group consisting of a) the nucleotide sequences set forth in SEQ ID NOs: 212 to 214, and b) nucleotide sequences derived from any one of SEQ ID NOs: 212 to 214 by 1 to 5, such as 1 to 2, nucleotide substitutions, provide that said nucleotide substitutions are not at position 31 of said derived sequence.

According to certain embodiments, the present invention provides a rainbow trout, such as an isolated rainbow trout, or a progeny thereof which comprises within its genome at least one nucleotide sequence selected from the group consisting of a) the nucleotide sequences set forth in SEQ ID NOs: 215 to 217, and b) nucleotide sequences derived from any one of SEQ ID NOs: 215 to 217 by 1 to 5, such as 1 to 2, nucleotide substitutions, provide that said nucleotide substitutions are not at position 31 of said derived sequence.

According to certain embodiments, the present invention provides a rainbow trout, such as an isolated rainbow trout, or a progeny thereof which comprises within its genome at least one nucleotide sequence selected from the group consisting of a) the nucleotide sequences set forth in SEQ ID NOs: 218 to 221, and b) nucleotide sequences derived from any one of SEQ ID NOs: 218 to 221 by 1 to 5, such as 1 to 2, nucleotide substitutions, provide that said nucleotide substitutions are not at position 31 of said derived sequence.

According to certain embodiments, the present invention provides a rainbow trout, such as an isolated rainbow trout, or a progeny thereof which comprises within its genome at least one nucleotide sequence selected from the group consisting of a) the nucleotide sequences set forth in SEQ ID NOs: 222 to 225, and b) nucleotide sequences derived from any one of SEQ ID NOs: 222 to 225 by 1 to 5, such as 1 to 2, nucleotide substitutions, provide that said nucleotide substitutions are not at position 31 of said derived sequence.

According to certain embodiments, the present invention provides a rainbow trout, such as an isolated rainbow trout, or a progeny thereof which comprises within its genome at least one nucleotide sequence selected from the group consisting of a) the nucleotide sequences set forth in SEQ ID NOs: 226 to 228, and b) nucleotide sequences derived from any one of SEQ ID NOs: 226 to 228 by 1 to 5, such as 1 to 2, nucleotide substitutions, provide that said nucleotide substitutions are not at position 31 of said derived sequence.

According to certain embodiments, the present invention provides a rainbow trout, such as an isolated rainbow trout, or a progeny thereof which comprises within its genome at least one nucleotide sequence selected from the group consisting of a) the nucleotide sequences set forth in SEQ ID NOs: 229 to 230, and b) nucleotide sequences derived from any one of SEQ ID NOs: 229 to 230 by 1 to 5, such as 1 to 2, nucleotide substitutions, provide that said nucleotide substitutions are not at position 31 of said derived sequence.

According to certain embodiments, the present invention provides a rainbow trout, such as an isolated rainbow trout, or a progeny thereof which comprises within its genome at least one nucleotide sequence selected from the group consisting of a) the nucleotide sequences set forth in SEQ ID NOs: 231 to 233, and b) nucleotide sequences derived from any one of SEQ ID NOs: 231 to 233 by 1 to 5, such as 1 to 2, nucleotide substitutions, provide that said nucleotide substitutions are not at position 31 of said derived sequence.

According to certain embodiments, the present invention provides a rainbow trout, such as an isolated rainbow trout, or a progeny thereof which comprises within its genome at least one nucleotide sequence selected from the group consisting of a) the nucleotide sequences set forth in SEQ ID NOs: 234 to 237, and b) nucleotide sequences derived from any one of SEQ ID NOs: 234 to 237 by 1 to 5, such as 1 to 2, nucleotide substitutions, provide that said nucleotide substitutions are not at position 31 of said derived sequence.

According to certain embodiments, the present invention provides a rainbow trout, such as an isolated rainbow trout, or a progeny thereof which comprises within its genome at least one nucleotide sequence selected from the group consisting of a) the nucleotide sequences set forth in SEQ ID NOs: 238 to 240, and b) nucleotide sequences derived from any one of SEQ ID NOs: 238 to 240 by 1 to 5, such as 1 to 2, nucleotide substitutions, provide that said nucleotide substitutions are not at position 31 of said derived sequence.

According to certain embodiments, the present invention provides a rainbow trout, such as an isolated rainbow trout, or a progeny thereof which comprises within its genome at least one nucleotide sequence selected from the group consisting of a) the nucleotide sequences set forth in SEQ ID NOs: 241 to 244, and b) nucleotide sequences derived from any one of SEQ ID NOs: 241 to 244 by 1 to 5, such as 1 to 2, nucleotide substitutions, provide that said nucleotide substitutions are not at position 31 of said derived sequence.

According to certain embodiments, the present invention provides a rainbow trout, such as an isolated rainbow trout, or a progeny thereof which comprises within its genome at least one nucleotide sequence selected from the group consisting of a) the nucleotide sequences set forth in SEQ ID NOs: 245 to 247, and b) nucleotide sequences derived from any one of SEQ ID NOs: 245 to 247 by 1 to 5, such as 1 to 2, nucleotide substitutions, provide that said nucleotide substitutions are not at position 31 of said derived sequence.

According to certain embodiments, the present invention provides a rainbow trout, such as an isolated rainbow trout, or a progeny thereof which comprises within its genome at least one nucleotide sequence selected from the group consisting of a) the nucleotide sequences set forth in SEQ ID NOs: 248 to 253, and b) nucleotide sequences derived from any one of SEQ ID NOs: 248 to 253 by 1 to 5, such as 1 to 2, nucleotide substitutions, provide that said nucleotide substitutions are not at position 31 of said derived sequence.

According to certain embodiments, the present invention provides a rainbow trout, such as an isolated rainbow trout, or a progeny thereof which comprises within its genome at least one nucleotide sequence selected from the group consisting of a) the nucleotide sequences set forth in SEQ ID NOs: 254 to 256, and b) nucleotide sequences derived from any one of SEQ ID NOs: 254 to 256 by 1 to 5, such as 1 to 2, nucleotide substitutions, provide that said nucleotide substitutions are not at position 31 of said derived sequence.

According to certain embodiments, the present invention provides a rainbow trout, such as an isolated rainbow trout, or a progeny thereof which comprises within its genome at least one nucleotide sequence selected from the group consisting of a) the nucleotide sequences set forth in SEQ ID NOs: 257 to 265, and b) nucleotide sequences derived from any one of SEQ ID NOs: 257 to 265 by 1 to 5, such as 1 to 2, nucleotide substitutions, provide that said nucleotide substitutions are not at position 31 of said derived sequence.

According to certain embodiments, the present invention provides a rainbow trout, such as an isolated rainbow trout, or a progeny thereof which comprises within its genome at least one nucleotide sequence selected from the group consisting of a) the nucleotide sequences set forth in SEQ ID NOs: 266 to 269, and b) nucleotide sequences derived from any one of SEQ ID NOs: 266 to 269 by 1 to 5, such as 1 to 2, nucleotide substitutions, provide that said nucleotide substitutions are not at position 31 of said derived sequence.

According to certain embodiments, the present invention provides a rainbow trout, such as an isolated rainbow trout, or a progeny thereof which comprises within its genome at least one nucleotide sequence selected from the group consisting of a) the nucleotide sequences set forth in SEQ ID NOs: 270 to 273, and b) nucleotide sequences derived from any one of SEQ ID NOs: 270 to 273 by 1 to 5, such as 1 to 2, nucleotide substitutions, provide that said nucleotide substitutions are not at position 31 of said derived sequence.

According to certain particularly preferred embodiments, the present invention provides a rainbow trout, such as an isolated rainbow trout, or a progeny thereof which comprises within its genome at least one nucleotide sequence selected from the group consisting of a) the nucleotide sequences set forth in SEQ ID NOs: 274 to 325, and b) nucleotide sequences derived from any one of SEQ ID NOs: 274 to 325 by 1 to 5, such as 1 to 2, nucleotide substitutions, provide that said nucleotide substitutions are not at position 31 of said derived sequence.

According to certain embodiments, the present invention provides a rainbow trout, such as an isolated rainbow trout, or a progeny thereof which comprises within its genome at least one nucleotide sequence selected from the group consisting of a) the nucleotide sequences set forth in SEQ ID NOs: 326 to 328, and b) nucleotide sequences derived from any one of SEQ ID NOs: 326 to 328 by 1 to 5, such as 1 to 2, nucleotide substitutions, provide that said nucleotide substitutions are not at position 31 of said derived sequence.

According to certain embodiments, the present invention provides a rainbow trout, such as an isolated rainbow trout, or a progeny thereof which comprises within its genome at least one nucleotide sequence selected from the group consisting of a) the nucleotide sequences set forth in SEQ ID NOs: 291, 292, 299, 301, 304, 306, 307, 308, 310 and 311, and b) nucleotide sequences derived from any one of SEQ ID NOs: 291, 292, 299, 301, 304, 306, 307, 308, 310 and 311 by 1 to 5, such as 1 to 2, nucleotide substitutions, provide that said nucleotide substitutions are not at position 31 of said derived sequence.

According to certain embodiments, the present invention provides a rainbow trout, such as an isolated rainbow trout, or a progeny thereof which comprises within its genome at least one nucleotide sequence selected from the group consisting of a) the nucleotide sequences set forth in SEQ ID NOs: 257, 278, 284, 293, 294, 295, 296, 298, 302 and 312, and b) nucleotide sequences derived from any one of SEQ ID NOs: 257, 278, 284, 293, 294, 295, 296, 298, 302 and 312 by 1 to 5, such as 1 to 2, nucleotide substitutions, provide that said nucleotide substitutions are not at position 31 of said derived sequence.

According to certain embodiments, the present invention provides a rainbow trout, such as an isolated rainbow trout, or a progeny thereof which comprises within its genome at least one nucleotide sequence selected from the group consisting of a) the nucleotide sequences set forth in SEQ ID NOs: 169, 188, 250, 285, 289, 290, 297, 305, 314 and 318, and b) nucleotide sequences derived from any one of SEQ ID NOs: 169, 188, 250, 285, 289, 290, 297, 305, 314 and 318 by 1 to 5, such as 1 to 2, nucleotide substitutions, provide that said nucleotide substitutions are not at position 31 of said derived sequence.

According to certain embodiments, the present invention provides a rainbow trout, such as an isolated rainbow trout, or a progeny thereof which comprises within its genome at least one nucleotide sequence selected from the group consisting of a) the nucleotide sequences set forth in SEQ ID NOs: 171, 173, 183, 249, 275, 280, 281, 283, 317 and 319, and b) nucleotide sequences derived from any one of SEQ ID NOs: 171, 173, 183, 249, 275, 280, 281, 283, 317 and 319 by 1 to 5, such as 1 to 2, nucleotide substitutions, provide that said nucleotide substitutions are not at position 31 of said derived sequence.

According to certain embodiments, the present invention provides a rainbow trout, such as an isolated rainbow trout, or a progeny thereof which comprises within its genome at least one nucleotide sequence selected from the group consisting of a) the nucleotide sequences set forth in SEQ ID NOs: 174, 175, 187, 252, 253, 255, 265, 288, 309 and 315, and b) nucleotide sequences derived from any one of SEQ ID NOs: 174, 175, 187, 252, 253, 255, 265, 288, 309 and 315 by 1 to 5, such as 1 to 2, nucleotide substitutions, provide that said nucleotide substitutions are not at position 31 of said derived sequence.

According to certain embodiments, the present invention provides a rainbow trout, such as an isolated rainbow trout, or a progeny thereof which comprises within its genome at least one nucleotide sequence selected from the group consisting of a) the nucleotide sequences set forth in SEQ ID NOs: 284, 291 to 295, 298, 299, 301, 302, 304, 306 to 308, 310 and 311, and b) nucleotide sequences derived from any one of SEQ ID NOs: 284, 291 to 295, 298, 299, 301, 302, 304, 306 to 308, 310 and 311 by 1 to 5, such as 1 to 2, nucleotide substitutions, provide that said nucleotide substitutions are not at position 31 of said derived sequence.

According to certain embodiments, the present invention provides a rainbow trout, such as an isolated rainbow trout, or a progeny thereof which comprises within its genome at least one nucleotide sequence selected from the group consisting of a) the nucleotide sequences set forth in SEQ ID NOs: 304, 299, 307 and 301, and b) nucleotide sequences derived from any one of SEQ ID NOs: 304, 299, 307 and 301 by 1 to 5, such as 1 to 2, nucleotide substitutions, provide that said nucleotide substitutions are not at position 31 of said derived sequence.

According to certain embodiments, the present invention provides a rainbow trout, such as an isolated rainbow trout, or a progeny thereof which comprises within its genome at least one nucleotide sequence selected from the group consisting of a) the nucleotide sequences set forth in SEQ ID NOs: 304, 299, 307, 301 and 292 and b) nucleotide sequences derived from any one of SEQ ID NOs: SEQ ID NOs: 304, 299, 307, 301 and 292 by 1 to 5, such as 1 to 2, nucleotide substitutions, provide that said nucleotide substitutions are not at position 31 of said derived sequence.

According to certain embodiments, the present invention provides a rainbow trout, such as an isolated rainbow trout, or a progeny thereof which comprises within its genome at least one nucleotide sequence selected from the group consisting of a) the nucleotide sequences set forth in SEQ ID NOs: 304, 299, 307, 301, 292 and 308 and b) nucleotide sequences derived from any one of SEQ ID NOs: 304, 299, 307, 301, 292 and 308 by 1 to 5, such as 1 to 2, nucleotide substitutions, provide that said nucleotide substitutions are not at position 31 of said derived sequence.

According to certain embodiments, the present invention provides a rainbow trout, such as an isolated rainbow trout, or a progeny thereof which comprises within its genome at least one nucleotide sequence selected from the group consisting of a) the nucleotide sequences set forth in SEQ ID NOs: 304, 299, 307, 301, 292, 308 and 306 and b) nucleotide sequences derived from any one of SEQ ID NOs: 304, 299, 307, 301, 292, 308 and 306 by 1 to 5, such as 1 to 2, nucleotide substitutions, provide that said nucleotide substitutions are not at position 31 of said derived sequence.

According to certain embodiments, the present invention provides a rainbow trout, such as an isolated rainbow trout, or a progeny thereof which comprises within its genome at least one nucleotide sequence selected from the group consisting of a) the nucleotide sequences set forth in SEQ ID NOs: 304, 299, 307, 301, 292, 308, 306 and 291 and b) nucleotide sequences derived from any one of SEQ ID NOs: 304, 299, 307, 301, 292, 308, 306 and 291 by 1 to 5, such as 1 to 2, nucleotide substitutions, provide that said nucleotide substitutions are not at position 31 of said derived sequence.

According to certain embodiments, the present invention provides a rainbow trout, such as an isolated rainbow trout, or a progeny thereof which comprises within its genome at least one nucleotide sequence selected from the group consisting of a) the nucleotide sequences set forth in SEQ ID NOs: 304, 299, 307, 301, 292, 308, 306, 291 and 310 and b) nucleotide sequences derived from any one of SEQ ID NOs: 304, 299, 307, 301, 292, 308, 306, 291 and 310 by 1 to 5, such as 1 to 2, nucleotide substitutions, provide that said nucleotide substitutions are not at position 31 of said derived sequence.

According to certain embodiments, the present invention provides a rainbow trout, such as an isolated rainbow trout, or a progeny thereof which comprises within its genome at least one nucleotide sequence selected from the group consisting of a) the nucleotide sequences set forth in SEQ ID NOs: 304, 299, 307, 301, 292, 308, 306, 291, 310 and 311 and b) nucleotide sequences derived from any one of SEQ ID NOs: 304, 299, 307, 301, 292, 308, 306, 291, 310 and 311 by 1 to 5, such as 1 to 2, nucleotide substitutions, provide that said nucleotide substitutions are not at position 31 of said derived sequence.

According to certain embodiments, the present invention provides a rainbow trout, such as an isolated rainbow trout, or a progeny thereof which comprises within its genome at least one nucleotide sequence selected from the group consisting of a) the nucleotide sequences set forth in SEQ ID NOs: 304, 299, 307, 301, 292, 308, 306, 291, 310, 311 and 295 and b) nucleotide sequences derived from any one of SEQ ID NOs: 304, 299, 307, 301, 292, 308, 306, 291, 310, 311 and 295 by 1 to 5, such as 1 to 2, nucleotide substitutions, provide that said nucleotide substitutions are not at position 31 of said derived sequence.

According to certain embodiments, the present invention provides a rainbow trout, such as an isolated rainbow trout, or a progeny thereof which comprises within its genome at least one nucleotide sequence selected from the group consisting of a) the nucleotide sequences set forth in SEQ ID NOs: 304, 299, 307, 301, 292, 308, 306, 291, 310, 311, 295 and 293 and b) nucleotide sequences derived from any one of SEQ ID NOs: 304, 299, 307, 301, 292, 308, 306, 291, 310, 311, 295 and 293 by 1 to 5, such as 1 to 2, nucleotide substitutions, provide that said nucleotide substitutions are not at position 31 of said derived sequence.

According to certain embodiments, the present invention provides a rainbow trout, such as an isolated rainbow trout, or a progeny thereof which comprises within its genome at least one nucleotide sequence selected from the group consisting of a) the nucleotide sequences set forth in SEQ ID NOs: 304, 299, 307, 301, 292, 308, 306, 291, 310, 311, 295, 293 and 284 and b) nucleotide sequences derived from any one of SEQ ID NOs: 304, 299, 307, 301, 292, 308, 306, 291, 310, 311, 295, 293 and 284 by 1 to 5, such as 1 to 2, nucleotide substitutions, provide that said nucleotide substitutions are not at position 31 of said derived sequence.

According to certain embodiments, the present invention provides a rainbow trout, such as an isolated rainbow trout, or a progeny thereof which comprises within its genome at least one nucleotide sequence selected from the group consisting of a) the nucleotide sequences set forth in SEQ ID NOs: 304, 299, 307, 301, 292, 308, 306, 291, 310, 311, 295, 293, 284 and 294 and b) nucleotide sequences derived from any one of SEQ ID NOs: 304, 299, 307, 301, 292, 308, 306, 291, 310, 311, 295, 293, 284 and 294 by 1 to 5, such as 1 to 2, nucleotide substitutions, provide that said nucleotide substitutions are not at position 31 of said derived sequence.

According to certain embodiments, the present invention provides a rainbow trout, such as an isolated rainbow trout, or a progeny thereof which comprises within its genome at least one nucleotide sequence selected from the group consisting of a) the nucleotide sequences set forth in SEQ ID NOs: 304, 299, 307, 301, 292, 308, 306, 291, 310, 311, 295, 293, 284, 294 and 302 and b) nucleotide sequences derived from any one of SEQ ID NOs: 304, 299, 307, 301, 292, 308, 306, 291, 310, 311, 295, 293, 284, 294 and 302 by 1 to 5, such as 1 to 2, nucleotide substitutions, provide that said nucleotide substitutions are not at position 31 of said derived sequence.

According to certain embodiments, the present invention provides a rainbow trout, such as an isolated rainbow trout, or a progeny thereof which comprises within its genome at least one nucleotide sequence selected from the group consisting of a) the nucleotide sequences set forth in SEQ ID NOs: 304, 299, 307 and 301 and b) nucleotide sequences derived from any one of SEQ ID NOs: 304, 299, 307 and 301 by 1 to 5, such as 1 to 2, nucleotide substitutions, provide that said nucleotide substitutions are not at position 31 of said derived sequence.

According to certain embodiments, the present invention provides a rainbow trout, such as an isolated rainbow trout, or a progeny thereof which comprises within its genome at least one nucleotide sequence selected from the group consisting of a) the nucleotide sequences set forth in SEQ ID NOs: 299, 301, 302, 304, 306 and 307 and b) nucleotide sequences derived from any one of SEQ ID NOs: 299, 301, 302, 304, 306 and 307 by 1 to 5, such as 1 to 2, nucleotide substitutions, provide that said nucleotide substitutions are not at position 31 of said derived sequence.

According to certain embodiments, the present invention provides a rainbow trout, such as an isolated rainbow trout, or a progeny thereof which comprises within its genome at least one nucleotide sequence selected from the group consisting of a) the nucleotide sequences set forth in SEQ ID NOs: 298, 299, 301, 302, 304, 306, 307 and 308 and b) nucleotide sequences derived from any one of SEQ ID NOs: 298, 299, 301, 302, 304, 306, 307 and 308 by 1 to 5, such as 1 to 2, nucleotide substitutions, provide that said nucleotide substitutions are not at position 31 of said derived sequence.

According to certain embodiments, the present invention provides a rainbow trout, such as an isolated rainbow trout, or a progeny thereof which comprises within its genome at least one nucleotide sequence selected from the group consisting of a) the nucleotide sequences set forth in SEQ ID NOs: 295, 298, 299, 301, 302, 304, 306, 307, 308 and 310 and b) nucleotide sequences derived from any one of SEQ ID NOs: 295, 298, 299, 301, 302, 304, 306, 307, 308 and 310 by 1 to 5, such as 1 to 2, nucleotide substitutions, provide that said nucleotide substitutions are not at position 31 of said derived sequence.

According to certain embodiments, the present invention provides a rainbow trout, such as an isolated rainbow trout, or a progeny thereof which comprises within its genome at least one nucleotide sequence selected from the group consisting of a) the nucleotide sequences set forth in SEQ ID NOs: 294, 295, 298, 299, 301, 302, 304, 306, 307, 308, 310 and 311 and b) nucleotide sequences derived from any one of SEQ ID NOs: 294, 295, 298, 299, 301, 302, 304, 306, 307, 308, 310 and 311 by 1 to 5, such as 1 to 2, nucleotide substitutions, provide that said nucleotide substitutions are not at position 31 of said derived sequence.

The rainbow trout has late onset of sexual maturation when the nucleotide of the at least one allele is a nucleotide corresponding to the late maturation allele of the respective SNP. The late maturation allele of each SNP is specified in Table 1.

The present invention provides in a further aspect a population of rainbow trout, such as an isolated population of rainbow trout, each individual rainbow trout within the population being a rainbow trout according to the further aspect as discussed above.

According to certain embodiments, the rainbow trout is a female.

According to certain other embodiments, the rainbow trout is a male.

According to certain embodiments, the rainbow trout or progeny thereof is obtained by a method according to the present invention.

In one further aspect of the present invention, a rainbow trout or progeny thereof comprises in its genome at least one allele conferring late sexual maturation obtainable by a process comprising the steps of:
 a) genotyping the trout,
 b) selecting individuals having at least one allele preferably two alleles conferring late onset of sexual maturation ("late maturation allele"); and
 c) mating individuals in such a way that at least one individual within each mated pair has two alleles conferring late onset of sexual maturation.

According to certain embodiments the mating in c) may also be conducted in such a way that the mated pair each has two alleles conferring late onset of sexual maturation, or that each mated pair has one allele conferring late onset of sexual maturation.

The rainbow trout has late onset of sexual maturation when the nucleotide of the at least one allele is a nucleotide corresponding to the late maturation allele of the respective SNP. The late maturation allele of each SNP is specified in Table 1.

Rainbow Trout Cell

The present invention provides in a third aspect, a rainbow trout cell, such as an isolated rainbow trout cell, comprising within its genome at least one allele conferring late onset of sexual maturation ("late maturation allele"); wherein the at least one late maturation allele is an allele of at least one single nucleotide polymorphism (SNP), the at least one SNP being selected from the SNPs listed in Table 1.

According to certain embodiments, the at least one late maturation allele is an allele of at least one single nucleotide polymorphism (SNP), the at least one SNP being located on chromosome 1 and being selected from SNP #1 to SNP #4 listed in table 1.

According to certain embodiments, the at least one late maturation allele is an allele of at least one single nucleotide polymorphism (SNP), the at least one SNP being located on chromosome 2 and being selected from SNP #5 to SNP #12 listed in table 1.

According to certain embodiments, the at least one late maturation allele is an allele of at least one single nucleotide polymorphism (SNP), the at least one SNP being located on chromosome 3 and being selected from SNP #13 to SNP #16 listed in table 1.

According to certain embodiments, the at least one late maturation allele is an allele of at least one single nucleotide polymorphism (SNP), the at least one SNP being located on chromosome 4 and being selected from SNP #17 to SNP #20 listed in table 1.

According to certain embodiments, the at least one late maturation allele is an allele of at least one single nucleotide polymorphism (SNP), the at least one SNP being located on chromosome 5 and being selected from SNP #21 to SNP #24 listed in table 1.

According to certain embodiments, the at least one late maturation allele is an allele of at least one single nucleotide polymorphism (SNP), the at least one SNP being located on chromosome 6 and being selected from SNP #25 to SNP #28 listed in table 1.

According to certain embodiments, the at least one late maturation allele is an allele of at least one single nucleotide polymorphism (SNP), the at least one SNP being located on chromosome 7 and being selected from SNP #29 to SNP #32 listed in table 1.

According to certain embodiments, the at least one late maturation allele is an allele of at least one single nucleotide polymorphism (SNP), the at least one SNP being located on chromosome 8 and being selected from SNP #33 to SNP #36 listed in table 1.

According to certain embodiments, the at least one late maturation allele is an allele of at least one single nucleotide polymorphism (SNP), the at least one SNP being located on chromosome 9 and being selected from SNP #37 to SNP #40 listed in table 1.

According to certain embodiments, the at least one late maturation allele is an allele of at least one single nucleotide polymorphism (SNP), the at least one SNP being located on chromosome 10 and being selected from SNP #41 to SNP #43 listed in table 1.

According to certain embodiments, the at least one late maturation allele is an allele of at least one single nucleotide polymorphism (SNP), the at least one SNP being located on chromosome 11 and being selected from SNP #44 to SNP #47 listed in table 1.

According to certain embodiments, the at least one late maturation allele is an allele of at least one single nucleotide polymorphism (SNP), the at least one SNP being located on chromosome 12 and being selected from SNP #48 to SNP #50 listed in table 1.

According to certain embodiments, the at least one late maturation allele is an allele of at least one single nucleotide polymorphism (SNP), the at least one SNP being located on chromosome 13 and being selected from SNP #51 to SNP #53 listed in table 1.

According to certain embodiments, the at least one late maturation allele is an allele of at least one single nucleotide polymorphism (SNP), the at least one SNP being located on chromosome 14 and being selected from SNP #54 to SNP #57 listed in table 1.

According to certain embodiments, the at least one late maturation allele is an allele of at least one single nucleotide polymorphism (SNP), the at least one SNP being located on chromosome 15 and being selected from SNP #58 to SNP #61 listed in table 1.

According to certain embodiments, the at least one late maturation allele is an allele of at least one single nucleotide polymorphism (SNP), the at least one SNP being located on chromosome 16 and being selected from SNP #62 to SNP #64 listed in table 1.

According to certain embodiments, the at least one late maturation allele is an allele of at least one single nucleotide polymorphism (SNP), the at least one SNP being located on chromosome 17 and being selected from SNP #65 to SNP #66 listed in table 1.

According to certain embodiments, the at least one late maturation allele is an allele of at least one single nucleotide polymorphism (SNP), the at least one SNP being located on chromosome 18 and being selected from SNP #67 to SNP #69 listed in table 1.

According to certain embodiments, the at least one late maturation allele is an allele of at least one single nucleotide polymorphism (SNP), the at least one SNP being located on chromosome 19 and being selected from SNP #70 to SNP #73 listed in table 1.

According to certain embodiments, the at least one late maturation allele is an allele of at least one single nucleotide polymorphism (SNP), the at least one SNP being located on chromosome 20 and being selected from SNP #74 to SNP #76 listed in table 1.

According to certain embodiments, the at least one late maturation allele is an allele of at least one single nucleotide polymorphism (SNP), the at least one SNP being located on chromosome 21 and being selected from SNP #77 to SNP #80 listed in table 1.

According to certain embodiments, the at least one late maturation allele is an allele of at least one single nucleotide polymorphism (SNP), the at least one SNP being located on chromosome 22 and being selected from SNP #81 to SNP #83 listed in table 1.

According to certain embodiments, the at least one late maturation allele is an allele of at least one single nucleotide polymorphism (SNP), the at least one SNP being located on chromosome 23 and being selected from SNP #84 to SNP #89 listed in table 1.

According to certain embodiments, the at least one late maturation allele is an allele of at least one single nucleotide polymorphism (SNP), the at least one SNP being located on chromosome 24 and being selected from SNP #90 to SNP #92 listed in table 1.

According to certain embodiments, the at least one late maturation allele is an allele of at least one single nucleotide polymorphism (SNP), the at least one SNP being located on chromosome 25 and being selected from SNP #93 to SNP #101 listed in table 1.

According to certain embodiments, the at least one late maturation allele is an allele of at least one single nucleotide polymorphism (SNP), the at least one SNP being located on chromosome 26 and being selected from SNP #102 to SNP #105 listed in table 1.

According to certain embodiments, the at least one late maturation allele is an allele of at least one single nucleotide polymorphism (SNP), the at least one SNP being located on chromosome 27 and being selected from SNP #106 to SNP #109 listed in table 1.

According to certain particularly preferred embodiments, the at least one late maturation allele is an allele of at least one single nucleotide polymorphism (SNP), the at least one SNP being located on chromosome 28 and being selected from SNP #110 to SNP #161 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #120, SNP #127 to SNP #131, SNP #134, SNP #135, SNP #137, SNP #138, SNP #140, SNP #142 to SNP #144, SNP #146 and SNP #147 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP #143 and SNP #137 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP #143, SNP #137 and SNP #128 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP #143, SNP #137, SNP #128 and SNP #144 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP #143, SNP #137, SNP #128, SNP #144 and SNP #142 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP #143, SNP #137, SNP #128, SNP #144, SNP #142, and SNP #127 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP #143, SNP #137, SNP #128, SNP #144, SNP #142, SNP #127 and SNP #146 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP #143, SNP #137, SNP #128, SNP #144, SNP #142, SNP #127, SNP #146 and SNP #147 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP #143, SNP #137, SNP #128, SNP #144, SNP #142, SNP #127, SNP #146, SNP #147 and SNP #131 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP #143, SNP #137, SNP #128, SNP #144, SNP #142, SNP #127, SNP #146, SNP #147, SNP #131 and SNP #129 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP #143, SNP #137, SNP #128, SNP #144, SNP #142, SNP #127, SNP #146, SNP #147, SNP #131, SNP #129 and SNP #120 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP #143, SNP #137, SNP #128, SNP #144, SNP #142, SNP #127, SNP #146, SNP #147, SNP #131, SNP #129, SNP #120 and SNP #130 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP #143, SNP #137, SNP #128, SNP #144, SNP #142, SNP #127, SNP #146, SNP #147, SNP #131, SNP #129, SNP #120, SNP #130 and SNP #138 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP #143 and SNP #137 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #135, SNP #137, SNP #138, SNP #140, SNP #142 and SNP #143 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #134, SNP #135, SNP #137, SNP #138, SNP #140, SNP #142, SNP #143 and SNP #144 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #131, SNP #134, SNP #135, SNP #137, SNP #138, SNP #140, SNP #142, SNP #143, SNP #144 and SNP #146 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #130, SNP #131, SNP #134, SNP #135, SNP #137, SNP #138, SNP #140, SNP #142, SNP #143, SNP #144, SNP #146 and SNP #147 listed in table 1.

According to certain embodiments, the at least one late maturation allele is an allele of at least one single nucleotide polymorphism (SNP), the at least one SNP being located on chromosome 29 and being selected from SNP #162 to SNP #164 listed in table 1.

According to certain embodiments, the at least one late maturation allele is an allele of at least one single nucleotide polymorphism (SNP), the at least one SNP being selected from the group consisting of SNP #127, SNP #128, SNP #135, SNP #137, SNP #140, SNP #142, SNP #143, SNP #144, SNP #146 and SNP #147 listed in table 1.

According to certain embodiments, the at least one late maturation allele is an allele of at least one single nucleotide polymorphism (SNP), the at least one SNP being selected from the group consisting of SNP #93, SNP #114, SNP #120, SNP #129, SNP #130, SNP #131, SNP #132, SNP #134, SNP #138 and SNP #148 listed in table 1.

According to certain embodiments, the at least one late maturation allele is an allele of at least one single nucleotide polymorphism (SNP), the at least one SNP being selected from the group consisting of SNP #5, SNP #24, SNP #86, SNP #121, SNP #125, SNP #126, SNP #133, SNP #141, SNP #150 and SNP #154 listed in table 1.

According to certain embodiments, the at least one late maturation allele is an allele of at least one single nucleotide polymorphism (SNP), the at least one SNP being selected from the group consisting of SNP #7, SNP #9, SNP #19, SNP #85, SNP #111, SNP #116, SNP #117, SNP #119, SNP #153 and SNP #155 listed in table 1.

According to certain embodiments, the at least one late maturation allele is an allele of at least one single nucleotide polymorphism (SNP), the at least one SNP being selected from the group consisting of SNP #10, SNP #11, SNP #23, SNP #88, SNP #89, SNP #91, SNP #101, SNP #124, SNP #145 and SNP #151 listed in table 1.

According to certain embodiments, the present invention provides a rainbow trout cell, such as an isolated rainbow trout cell which comprises within its genome at least one nucleotide sequence selected from the group consisting of a) the nucleotide sequences set forth in SEQ ID NOs: 165 to 328, and b) nucleotide sequences derived from any one of SEQ ID NOs: 165 to 328 by 1 to 5, such as 1 to 2, nucleotide substitutions, provide that said nucleotide substitutions are not at position 31 of said derived sequence.

According to certain embodiments, the present invention provides a rainbow trout cell, such as an isolated rainbow trout cell, which comprises within its genome at least one nucleotide sequence selected from the group consisting of a) the nucleotide sequences set forth in SEQ ID NOs: 165 to 168, and b) nucleotide sequences derived from any one of SEQ ID NOs: 165 to 168 by 1 to 5, such as 1 to 2, nucleotide substitutions, provide that said nucleotide substitutions are not at position 31 of said derived sequence.

According to certain embodiments, the present invention provides a rainbow trout cell, such as an isolated rainbow trout cell, which comprises within its genome at least one nucleotide sequence selected from the group consisting of a) the nucleotide sequences set forth in SEQ ID NOs: 169 to 176, and b) nucleotide sequences derived from any one of SEQ ID NOs: 169 to 176 by 1 to 5, such as 1 to 2, nucleotide substitutions, provide that said nucleotide substitutions are not at position 31 of said derived sequence.

According to certain embodiments, the present invention provides a rainbow trout cell, such as an isolated rainbow trout cell, which comprises within its genome at least one nucleotide sequence selected from the group consisting of a) the nucleotide sequences set forth in SEQ ID NOs: 177 to 180, and b) nucleotide sequences derived from any one of SEQ ID NOs: 177 to 180 by 1 to 5, such as 1 to 2, nucleotide substitutions, provide that said nucleotide substitutions are not at position 31 of said derived sequence.

According to certain embodiments, the present invention provides a rainbow trout cell, such as an isolated rainbow trout cell, which comprises within its genome at least one nucleotide sequence selected from the group consisting of a) the nucleotide sequences set forth in SEQ ID NOs: 181 to 184, and b) nucleotide sequences derived from any one of SEQ ID NOs: 181 to 184 by 1 to 5, such as 1 to 2, nucleotide substitutions, provide that said nucleotide substitutions are not at position 31 of said derived sequence.

According to certain embodiments, the present invention provides a rainbow trout cell, such as an isolated rainbow trout cell, which comprises within its genome at least one nucleotide sequence selected from the group consisting of a) the nucleotide sequences set forth in SEQ ID NOs: 185 to 188, and b) nucleotide sequences derived from any one of SEQ ID NOs: 185 to 188 by 1 to 5, such as 1 to 2, nucleotide substitutions, provide that said nucleotide substitutions are not at position 31 of said derived sequence.

According to certain embodiments, the present invention provides a rainbow trout cell, such as an isolated rainbow trout cell, which comprises within its genome at least one nucleotide sequence selected from the group consisting of a) the nucleotide sequences set forth in SEQ ID NOs: 189 to 192, and b) nucleotide sequences derived from any one of SEQ ID NOs: 189 to 192 by 1 to 5, such as 1 to 2, nucleotide substitutions, provide that said nucleotide substitutions are not at position 31 of said derived sequence.

According to certain embodiments, the present invention provides a rainbow trout cell, such as an isolated rainbow trout cell, which comprises within its genome at least one nucleotide sequence selected from the group consisting of a) the nucleotide sequences set forth in SEQ ID NOs: 193 to 196, and b) nucleotide sequences derived from any one of SEQ ID NOs: 193 to 196 by 1 to 5, such as 1 to 2, nucleotide substitutions, provide that said nucleotide substitutions are not at position 31 of said derived sequence.

According to certain embodiments, the present invention provides a rainbow trout cell, such as an isolated rainbow trout cell, which comprises within its genome at least one nucleotide sequence selected from the group consisting of a) the nucleotide sequences set forth in SEQ ID NOs: 197 to 200, and b) nucleotide sequences derived from any one of SEQ ID NOs: 197 to 200 by 1 to 5, such as 1 to 2, nucleotide substitutions, provide that said nucleotide substitutions are not at position 31 of said derived sequence.

According to certain embodiments, the present invention provides a rainbow trout cell, such as an isolated rainbow trout cell, which comprises within its genome at least one nucleotide sequence selected from the group consisting of a) the nucleotide sequences set forth in SEQ ID NOs: 201 to 204, and b) nucleotide sequences derived from any one of SEQ ID NOs: 201 to 204 by 1 to 5, such as 1 to 2, nucleotide substitutions, provide that said nucleotide substitutions are not at position 31 of said derived sequence.

According to certain embodiments, the present invention provides a rainbow trout cell, such as an isolated rainbow trout cell, which comprises within its genome at least one nucleotide sequence selected from the group consisting of a) the nucleotide sequences set forth in SEQ ID NOs: 205 to 207, and b) nucleotide sequences derived from any one of SEQ ID NOs: 205 to 207 by 1 to 5, such as 1 to 2, nucleotide substitutions, provide that said nucleotide substitutions are not at position 31 of said derived sequence.

According to certain embodiments, the present invention provides a rainbow trout cell, such as an isolated rainbow trout cell, which comprises within its genome at least one nucleotide sequence selected from the group consisting of a) the nucleotide sequences set forth in SEQ ID NOs: 208 to 211, and b) nucleotide sequences derived from any one of SEQ ID NOs: 208 to 211 by 1 to 5, such as 1 to 2, nucleotide substitutions, provide that said nucleotide substitutions are not at position 31 of said derived sequence.

According to certain embodiments, the present invention provides a rainbow trout cell, such as an isolated rainbow trout cell, which comprises within its genome at least one nucleotide sequence selected from the group consisting of a) the nucleotide sequences set forth in SEQ ID NOs: 212 to 214, and b) nucleotide sequences derived from any one of SEQ ID NOs: 212 to 214 by 1 to 5, such as 1 to 2, nucleotide substitutions, provide that said nucleotide substitutions are not at position 31 of said derived sequence.

According to certain embodiments, the present invention provides a rainbow trout cell, such as an isolated rainbow trout cell, which comprises within its genome at least one nucleotide sequence selected from the group consisting of a) the nucleotide sequences set forth in SEQ ID NOs: 215 to 217, and b) nucleotide sequences derived from any one of SEQ ID NOs: 215 to 217 by 1 to 5, such as 1 to 2, nucleotide substitutions, provide that said nucleotide substitutions are not at position 31 of said derived sequence.

According to certain embodiments, the present invention provides a rainbow trout cell, such as an isolated rainbow trout cell, which comprises within its genome at least one nucleotide sequence selected from the group consisting of a) the nucleotide sequences set forth in SEQ ID NOs: 218 to 221, and b) nucleotide sequences derived from any one of SEQ ID NOs: 218 to 221 by 1 to 5, such as 1 to 2, nucleotide substitutions, provide that said nucleotide substitutions are not at position 31 of said derived sequence.

According to certain embodiments, the present invention provides a rainbow trout cell, such as an isolated rainbow trout cell, which comprises within its genome at least one nucleotide sequence selected from the group consisting of a) the nucleotide sequences set forth in SEQ ID NOs: 222 to 225, and b) nucleotide sequences derived from any one of SEQ ID NOs: 222 to 225 by 1 to 5, such as 1 to 2, nucleotide substitutions, provide that said nucleotide substitutions are not at position 31 of said derived sequence.

According to certain embodiments, the present invention provides a rainbow trout cell, such as an isolated rainbow trout cell, which comprises within its genome at least one nucleotide sequence selected from the group consisting of a) the nucleotide sequences set forth in SEQ ID NOs: 226 to 228, and b) nucleotide sequences derived from any one of SEQ ID NOs: 226 to 228 by 1 to 5, such as 1 to 2, nucleotide substitutions, provide that said nucleotide substitutions are not at position 31 of said derived sequence.

According to certain embodiments, the present invention provides a rainbow trout cell, such as an isolated rainbow trout cell, which comprises within its genome at least one nucleotide sequence selected from the group consisting of a) the nucleotide sequences set forth in SEQ ID NOs: 229 to 230, and b) nucleotide sequences derived from any one of SEQ ID NOs: 229 to 230 by 1 to 5, such as 1 to 2, nucleotide substitutions, provide that said nucleotide substitutions are not at position 31 of said derived sequence.

According to certain embodiments, the present invention provides a rainbow trout cell, such as an isolated rainbow trout cell, which comprises within its genome at least one nucleotide sequence selected from the group consisting of a) the nucleotide sequences set forth in SEQ ID NOs: 231 to 233, and b) nucleotide sequences derived from any one of SEQ ID NOs: 231 to 233 by 1 to 5, such as 1 to 2, nucleotide substitutions, provide that said nucleotide substitutions are not at position 31 of said derived sequence.

According to certain embodiments, the present invention provides a rainbow trout cell, such as an isolated rainbow trout cell, which comprises within its genome at least one nucleotide sequence selected from the group consisting of a) the nucleotide sequences set forth in SEQ ID NOs: 234 to 237, and b) nucleotide sequences derived from any one of SEQ ID NOs: 234 to 237 by 1 to 5, such as 1 to 2, nucleotide substitutions, provide that said nucleotide substitutions are not at position 31 of said derived sequence.

According to certain embodiments, the present invention provides a rainbow trout cell, such as an isolated rainbow trout cell, which comprises within its genome at least one nucleotide sequence selected from the group consisting of a) the nucleotide sequences set forth in SEQ ID NOs: 238 to 240, and b) nucleotide sequences derived from any one of SEQ ID NOs: 238 to 240 by 1 to 5, such as 1 to 2, nucleotide substitutions, provide that said nucleotide substitutions are not at position 31 of said derived sequence.

According to certain embodiments, the present invention provides a rainbow trout cell, such as an isolated rainbow trout cell, which comprises within its genome at least one nucleotide sequence selected from the group consisting of a) the nucleotide sequences set forth in SEQ ID NOs: 241 to 244, and b) nucleotide sequences derived from any one of SEQ ID NOs: 241 to 244 by 1 to 5, such as 1 to 2, nucleotide substitutions, provide that said nucleotide substitutions are not at position 31 of said derived sequence.

According to certain embodiments, the present invention provides a rainbow trout cell, such as an isolated rainbow trout cell, which comprises within its genome at least one nucleotide sequence selected from the group consisting of a) the nucleotide sequences set forth in SEQ ID NOs: 245 to 247, and b) nucleotide sequences derived from any one of SEQ ID NOs: 245 to 247 by 1 to 5, such as 1 to 2, nucleotide substitutions, provide that said nucleotide substitutions are not at position 31 of said derived sequence.

According to certain embodiments, the present invention provides a rainbow trout cell, such as an isolated rainbow trout cell, which comprises within its genome at least one nucleotide sequence selected from the group consisting of a) the nucleotide sequences set forth in SEQ ID NOs: 248 to 253, and b) nucleotide sequences derived from any one of SEQ ID NOs: 248 to 253 by 1 to 5, such as 1 to 2, nucleotide substitutions, provide that said nucleotide substitutions are not at position 31 of said derived sequence.

According to certain embodiments, the present invention provides a rainbow trout cell, such as an isolated rainbow trout cell, which comprises within its genome at least one nucleotide sequence selected from the group consisting of a) the nucleotide sequences set forth in SEQ ID NOs: 254 to 256, and b) nucleotide sequences derived from any one of SEQ ID NOs: 254 to 256 by 1 to 5, such as 1 to 2, nucleotide substitutions, provide that said nucleotide substitutions are not at position 31 of said derived sequence.

According to certain embodiments, the present invention provides a rainbow trout cell, such as an isolated rainbow trout cell, which comprises within its genome at least one nucleotide sequence selected from the group consisting of a) the nucleotide sequences set forth in SEQ ID NOs: 257 to 265, and b) nucleotide sequences derived from any one of SEQ ID NOs: 257 to 265 by 1 to 5, such as 1 to 2, nucleotide substitutions, provide that said nucleotide substitutions are not at position 31 of said derived sequence.

According to certain embodiments, the present invention provides a rainbow trout cell, such as an isolated rainbow trout cell, which comprises within its genome at least one nucleotide sequence selected from the group consisting of a) the nucleotide sequences set forth in SEQ ID NOs: 266 to 269, and b) nucleotide sequences derived from any one of SEQ ID NOs: 266 to 269 by 1 to 5, such as 1 to 2, nucleotide substitutions, provide that said nucleotide substitutions are not at position 31 of said derived sequence.

According to certain embodiments, the present invention provides a rainbow trout cell, such as an isolated rainbow trout cell, which comprises within its genome at least one nucleotide sequence selected from the group consisting of a) the nucleotide sequences set forth in SEQ ID NOs: 270 to 273, and b) nucleotide sequences derived from any one of SEQ ID NOs: 270 to 273 by 1 to 5, such as 1 to 2, nucleotide substitutions, provide that said nucleotide substitutions are not at position 31 of said derived sequence.

According to certain particularly preferred embodiments, the present invention provides a rainbow trout cell, such as an isolated rainbow trout cell, which comprises within its genome at least one nucleotide sequence selected from the group consisting of a) the nucleotide sequences set forth in SEQ ID NOs: 274 to 325, and b) nucleotide sequences derived from any one of SEQ ID NOs: 274 to 325 by 1 to 5, such as 1 to 2, nucleotide substitutions, provide that said nucleotide substitutions are not at position 31 of said derived sequence.

According to certain embodiments, the present invention provides a rainbow trout cell, such as an isolated rainbow trout cell, which comprises within its genome at least one nucleotide sequence selected from the group consisting of a) the nucleotide sequences set forth in SEQ ID NOs: 326 to 328, and b) nucleotide sequences derived from any one of SEQ ID NOs: 326 to 328 by 1 to 5, such as 1 to 2, nucleotide substitutions, provide that said nucleotide substitutions are not at position 31 of said derived sequence.

According to certain embodiments, the present invention provides a rainbow trout cell, such as an isolated rainbow trout cell, which comprises within its genome at least one nucleotide sequence selected from the group consisting of a) the nucleotide sequences set forth in SEQ ID NOs: 291, 292, 299, 301, 304, 306, 307, 308, 310 and 311, and b) nucleotide sequences derived from any one of SEQ ID NOs: 291, 292, 299, 301, 304, 306, 307, 308, 310 and 311 by 1 to 5, such as 1 to 2, nucleotide substitutions, provide that said nucleotide substitutions are not at position 31 of said derived sequence.

According to certain embodiments, the present invention provides a rainbow trout cell, such as an isolated rainbow trout cell, which comprises within its genome at least one nucleotide sequence selected from the group consisting of a) the nucleotide sequences set forth in SEQ ID NOs: 257, 278, 284, 293, 294, 295, 296, 298, 302 and 312, and b) nucleotide sequences derived from any one of SEQ ID NOs: 257, 278, 284, 293, 294, 295, 296, 298, 302 and 312 by 1 to 5, such as 1 to 2, nucleotide substitutions, provide that said nucleotide substitutions are not at position 31 of said derived sequence.

According to certain embodiments, the present invention provides a rainbow trout cell, such as an isolated rainbow trout cell, which comprises within its genome at least one nucleotide sequence selected from the group consisting of a) the nucleotide sequences set forth in SEQ ID NOs: 169, 188, 250, 285, 289, 290, 297, 305, 314 and 318, and b) nucleotide sequences derived from any one of SEQ ID NOs: 169, 188, 250, 285, 289, 290, 297, 305, 314 and 318 by 1 to 5, such as 1 to 2, nucleotide substitutions, provide that said nucleotide substitutions are not at position 31 of said derived sequence.

According to certain embodiments, the present invention provides a rainbow trout cell, such as an isolated rainbow trout cell, which comprises within its genome at least one nucleotide sequence selected from the group consisting of a) the nucleotide sequences set forth in SEQ ID NOs: 171, 173, 183, 249, 275, 280, 281, 283, 317 and 319, and b) nucleotide sequences derived from any one of SEQ ID NOs: 171, 173, 183, 249, 275, 280, 281, 283, 317 and 319 by 1 to 5, such as 1 to 2, nucleotide substitutions, provide that said nucleotide substitutions are not at position 31 of said derived sequence.

According to certain embodiments, the present invention provides a rainbow trout cell, such as an isolated rainbow trout cell, which comprises within its genome at least one nucleotide sequence selected from the group consisting of a) the nucleotide sequences set forth in SEQ ID NOs: 174, 175, 187, 252, 253, 255, 265, 288, 309 and 315, and b) nucleotide sequences derived from any one of SEQ ID NOs: 174, 175, 187, 252, 253, 255, 265, 288, 309 and 315 by 1 to 5, such as 1 to 2, nucleotide substitutions, provide that said nucleotide substitutions are not at position 31 of said derived sequence.

According to certain embodiments, the present invention provides a rainbow trout cell, such as an isolated rainbow trout cell, which comprises within its genome at least one nucleotide sequence selected from the group consisting of a) the nucleotide sequences set forth in SEQ ID NOs: 284, 291 to 295, 298, 299, 301, 302, 304, 306 to 308, 310 and 311, and b) nucleotide sequences derived from any one of SEQ ID NOs: 284, 291 to 295, 298, 299, 301, 302, 304, 306 to 308, 310 and 311 by 1 to 5, such as 1 to 2, nucleotide substitutions, provide that said nucleotide substitutions are not at position 31 of said derived sequence.

According to certain embodiments, the present invention provides a rainbow trout cell, such as an isolated rainbow trout cell, which comprises within its genome at least one nucleotide sequence selected from the group consisting of a) the nucleotide sequences set forth in SEQ ID NOs: 304, 299, 307 and 301, and b) nucleotide sequences derived from any one of SEQ ID NOs: 304, 299, 307 and 301 by 1 to 5, such as 1 to 2, nucleotide substitutions, provide that said nucleotide substitutions are not at position 31 of said derived sequence.

According to certain embodiments, the present invention provides a rainbow trout cell, such as an isolated rainbow trout cell, which comprises within its genome at least one nucleotide sequence selected from the group consisting of a) the nucleotide sequences set forth in SEQ ID NOs: 304, 299, 307, 301 and 292 and b) nucleotide sequences derived from any one of SEQ ID NOs: SEQ ID NOs: 304, 299, 307, 301 and 292 by 1 to 5, such as 1 to 2, nucleotide substitutions, provide that said nucleotide substitutions are not at position 31 of said derived sequence.

According to certain embodiments, the present invention provides a rainbow trout cell, such as an isolated rainbow trout cell, which comprises within its genome at least one nucleotide sequence selected from the group consisting of a) the nucleotide sequences set forth in SEQ ID NOs: 304, 299, 307, 301, 292 and 308 and b) nucleotide sequences derived from any one of SEQ ID NOs: 304, 299, 307, 301, 292 and 308 by 1 to 5, such as 1 to 2, nucleotide substitutions, provide that said nucleotide substitutions are not at position 31 of said derived sequence.

According to certain embodiments, the present invention provides a rainbow trout cell, such as an isolated rainbow trout cell, which comprises within its genome at least one nucleotide sequence selected from the group consisting of a) the nucleotide sequences set forth in SEQ ID NOs: 304, 299, 307, 301, 292, 308 and 306 and b) nucleotide sequences derived from any one of SEQ ID NOs: 304, 299, 307, 301, 292, 308 and 306 by 1 to 5, such as 1 to 2, nucleotide substitutions, provide that said nucleotide substitutions are not at position 31 of said derived sequence.

According to certain embodiments, the present invention provides a rainbow trout cell, such as an isolated rainbow trout cell, which comprises within its genome at least one nucleotide sequence selected from the group consisting of a) the nucleotide sequences set forth in SEQ ID NOs: 304, 299, 307, 301, 292, 308, 306 and 291 and b) nucleotide sequences derived from any one of SEQ ID NOs: 304, 299, 307, 301, 292, 308, 306 and 291 by 1 to 5, such as 1 to 2, nucleotide substitutions, provide that said nucleotide substitutions are not at position 31 of said derived sequence.

According to certain embodiments, the present invention provides a rainbow trout cell, such as an isolated rainbow trout cell, which comprises within its genome at least one nucleotide sequence selected from the group consisting of a) the nucleotide sequences set forth in SEQ ID NOs: 304, 299, 307, 301, 292, 308, 306, 291 and 310 and b) nucleotide sequences derived from any one of SEQ ID NOs: 304, 299, 307, 301, 292, 308, 306, 291 and 310 by 1 to 5, such as 1 to 2, nucleotide substitutions, provide that said nucleotide substitutions are not at position 31 of said derived sequence.

According to certain embodiments, the present invention provides a rainbow trout cell, such as an isolated rainbow trout cell, which comprises within its genome at least one nucleotide sequence selected from the group consisting of a) the nucleotide sequences set forth in SEQ ID NOs: 304, 299, 307, 301, 292, 308, 306, 291, 310 and 311 and b) nucleotide sequences derived from any one of SEQ ID NOs: 304, 299, 307, 301, 292, 308, 306, 291, 310 and 311 by 1 to 5, such as 1 to 2, nucleotide substitutions, provide that said nucleotide substitutions are not at position 31 of said derived sequence.

According to certain embodiments, the present invention provides a rainbow trout cell, such as an isolated rainbow trout cell, which comprises within its genome at least one nucleotide sequence selected from the group consisting of a) the nucleotide sequences set forth in SEQ ID NOs: 304, 299, 307, 301, 292, 308, 306, 291, 310, 311 and 295 and b) nucleotide sequences derived from any one of SEQ ID NOs: 304, 299, 307, 301, 292, 308, 306, 291, 310, 311 and 295 by 1 to 5, such as 1 to 2, nucleotide substitutions, provide that said nucleotide substitutions are not at position 31 of said derived sequence.

According to certain embodiments, the present invention provides a rainbow trout cell, such as an isolated rainbow trout cell, which comprises within its genome at least one nucleotide sequence selected from the group consisting of a) the nucleotide sequences set forth in SEQ ID NOs: 304, 299, 307, 301, 292, 308, 306, 291, 310, 311, 295 and 293 and b) nucleotide sequences derived from any one of SEQ ID NOs: 304, 299, 307, 301, 292, 308, 306, 291, 310, 311, 295 and 293 by 1 to 5, such as 1 to 2, nucleotide substitutions, provide that said nucleotide substitutions are not at position 31 of said derived sequence.

According to certain embodiments, the present invention provides a rainbow trout cell, such as an isolated rainbow trout cell, which comprises within its genome at least one nucleotide sequence selected from the group consisting of a) the nucleotide sequences set forth in SEQ ID NOs: 304, 299, 307, 301, 292, 308, 306, 291, 310, 311, 295, 293 and 284 and b) nucleotide sequences derived from any one of SEQ ID NOs: 304, 299, 307, 301, 292, 308, 306, 291, 310, 311, 295, 293 and 284 by 1 to 5, such as 1 to 2, nucleotide substitutions, provide that said nucleotide substitutions are not at position 31 of said derived sequence.

According to certain embodiments, the present invention provides a rainbow trout cell, such as an isolated rainbow trout cell, which comprises within its genome at least one nucleotide sequence selected from the group consisting of a) the nucleotide sequences set forth in SEQ ID NOs: 304, 299, 307, 301, 292, 308, 306, 291, 310, 311, 295, 293, 284 and 294 and b) nucleotide sequences derived from any one of SEQ ID NOs: 304, 299, 307, 301, 292, 308, 306, 291, 310, 311, 295, 293, 284 and 294 by 1 to 5, such as 1 to 2, nucleotide substitutions, provide that said nucleotide substitutions are not at position 31 of said derived sequence.

According to certain embodiments, the present invention provides a rainbow trout cell, such as an isolated rainbow trout cell, which comprises within its genome at least one nucleotide sequence selected from the group consisting of a) the nucleotide sequences set forth in SEQ ID NOs: 304, 299, 307, 301, 292, 308, 306, 291, 310, 311, 295, 293, 284, 294 and 302 and b) nucleotide sequences derived from any one of SEQ ID NOs: 304, 299, 307, 301, 292, 308, 306, 291, 310, 311, 295, 293, 284, 294 and 302 by 1 to 5, such as 1 to 2, nucleotide substitutions, provide that said nucleotide substitutions are not at position 31 of said derived sequence.

According to certain embodiments, the present invention provides a rainbow trout cell, such as an isolated rainbow trout cell, which comprises within its genome at least one nucleotide sequence selected from the group consisting of a) the nucleotide sequences set forth in SEQ ID NOs: 304, 299, 307 and 301 and b) nucleotide sequences derived from any one of SEQ ID NOs: 304, 299, 307 and 301 by 1 to 5, such as 1 to 2, nucleotide substitutions, provide that said nucleotide substitutions are not at position 31 of said derived sequence.

According to certain embodiments, the present invention provides a rainbow trout cell, such as an isolated rainbow trout cell, which comprises within its genome at least one nucleotide sequence selected from the group consisting of a) the nucleotide sequences set forth in SEQ ID NOs: 299, 301, 302, 304, 306 and 307 and b) nucleotide sequences derived from any one of SEQ ID NOs: 299, 301, 302, 304, 306 and 307 by 1 to 5, such as 1 to 2, nucleotide substitutions, provide that said nucleotide substitutions are not at position 31 of said derived sequence.

According to certain embodiments, the present invention provides a rainbow trout cell, such as an isolated rainbow trout cell, which comprises within its genome at least one nucleotide sequence selected from the group consisting of a) the nucleotide sequences set forth in SEQ ID NOs: 298, 299, 301, 302, 304, 306, 307 and 308 and b) nucleotide sequences derived from any one of SEQ ID NOs: 298, 299, 301, 302, 304, 306, 307 and 308 by 1 to 5, such as 1 to 2, nucleotide substitutions, provide that said nucleotide substitutions are not at position 31 of said derived sequence.

According to certain embodiments, the present invention provides a rainbow trout cell, such as an isolated rainbow trout cell, which comprises within its genome at least one nucleotide sequence selected from the group consisting of a) the nucleotide sequences set forth in SEQ ID NOs: 295, 298, 299, 301, 302, 304, 306, 307, 308 and 310 and b) nucleotide sequences derived from any one of SEQ ID NOs: 295, 298, 299, 301, 302, 304, 306, 307, 308 and 310 by 1 to 5, such as 1 to 2, nucleotide substitutions, provide that said nucleotide substitutions are not at position 31 of said derived sequence.

According to certain embodiments, the present invention provides a rainbow trout cell, such as an isolated rainbow trout cell, which comprises within its genome at least one nucleotide sequence selected from the group consisting of a) the nucleotide sequences set forth in SEQ ID NOs: 294, 295, 298, 299, 301, 302, 304, 306, 307, 308, 310 and 311 and b) nucleotide sequences derived from any one of SEQ ID NOs: 294, 295, 298, 299, 301, 302, 304, 306, 307, 308, 310 and 311 by 1 to 5, such as 1 to 2, nucleotide substitutions, provide that said nucleotide substitutions are not at position 31 of said derived sequence.

The rainbow trout has late onset of sexual maturation when the nucleotide of the at least one allele is a nucleotide corresponding to the late maturation allele of the respective SNP. The late maturation allele of each SNP is specified in Table 1.

The present invention provides in a further aspect a population of rainbow trout cells, such as an isolated population of rainbow trout cells, each individual cell within the population being a cell according to the third aspect of the present invention.

According to certain embodiments, the rainbow trout cell is a gamete.

According to certain embodiments, the rainbow trout cell is not a gamete.

According to particular embodiments, the rainbow trout cell is an egg, such as an eyed egg. According to more particular embodiments, the egg is unfertilized. According to other more particular embodiments, the egg is fertilized.

According to particular embodiments, the rainbow trout cell is a sperm cell.

According to certain other embodiments, the rainbow trout cell is a somatic cell.

According to certain embodiments, the rainbow trout cell has been isolated from a rainbow trout of the invention.

According to particular embodiments, the rainbow trout cell has been isolated from a female rainbow trout of the invention.

According to particular embodiments, the rainbow trout cell has been isolated from a male rainbow trout of the invention.

Rainbow Trout Egg or Spermatozoa

The present invention provides in a fourth aspect, a rainbow trout egg or spermatozoa, such as an isolated rainbow trout egg or spermatozoa, comprising within its genome at least one allele conferring late onset of sexual maturation ("late maturation allele"); wherein the isolated rainbow trout egg is unfertilized; and the at least one late maturation allele is an allele of at least one single nucleotide polymorphism (SNP), the at least one SNP being selected from the SNPs listed in Table 1.

According to certain embodiments, the at least one late maturation allele is an allele of at least one single nucleotide polymorphism (SNP), the at least one SNP being located on chromosome 1 and being selected from SNP #1 to SNP #4 listed in table 1.

According to certain embodiments, the at least one late maturation allele is an allele of at least one single nucleotide polymorphism (SNP), the at least one SNP being located on chromosome 2 and being selected from SNP #5 to SNP #12 listed in table 1.

According to certain embodiments, the at least one late maturation allele is an allele of at least one single nucleotide polymorphism (SNP), the at least one SNP being located on chromosome 3 and being selected from SNP #13 to SNP #16 listed in table 1.

According to certain embodiments, the at least one late maturation allele is an allele of at least one single nucleotide polymorphism (SNP), the at least one SNP being located on chromosome 4 and being selected from SNP #17 to SNP #20 listed in table 1.

According to certain embodiments, the at least one late maturation allele is an allele of at least one single nucleotide polymorphism (SNP), the at least one SNP being located on chromosome 5 and being selected from SNP #21 to SNP #24 listed in table 1.

According to certain embodiments, the at least one late maturation allele is an allele of at least one single nucleotide polymorphism (SNP), the at least one SNP being located on chromosome 6 and being selected from SNP #25 to SNP #28 listed in table 1.

According to certain embodiments, the at least one late maturation allele is an allele of at least one single nucleotide polymorphism (SNP), the at least one SNP being located on chromosome 7 and being selected from SNP #29 to SNP #32 listed in table 1.

According to certain embodiments, the at least one late maturation allele is an allele of at least one single nucleotide polymorphism (SNP), the at least one SNP being located on chromosome 8 and being selected from SNP #33 to SNP #36 listed in table 1.

According to certain embodiments, the at least one late maturation allele is an allele of at least one single nucleotide polymorphism (SNP), the at least one SNP being located on chromosome 9 and being selected from SNP #37 to SNP #40 listed in table 1.

According to certain embodiments, the at least one late maturation allele is an allele of at least one single nucleotide polymorphism (SNP), the at least one SNP being located on chromosome 10 and being selected from SNP #41 to SNP #43 listed in table 1.

According to certain embodiments, the at least one late maturation allele is an allele of at least one single nucleotide polymorphism (SNP), the at least one SNP being located on chromosome 11 and being selected from SNP #44 to SNP #47 listed in table 1.

According to certain embodiments, the at least one late maturation allele is an allele of at least one single nucleotide polymorphism (SNP), the at least one SNP being located on chromosome 12 and being selected from SNP #48 to SNP #50 listed in table 1.

According to certain embodiments, the at least one late maturation allele is an allele of at least one single nucleotide polymorphism (SNP), the at least one SNP being located on chromosome 13 and being selected from SNP #51 to SNP #53 listed in table 1.

According to certain embodiments, the at least one late maturation allele is an allele of at least one single nucleotide polymorphism (SNP), the at least one SNP being located on chromosome 14 and being selected from SNP #54 to SNP #57 listed in table 1.

According to certain embodiments, the at least one late maturation allele is an allele of at least one single nucleotide polymorphism (SNP), the at least one SNP being located on chromosome 15 and being selected from SNP #58 to SNP #61 listed in table 1.

According to certain embodiments, the at least one late maturation allele is an allele of at least one single nucleotide polymorphism (SNP), the at least one SNP being located on chromosome 16 and being selected from SNP #62 to SNP #64 listed in table 1.

According to certain embodiments, the at least one late maturation allele is an allele of at least one single nucleotide polymorphism (SNP), the at least one SNP being located on chromosome 17 and being selected from SNP #65 to SNP #66 listed in table 1.

According to certain embodiments, the at least one late maturation allele is an allele of at least one single nucleotide polymorphism (SNP), the at least one SNP being located on chromosome 18 and being selected from SNP #67 to SNP #69 listed in table 1.

According to certain embodiments, the at least one late maturation allele is an allele of at least one single nucleotide polymorphism (SNP), the at least one SNP being located on chromosome 19 and being selected from SNP #70 to SNP #73 listed in table 1.

According to certain embodiments, the at least one late maturation allele is an allele of at least one single nucleotide polymorphism (SNP), the at least one SNP being located on chromosome 20 and being selected from SNP #74 to SNP #76 listed in table 1.

According to certain embodiments, the at least one late maturation allele is an allele of at least one single nucleotide polymorphism (SNP), the at least one SNP being located on chromosome 21 and being selected from SNP #77 to SNP #80 listed in table 1.

According to certain embodiments, the at least one late maturation allele is an allele of at least one single nucleotide polymorphism (SNP), the at least one SNP being located on chromosome 22 and being selected from SNP #81 to SNP #83 listed in table 1.

According to certain embodiments, the at least one late maturation allele is an allele of at least one single nucleotide polymorphism (SNP), the at least one SNP being located on chromosome 23 and being selected from SNP #84 to SNP #89 listed in table 1.

According to certain embodiments, the at least one late maturation allele is an allele of at least one single nucleotide polymorphism (SNP), the at least one SNP being located on chromosome 24 and being selected from SNP #90 to SNP #92 listed in table 1.

According to certain embodiments, the at least one late maturation allele is an allele of at least one single nucleotide polymorphism (SNP), the at least one SNP being located on chromosome 25 and being selected from SNP #93 to SNP #101 listed in table 1.

According to certain embodiments, the at least one late maturation allele is an allele of at least one single nucleotide polymorphism (SNP), the at least one SNP being located on chromosome 26 and being selected from SNP #102 to SNP #105 listed in table 1.

According to certain embodiments, the at least one late maturation allele is an allele of at least one single nucleotide polymorphism (SNP), the at least one SNP being located on chromosome 27 and being selected from SNP #106 to SNP #109 listed in table 1.

According to certain particularly preferred embodiments, the at least one late maturation allele is an allele of at least one single nucleotide polymorphism (SNP), the at least one SNP being located on chromosome 28 and being selected from SNP #110 to SNP #161 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #120, SNP #127 to SNP #131, SNP #134, SNP #135, SNP #137, SNP #138, SNP #140, SNP #142 to SNP #144, SNP #146 and SNP #147 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP #143 and SNP #137 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP #143, SNP #137 and SNP #128 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP #143, SNP #137, SNP #128 and SNP #144 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP #143, SNP #137, SNP #128, SNP #144 and SNP #142 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP #143, SNP #137, SNP #128, SNP #144, SNP #142, and SNP #127 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP #143, SNP #137, SNP #128, SNP #144, SNP #142, SNP #127 and SNP #146 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP #143, SNP #137, SNP #128, SNP #144, SNP #142, SNP #127, SNP #146 and SNP #147 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP

143, SNP #137, SNP #128, SNP #144, SNP #142, SNP #127, SNP #146, SNP #147 and SNP #131 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP #143, SNP #137, SNP #128, SNP #144, SNP #142, SNP #127, SNP #146, SNP #147, SNP #131 and SNP #129 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP #143, SNP #137, SNP #128, SNP #144, SNP #142, SNP #127, SNP #146, SNP #147, SNP #131, SNP #129 and SNP #120 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP #143, SNP #137, SNP #128, SNP #144, SNP #142, SNP #127, SNP #146, SNP #147, SNP #131, SNP #129, SNP #120 and SNP #130 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP #143, SNP #137, SNP #128, SNP #144, SNP #142, SNP #127, SNP #146, SNP #147, SNP #131, SNP #129, SNP #120, SNP #130 and SNP #138 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #140, SNP #135, SNP #143 and SNP #137 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #135, SNP #137, SNP #138, SNP #140, SNP #142 and SNP #143 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #134, SNP #135, SNP #137, SNP #138, SNP #140, SNP #142, SNP #143 and SNP #144 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #131, SNP #134, SNP #135, SNP #137, SNP #138, SNP #140, SNP #142, SNP #143, SNP #144 and SNP #146 listed in table 1.

According to certain particularly preferred embodiments, the at least one late maturation allele is an allele of at least one single nucleotide polymorphism (SNP), the at least one SNP being located on chromosome 28 and being selected from the group consisting of SNP #130, SNP #131, SNP #134, SNP #135, SNP #137, SNP #138, SNP #140, SNP #142, SNP #143, SNP #144, SNP #146 and SNP #147 listed in table 1.

According to certain embodiments, the at least one late maturation allele is an allele of at least one single nucleotide polymorphism (SNP), the at least one SNP being located on chromosome 29 and being selected from SNP #162 to SNP #164 listed in table 1.

According to certain embodiments, the at least one late maturation allele is an allele of at least one single nucleotide polymorphism (SNP), the at least one SNP being selected from the group consisting of SNP #127, SNP #128, SNP #135, SNP #137, SNP #140, SNP #142, SNP #143, SNP #144, SNP #146 and SNP #147 listed in table 1.

According to certain embodiments, the at least one late maturation allele is an allele of at least one single nucleotide polymorphism (SNP), the at least one SNP being selected from the group consisting of SNP #93, SNP #114, SNP #120, SNP #129, SNP #130, SNP #131, SNP #132, SNP #134, SNP #138 and SNP #148 listed in table 1.

According to certain embodiments, the at least one late maturation allele is an allele of at least one single nucleotide polymorphism (SNP), the at least one SNP being selected from the group consisting of SNP #5, SNP #24, SNP #86, SNP #121, SNP #125, SNP #126, SNP #133, SNP #141, SNP #150 and SNP #154 listed in table 1.

According to certain embodiments, the at least one late maturation allele is an allele of at least one single nucleotide polymorphism (SNP), the at least one SNP being selected from the group consisting of SNP #7, SNP #9, SNP #19, SNP #85, SNP #111, SNP #116, SNP #117, SNP #119, SNP #153 and SNP #155 listed in table 1.

According to certain embodiments, the at least one late maturation allele is an allele of at least one single nucleotide polymorphism (SNP), the at least one SNP being selected from the group consisting of SNP #10, SNP #11, SNP #23, SNP #88, SNP #89, SNP #91, SNP #101, SNP #124, SNP #145 and SNP #151 listed in table 1.

According to certain embodiments, the present invention provides a rainbow trout egg or spermatozoa, such as an isolated rainbow trout egg or spermatozoa, which comprises within its genome at least one nucleotide sequence selected from the group consisting of a) the nucleotide sequences set forth in SEQ ID NOs: 165 to 328, and b) nucleotide sequences derived from any one of SEQ ID NOs: 165 to 328 by 1 to 5, such as 1 to 2, nucleotide substitutions, provide that said nucleotide substitutions are not at position 31 of said derived sequence.

According to certain embodiments, the present invention provides a rainbow trout egg or spermatozoa, such as an isolated rainbow trout egg or spermatozoa, which comprises within its genome at least one nucleotide sequence selected from the group consisting of a) the nucleotide sequences set forth in SEQ ID NOs: 165 to 168, and b) nucleotide sequences derived from any one of SEQ ID NOs: 165 to 168 by 1 to 5, such as 1 to 2, nucleotide substitutions, provide that said nucleotide substitutions are not at position 31 of said derived sequence.

According to certain embodiments, the present invention provides a rainbow trout egg or spermatozoa, such as an isolated rainbow trout egg or spermatozoa, which comprises within its genome at least one nucleotide sequence selected from the group consisting of a) the nucleotide sequences set forth in SEQ ID NOs: 169 to 176, and b) nucleotide sequences derived from any one of SEQ ID NOs: 169 to 176 by 1 to 5, such as 1 to 2, nucleotide substitutions, provide that said nucleotide substitutions are not at position 31 of said derived sequence.

According to certain embodiments, the present invention provides a rainbow trout egg or spermatozoa, such as an isolated rainbow trout egg or spermatozoa, which comprises within its genome at least one nucleotide sequence selected from the group consisting of a) the nucleotide sequences set forth in SEQ ID NOs: 177 to 180, and b) nucleotide sequences derived from any one of SEQ ID NOs: 177 to 180 by 1 to 5, such as 1 to 2, nucleotide substitutions, provide that said nucleotide substitutions are not at position 31 of said derived sequence.

According to certain embodiments, the present invention provides a rainbow trout egg or spermatozoa, such as an isolated rainbow trout egg or spermatozoa, which comprises within its genome at least one nucleotide sequence selected from the group consisting of a) the nucleotide sequences set forth in SEQ ID NOs: 181 to 184, and b) nucleotide sequences derived from any one of SEQ ID NOs: 181 to 184 by 1 to 5, such as 1 to 2, nucleotide substitutions, provide that said nucleotide substitutions are not at position 31 of said derived sequence.

According to certain embodiments, the present invention provides a rainbow trout egg or spermatozoa, such as an isolated rainbow trout egg or spermatozoa, which comprises within its genome at least one nucleotide sequence selected from the group consisting of a) the nucleotide sequences set forth in SEQ ID NOs: 185 to 188, and b) nucleotide sequences derived from any one of SEQ ID NOs: 185 to 188 by 1 to 5, such as 1 to 2, nucleotide substitutions, provide that said nucleotide substitutions are not at position 31 of said derived sequence.

According to certain embodiments, the present invention provides a rainbow trout egg or spermatozoa, such as an isolated rainbow trout egg or spermatozoa, which comprises within its genome at least one nucleotide sequence selected from the group consisting of a) the nucleotide sequences set forth in SEQ ID NOs: 189 to 192, and b) nucleotide sequences derived from any one of SEQ ID NOs: 189 to 192 by 1 to 5, such as 1 to 2, nucleotide substitutions, provide that said nucleotide substitutions are not at position 31 of said derived sequence.

According to certain embodiments, the present invention provides a rainbow trout egg or spermatozoa, such as an isolated rainbow trout egg or spermatozoa, which comprises within its genome at least one nucleotide sequence selected from the group consisting of a) the nucleotide sequences set forth in SEQ ID NOs: 193 to 196, and b) nucleotide sequences derived from any one of SEQ ID NOs: 193 to 196 by 1 to 5, such as 1 to 2, nucleotide substitutions, provide that said nucleotide substitutions are not at position 31 of said derived sequence.

According to certain embodiments, the present invention provides a rainbow trout egg or spermatozoa, such as an isolated rainbow trout egg or spermatozoa, which comprises within its genome at least one nucleotide sequence selected from the group consisting of a) the nucleotide sequences set forth in SEQ ID NOs: 197 to 200, and b) nucleotide sequences derived from any one of SEQ ID NOs: 197 to 200 by 1 to 5, such as 1 to 2, nucleotide substitutions, provide that said nucleotide substitutions are not at position 31 of said derived sequence.

According to certain embodiments, the present invention provides a rainbow trout egg or spermatozoa, such as an isolated rainbow trout egg or spermatozoa, which comprises within its genome at least one nucleotide sequence selected from the group consisting of a) the nucleotide sequences set forth in SEQ ID NOs: 201 to 204, and b) nucleotide sequences derived from any one of SEQ ID NOs: 201 to 204 by 1 to 5, such as 1 to 2, nucleotide substitutions, provide that said nucleotide substitutions are not at position 31 of said derived sequence.

According to certain embodiments, the present invention provides a rainbow trout egg or spermatozoa, such as an isolated rainbow trout egg or spermatozoa, which comprises within its genome at least one nucleotide sequence selected from the group consisting of a) the nucleotide sequences set forth in SEQ ID NOs: 205 to 207, and b) nucleotide sequences derived from any one of SEQ ID NOs: 205 to 207 by 1 to 5, such as 1 to 2, nucleotide substitutions, provide that said nucleotide substitutions are not at position 31 of said derived sequence.

According to certain embodiments, the present invention provides a rainbow trout egg or spermatozoa, such as an isolated rainbow trout egg or spermatozoa, which comprises within its genome at least one nucleotide sequence selected from the group consisting of a) the nucleotide sequences set forth in SEQ ID NOs: 208 to 211, and b) nucleotide sequences derived from any one of SEQ ID NOs: 208 to 211 by 1 to 5, such as 1 to 2, nucleotide substitutions, provide that said nucleotide substitutions are not at position 31 of said derived sequence.

According to certain embodiments, the present invention provides a rainbow trout egg or spermatozoa, such as an isolated rainbow trout egg or spermatozoa, which comprises within its genome at least one nucleotide sequence selected from the group consisting of a) the nucleotide sequences set forth in SEQ ID NOs: 212 to 214, and b) nucleotide sequences derived from any one of SEQ ID NOs: 212 to 214 by 1 to 5, such as 1 to 2, nucleotide substitutions, provide that said nucleotide substitutions are not at position 31 of said derived sequence.

According to certain embodiments, the present invention provides a rainbow trout egg or spermatozoa, such as an isolated rainbow trout egg or spermatozoa, which comprises within its genome at least one nucleotide sequence selected from the group consisting of a) the nucleotide sequences set forth in SEQ ID NOs: 215 to 217, and b) nucleotide sequences derived from any one of SEQ ID NOs: 215 to 217 by 1 to 5, such as 1 to 2, nucleotide substitutions, provide that said nucleotide substitutions are not at position 31 of said derived sequence.

According to certain embodiments, the present invention provides a rainbow trout egg or spermatozoa, such as an isolated rainbow trout egg or spermatozoa, which comprises within its genome at least one nucleotide sequence selected from the group consisting of a) the nucleotide sequences set forth in SEQ ID NOs: 218 to 221, and b) nucleotide sequences derived from any one of SEQ ID NOs: 218 to 221 by 1 to 5, such as 1 to 2, nucleotide substitutions, provide that said nucleotide substitutions are not at position 31 of said derived sequence.

According to certain embodiments, the present invention provides a rainbow trout egg or spermatozoa, such as an isolated rainbow trout egg or spermatozoa, which comprises within its genome at least one nucleotide sequence selected from the group consisting of a) the nucleotide sequences set forth in SEQ ID NOs: 222 to 225, and b) nucleotide sequences derived from any one of SEQ ID NOs: 222 to 225 by 1 to 5, such as 1 to 2, nucleotide substitutions, provide that said nucleotide substitutions are not at position 31 of said derived sequence.

According to certain embodiments, the present invention provides a rainbow trout egg or spermatozoa, such as an isolated rainbow trout egg or spermatozoa, which comprises within its genome at least one nucleotide sequence selected from the group consisting of a) the nucleotide sequences set forth in SEQ ID NOs: 226 to 228, and b) nucleotide sequences derived from any one of SEQ ID NOs: 226 to 228 by 1 to 5, such as 1 to 2, nucleotide substitutions, provide that said nucleotide substitutions are not at position 31 of said derived sequence.

According to certain embodiments, the present invention provides a rainbow trout egg or spermatozoa, such as an isolated rainbow trout egg or spermatozoa, which comprises within its genome at least one nucleotide sequence selected from the group consisting of a) the nucleotide sequences set forth in SEQ ID NOs: 229 to 230, and b) nucleotide sequences derived from any one of SEQ ID NOs: 229 to 230 by 1 to 5, such as 1 to 2, nucleotide substitutions, provide that said nucleotide substitutions are not at position 31 of said derived sequence.

According to certain embodiments, the present invention provides a rainbow trout egg or spermatozoa, such as an isolated rainbow trout egg or spermatozoa, which comprises within its genome at least one nucleotide sequence selected from the group consisting of a) the nucleotide sequences set forth in SEQ ID NOs: 231 to 233, and b) nucleotide sequences derived from any one of SEQ ID NOs: 231 to 233 by 1 to 5, such as 1 to 2, nucleotide substitutions, provide that said nucleotide substitutions are not at position 31 of said derived sequence.

According to certain embodiments, the present invention provides a rainbow trout egg or spermatozoa, such as an isolated rainbow trout egg or spermatozoa, which comprises within its genome at least one nucleotide sequence selected from the group consisting of a) the nucleotide sequences set forth in SEQ ID NOs: 234 to 237, and b) nucleotide sequences derived from any one of SEQ ID NOs: 234 to 237 by 1 to 5, such as 1 to 2, nucleotide substitutions, provide that said nucleotide substitutions are not at position 31 of said derived sequence.

According to certain embodiments, the present invention provides a rainbow trout egg or spermatozoa, such as an isolated rainbow trout egg or spermatozoa, which comprises within its genome at least one nucleotide sequence selected from the group consisting of a) the nucleotide sequences set forth in SEQ ID NOs: 238 to 240, and b) nucleotide sequences derived from any one of SEQ ID NOs: 238 to 240 by 1 to 5, such as 1 to 2, nucleotide substitutions, provide that said nucleotide substitutions are not at position 31 of said derived sequence.

According to certain embodiments, the present invention provides a rainbow trout egg or spermatozoa, such as an isolated rainbow trout egg or spermatozoa, which comprises within its genome at least one nucleotide sequence selected from the group consisting of a) the nucleotide sequences set forth in SEQ ID NOs: 241 to 244, and b) nucleotide sequences derived from any one of SEQ ID NOs: 241 to 244 by 1 to 5, such as 1 to 2, nucleotide substitutions, provide that said nucleotide substitutions are not at position 31 of said derived sequence.

According to certain embodiments, the present invention provides a rainbow trout egg or spermatozoa, such as an isolated rainbow trout egg or spermatozoa, which comprises within its genome at least one nucleotide sequence selected from the group consisting of a) the nucleotide sequences set forth in SEQ ID NOs: 245 to 247, and b) nucleotide sequences derived from any one of SEQ ID NOs: 245 to 247 by 1 to 5, such as 1 to 2, nucleotide substitutions, provide that said nucleotide substitutions are not at position 31 of said derived sequence.

According to certain embodiments, the present invention provides a rainbow trout egg or spermatozoa, such as an isolated rainbow trout egg or spermatozoa, which comprises within its genome at least one nucleotide sequence selected from the group consisting of a) the nucleotide sequences set forth in SEQ ID NOs: 248 to 253, and b) nucleotide sequences derived from any one of SEQ ID NOs: 248 to 253 by 1 to 5, such as 1 to 2, nucleotide substitutions, provide that said nucleotide substitutions are not at position 31 of said derived sequence.

According to certain embodiments, the present invention provides a rainbow trout egg or spermatozoa, such as an isolated rainbow trout egg or spermatozoa, which comprises within its genome at least one nucleotide sequence selected from the group consisting of a) the nucleotide sequences set forth in SEQ ID NOs: 254 to 256, and b) nucleotide sequences derived from any one of SEQ ID NOs: 254 to 256 by 1 to 5, such as 1 to 2, nucleotide substitutions, provide that said nucleotide substitutions are not at position 31 of said derived sequence.

According to certain embodiments, the present invention provides a rainbow trout egg or spermatozoa, such as an isolated rainbow trout egg or spermatozoa, which comprises within its genome at least one nucleotide sequence selected from the group consisting of a) the nucleotide sequences set forth in SEQ ID NOs: 257 to 265, and b) nucleotide sequences derived from any one of SEQ ID NOs: 257 to 265 by 1 to 5, such as 1 to 2, nucleotide substitutions, provide that said nucleotide substitutions are not at position 31 of said derived sequence.

According to certain embodiments, the present invention provides a rainbow trout egg or spermatozoa, such as an isolated rainbow trout egg or spermatozoa, which comprises within its genome at least one nucleotide sequence selected from the group consisting of a) the nucleotide sequences set forth in SEQ ID NOs: 266 to 269, and b) nucleotide sequences derived from any one of SEQ ID NOs: 266 to 269 by 1 to 5, such as 1 to 2, nucleotide substitutions, provide that said nucleotide substitutions are not at position 31 of said derived sequence.

According to certain embodiments, the present invention provides a rainbow trout egg or spermatozoa, such as an isolated rainbow trout egg or spermatozoa, which comprises within its genome at least one nucleotide sequence selected from the group consisting of a) the nucleotide sequences set forth in SEQ ID NOs: 270 to 273, and b) nucleotide sequences derived from any one of SEQ ID NOs: 270 to 273 by 1 to 5, such as 1 to 2, nucleotide substitutions, provide that said nucleotide substitutions are not at position 31 of said derived sequence.

According to certain embodiments, the present invention provides a rainbow trout egg or spermatozoa, such as an isolated rainbow trout egg or spermatozoa, which comprises within its genome at least one nucleotide sequence selected from the group consisting of a) the nucleotide sequences set forth in SEQ ID NOs: 274 to 325, and b) nucleotide sequences derived from any one of SEQ ID NOs: 274 to 325 by 1 to 5, such as 1 to 2, nucleotide substitutions, provide that said nucleotide substitutions are not at position 31 of said derived sequence.

According to certain embodiments, the present invention provides a rainbow trout egg or spermatozoa, such as an isolated rainbow trout egg or spermatozoa, which comprises within its genome at least one nucleotide sequence selected from the group consisting of a) the nucleotide sequences set forth in SEQ ID NOs: 326 to 328, and b) nucleotide sequences derived from any one of SEQ ID NOs: 326 to 328 by 1 to 5, such as 1 to 2, nucleotide substitutions, provide that said nucleotide substitutions are not at position 31 of said derived sequence.

According to certain embodiments, the present invention provides a rainbow trout egg or spermatozoa, such as an isolated rainbow trout egg or spermatozoa, which comprises within its genome at least one nucleotide sequence selected from the group consisting of a) the nucleotide sequences set forth in SEQ ID NOs: 291, 292, 299, 301, 304, 306, 307, 308, 310 and 311, and b) nucleotide sequences derived from any one of SEQ ID NOs: 291, 292, 299, 301, 304, 306, 307, 308, 310 and 311 by 1 to 5, such as 1 to 2, nucleotide substitutions, provide that said nucleotide substitutions are not at position 31 of said derived sequence.

According to certain embodiments, the present invention provides a rainbow trout egg or spermatozoa, such as an isolated rainbow trout egg or spermatozoa, which comprises within its genome at least one nucleotide sequence selected from the group consisting of a) the nucleotide sequences set forth in SEQ ID NOs: 257, 278, 284, 293, 294, 295, 296, 298, 302 and 312, and b) nucleotide sequences derived from any one of SEQ ID NOs: 257, 278, 284, 293, 294, 295, 296, 298, 302 and 312 by 1 to 5, such as 1 to 2, nucleotide substitutions, provide that said nucleotide substitutions are not at position 31 of said derived sequence.

According to certain embodiments, the present invention provides a rainbow trout egg or spermatozoa, such as an isolated rainbow trout egg or spermatozoa, which comprises within its genome at least one nucleotide sequence selected from the group consisting of a) the nucleotide sequences set forth in SEQ ID NOs: 169, 188, 250, 285, 289, 290, 297, 305, 314 and 318, and b) nucleotide sequences derived from any one of SEQ ID NOs: 169, 188, 250, 285, 289, 290, 297, 305, 314 and 318 by 1 to 5, such as 1 to 2, nucleotide substitutions, provide that said nucleotide substitutions are not at position 31 of said derived sequence.

According to certain embodiments, the present invention provides a rainbow trout egg or spermatozoa, such as an isolated rainbow trout egg or spermatozoa, which comprises within its genome at least one nucleotide sequence selected from the group consisting of a) the nucleotide sequences set forth in SEQ ID NOs: 171, 173, 183, 249, 275, 280, 281, 283, 317 and 319, and b) nucleotide sequences derived from any one of SEQ ID NOs: 171, 173, 183, 249, 275, 280, 281, 283, 317 and 319 by 1 to 5, such as 1 to 2, nucleotide substitutions, provide that said nucleotide substitutions are not at position 31 of said derived sequence.

According to certain embodiments, the present invention provides a rainbow trout egg or spermatozoa, such as an isolated rainbow trout egg or spermatozoa, which comprises within its genome at least one nucleotide sequence selected from the group consisting of a) the nucleotide sequences set forth in SEQ ID NOs: 174, 175, 187, 252, 253, 255, 265, 288, 309 and 315, and b) nucleotide sequences derived from any one of SEQ ID NOs: 174, 175, 187, 252, 253, 255, 265, 288, 309 and 315 by 1 to 5, such as 1 to 2, nucleotide substitutions, provide that said nucleotide substitutions are not at position 31 of said derived sequence.

According to certain embodiments, the present invention provides a rainbow trout egg or spermatozoa, such as an isolated rainbow trout egg or spermatozoa, which comprises within its genome at least one nucleotide sequence selected from the group consisting of a) the nucleotide sequences set forth in SEQ ID NOs: 284, 291 to 295, 298, 299, 301, 302, 304, 306 to 308, 310 and 311, and b) nucleotide sequences derived from any one of SEQ ID NOs: 284, 291 to 295, 298, 299, 301, 302, 304, 306 to 308, 310 and 311 by 1 to 5, such as 1 to 2, nucleotide substitutions, provide that said nucleotide substitutions are not at position 31 of said derived sequence.

According to certain embodiments, the present invention provides a rainbow trout egg or spermatozoa, such as an isolated rainbow trout egg or spermatozoa, which comprises within its genome at least one nucleotide sequence selected from the group consisting of a) the nucleotide sequences set forth in SEQ ID NOs: 304, 299, 307 and 301, and b) nucleotide sequences derived from any one of SEQ ID NOs: 304, 299, 307 and 301 by 1 to 5, such as 1 to 2, nucleotide substitutions, provide that said nucleotide substitutions are not at position 31 of said derived sequence.

According to certain embodiments, the present invention provides a rainbow trout egg or spermatozoa, such as an isolated rainbow trout egg or spermatozoa, which comprises within its genome at least one nucleotide sequence selected from the group consisting of a) the nucleotide sequences set forth in SEQ ID NOs: 304, 299, 307, 301 and 292 and b) nucleotide sequences derived from any one of SEQ ID NOs: 304, 299, 307, 301 and 292 by 1 to 5, such as 1 to 2, nucleotide substitutions, provide that said nucleotide substitutions are not at position 31 of said derived sequence.

According to certain embodiments, the present invention provides a rainbow trout egg or spermatozoa, such as an isolated rainbow trout egg or spermatozoa, which comprises within its genome at least one nucleotide sequence selected from the group consisting of a) the nucleotide sequences set forth in SEQ ID NOs: 304, 299, 307, 301, 292 and 308 and b) nucleotide sequences derived from any one of SEQ ID NOs: 304, 299, 307, 301, 292 and 308 by 1 to 5, such as 1 to 2, nucleotide substitutions, provide that said nucleotide substitutions are not at position 31 of said derived sequence.

According to certain embodiments, the present invention provides a rainbow trout egg or spermatozoa, such as an isolated rainbow trout egg or spermatozoa, which comprises within its genome at least one nucleotide sequence selected from the group consisting of a) the nucleotide sequences set forth in SEQ ID NOs: 304, 299, 307, 301, 292, 308 and 306 and b) nucleotide sequences derived from any one of SEQ ID NOs: 304, 299, 307, 301, 292, 308 and 306 by 1 to 5, such as 1 to 2, nucleotide substitutions, provide that said nucleotide substitutions are not at position 31 of said derived sequence.

According to certain embodiments, the present invention provides a rainbow trout egg or spermatozoa, such as an isolated rainbow trout egg or spermatozoa, which comprises within its genome at least one nucleotide sequence selected from the group consisting of a) the nucleotide sequences set forth in SEQ ID NOs: 304, 299, 307, 301, 292, 308, 306 and 291 and b) nucleotide sequences derived from any one of SEQ ID NOs: 304, 299, 307, 301, 292, 308, 306 and 291 by 1 to 5, such as 1 to 2, nucleotide substitutions, provide that said nucleotide substitutions are not at position 31 of said derived sequence.

According to certain embodiments, the present invention provides a rainbow trout egg or spermatozoa, such as an isolated rainbow trout egg or spermatozoa, which comprises within its genome at least one nucleotide sequence selected from the group consisting of a) the nucleotide sequences set forth in SEQ ID NOs: 304, 299, 307, 301, 292, 308, 306, 291 and 310 and b) nucleotide sequences derived from any one of SEQ ID NOs: 304, 299, 307, 301, 292, 308, 306, 291 and 310 by 1 to 5, such as 1 to 2, nucleotide substitutions, provide that said nucleotide substitutions are not at position 31 of said derived sequence.

According to certain embodiments, the present invention provides a rainbow trout egg or spermatozoa, such as an isolated rainbow trout egg or spermatozoa, which comprises within its genome at least one nucleotide sequence selected from the group consisting of a) the nucleotide sequences set forth in SEQ ID NOs: 304, 299, 307, 301, 292, 308, 306, 291, 310 and 311 and b) nucleotide sequences derived from any one of SEQ ID NOs: 304, 299, 307, 301, 292, 308, 306, 291, 310 and 311 by 1 to 5, such as 1 to 2, nucleotide substitutions, provide that said nucleotide substitutions are not at position 31 of said derived sequence.

According to certain embodiments, the present invention provides a rainbow trout egg or spermatozoa, such as an isolated rainbow trout egg or spermatozoa, which comprises within its genome at least one nucleotide sequence selected from the group consisting of a) the nucleotide sequences set forth in SEQ ID NOs: 304, 299, 307, 301, 292, 308, 306, 291, 310, 311 and 295 and b) nucleotide sequences derived from any one of SEQ ID NOs: 304, 299, 307, 301, 292, 308, 306, 291, 310, 311 and 295 by 1 to 5, such as 1 to 2, nucleotide substitutions, provide that said nucleotide substitutions are not at position 31 of said derived sequence.

According to certain embodiments, the present invention provides a rainbow trout egg or spermatozoa, such as an isolated rainbow trout egg or spermatozoa, which comprises within its genome at least one nucleotide sequence selected from the group consisting of a) the nucleotide sequences set forth in SEQ ID NOs: 304, 299, 307, 301, 292, 308, 306, 291, 310, 311, 295 and 293 and b) nucleotide sequences derived from any one of SEQ ID NOs: 304, 299, 307, 301, 292, 308, 306, 291, 310, 311, 295 and 293 by 1 to 5, such as 1 to 2, nucleotide substitutions, provide that said nucleotide substitutions are not at position 31 of said derived sequence.

According to certain embodiments, the present invention provides a rainbow trout egg or spermatozoa, such as an isolated rainbow trout egg or spermatozoa, which comprises within its genome at least one nucleotide sequence selected from the group consisting of a) the nucleotide sequences set forth in SEQ ID NOs: 304, 299, 307, 301, 292, 308, 306, 291, 310, 311, 295, 293 and 284 and b) nucleotide sequences derived from any one of SEQ ID NOs: 304, 299, 307, 301, 292, 308, 306, 291, 310, 311, 295, 293 and 284 by 1 to 5, such as 1 to 2, nucleotide substitutions, provide that said nucleotide substitutions are not at position 31 of said derived sequence.

According to certain embodiments, the present invention provides a rainbow trout egg or spermatozoa, such as an isolated rainbow trout egg or spermatozoa, which comprises within its genome at least one nucleotide sequence selected from the group consisting of a) the nucleotide sequences set forth in SEQ ID NOs: 304, 299, 307, 301, 292, 308, 306, 291, 310, 311, 295, 293, 284 and 294 and b) nucleotide sequences derived from any one of SEQ ID NOs: 304, 299, 307, 301, 292, 308, 306, 291, 310, 311, 295, 293, 284 and 294 by 1 to 5, such as 1 to 2, nucleotide substitutions, provide that said nucleotide substitutions are not at position 31 of said derived sequence.

According to certain embodiments, the present invention provides a rainbow trout egg or spermatozoa, such as an isolated rainbow trout egg or spermatozoa, which comprises within its genome at least one nucleotide sequence selected from the group consisting of a) the nucleotide sequences set forth in SEQ ID NOs: 304, 299, 307, 301, 292, 308, 306, 291, 310, 311, 295, 293, 284, 294 and 302 and b) nucleotide sequences derived from any one of SEQ ID NOs: 304, 299, 307, 301, 292, 308, 306, 291, 310, 311, 295, 293, 284, 294 and 302 by 1 to 5, such as 1 to 2, nucleotide substitutions, provide that said nucleotide substitutions are not at position 31 of said derived sequence.

According to certain embodiments, the present invention provides a rainbow trout egg or spermatozoa, such as an isolated rainbow trout egg or spermatozoa, which comprises within its genome at least one nucleotide sequence selected from the group consisting of a) the nucleotide sequences set forth in SEQ ID NOs: 304, 299, 307 and 301 and b) nucleotide sequences derived from any one of SEQ ID NOs: 304, 299, 307 and 301 by 1 to 5, such as 1 to 2, nucleotide substitutions, provide that said nucleotide substitutions are not at position 31 of said derived sequence.

According to certain embodiments, the present invention provides a rainbow trout egg or spermatozoa, such as an isolated rainbow trout egg or spermatozoa, which comprises within its genome at least one nucleotide sequence selected from the group consisting of a) the nucleotide sequences set forth in SEQ ID NOs: 299, 301, 302, 304, 306 and 307 and b) nucleotide sequences derived from any one of SEQ ID NOs: 299, 301, 302, 304, 306 and 307 by 1 to 5, such as 1 to 2, nucleotide substitutions, provide that said nucleotide substitutions are not at position 31 of said derived sequence.

According to certain embodiments, the present invention provides a rainbow trout egg or spermatozoa, such as an isolated rainbow trout egg or spermatozoa, which comprises within its genome at least one nucleotide sequence selected from the group consisting of a) the nucleotide sequences set forth in SEQ ID NOs: 298, 299, 301, 302, 304, 306, 307 and 308 and b) nucleotide sequences derived from any one of SEQ ID NOs: 298, 299, 301, 302, 304, 306, 307 and 308 by 1 to 5, such as 1 to 2, nucleotide substitutions, provide that said nucleotide substitutions are not at position 31 of said derived sequence.

According to certain embodiments, the present invention provides a rainbow trout egg or spermatozoa, such as an isolated rainbow trout egg or spermatozoa, which comprises within its genome at least one nucleotide sequence selected from the group consisting of a) the nucleotide sequences set forth in SEQ ID NOs: 295, 298, 299, 301, 302, 304, 306, 307, 308 and 310 and b) nucleotide sequences derived from any one of SEQ ID NOs: 295, 298, 299, 301, 302, 304, 306, 307, 308 and 310 by 1 to 5, such as 1 to 2, nucleotide substitutions, provide that said nucleotide substitutions are not at position 31 of said derived sequence.

According to certain embodiments, the present invention provides a rainbow trout egg or spermatozoa, such as an isolated rainbow trout egg or spermatozoa, which comprises within its genome at least one nucleotide sequence selected from the group consisting of a) the nucleotide sequences set forth in SEQ ID NOs: 294, 295, 298, 299, 301, 302, 304, 306, 307, 308, 310 and 311 and b) nucleotide sequences derived from any one of SEQ ID NOs: 294, 295, 298, 299, 301, 302, 304, 306, 307, 308, 310 and 311 by 1 to 5, such as 1 to 2, nucleotide substitutions, provide that said nucleotide substitutions are not at position 31 of said derived sequence.

The rainbow trout has late onset of sexual maturation when the nucleotide of the at least one allele is a nucleotide corresponding to the late maturation allele of the respective SNP. The late maturation allele of each SNP is specified in Table 1.

The present invention provides in a further aspect a population of rainbow trout egg or spermatozoa, such as an isolated population of rainbow trout egg or spermatozoa, each individual egg or spermatozoa within the population being an egg or spermatozoa according to the fourth aspect of the present invention.

According to certain embodiments, the rainbow trout egg is unfertilized.

According to certain other embodiments, the rainbow trout egg is fertilized.

According to particular embodiments, the rainbow trout egg is an eyed egg.

According to certain embodiments, the rainbow trout egg has been isolated from a female rainbow trout of the invention.

Oligonucleotide

The present invention provides in a fifth aspect, an oligonucleotide, such as an isolated oligonucleotide, comprising at least 8 contiguous nucleotides, such as at least 10 contiguous nucleotides, at least 12 contiguous nucleotides, at least 14 contiguous nucleotides, at least 16 contiguous nucleotides, at least 18 contiguous nucleotides or at least 20 contiguous nucleotides, of a nucleotide sequence set forth in any one of SEQ ID NOs: 1 to 164, or a complementary sequence thereof; or of a nucleotide sequence derived from any one of SEQ ID NOs: 1 to 164 by 1 to 5, such as 1 to 2, nucleotide substitutions, or a complementary sequence thereof; with the proviso that that the oligonucleotide includes a late maturation allele or a normal maturation allele, the late maturation allele and the normal maturation allele being alleles of single nucleotide polymorphisms (SNP), the SNP being selected from the SNPs listed in Table 1.

In one embodiment according to the fifth aspect of the present invention, the oligonucleotide has a total length of 8 to 61 nucleotides, such as a total length of 10 to 61 nucleotides, a total length of 12 to 61 nucleotides, a total length of 14 to 61 nucleotides, a total length of 16 to 61 nucleotides, a total length of 18 to 61 nucleotides or a total length of 20 to 61 nucleotides.

In another embodiment according to the fifth aspect of the present invention, the oligonucleotide has a total length of 8 to 50 nucleotides, such as a total length of 10 to 50 nucleotides, a total length of 12 to 50 nucleotides, a total length of 14 to 50 nucleotides, a total length of 16 to 50 nucleotides, a total length of 18 to 50 nucleotides or a total length of 20 to 50 nucleotides.

In another embodiment according to the fifth aspect of the present invention, the oligonucleotide has a total length of 8 to 40 nucleotides, such as a total length of 10 to 40 nucleotides, a total length of 12 to 40 nucleotides, a total length of 14 to 40 nucleotides, a total length of 16 to 40 nucleotides, a total length of 18 to 40 nucleotides or a total length of 20 to 40 nucleotides.

In certain embodiments, the (isolated) oligonucleotide comprises at least 8 contiguous nucleotides, such as at least 10 contiguous nucleotides, at least 12 contiguous nucleotides, at least 14 contiguous nucleotides, at least 16 contiguous nucleotides, at least 18 contiguous nucleotides or at least 20 contiguous nucleotides, of a nucleotide sequence set forth in any one of SEQ ID NOs: 1 to 4, or a complementary sequence thereof; or of a nucleotide sequence derived from any one of SEQ ID NOs: 1 to 4 by 1 to 5, such as 1 to 2, nucleotide substitutions, or a complementary sequence thereof; with the proviso that that the oligonucleotide includes a late maturation allele or a normal maturation allele, the late maturation allele and the normal maturation allele being alleles of single nucleotide polymorphisms (SNP), the SNP being selected from the SNPs listed in Table 1.

In certain embodiments, the (isolated) oligonucleotide comprises at least 8 contiguous nucleotides, such as at least 10 contiguous nucleotides, at least 12 contiguous nucleotides, at least 14 contiguous nucleotides, at least 16 contiguous nucleotides, at least 18 contiguous nucleotides or at least 20 contiguous nucleotides, of a nucleotide sequence set forth in any one of SEQ ID NOs: 5 to 12, or a complementary sequence thereof; or of a nucleotide sequence derived from any one of SEQ ID NOs: 5 to 12 by 1 to 5, such as 1 to 2, nucleotide substitutions, or a complementary sequence thereof; with the proviso that that the oligonucleotide includes a late maturation allele or a normal maturation allele, the late maturation allele and the normal maturation allele being alleles of single nucleotide polymorphisms (SNP), the SNP being selected from the SNPs listed in Table 1.

In certain embodiments, the (isolated) oligonucleotide comprises at least 8 contiguous nucleotides, such as at least 10 contiguous nucleotides, at least 12 contiguous nucleotides, at least 14 contiguous nucleotides, at least 16 contiguous nucleotides, at least 18 contiguous nucleotides or at least 20 contiguous nucleotides, of a nucleotide sequence set forth in any one of SEQ ID NOs: 13 to 16, or a complementary sequence thereof; or of a nucleotide sequence derived from any one of SEQ ID NOs: 13 to 16 by 1 to 5, such as 1 to 2, nucleotide substitutions, or a complementary sequence thereof; with the proviso that that the oligonucleotide includes a late maturation allele or a normal maturation allele, the late maturation allele and the normal maturation allele being alleles of single nucleotide polymorphisms (SNP), the SNP being selected from the SNPs listed in Table 1.

In certain embodiments, the (isolated) oligonucleotide comprises at least 8 contiguous nucleotides, such as at least 10 contiguous nucleotides, at least 12 contiguous nucleotides, at least 14 contiguous nucleotides, at least 16 contiguous nucleotides, at least 18 contiguous nucleotides or at least 20 contiguous nucleotides, of a nucleotide sequence set forth in any one of SEQ ID NOs: 17 to 20, or a complementary sequence thereof; or of a nucleotide sequence derived from any one of SEQ ID NOs: 17 to 20 by 1 to 5, such as 1 to 2, nucleotide substitutions, or a complementary sequence thereof; with the proviso that that the oligonucleotide includes a late maturation allele or a normal maturation allele, the late maturation allele and the normal maturation allele being alleles of single nucleotide polymorphisms (SNP), the SNP being selected from the SNPs listed in Table 1.

In certain embodiments, the (isolated) oligonucleotide comprises at least 8 contiguous nucleotides, such as at least 10 contiguous nucleotides, at least 12 contiguous nucleotides, at least 14 contiguous nucleotides, at least 16 contiguous nucleotides, at least 18 contiguous nucleotides or at least 20 contiguous nucleotides, of a nucleotide sequence set forth in any one of SEQ ID NOs: 21 to 24, or a complementary sequence thereof; or of a nucleotide sequence derived from any one of SEQ ID NOs: 21 to 24 by 1 to 5, such as 1 to 2, nucleotide substitutions, or a complementary sequence thereof; with the proviso that that the oligonucleotide includes a late maturation allele or a normal maturation allele, the late maturation allele and the normal maturation allele being alleles of single nucleotide polymorphisms (SNP), the SNP being selected from the SNPs listed in Table 1.

In certain embodiments, the (isolated) oligonucleotide comprises at least 8 contiguous nucleotides, such as at least 10 contiguous nucleotides, at least 12 contiguous nucleotides, at least 14 contiguous nucleotides, at least 16 contiguous nucleotides, at least 18 contiguous nucleotides or at least 20 contiguous nucleotides, of a nucleotide sequence set forth in any one of SEQ ID NOs: 25 to 28, or a complementary sequence thereof; or of a nucleotide sequence derived from any one of SEQ ID NOs: 25 to 28 by 1 to 5, such as 1 to 2, nucleotide substitutions, or a complementary sequence thereof; with the proviso that that the oligonucleotide includes a late maturation allele or a normal maturation allele, the late maturation allele and the normal maturation allele being alleles of single nucleotide polymorphisms (SNP), the SNP being selected from the SNPs listed in Table 1.

In certain embodiments, the (isolated) oligonucleotide comprises at least 8 contiguous nucleotides, such as at least 10 contiguous nucleotides, at least 12 contiguous nucleotides, at least 14 contiguous nucleotides, at least 16 contiguous nucleotides, at least 18 contiguous nucleotides or at least 20 contiguous nucleotides, of a nucleotide sequence set forth in any one of SEQ ID NOs: 29 to 32, or a complementary sequence thereof; or of a nucleotide sequence derived from any one of SEQ ID NOs: 29 to 32 by 1 to 5, such as 1 to 2, nucleotide substitutions, or a complementary sequence thereof; with the proviso that that the oligonucleotide includes a late maturation allele or a normal maturation allele, the late maturation allele and the normal maturation allele being alleles of single nucleotide polymorphisms (SNP), the SNP being selected from the SNPs listed in Table 1.

In certain embodiments, the (isolated) oligonucleotide comprises at least 8 contiguous nucleotides, such as at least 10 contiguous nucleotides, at least 12 contiguous nucleotides, at least 14 contiguous nucleotides, at least 16 contiguous nucleotides, at least 18 contiguous nucleotides or at least 20 contiguous nucleotides, of a nucleotide sequence set forth in any one of SEQ ID NOs: 33 to 36, or a complementary sequence thereof; or of a nucleotide sequence derived from any one of SEQ ID NOs: 33 to 36 by 1 to 5, such as 1 to 2, nucleotide substitutions, or a complementary sequence thereof; with the proviso that that the oligonucleotide includes a late maturation allele or a normal maturation allele, the late maturation allele and the normal maturation allele being alleles of single nucleotide polymorphisms (SNP), the SNP being selected from the SNPs listed in Table 1.

In certain embodiments, the (isolated) oligonucleotide comprises at least 8 contiguous nucleotides, such as at least 10 contiguous nucleotides, at least 12 contiguous nucleotides, at least 14 contiguous nucleotides, at least 16 contiguous nucleotides, at least 18 contiguous nucleotides or at least 20 contiguous nucleotides, of a nucleotide sequence set forth in any one of SEQ ID NOs: 37 to 40, or a complementary sequence thereof; or of a nucleotide sequence derived from any one of SEQ ID NOs: 37 to 40 by 1 to 5, such as 1 to 2, nucleotide substitutions, or a complementary sequence thereof; with the proviso that that the oligonucleotide includes a late maturation allele or a normal maturation allele, the late maturation allele and the normal maturation allele being alleles of single nucleotide polymorphisms (SNP), the SNP being selected from the SNPs listed in Table 1.

In certain embodiments, the (isolated) oligonucleotide comprises at least 8 contiguous nucleotides, such as at least 10 contiguous nucleotides, at least 12 contiguous nucleotides, at least 14 contiguous nucleotides, at least 16 contiguous nucleotides, at least 18 contiguous nucleotides or at least 20 contiguous nucleotides, of a nucleotide sequence set forth in any one of SEQ ID NOs: 41 to 43, or a complementary sequence thereof; or of a nucleotide sequence derived from any one of SEQ ID NOs: 41 to 43 by 1 to 5, such as 1 to 2, nucleotide substitutions, or a complementary sequence thereof; with the proviso that that the oligonucleotide includes a late maturation allele or a normal maturation allele, the late maturation allele and the normal maturation allele being alleles of single nucleotide polymorphisms (SNP), the SNP being selected from the SNPs listed in Table 1.

In certain embodiments, the (isolated) oligonucleotide comprises at least 8 contiguous nucleotides, such as at least 10 contiguous nucleotides, at least 12 contiguous nucleotides, at least 14 contiguous nucleotides, at least 16 contiguous nucleotides, at least 18 contiguous nucleotides or at least 20 contiguous nucleotides, of a nucleotide sequence set forth in any one of SEQ ID NOs: 44 to 47, or a complementary sequence thereof; or of a nucleotide sequence derived from any one of SEQ ID NOs: 44 to 47 by 1 to 5, such as 1 to 2, nucleotide substitutions, or a complementary sequence thereof; with the proviso that that the oligonucleotide includes a late maturation allele or a normal maturation allele, the late maturation allele and the normal maturation allele being alleles of single nucleotide polymorphisms (SNP), the SNP being selected from the SNPs listed in Table 1.

In certain embodiments, the (isolated) oligonucleotide comprises at least 8 contiguous nucleotides, such as at least 10 contiguous nucleotides, at least 12 contiguous nucleotides, at least 14 contiguous nucleotides, at least 16 contiguous nucleotides, at least 18 contiguous nucleotides or at least 20 contiguous nucleotides, of a nucleotide sequence set forth in any one of SEQ ID NOs: 48 to 50, or a complementary sequence thereof; or of a nucleotide sequence derived from any one of SEQ ID NOs: 48 to 50 by 1 to 5, such as 1 to 2, nucleotide substitutions, or a complementary sequence thereof; with the proviso that that the oligonucleotide includes a late maturation allele or a normal maturation allele, the late maturation allele and the normal maturation allele being alleles of single nucleotide polymorphisms (SNP), the SNP being selected from the SNPs listed in Table 1.

In certain embodiments, the (isolated) oligonucleotide comprises at least 8 contiguous nucleotides, such as at least 10 contiguous nucleotides, at least 12 contiguous nucleotides, at least 14 contiguous nucleotides, at least 16 contiguous nucleotides, at least 18 contiguous nucleotides or at least 20 contiguous nucleotides, of a nucleotide sequence set forth in any one of SEQ ID NOs: 51 to 53, or a complementary sequence thereof; or of a nucleotide sequence derived from any one of SEQ ID NOs: 51 to 53 by 1 to 5, such as 1 to 2, nucleotide substitutions, or a complementary sequence thereof; with the proviso that that the oligonucleotide includes a late maturation allele or a normal maturation allele, the late maturation allele and the normal maturation allele being alleles of single nucleotide polymorphisms (SNP), the SNP being selected from the SNPs listed in Table 1.

In certain embodiments, the (isolated) oligonucleotide comprises at least 8 contiguous nucleotides, such as at least 10 contiguous nucleotides, at least 12 contiguous nucleotides, at least 14 contiguous nucleotides, at least 16 contiguous nucleotides, at least 18 contiguous nucleotides or at least 20 contiguous nucleotides, of a nucleotide sequence set forth in any one of SEQ ID NOs: 54 to 57, or a complementary sequence thereof; or of a nucleotide sequence derived from any one of SEQ ID NOs: 54 to 57 by 1 to 5, such as 1 to 2, nucleotide substitutions, or a complementary sequence thereof; with the proviso that that the oligonucleotide includes a late maturation allele or a normal maturation allele, the late maturation allele and the normal maturation allele being alleles of single nucleotide polymorphisms (SNP), the SNP being selected from the SNPs listed in Table 1.

In certain embodiments, the (isolated) oligonucleotide comprises at least 8 contiguous nucleotides, such as at least 10 contiguous nucleotides, at least 12 contiguous nucleotides, at least 14 contiguous nucleotides, at least 16 contiguous nucleotides, at least 18 contiguous nucleotides or at least 20 contiguous nucleotides, of a nucleotide sequence set forth in any one of SEQ ID NOs: 58 to 61, or a complementary sequence thereof; or of a nucleotide sequence derived from any one of SEQ ID NOs: 58 to 61 by 1 to 5, such as 1 to 2, nucleotide substitutions, or a complementary sequence thereof; with the proviso that that the oligonucleotide includes a late maturation allele or a normal maturation allele, the late maturation allele and the normal maturation allele being alleles of single nucleotide polymorphisms (SNP), the SNP being selected from the SNPs listed in Table 1.

In certain embodiments, the (isolated) oligonucleotide comprises at least 8 contiguous nucleotides, such as at least 10 contiguous nucleotides, at least 12 contiguous nucleotides, at least 14 contiguous nucleotides, at least 16 contiguous nucleotides, at least 18 contiguous nucleotides or at least 20 contiguous nucleotides, of a nucleotide sequence set forth in any one of SEQ ID NOs: 62 to 64, or a complementary sequence thereof; or of a nucleotide sequence derived from any one of SEQ ID NOs: 62 to 64 by 1 to 5, such as 1 to 2, nucleotide substitutions, or a complementary sequence thereof; with the proviso that that the oligonucleotide includes a late maturation allele or a normal maturation allele, the late maturation allele and the normal maturation allele being alleles of single nucleotide polymorphisms (SNP), the SNP being selected from the SNPs listed in Table 1.

In certain embodiments, the (isolated) oligonucleotide comprises at least 8 contiguous nucleotides, such as at least 10 contiguous nucleotides, at least 12 contiguous nucleotides, at least 14 contiguous nucleotides, at least 16 contiguous nucleotides, at least 18 contiguous nucleotides or at least 20 contiguous nucleotides, of a nucleotide sequence set forth in any one of SEQ ID NOs: 65 to 66, or a complementary sequence thereof; or of a nucleotide sequence derived from any one of SEQ ID NOs: 65 to 66 by 1 to 5, such as 1 to 2, nucleotide substitutions, or a complementary sequence thereof; with the proviso that that the oligonucleotide includes a late maturation allele or a normal maturation allele, the late maturation allele and the normal maturation allele being alleles of single nucleotide polymorphisms (SNP), the SNP being selected from the SNPs listed in Table 1.

In certain embodiments, the (isolated) oligonucleotide comprises at least 8 contiguous nucleotides, such as at least 10 contiguous nucleotides, at least 12 contiguous nucleotides, at least 14 contiguous nucleotides, at least 16 contiguous nucleotides, at least 18 contiguous nucleotides or at least 20 contiguous nucleotides, of a nucleotide sequence set forth in any one of SEQ ID NOs: 67 to 69, or a complementary sequence thereof; or of a nucleotide sequence derived from any one of SEQ ID NOs: 67 to 69 by 1 to 5, such as 1 to 2, nucleotide substitutions, or a complementary sequence thereof; with the proviso that that the oligonucleotide includes a late maturation allele or a normal maturation allele, the late maturation allele and the normal maturation allele being alleles of single nucleotide polymorphisms (SNP), the SNP being selected from the SNPs listed in Table 1.

In certain embodiments, the (isolated) oligonucleotide comprises at least 8 contiguous nucleotides, such as at least 10 contiguous nucleotides, at least 12 contiguous nucleotides, at least 14 contiguous nucleotides, at least 16 contiguous nucleotides, at least 18 contiguous nucleotides or at least 20 contiguous nucleotides, of a nucleotide sequence set forth in any one of SEQ ID NOs: 70 to 73, or a complementary sequence thereof; or of a nucleotide sequence derived from any one of SEQ ID NOs: 70 to 73 by 1 to 5, such as 1 to 2, nucleotide substitutions, or a complementary sequence thereof; with the proviso that that the oligonucleotide includes a late maturation allele or a normal maturation allele, the late maturation allele and the normal maturation allele being alleles of single nucleotide polymorphisms (SNP), the SNP being selected from the SNPs listed in Table 1.

In certain embodiments, the (isolated) oligonucleotide comprises at least 8 contiguous nucleotides, such as at least 10 contiguous nucleotides, at least 12 contiguous nucleotides, at least 14 contiguous nucleotides, at least 16 contiguous nucleotides, at least 18 contiguous nucleotides or at least 20 contiguous nucleotides, of a nucleotide sequence set forth in any one of SEQ ID NOs: 74 to 76, or a complementary sequence thereof; or of a nucleotide sequence derived from any one of SEQ ID NOs: 74 to 76 by 1 to 5, such as 1 to 2, nucleotide substitutions, or a complementary sequence thereof; with the proviso that that the oligonucleotide includes a late maturation allele or a normal maturation allele, the late maturation allele and the normal maturation allele being alleles of single nucleotide polymorphisms (SNP), the SNP being selected from the SNPs listed in Table 1.

In certain embodiments, the (isolated) oligonucleotide comprises at least 8 contiguous nucleotides, such as at least 10 contiguous nucleotides, at least 12 contiguous nucleotides, at least 14 contiguous nucleotides, at least 16 contiguous nucleotides, at least 18 contiguous nucleotides or at least 20 contiguous nucleotides, of a nucleotide sequence set forth in any one of SEQ ID NOs: 77 to 80, or a complementary sequence thereof; or of a nucleotide sequence derived from any one of SEQ ID NOs: 77 to 80 by 1 to 5, such as 1 to 2, nucleotide substitutions, or a complementary sequence thereof; with the proviso that that the oligonucleotide includes a late maturation allele or a normal maturation allele, the late maturation allele and the normal maturation allele being alleles of single nucleotide polymorphisms (SNP), the SNP being selected from the SNPs listed in Table 1.

In certain embodiments, the (isolated) oligonucleotide comprises at least 8 contiguous nucleotides, such as at least 10 contiguous nucleotides, at least 12 contiguous nucleotides, at least 14 contiguous nucleotides, at least 16 contiguous nucleotides, at least 18 contiguous nucleotides or at least 20 contiguous nucleotides, of a nucleotide sequence set forth in any one of SEQ ID NOs: 81 to 83, or a complementary sequence thereof; or of a nucleotide sequence derived from any one of SEQ ID NOs: 81 to 83 by 1 to 5, such as 1 to 2, nucleotide substitutions, or a complementary sequence thereof; with the proviso that that the oligonucleotide includes a late maturation allele or a normal maturation allele, the late maturation allele and the normal maturation allele being alleles of single nucleotide polymorphisms (SNP), the SNP being selected from the SNPs listed in Table 1.

In certain embodiments, the (isolated) oligonucleotide comprises at least 8 contiguous nucleotides, such as at least 10 contiguous nucleotides, at least 12 contiguous nucleotides, at least 14 contiguous nucleotides, at least 16 contiguous nucleotides, at least 18 contiguous nucleotides or at least 20 contiguous nucleotides, of a nucleotide sequence set forth in any one of SEQ ID NOs: 84 to 89, or a complementary sequence thereof; or of a nucleotide sequence derived from any one of SEQ ID NOs: 84 to 89 by 1 to 5, such as 1 to 2, nucleotide substitutions, or a complementary sequence thereof; with the proviso that that the oligonucleotide includes a late maturation allele or a normal maturation allele, the late maturation allele and the normal maturation allele being alleles of single nucleotide polymorphisms (SNP), the SNP being selected from the SNPs listed in Table 1.

In certain embodiments, the (isolated) oligonucleotide comprises at least 8 contiguous nucleotides, such as at least 10 contiguous nucleotides, at least 12 contiguous nucleotides, at least 14 contiguous nucleotides, at least 16 contiguous nucleotides, at least 18 contiguous nucleotides or at least 20 contiguous nucleotides, of a nucleotide sequence set forth in any one of SEQ ID NOs: 90 to 92, or a complementary sequence thereof; or of a nucleotide sequence derived from any one of SEQ ID NOs: 90 to 92 by 1 to 5, such as 1 to 2, nucleotide substitutions, or a complementary sequence thereof; with the proviso that that the oligonucleotide includes a late maturation allele or a normal maturation allele, the late maturation allele and the normal maturation allele being alleles of single nucleotide polymorphisms (SNP), the SNP being selected from the SNPs listed in Table 1.

In certain embodiments, the (isolated) oligonucleotide comprises at least 8 contiguous nucleotides, such as at least 10 contiguous nucleotides, at least 12 contiguous nucleotides, at least 14 contiguous nucleotides, at least 16 contiguous nucleotides, at least 18 contiguous nucleotides or at least 20 contiguous nucleotides, of a nucleotide sequence set forth in any one of SEQ ID NOs: 93 to 101, or a complementary sequence thereof; or of a nucleotide sequence derived from any one of SEQ ID NOs: 93 to 101 by 1 to 5, such as 1 to 2, nucleotide substitutions, or a complementary sequence thereof; with the proviso that that the oligonucleotide includes a late maturation allele or a normal maturation allele, the late maturation allele and the normal maturation allele being alleles of single nucleotide polymorphisms (SNP), the SNP being selected from the SNPs listed in Table 1.

In certain embodiments, the (isolated) oligonucleotide comprises at least 8 contiguous nucleotides, such as at least 10 contiguous nucleotides, at least 12 contiguous nucleotides, at least 14 contiguous nucleotides, at least 16 contiguous nucleotides, at least 18 contiguous nucleotides or at least 20 contiguous nucleotides, of a nucleotide sequence set forth in any one of SEQ ID NOs: 102 to 105, or a complementary sequence thereof; or of a nucleotide sequence derived from any one of SEQ ID NOs: 102 to 105 by 1 to 5, such as 1 to 2, nucleotide substitutions, or a complementary sequence thereof; with the proviso that that the oligonucleotide includes a late maturation allele or a normal maturation allele, the late maturation allele and the normal maturation allele being alleles of single nucleotide polymorphisms (SNP), the SNP being selected from the SNPs listed in Table 1.

In certain embodiments, the (isolated) oligonucleotide comprises at least 8 contiguous nucleotides, such as at least 10 contiguous nucleotides, at least 12 contiguous nucleotides, at least 14 contiguous nucleotides, at least 16 contiguous nucleotides, at least 18 contiguous nucleotides or at least 20 contiguous nucleotides, of a nucleotide sequence set forth in any one of SEQ ID NOs: 106 to 109, or a complementary sequence thereof; or of a nucleotide sequence derived from any one of SEQ ID NOs: 106 to 109 by 1 to 5, such as 1 to 2, nucleotide substitutions, or a complementary sequence thereof; with the proviso that that the oligonucleotide includes a late maturation allele or a normal maturation allele, the late maturation allele and the normal maturation allele being alleles of single nucleotide polymorphisms (SNP), the SNP being selected from the SNPs listed in Table 1.

In certain particularly preferred embodiments, the (isolated) oligonucleotide comprises at least 8 contiguous nucleotides, such as at least 10 contiguous nucleotides, at least 12 contiguous nucleotides, at least 14 contiguous nucleotides, at least 16 contiguous nucleotides, at least 18 contiguous nucleotides or at least 20 contiguous nucleotides, of a nucleotide sequence set forth in any one of SEQ ID NOs: 110 to 161, or a complementary sequence thereof; or of a nucleotide sequence derived from any one of SEQ ID NOs: 110 to 161 by 1 to 5, such as 1 to 2, nucleotide substitutions, or a complementary sequence thereof; with the proviso that that the oligonucleotide includes a late maturation allele or a normal maturation allele, the late maturation allele and the normal maturation allele being alleles of single nucleotide polymorphisms (SNP), the SNP being selected from the SNPs listed in Table 1.

In certain embodiments, the (isolated) oligonucleotide comprises at least 8 contiguous nucleotides, such as at least 10 contiguous nucleotides, at least 12 contiguous nucleotides, at least 14 contiguous nucleotides, at least 16 contiguous nucleotides, at least 18 contiguous nucleotides or at least 20 contiguous nucleotides, of a nucleotide sequence set forth in any one of SEQ ID NOs: 162 to 164, or a complementary sequence thereof; or of a nucleotide sequence derived from any one of SEQ ID NOs: 162 to 164 by 1 to 5, such as 1 to 2, nucleotide substitutions, or a complementary sequence thereof; with the proviso that that the oligonucleotide includes a late maturation allele or a normal maturation allele, the late maturation allele and the normal maturation allele being alleles of single nucleotide polymorphisms (SNP), the SNP being selected from the SNPs listed in Table 1.

In certain embodiments, the (isolated) oligonucleotide comprises at least 8 contiguous nucleotides, such as at least 10 contiguous nucleotides, at least 12 contiguous nucleotides, at least 14 contiguous nucleotides, at least 16 contiguous nucleotides, at least 18 contiguous nucleotides or at least 20 contiguous nucleotides, of a nucleotide sequence set forth in any one of SEQ ID NOs: 127, 128, 135, 137, 140, 142, 143, 144, 146 and 147, or a complementary sequence thereof; or of a nucleotide sequence derived from any one of SEQ ID NOs: 127, 128, 135, 137, 140, 142, 143, 144, 146 and 147 by 1 to 5, such as 1 to 2, nucleotide substitutions, or a complementary sequence thereof; with the proviso that that the oligonucleotide includes a late maturation allele or a normal maturation allele, the late maturation allele and the normal maturation allele being alleles of single nucleotide polymorphisms (SNP), the SNP being selected from the SNPs listed in Table 1.

In certain embodiments, the (isolated) oligonucleotide comprises at least 8 contiguous nucleotides, such as at least 10 contiguous nucleotides, at least 12 contiguous nucleotides, at least 14 contiguous nucleotides, at least 16 contiguous nucleotides, at least 18 contiguous nucleotides or at least 20 contiguous nucleotides, of a nucleotide sequence set forth in any one of SEQ ID NOs: 93, 114, 120, 129, 130, 131, 132, 134, 138 and 148, or a complementary sequence thereof; or of a nucleotide sequence derived from any one of SEQ ID NOs: 93, 114, 120, 129, 130, 131, 132, 134, 138 and 148 by 1 to 5, such as 1 to 2, nucleotide substitutions, or a complementary sequence thereof; with the proviso that that the oligonucleotide includes a late maturation allele or a normal maturation allele, the late maturation allele and the normal maturation allele being alleles of single nucleotide polymorphisms (SNP), the SNP being selected from the SNPs listed in Table 1.

In certain embodiments, the (isolated) oligonucleotide comprises at least 8 contiguous nucleotides, such as at least 10 contiguous nucleotides, at least 12 contiguous nucleotides, at least 14 contiguous nucleotides, at least 16 contiguous nucleotides, at least 18 contiguous nucleotides or at least 20 contiguous nucleotides, of a nucleotide sequence set forth in any one of SEQ ID NOs: 5, 24, 86, 121, 125, 126, 133, 141, 150 and 154, or a complementary sequence thereof; or of a nucleotide sequence derived from any one of SEQ ID NOs: 5, 24, 86, 121, 125, 126, 133, 141, 150 and 154 by 1 to 5, such as 1 to 2, nucleotide substitutions, or a complementary sequence thereof; with the proviso that that the oligonucleotide includes a late maturation allele or a normal maturation allele, the late maturation allele and the normal maturation allele being alleles of single nucleotide polymorphisms (SNP), the SNP being selected from the SNPs listed in Table 1.

In certain embodiments, the (isolated) oligonucleotide comprises at least 8 contiguous nucleotides, such as at least 10 contiguous nucleotides, at least 12 contiguous nucleotides, at least 14 contiguous nucleotides, at least 16 contiguous nucleotides, at least 18 contiguous nucleotides or at least 20 contiguous nucleotides, of a nucleotide sequence set forth in any one of SEQ ID NOs: 7, 9, 19, 85, 111, 116, 117, 119, 153 and 155, or a complementary sequence thereof; or of a nucleotide sequence derived from any one of SEQ ID NOs: 7, 9, 19, 85, 111, 116, 117, 119, 153 and 155 by 1 to 5, such as 1 to 2, nucleotide substitutions, or a complementary sequence thereof; with the proviso that that the oligonucleotide includes a late maturation allele or a normal maturation allele, the late maturation allele and the normal maturation allele being alleles of single nucleotide polymorphisms (SNP), the SNP being selected from the SNPs listed in Table 1.

In certain embodiments, the (isolated) oligonucleotide comprises at least 8 contiguous nucleotides, such as at least 10 contiguous nucleotides, at least 12 contiguous nucleotides, at least 14 contiguous nucleotides, at least 16 contiguous nucleotides, at least 18 contiguous nucleotides or at least 20 contiguous nucleotides, of a nucleotide sequence set forth in any one of SEQ ID NOs: 10, 11, 23, 88, 89, 91, 101, 124, 145 and 151, or a complementary sequence thereof; or of a nucleotide sequence derived from any one of SEQ ID NOs: 10, 11, 23, 88, 89, 91, 101, 124, 145 and 151 by 1 to 5, such as 1 to 2, nucleotide substitutions, or a complementary sequence thereof; with the proviso that that the oligonucleotide includes a late maturation allele or a normal maturation allele, the late maturation allele and the normal maturation allele being alleles of single nucleotide polymorphisms (SNP), the SNP being selected from the SNPs listed in Table 1.

In certain embodiments, the (isolated) oligonucleotide comprises at least 8 contiguous nucleotides, such as at least 10 contiguous nucleotides, at least 12 contiguous nucleotides, at least 14 contiguous nucleotides, at least 16 contiguous nucleotides, at least 18 contiguous nucleotides or at least 20 contiguous nucleotides, of a nucleotide sequence set forth in any one of SEQ ID NOs: 120, 127 to 131, 134, 135, 137, 138, 140, 142 to 144, 146 and 147, or a complementary sequence thereof; or of a nucleotide sequence derived from any one of SEQ ID NOs: 120, 127 to 131, 134, 135, 137, 138, 140, 142 to 144, 146 and 147 by 1 to 5, such as 1 to 2, nucleotide substitutions, or a complementary sequence thereof; with the proviso that that the oligonucleotide includes a late maturation allele or a normal maturation allele, the late maturation allele and the normal maturation allele being alleles of single nucleotide polymorphisms (SNP), the SNP being selected from the SNPs listed in Table 1.

In certain embodiments, the (isolated) oligonucleotide comprises at least 8 contiguous nucleotides, such as at least 10 contiguous nucleotides, at least 12 contiguous nucleotides, at least 14 contiguous nucleotides, at least 16 contiguous nucleotides, at least 18 contiguous nucleotides or at least 20 contiguous nucleotides, of a nucleotide sequence set forth in any one of SEQ ID NOs: 140, 135, 143 and 137, or a complementary sequence thereof; or of a nucleotide sequence derived from any one of SEQ ID NOs: 140, 135, 143 and 137 by 1 to 5, such as 1 to 2, nucleotide substitutions, or a complementary sequence thereof; with the proviso that that the oligonucleotide includes a late maturation allele or a normal maturation allele, the late maturation allele and the normal maturation allele being alleles of single nucleotide polymorphisms (SNP), the SNP being selected from the SNPs listed in Table 1.

In certain embodiments, the (isolated) oligonucleotide comprises at least 8 contiguous nucleotides, such as at least 10 contiguous nucleotides, at least 12 contiguous nucleotides, at least 14 contiguous nucleotides, at least 16 contiguous nucleotides, at least 18 contiguous nucleotides or at least 20 contiguous nucleotides, of a nucleotide sequence set forth in any one of SEQ ID NOs: 140, 135, 143, 137 and 128 or a complementary sequence thereof; or of a nucleotide sequence derived from any one of SEQ ID NOs: 140, 135, 143 and 128 by 1 to 5, such as 1 to 2, nucleotide substitutions, or a complementary sequence thereof; with the proviso that that the oligonucleotide includes a late maturation allele or a normal maturation allele, the late maturation allele and the normal maturation allele being alleles of single nucleotide polymorphisms (SNP), the SNP being selected from the SNPs listed in Table 1.

In certain embodiments, the (isolated) oligonucleotide comprises at least 8 contiguous nucleotides, such as at least 10 contiguous nucleotides, at least 12 contiguous nucleotides, at least 14 contiguous nucleotides, at least 16 contiguous nucleotides, at least 18 contiguous nucleotides or at least 20 contiguous nucleotides, of a nucleotide sequence set forth in any one of SEQ ID NOs: 140, 135, 143, 137, 128 and 144 or a complementary sequence thereof; or of a nucleotide sequence derived from any one of SEQ ID NOs: 140, 135, 143, 128 and 144 by 1 to 5, such as 1 to 2, nucleotide substitutions, or a complementary sequence thereof; with the proviso that that the oligonucleotide includes a late maturation allele or a normal maturation allele, the late maturation allele and the normal maturation allele being alleles of single nucleotide polymorphisms (SNP), the SNP being selected from the SNPs listed in Table 1.

In certain embodiments, the (isolated) oligonucleotide comprises at least 8 contiguous nucleotides, such as at least 10 contiguous nucleotides, at least 12 contiguous nucleotides, at least 14 contiguous nucleotides, at least 16 contiguous nucleotides, at least 18 contiguous nucleotides or at least 20 contiguous nucleotides, of a nucleotide sequence set forth in any one of SEQ ID NOs: 140, 135, 143, 137, 128, 144 and 142 or a complementary sequence thereof; or of a nucleotide sequence derived from any one of SEQ ID NOs: 140, 135, 143, 137, 128, 144 and 142 by 1 to 5, such as 1 to 2, nucleotide substitutions, or a complementary sequence thereof; with the proviso that that the oligonucleotide includes a late maturation allele or a normal maturation allele, the late maturation allele and the normal maturation allele being alleles of single nucleotide polymorphisms (SNP), the SNP being selected from the SNPs listed in Table 1.

In certain embodiments, the (isolated) oligonucleotide comprises at least 8 contiguous nucleotides, such as at least 10 contiguous nucleotides, at least 12 contiguous nucleotides, at least 14 contiguous nucleotides, at least 16 contiguous nucleotides, at least 18 contiguous nucleotides or at least 20 contiguous nucleotides, of a nucleotide sequence set forth in any one of SEQ ID NOs: 140, 135, 143, 137, 128, 144, 142 and 127 or a complementary sequence thereof; or of a nucleotide sequence derived from any one of SEQ ID NOs: 140, 135, 143, 137, 128, 144, 142 and 127 by 1 to 5, such as 1 to 2, nucleotide substitutions, or a complementary sequence thereof; with the proviso that that the oligonucleotide includes a late maturation allele or a normal maturation allele, the late maturation allele and the normal maturation allele being alleles of single nucleotide polymorphisms (SNP), the SNP being selected from the SNPs listed in Table 1.

In certain embodiments, the (isolated) oligonucleotide comprises at least 8 contiguous nucleotides, such as at least 10 contiguous nucleotides, at least 12 contiguous nucleotides, at least 14 contiguous nucleotides, at least 16 contiguous nucleotides, at least 18 contiguous nucleotides or at least 20 contiguous nucleotides, of a nucleotide sequence set forth in any one of SEQ ID NOs: 140, 135, 143, 137, 128, 144, 142, 127 and 146 or a complementary sequence thereof; or of a nucleotide sequence derived from any one of SEQ ID NOs: 140, 135, 143, 137, 128, 144, 142, 127 and 146 by 1 to 5, such as 1 to 2, nucleotide substitutions, or a complementary sequence thereof; with the proviso that that the oligonucleotide includes a late maturation allele or a normal maturation allele, the late maturation allele and the normal maturation allele being alleles of single nucleotide polymorphisms (SNP), the SNP being selected from the SNPs listed in Table 1.

In certain embodiments, the (isolated) oligonucleotide comprises at least 8 contiguous nucleotides, such as at least 10 contiguous nucleotides, at least 12 contiguous nucleotides, at least 14 contiguous nucleotides, at least 16 contiguous nucleotides, at least 18 contiguous nucleotides or at least 20 contiguous nucleotides, of a nucleotide sequence set forth in any one of SEQ ID NOs: 140, 135, 143, 137, 128, 144, 142, 127, 146 and 147 or a complementary sequence thereof; or of a nucleotide sequence derived from any one of SEQ ID NOs: 140, 135, 143, 137, 128, 144, 142, 127, 146 and 147 by 1 to 5, such as 1 to 2, nucleotide substitutions, or a complementary sequence thereof; with the proviso that that the oligonucleotide includes a late maturation allele or a normal maturation allele, the late maturation allele and the normal maturation allele being alleles of single nucleotide polymorphisms (SNP), the SNP being selected from the SNPs listed in Table 1.

In certain embodiments, the (isolated) oligonucleotide comprises at least 8 contiguous nucleotides, such as at least 10 contiguous nucleotides, at least 12 contiguous nucleotides, at least 14 contiguous nucleotides, at least 16 contiguous nucleotides, at least 18 contiguous nucleotides or at least 20 contiguous nucleotides, of a nucleotide sequence set forth in any one of SEQ ID NOs: 140, 135, 143, 137, 128, 144, 142, 127, 146, 147 and 131 or a complementary sequence thereof; or of a nucleotide sequence derived from any one of SEQ ID NOs: 140, 135, 143, 137, 128, 144, 142, 127, 146, 147 and 131 by 1 to 5, such as 1 to 2, nucleotide substitutions, or a complementary sequence thereof; with the proviso that that the oligonucleotide includes a late maturation allele or a normal maturation allele, the late maturation allele and the normal maturation allele being alleles of single nucleotide polymorphisms (SNP), the SNP being selected from the SNPs listed in Table 1.

In certain embodiments, the (isolated) oligonucleotide comprises at least 8 contiguous nucleotides, such as at least 10 contiguous nucleotides, at least 12 contiguous nucleotides, at least 14 contiguous nucleotides, at least 16 contiguous nucleotides, at least 18 contiguous nucleotides or at least 20 contiguous nucleotides, of a nucleotide sequence set forth in any one of SEQ ID NOs: 140, 135, 143, 137, 128, 144, 142, 127, 146, 147, 131 and 129 or a complementary sequence thereof; or of a nucleotide sequence derived from any one of SEQ ID NOs: 140, 135, 143, 137, 128, 144, 142, 127, 146, 147, 131 and 129 by 1 to 5, such as 1 to 2, nucleotide substitutions, or a complementary sequence thereof; with the proviso that that the oligonucleotide includes a late maturation allele or a normal maturation allele, the late maturation allele and the normal maturation allele being alleles of single nucleotide polymorphisms (SNP), the SNP being selected from the SNPs listed in Table 1.

In certain embodiments, the (isolated) oligonucleotide comprises at least 8 contiguous nucleotides, such as at least 10 contiguous nucleotides, at least 12 contiguous nucleotides, at least 14 contiguous nucleotides, at least 16 contiguous nucleotides, at least 18 contiguous nucleotides or at least 20 contiguous nucleotides, of a nucleotide sequence set forth in any one of SEQ ID NOs: 140, 135, 143, 137, 128, 144, 142, 127, 146, 147, 131, 129 and 120 or a complementary sequence thereof; or of a nucleotide sequence derived from any one of SEQ ID NOs: 140, 135, 143, 137, 128, 144, 142, 127, 146, 147, 131, 129 and 120 by 1 to 5, such as 1 to 2, nucleotide substitutions, or a complementary sequence thereof; with the proviso that that the oligonucleotide includes a late maturation allele or a normal maturation allele, the late maturation allele and the normal maturation allele being alleles of single nucleotide polymorphisms (SNP), the SNP being selected from the SNPs listed in Table 1.

In certain embodiments, the (isolated) oligonucleotide comprises at least 8 contiguous nucleotides, such as at least 10 contiguous nucleotides, at least 12 contiguous nucleotides, at least 14 contiguous nucleotides, at least 16 contiguous nucleotides, at least 18 contiguous nucleotides or at least 20 contiguous nucleotides, of a nucleotide sequence set forth in any one of SEQ ID NOs: 140, 135, 143, 137, 128, 144, 142, 127, 146, 147, 131, 129, 120 and 130 or a complementary sequence thereof; or of a nucleotide sequence derived from any one of SEQ ID NOs: 140, 135, 143, 137, 128, 144, 142, 127, 146, 147, 131, 129, 120 and 130 by 1 to 5, such as 1 to 2, nucleotide substitutions, or a complementary sequence thereof; with the proviso that that the oligonucleotide includes a late maturation allele or a normal maturation allele, the late maturation allele and the normal maturation allele being alleles of single nucleotide polymorphisms (SNP), the SNP being selected from the SNPs listed in Table 1.

In certain embodiments, the (isolated) oligonucleotide comprises at least 8 contiguous nucleotides, such as at least 10 contiguous nucleotides, at least 12 contiguous nucleotides, at least 14 contiguous nucleotides, at least 16 contiguous nucleotides, at least 18 contiguous nucleotides or at least 20 contiguous nucleotides, of a nucleotide sequence set forth in any one of SEQ ID NOs: 140, 135, 143, 137, 128, 144, 142, 127, 146, 147, 131, 129, 120, 130 and 138 or a complementary sequence thereof; or of a nucleotide sequence derived from any one of SEQ ID NOs: 140, 135, 143, 137, 128, 144, 142, 127, 146, 147, 131, 129, 120, 130 and 138 by 1 to 5, such as 1 to 2, nucleotide substitutions, or a complementary sequence thereof; with the proviso that that the oligonucleotide includes a late maturation allele or a normal maturation allele, the late maturation allele and the normal maturation allele being alleles of single nucleotide polymorphisms (SNP), the SNP being selected from the SNPs listed in Table 1.

In certain embodiments, the (isolated) oligonucleotide comprises at least 8 contiguous nucleotides, such as at least 10 contiguous nucleotides, at least 12 contiguous nucleotides, at least 14 contiguous nucleotides, at least 16 contiguous nucleotides, at least 18 contiguous nucleotides or at least 20 contiguous nucleotides, of a nucleotide sequence set forth in any one of SEQ ID NOs: 140, 135, 143 and 137 or a complementary sequence thereof; or of a nucleotide sequence derived from any one of SEQ ID NOs: 140, 135, 143 and 137 by 1 to 5, such as 1 to 2, nucleotide substitutions, or a complementary sequence thereof; with the proviso that that the oligonucleotide includes a late maturation allele or a normal maturation allele, the late maturation allele and the normal maturation allele being alleles of single nucleotide polymorphisms (SNP), the SNP being selected from the SNPs listed in Table 1.

In certain embodiments, the (isolated) oligonucleotide comprises at least 8 contiguous nucleotides, such as at least 10 contiguous nucleotides, at least 12 contiguous nucleotides, at least 14 contiguous nucleotides, at least 16 contiguous nucleotides, at least 18 contiguous nucleotides or at least 20 contiguous nucleotides, of a nucleotide sequence set forth in any one of SEQ ID NOs: 135, 137, 138, 140, 142 and 143 or a complementary sequence thereof; or of a nucleotide sequence derived from any one of SEQ ID NOs: 135, 137, 138, 140, 142 and 143 by 1 to 5, such as 1 to 2, nucleotide substitutions, or a complementary sequence thereof; with the proviso that that the oligonucleotide includes a late maturation allele or a normal maturation allele, the late maturation allele and the normal maturation allele being alleles of single nucleotide polymorphisms (SNP), the SNP being selected from the SNPs listed in Table 1.

In certain embodiments, the (isolated) oligonucleotide comprises at least 8 contiguous nucleotides, such as at least 10 contiguous nucleotides, at least 12 contiguous nucleotides, at least 14 contiguous nucleotides, at least 16 contiguous nucleotides, at least 18 contiguous nucleotides or at least 20 contiguous nucleotides, of a nucleotide sequence set forth in any one of SEQ ID NOs: 134, 135, 137, 138, 140, 142, 143 and 144 or a complementary sequence thereof; or of a nucleotide sequence derived from any one of SEQ ID NOs: 134, 135, 137, 138, 140, 142, 143 and 144 by 1 to 5, such as 1 to 2, nucleotide substitutions, or a complementary sequence thereof; with the proviso that that the oligonucleotide includes a late maturation allele or a normal maturation allele, the late maturation allele and the normal maturation allele being alleles of single nucleotide polymorphisms (SNP), the SNP being selected from the SNPs listed in Table 1.

In certain embodiments, the (isolated) oligonucleotide comprises at least 8 contiguous nucleotides, such as at least 10 contiguous nucleotides, at least 12 contiguous nucleotides, at least 14 contiguous nucleotides, at least 16 contiguous nucleotides, at least 18 contiguous nucleotides or at least 20 contiguous nucleotides, of a nucleotide sequence set forth in any one of SEQ ID NOs: 131, 134, 135, 137, 138, 140, 142, 143, 144 and 146 or a complementary sequence thereof; or of a nucleotide sequence derived from any one of SEQ ID NOs: 131, 134, 135, 137, 138, 140, 142, 143, 144 and 146 by 1 to 5, such as 1 to 2, nucleotide substitutions, or a complementary sequence thereof; with the proviso that that the oligonucleotide includes a late maturation allele or a normal maturation allele, the late maturation allele and the normal maturation allele being alleles of single nucleotide polymorphisms (SNP), the SNP being selected from the SNPs listed in Table 1.

In certain embodiments, the (isolated) oligonucleotide comprises at least 8 contiguous nucleotides, such as at least 10 contiguous nucleotides, at least 12 contiguous nucleotides, at least 14 contiguous nucleotides, at least 16 contiguous nucleotides, at least 18 contiguous nucleotides or at least 20 contiguous nucleotides, of a nucleotide sequence set forth in any one of SEQ ID NOs: 130, 131, 134, 135, 137, 138, 140, 142, 143, 144, 146 and 147 or a complementary sequence thereof; or of a nucleotide sequence derived from any one of SEQ ID NOs: 131, 134, 135, 137, 138, 140, 142, 143, 144 and 146 by 1 to 5, such as 1 to 2, nucleotide substitutions, or a complementary sequence thereof; with the proviso that that the oligonucleotide includes a late maturation allele or a normal maturation allele, the late maturation allele and the normal maturation allele being alleles of single nucleotide polymorphisms (SNP), the SNP being selected from the SNPs listed in Table 1.

According to certain embodiments, the oligonucleotide or complement thereof has a length of at least 10 nucleotides, such as at least 16 nucleotides.

According to certain embodiments, the oligonucleotide or complement thereof has a length of at least 16 nucleotides, such as at least 20 nucleotides.

According to certain embodiments, the oligonucleotide or complement thereof has a length of at least 20 nucleotides, such as at least 25 nucleotides.

According to certain embodiments, the oligonucleotide or complement thereof has a length of 10 to 200 nucleotides, such as 10 to 150 nucleotides.

According to certain embodiments, the oligonucleotide or complement thereof has a length of 10 to 100 nucleotides, such as 10 to 70 nucleotides.

According to certain embodiments, the oligonucleotide or complement thereof has a length of 16 to 100 nucleotides, such as 16 to 70 nucleotides.

According to certain embodiments, the oligonucleotide or complement thereof has a length of 10 to 50 nucleotides, such as 10 to 40 nucleotides.

According to certain embodiments, the oligonucleotide or complement thereof has a length of 16 to 50 nucleotides, such as 16 to 40 nucleotides.

According to certain embodiments, the oligonucleotide or complement thereof has a length of 10 to 30 nucleotides, such as 8 to 25 nucleotides.

According to certain embodiments, the oligonucleotide or complement thereof has a length of 16 to 30 nucleotides, such as 16 to 25 nucleotides.

According to certain embodiments, the oligonucleotide or complement thereof is a primer, such as a PCR primer.

According to certain embodiments, the oligonucleotide or complement thereof is a probe, such as a hybridization probe.

According to certain embodiments, the present invention provides a complement to the oligonucleotide specified above. Such complement may be used as a probe, such as a hybridization probe.

A probe or primer according to the present invention may have attached to it a detectable label or reporter molecule. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, for example, in Sambrook et al. (In Molecular Cloning, A Laboratory Manual, CSHL, New York, 1989) and Ausubel et al. (In Current Protocols in Molecular Biology, John Wiley & Sons, New York, 1998). As a particular example, a probe or primer may include one fluorophor, such as an acceptor fluorophore or donor fluorophore. Such fluorophore may be attached at the 5'- or 3' end of the probe/primer.

Probes are generally at least 15 nucleotides in length, such as at least 16, at least 17, at least 18, at least 19, at least 20, at least 25, at least 30, at least 35, at least 40, at least 45, at least 50, at least 55, at least 60, at least 65, at least 70, or more contiguous nucleotides complementary to the target nucleic acid molecule, such as 20 to 70 nucleotides, 20 to 60 nucleotides, 20 to 50 nucleotides, 20 to 40 nucleotides, or 20 to 30 nucleotides.

Primers are typically shorter in length. An oligonucleotide used as primer may be at least 10 nucleotides in length. The specificity of a primer increases with its length. Thus, for example, a primer that includes 30 consecutive nucleotides will anneal to a target sequence with a higher specificity that a corresponding primer of only 15 nucleotides. Thus, to obtain greater specificity, primers of the invention are at least 15 nucleotides in length, such as at least 16, at least 17, at least 18, at least 19, at least 20, at least 25, at least 30, at least 35, at least 40, at least 45, at least 50, at least 55, at least 60, at least 65, at least 70, or more contiguous nucleotides complementary to the target nucleic acid molecule, such as 15 to 70 nucleotides, 15 to 60 nucleotides, 15 to 50 nucleotides, 15 to 40 nucleotides, or 15 to 30 nucleotides. Primer pairs can be used for amplification of nucleic acid sequences, for example, by PCT, real-time-PCR, or other nucleic-acid amplification methods known in the art.

Kit

The present invention provides in a sixth aspect, a kit for predicting late onset of sexual maturation in rainbow trout, the kit comprising at least one of the oligonucleotides according to the fifth aspect of the present invention.

The present invention provides in a seventh aspect, a kit for selecting a rainbow trout having late onset of sexual maturation, the kit comprising at least one of the oligonucleotides according to the fifth aspect of the present invention.

Having generally described this invention, a further understanding can be obtained by reference to certain specific examples, which are provided herein for purposes of illustration only, and are not intended to be limiting unless otherwise specified.

EXAMPLES

Example 1: Genome Wide Association Study (GWAS)

Dataset: The dataset was acquired from rainbow trout (*Oncorhynchus mykiss*) from AquaGen's breeding nucleus population of the 2017 year-class.

Egg incubation and first feeding: Eggs were fertilized in freshwater in February 2017. The eggs and yolk sac larvae were kept in covered trays with 8 h background light and 16 h darkness, and the mean water temperature was 8° C., until first feeding in April 2017. During egg incubation and first feeding each family group was kept separate, in 250 single tanks. Each first-feeding tank had 80 L, and 1000 fish per family. The fish were fed by a Storvik robot feeder, every 10 minutes 24 h per day. When the mean weight was 2.5 g the number of fish per tank was reduced to 250. All deformed and small fish were culled at this step.

Smoltification & vaccination: In June 2017, when the mean fish weight was more than 5 g, 140 fish per family were PIT-tagged (Passive Integrated Transponder, Smartrac Unique 12×2 mm, supplied by RFID-solution). After tagging, fish from different families were mixed in three 6 m$^3$ tanks, and kept at 24 h light and 13° C. In late July 2017, when the ambient water temperature was 12° C., all fish were transferred to two 50 m$^3$ outdoor tanks, with ambient light and water temperature. Feeding in these tanks was done by Betten automatic feeders. All fish were manually vaccinated in September 2017, by injection of AlphaJect® 5-3. At this stage all fish were individually weighed, and PIT tag registered. Fish weighing less than 20 g and fish with deviations were culled.

Freshwater to Seawater: 25 798 fish with a mean weight of 76 g were transferred to seawater in October 2017. From first feeding until transfer to outdoor tanks the fish were kept at 24 h light and 13° C. The fish were fed commercially available feed for rainbow trout, with nutritional composition and pellet size adjusted to the fish developmental stage and body size.

The 25 798 smolts that were transferred to seawater were reared in a 90-meter polar circle cage under ambient light and sea water temperature, similar to national statistics for the Trondheim area. The fish were fed according to feeding tables adjusted for weight, with automatic feeding systems from Aqua.

Selection & Identification of control fish: In October 2018, the remaining 25.548 fish were anaesthetised and inspected for deformities, skin colour and body shape. Weight and length were measured, and a photo stored for each fish. The purpose of the measurements was to calculate breeding values and select the best fish to be parents for a new generation trout.

At this stage, the 30% biggest trout, with the silveriest skin colour, were kept as breeding candidates. 7 000 fish were pre-selected, at a mean weight of 3.93 kg. The culled ones, 18 547 fish, had a mean weight of 3.00 kg. These fish were transported to a processing plant for harvest during October 2018.

At the processing plant, a group of 1 526 non-maturing fish (average weight of 3.1 kg), with maximum 7 fish per 250 family, were selected for registration of yield and analysis of pigment and DNA. The gender of these fish was determined when the fish were opened, and the gonads could be seen. This group of fish was considered the control group, i.e. non-maturing fish with known gender.

Seawater to freshwater for spawning: 6900 fish of the pre-selected fish, with a mean weight of 5.11 kg, were sorted again in December 2018. All fish with a tendency for maturation were selected. Maturation is more difficult to determine in fish less than 2 years of age, as they have a silverier skin colour and less clear external sexual maturation characteristics. 1 748 fish were selected as broodstock candidates, and tissue samples were taken from all these fish for DNA analysis.

The selected fish were transferred to freshwater in Aqua-Gen's broodstock facilities in Kyrksæterøra, Norway, for spawning in February 2019. Included in this group were also fish of the type neo-males, which are sex-reversed so that genetic females develop masculine reproductive organs and produce sperm. This is done by administering testosterone to the fish at the time when the reproductive organs are first developed (at first feeding, around 0.15 g) (Biotechnology & Biotechnological Equipment, 2009, 23:4, 1509-1514, DOI: 10.2478/V10133-009-0002-X). The change in hormone levels stimulates females to develop male gonads, and they develop male external characteristics when they mature 2 years later. All neo-males were genotyped in advance to ensure that only genetic females were present.

During the last period in freshwater (1 month) around 60% of the fish went through final maturation and became ready to spawn. Fish that did not go through final maturation, were culled. The gender of these fish was not checked. For the fish that went through final maturation, gender was determined by whether the spawning product was eggs (from females) or sperm (from males). The fish were kept at a 24 h light, and the mean water temperature was 10° C. during the month in freshwater.

Genotyping: As already described above, tissue samples were taken from control fish and broodstock candidates. All tissue samples were taken from the tail fin of the fish for DNA-extraction and genotyping. DNA was extracted from the tissue samples, using a standard method (DNAdvance™ kit from Beckman Coulter, Indianapolis, United States). The DNA was genotyped using the Axiom® Trout genotyping Array, a SNP-chip harbouring 57,501 single nucleotide polymorphisms (SNPs) in 96-well format. This SNP-chip was developed by AquaGen in collaboration with the United Stated Department of Agriculture 20 (USDA) and Affymetrix, and is commercially available from Affymetrix (San Diego, USA). Genotyping was performed using the Affymetrix' proprietary Axiom® platform, following the Axiom® 2.0 Assay Automated Workflow User Guide.

Based on the raw data provided by the Axiom® machinery, genotypes were called using the Affymetrix PowerTools software. The analysis and interpretation of the raw data was done according to the Best Practices 30 Workflow provided by Affymetrix. SNPs and animals having quality parameters below the default thresholds, provided in the Best Practices Workflow, were not considered for further analyses.

Only markers in the PolyHighResolution and NoMinorHom categories were analysed, as recommended by the genotyping platform producer. SNP markers with missingness above 10% and animals with missing data above 15% was removed, resulting in a dataset of 42,314 SNP markers and 1,647 fish with recorded maturation status and sex.

GWAS: To search for DNA markers associated with late maturation in the sampled rainbow trout population, a single marker genome-wide association study was conducted using genotypes for 1 647 fish with recorded maturation status. Sex was included as a covariate in the analysis. The association study was conducted with the GCTA software (Yang et al., 2011, Am J Hum Genet. 2011 88(1): 76-82) which implements a mixed linear model single-marker association analysis using the -mlma-loco option of GCTA (Yang et al., 2014, Nat Genet. February; 46(2):100-6). Sex was included as a covariate in the analysis using the covar parameter. The model fitted to the performance information for each trait and each SNP was:

$$LATEMAT = a + bx + g- + e$$

where LATEMAT is the maturation status of the fish coded as 0 or 1 (0=immature; 1=mature), a is the mean term, b is the fixed additive effect of the candidate SNP to be tested for association, x is the SNP genotype indicator variable coded as 0, 1 or 2, g- is the random polygenic effect, i.e. the accumulated effect of all SNPs except those on the chromosome where the candidate SNP is located, and e is the residual. The var(g-) is re-estimated each time when a chromosome is excluded from calculating the genomic relationship matrix.

The results of the genome-wide association study are presented in table 1 and table 3.

TABLE 3

| SNP # | b | p | se |
|---|---|---|---|
| 1 | 0.072621 | 0.000116 | 0.018841 |
| 2 | 0.066487 | 0.000363 | 0.018646 |
| 3 | -0.0733 | 0.000143 | 0.019278 |
| 4 | 0.069419 | 0.000374 | 0.01951 |
| 5 | 0.232912 | 1.39E-06 | 0.048258 |
| 6 | -0.20478 | 1.21E-05 | 0.046799 |
| 7 | -0.0878 | 3.16E-06 | 0.018842 |
| 8 | 0.155719 | 2.26E-05 | 0.036752 |
| 9 | 0.20537 | 3.29E-06 | 0.044148 |
| 10 | -0.19734 | 9.78E-06 | 0.044628 |
| 11 | -0.19984 | 7.04E-06 | 0.044482 |
| 12 | 0.19337 | 1.58E-05 | 0.044785 |
| 13 | 0.053904 | 0.006195 | 0.019693 |
| 14 | 0.066758 | 0.006195 | 0.024389 |
| 15 | -0.07529 | 0.001926 | 0.024278 |
| 16 | 0.062764 | 0.003561 | 0.021534 |
| 17 | -0.09764 | 3.73E-05 | 0.023679 |
| 18 | -0.09032 | 2.55E-05 | 0.021452 |
| 19 | 0.125808 | 4.33E-06 | 0.02738 |
| 20 | -0.07647 | 0.000213 | 0.020651 |
| 21 | 0.115704 | 1.72E-05 | 0.026915 |
| 22 | 0.111758 | 1.22E-05 | 0.025546 |
| 23 | 0.091821 | 6.78E-06 | 0.020402 |
| 24 | -0.0919 | 1.31E-06 | 0.018996 |
| 25 | -0.09971 | 0.005334 | 0.035786 |
| 26 | -0.05523 | 0.006552 | 0.020316 |
| 27 | 0.126665 | 0.00635 | 0.046413 |
| 28 | 0.05894 | 0.001665 | 0.018745 |
| 29 | -0.1057 | 0.000305 | 0.029273 |
| 30 | 0.147067 | 0.00117 | 0.045304 |
| 31 | -0.16004 | 0.000784 | 0.047657 |
| 32 | -0.10704 | 0.000775 | 0.031843 |
| 33 | 0.115041 | 0.000899 | 0.034647 |
| 34 | 0.12055 | 0.000502 | 0.034646 |
| 35 | 0.119566 | 0.000526 | 0.034488 |
| 36 | -0.08267 | 0.000725 | 0.024459 |
| 37 | 0.108508 | 0.002291 | 0.03558 |
| 38 | 0.110396 | 0.001872 | 0.035499 |
| 39 | 0.108853 | 0.002157 | 0.035483 |
| 40 | 0.110637 | 0.002715 | 0.0369 |
| 41 | -0.14723 | 0.000184 | 0.039366 |
| 42 | 0.070596 | 0.000442 | 0.020092 |
| 43 | 0.069851 | 0.00041 | 0.019768 |
| 44 | -0.06207 | 0.000744 | 0.018403 |
| 45 | -0.07639 | 0.000417 | 0.021643 |
| 46 | 0.073182 | 0.000715 | 0.021626 |
| 47 | -0.06458 | 0.000603 | 0.018827 |
| 48 | -0.13404 | 0.003149 | 0.045395 |

TABLE 3-continued

| SNP # | b | p | se |
|---|---|---|---|
| 49 | −0.10799 | 0.003762 | 0.037271 |
| 50 | 0.056679 | 0.006409 | 0.020791 |
| 51 | −0.06892 | 0.000714 | 0.020366 |
| 52 | −0.14191 | 0.000392 | 0.040027 |
| 53 | −0.05961 | 0.001254 | 0.018476 |
| 54 | −0.06682 | 0.000265 | 0.018321 |
| 55 | −0.06498 | 0.000317 | 0.018043 |
| 56 | 0.127081 | 0.00027 | 0.034891 |
| 57 | −0.11243 | 0.000252 | 0.030712 |
| 58 | 0.159429 | 0.000285 | 0.043937 |
| 59 | 0.069496 | 0.000553 | 0.020121 |
| 60 | −0.09543 | 0.000307 | 0.026438 |
| 61 | −0.08153 | 0.000847 | 0.02443 |
| 62 | 0.05459 | 0.002727 | 0.018216 |
| 63 | 0.072264 | 0.003723 | 0.024912 |
| 64 | 0.09553 | 0.003666 | 0.032879 |
| 65 | 0.061393 | 0.001841 | 0.019711 |
| 66 | −0.06519 | 0.001032 | 0.019865 |
| 67 | 0.063174 | 0.000705 | 0.018649 |
| 68 | −0.06968 | 0.000576 | 0.020241 |
| 69 | −0.07971 | 0.00024 | 0.021706 |
| 70 | −0.08226 | 0.000214 | 0.02222 |
| 71 | 0.099409 | 1.23E−05 | 0.022736 |
| 72 | −0.08576 | 0.000127 | 0.022383 |
| 73 | −0.08458 | 0.000187 | 0.022635 |
| 74 | −0.08047 | 0.000126 | 0.020985 |
| 75 | 0.064418 | 0.000812 | 0.019236 |
| 76 | 0.063253 | 0.000951 | 0.019141 |
| 77 | 0.044405 | 0.021796 | 0.019358 |
| 78 | 0.066171 | 0.011509 | 0.026187 |
| 79 | −0.04933 | 0.015787 | 0.020436 |
| 80 | 0.042566 | 0.024577 | 0.018935 |
| 81 | 0.060481 | 0.014357 | 0.024704 |
| 82 | −0.09819 | 0.011979 | 0.039075 |
| 83 | 0.110566 | 0.009111 | 0.042397 |
| 84 | 0.111622 | 1.93E−05 | 0.026122 |
| 85 | 0.105807 | 3.43E−06 | 0.022787 |
| 86 | 0.104419 | 2.28E−06 | 0.022091 |
| 87 | −0.09058 | 1.21E−05 | 0.020704 |
| 88 | −0.11374 | 1.08E−05 | 0.025847 |
| 89 | 0.096867 | 9.5E−06 | 0.021875 |
| 90 | 0.104326 | 5.27E−05 | 0.025802 |
| 91 | 0.108363 | 1E−05 | 0.024537 |
| 92 | 0.105876 | 1.7E−05 | 0.024617 |
| 93 | −0.1047 | 1.33E−07 | 0.019847 |
| 94 | 0.079676 | 2.82E−05 | 0.019027 |
| 95 | 0.077646 | 4.61E−05 | 0.019056 |
| 96 | −0.0792 | 3.17E−05 | 0.019034 |
| 97 | 0.120882 | 4.93E−05 | 0.029782 |
| 98 | −0.12623 | 2.36E−05 | 0.029858 |
| 99 | 0.123603 | 3.31E−05 | 0.029775 |
| 100 | −0.12114 | 4.72E−05 | 0.02977 |
| 101 | −0.13242 | 9.56E−06 | 0.029912 |
| 102 | 0.075256 | 0.010179 | 0.029286 |
| 103 | 0.043721 | 0.014083 | 0.017808 |
| 104 | −0.065 | 0.004754 | 0.023025 |
| 105 | −0.04499 | 0.016455 | 0.018755 |
| 106 | −0.07967 | 0.000102 | 0.020501 |
| 107 | −0.07302 | 9.19E−05 | 0.018671 |
| 108 | −0.0709 | 0.000138 | 0.018599 |
| 109 | −0.07402 | 0.00024 | 0.020152 |
| 110 | −0.09654 | 4.21E−05 | 0.023571 |
| 111 | −0.08881 | 4.36E−06 | 0.019335 |
| 112 | −0.09654 | 4.21E−05 | 0.023571 |
| 113 | 0.09124 | 2.02E−05 | 0.021402 |
| 114 | 0.094936 | 3.3E−07 | 0.018595 |
| 115 | 0.081369 | 1.22E−05 | 0.018605 |
| 116 | −0.08526 | 2.5E−06 | 0.018109 |
| 117 | 0.081366 | 4.64E−06 | 0.017763 |
| 118 | 0.07669 | 1.78E−05 | 0.017876 |
| 119 | 0.104425 | 2.77E−06 | 0.02228 |
| 120 | −0.1101 | 1.97E−07 | 0.021165 |
| 121 | 0.090614 | 5.93E−07 | 0.018147 |
| 122 | −0.07324 | 4.21E−05 | 0.017881 |
| 123 | −0.07727 | 1.56E−05 | 0.017885 |
| 124 | 0.162104 | 6.3E−06 | 0.035896 |
| 125 | −0.08414 | 1.63E−06 | 0.017546 |
| 126 | −0.09229 | 8.96E−07 | 0.018783 |
| 127 | 0.112832 | 9.8E−08 | 0.021168 |
| 128 | −0.1145 | 6.4E−08 | 0.021176 |
| 129 | −0.11025 | 1.84E−07 | 0.02114 |
| 130 | −0.10958 | 2.43E−07 | 0.021225 |
| 131 | 0.111905 | 1.32E−07 | 0.021211 |
| 132 | 0.093353 | 3.85E−07 | 0.018391 |
| 133 | 0.088411 | 1.81E−06 | 0.018519 |
| 134 | 0.09229 | 3.12E−07 | 0.018039 |
| 135 | −0.1046 | 1.68E−08 | 0.018538 |
| 136 | −0.08991 | 1.52E−05 | 0.020784 |
| 137 | 0.10297 | 2.56E−08 | 0.018489 |
| 138 | −0.09344 | 3.12E−07 | 0.018263 |
| 139 | −0.08991 | 1.52E−05 | 0.020784 |
| 140 | 0.112587 | 6.95E−10 | 0.018256 |
| 141 | −0.09459 | 5.24E−07 | 0.018852 |
| 142 | 0.096872 | 8.73E−08 | 0.018103 |
| 143 | 0.101851 | 1.87E−08 | 0.018112 |
| 144 | 0.096511 | 8.44E−08 | 0.018014 |
| 145 | 0.080036 | 5.37E−06 | 0.017591 |
| 146 | 0.117443 | 1.18E−07 | 0.022174 |
| 147 | 0.084425 | 1.2E−07 | 0.015949 |
| 148 | −0.11203 | 4.33E−07 | 0.022169 |
| 149 | −0.09458 | 2.84E−05 | 0.022593 |
| 150 | 0.106663 | 1E−06 | 0.021805 |
| 151 | −0.08603 | 1.17E−05 | 0.019631 |
| 152 | 0.08138 | 2.35E−05 | 0.019247 |
| 153 | −0.09825 | 2.32E−06 | 0.0208 |
| 154 | −0.10695 | 6.85E−07 | 0.021539 |
| 155 | 0.10169 | 2.53E−06 | 0.021609 |
| 156 | 0.096217 | 2.48E−05 | 0.022817 |
| 157 | 0.097621 | 1.77E−05 | 0.022743 |
| 158 | −0.09713 | 1.93E−05 | 0.022735 |
| 159 | −0.09638 | 2.24E−05 | 0.022737 |
| 160 | −0.09391 | 3.63E−05 | 0.02274 |
| 161 | −0.09331 | 2.82E−05 | 0.022282 |
| 162 | −0.10438 | 0.008011 | 0.039364 |
| 163 | 0.132686 | 0.008268 | 0.050242 |
| 164 | 0.051735 | 0.01064 | 0.020254 | b (also referred to as the beta value) is also called the allele substitution effect and refers to the estimated effect of receiving one copy of the tested allele (the "normal maturation allele" in table 1). Reference is e.g. made to SNP #140, wherein the mean effect on the phenotype of going from genotype TT to TC is 0.112587 while going from TT to CC is 0.112587 X2 = 0.225174. The phenotype in the present case is maturation status coded as 0 when immature and 1 when mature, the effect of 0.112587 translates to an 11 percentage point increase in percentage of mature fish in the data set.
p measure of statistical evidence against a null hypothesis. A smaller p-value indicates stronger evidence substantiating the alternative hypothesis. In practice, the p-value indicates how likely a putative characteristic associated variant is due to random chance. High beta value and low se value will provide a low p-value, while low beta value and high se value will provide a high p-value.
se represents the standard error which depends on the sample size and how well the observed data fits the linear model.

Linkage Disequilibrium (LD)

LD or, more precisely, gametic phase linkage disequilibrium, is used in order to describe the co-inheritance of alleles at genetically linked polymorphisms, at the population level. Two polymorphisms are defined to be in strong LD if the square of the correlation coefficient between the two loci (r2, the most commonly used measure of LD) is equal to or larger than 0.5, more preferably equal to or larger than 0.7, even more preferably equal to or larger than 0.8 and most preferably equal to or larger than 0.9.

A distinctive and highly significant QTL for maturity has been detected on chromosome 28 (see FIGS. 1a and 1b), and among these are 16 SNPs of particular interest (SNP #120, 127-131, 134-135, 137-138, 140, 142-144 and 146-147). All 16 of the SNPs are located within a genomic region of 1.9 megabases (FIG. 1b), and all show varying degree of elevated squared correlations to each other (FIG. 3).

Table 4 provides a list of the 16 SNPs on chromosome 28 that are of particular interest and their position on the chromosome. Further, the list is sorted according to the square of the correlation coefficient between two loci.

TABLE 4

| A_SNP # | A_BP # | B_SNP # | B_BP # | R2 |
|---|---|---|---|---|
| 135 | 11414120 | 137 | 11414399 | 0.996177 |
| 128 | 11093692 | 129 | 11096202 | 0.995723 |
| 120 | 10378833 | 129 | 11096202 | 0.990043 |
| 120 | 10378833 | 128 | 11093692 | 0.988618 |
| 142 | 11667915 | 143 | 11704242 | 0.980364 |
| 143 | 11704242 | 144 | 11745469 | 0.979454 |
| 142 | 11667915 | 144 | 11745469 | 0.976509 |
| 129 | 11096202 | 131 | 11148320 | 0.97439 |
| 128 | 11093692 | 131 | 11148320 | 0.974313 |
| 120 | 10378833 | 131 | 11148320 | 0.967308 |
| 134 | 11382381 | 138 | 11487704 | 0.961402 |
| 128 | 11093692 | 130 | 11139401 | 0.934455 |
| 129 | 11096202 | 130 | 11139401 | 0.934442 |
| 120 | 10378833 | 130 | 11139401 | 0.927666 |
| 130 | 11139401 | 131 | 11148320 | 0.923362 |
| 138 | 11487704 | 140 | 11537736 | 0.870889 |
| 127 | 10605800 | 130 | 11139401 | 0.854619 |
| 134 | 11382381 | 140 | 11537736 | 0.841967 |
| 127 | 10605800 | 128 | 11093692 | 0.82477 |
| 127 | 10605800 | 129 | 11096202 | 0.824571 |
| 120 | 10378833 | 127 | 10605800 | 0.818416 |
| 127 | 10605800 | 131 | 11148320 | 0.813752 |
| 131 | 11148320 | 146 | 12063041 | 0.801846 |
| 134 | 11382381 | 137 | 11414399 | 0.776771 |
| 134 | 11382381 | 135 | 11414120 | 0.775718 |
| 137 | 11414399 | 138 | 11487704 | 0.755322 |
| 135 | 11414120 | 138 | 11487704 | 0.754192 |
| 137 | 11414399 | 140 | 11537736 | 0.640884 |
| 135 | 11414120 | 140 | 11537736 | 0.638918 |
| 134 | 11382381 | 147 | 12252318 | 0.63764 |
| 138 | 11487704 | 147 | 12252318 | 0.629467 |
| 137 | 11414399 | 142 | 11667915 | 0.571017 |
| 135 | 11414120 | 142 | 11667915 | 0.569716 |
| 137 | 11414399 | 143 | 11704242 | 0.568289 |
| 137 | 11414399 | 144 | 11745469 | 0.567879 |
| 135 | 11414120 | 143 | 11704242 | 0.566992 |
| 135 | 11414120 | 144 | 11745469 | 0.566587 |
| 137 | 11414399 | 147 | 12252318 | 0.555781 |
| 135 | 11414120 | 147 | 12252318 | 0.553991 |
| 140 | 11537736 | 147 | 12252318 | 0.547934 |
| 140 | 11537736 | 143 | 11704242 | 0.458642 |
| 140 | 11537736 | 144 | 11745469 | 0.456815 |
| 140 | 11537736 | 142 | 11667915 | 0.456404 |
| 134 | 11382381 | 143 | 11704242 | 0.439942 |
| 134 | 11382381 | 142 | 11667915 | 0.439518 |
| 134 | 11382381 | 144 | 11745469 | 0.43747 |
| 138 | 11487704 | 142 | 11667915 | 0.428019 |
| 138 | 11487704 | 144 | 11745469 | 0.425464 |
| 138 | 11487704 | 143 | 11704242 | 0.425421 |
| 129 | 11096202 | 143 | 11704242 | 0.399344 |
| 129 | 11096202 | 142 | 11667915 | 0.397379 |
| 128 | 11093692 | 142 | 11667915 | 0.395977 |
| 131 | 11148320 | 143 | 11704242 | 0.390864 |
| 131 | 11148320 | 142 | 11667915 | 0.388907 |
| 131 | 11148320 | 144 | 11745469 | 0.387393 |
| 130 | 11139401 | 143 | 11704242 | 0.362932 |
| 130 | 11139401 | 142 | 11667915 | 0.360975 |
| 130 | 11139401 | 144 | 11745469 | 0.359626 |
| 143 | 11704242 | 146 | 12063041 | 0.316434 |
| 144 | 11745469 | 147 | 12252318 | 0.3161 |
| 144 | 11745469 | 146 | 12063041 | 0.315437 |
| 142 | 11667915 | 146 | 12063041 | 0.313873 |
| 143 | 11704242 | 147 | 12252318 | 0.313531 |
| 142 | 11667915 | 147 | 12252318 | 0.312988 |
| 130 | 11139401 | 137 | 11414399 | 0.227957 |
| 130 | 11139401 | 135 | 11414120 | 0.227507 |
| 127 | 10605800 | 137 | 11414399 | 0.226163 |
| 127 | 10605800 | 135 | 11414120 | 0.225741 |
| 129 | 11096202 | 137 | 11414399 | 0.219178 |
| 128 | 11093692 | 137 | 11414399 | 0.219139 |
| 129 | 11096202 | 135 | 11414120 | 0.218713 |
| 128 | 11093692 | 135 | 11414120 | 0.218672 |
| 131 | 11148320 | 137 | 11414399 | 0.216527 |
| 131 | 11148320 | 135 | 11414120 | 0.216046 |
| 127 | 10605800 | 140 | 11537736 | 0.211376 |
| 127 | 10605800 | 134 | 11382381 | 0.192605 |
| 146 | 12063041 | 147 | 12252318 | 0.191637 |
| 130 | 11139401 | 140 | 11537736 | 0.188975 |
| 127 | 10605800 | 138 | 11487704 | 0.185399 |
| 128 | 11093692 | 140 | 11537736 | 0.182801 |
| 129 | 11096202 | 140 | 11537736 | 0.182682 |
| 131 | 11148320 | 140 | 11537736 | 0.179886 |
| 130 | 11139401 | 134 | 11382381 | 0.17262 |
| 130 | 11139401 | 138 | 11487704 | 0.166937 |
| 128 | 11093692 | 134 | 11382381 | 0.16544 |
| 129 | 11096202 | 134 | 11382381 | 0.16483 |
| 131 | 11148320 | 134 | 11382381 | 0.163749 |
| 137 | 11414399 | 146 | 12063041 | 0.160392 |
| 135 | 11414120 | 146 | 12063041 | 0.160383 |
| 128 | 11093692 | 138 | 11487704 | 0.159903 |
| 129 | 11096202 | 138 | 11487704 | 0.159742 |
| 131 | 11148320 | 138 | 11487704 | 0.158182 |
| 140 | 11537736 | 146 | 12063041 | 0.133768 |
| 138 | 11487704 | 146 | 12063041 | 0.115124 |
| 134 | 11382381 | 146 | 12063041 | 0.114512 |

A_SNP # a first SNP, wherein the number refers to the SNP # according to table 1.
A_BP # position of the A_SNP # (first SNP) on chromosome 28.
B_SNP # a second SNP, wherein the number refers to the SNP # according to table 1.
B_BP # position of the B_SNP # (second SNP) on chromosome 28.
R2 correlation coefficient between A_SNP # and B_SNP #.

TABLE 5A AND TABLE 5B PROVIDES A LIST OF THE 16 SNPS ON CHROMOSOME 28 THAT ARE OF PARTICULAR INTEREST, THEIR POSITION ALONG THE CHROMOSOME AND THEIR P-VALUE. TABLE 5A IS SORTED ACCORDING TO THE POSITION OF THE SNPS ALONG CHROMOSOME 28 WHILE TABLE 5B IS SORTED ACCORDING TO THE P-VALUE OF THE SNPS.

TABLE 5a

| SNP # | BP # | p |
|---|---|---|
| 120 | 10378833 | 1.97073E−07 |
| 127 | 10605800 | 9.79982E−08 |
| 128 | 11093692 | 6.40093E−08 |
| 129 | 11096202 | 1.83833E−07 |
| 130 | 11139401 | 2.43284E−07 |
| 131 | 11148320 | 1.32183E−07 |
| 134 | 11382381 | 3.11917E−07 |
| 135 | 11414120 | 1.67786E−08 |
| 137 | 11414399 | 2.55833E−08 |
| 138 | 11487704 | 3.11633E−07 |
| 140 | 11537736 | 6.95304E−10 |
| 142 | 11667915 | 8.7344E−08 |
| 143 | 11704242 | 1.87124E−08 |
| 144 | 11745469 | 8.4426E−08 |
| 146 | 12063041 | 1.18044E−07 |
| 147 | 12252318 | 1.20003E−07 |

TABLE 5b

| SNP # | BP # | p |
|---|---|---|
| 140 | 11537736 | 6.95304E−10 |
| 135 | 11414120 | 1.67786E−08 |
| 143 | 11704242 | 1.87124E−08 |
| 137 | 11414399 | 2.55833E−08 |
| 128 | 11093692 | 6.40093E−08 |
| 144 | 11745469 | 8.4426E−08 |
| 142 | 11667915 | 8.7344E−08 |
| 127 | 10605800 | 9.79982E−08 |
| 146 | 12063041 | 1.18044E−07 |
| 147 | 12252318 | 1.20003E−07 |

TABLE 5b-continued

| SNP # | BP # | p |
|---|---|---|
| 131 | 11148320 | 1.32183E-07 |
| 129 | 11096202 | 1.83833E-07 |
| 120 | 10378833 | 1.97073E-07 |
| 130 | 11139401 | 2.43284E-07 |
| 138 | 11487704 | 3.11633E-07 |
| 134 | 11382381 | 3.11917E-07 |

SNP # the number refers to the SNP # according to table 1.
BP # position of the SNP along chromosome 28.
p measure of statistical evidence against a null hypothesis. A smaller p-value indicates stronger evidence substantiating the alternative hypothesis. In practice, the p-value indicates how likely a putative characteristic associated variant is due to random chance. High beta value and low se value will provide a low p-value, while low beta value and high se value will provide a high p-value.

The invention claimed is:

1. A method for obtaining rainbow trout having late onset of sexual maturation, said method comprising:
   providing an initial population of rainbow trout;
   obtaining a nucleic acid sample from at least one individual rainbow trout within said initial population;
   detecting in each of said nucleic acid samples the presence of at least one allele conferring late onset of sexual maturation ("late maturation allele") within the genome of said rainbow trout; wherein the at least one late maturation allele is an allele of at least one single nucleotide polymorphism (SNP), the at least one SNP being selected from the SNPs listed in the following table;

| SNP # | Seq ID NO: | Affymetrix ID | Chromosome | GenBank contig | Position in Genbank contig | Late maturation allele | Normal maturation allele |
|---|---|---|---|---|---|---|---|
| 134 | 134 | Affx-88927547 | chr28 | CM007962.1 | 11382381 | A | C |
| 135 | 135 | Affx-88946147 | chr28 | CM007962.1 | 11414120 | G | A |
| 137 | 137 | Affx-88953900 | chr28 | CM007962.1 | 11414399 | A | G |
| 138 | 138 | Affx-88947402 | chr28 | CM007962.1 | 11487704 | C | T |
| 140 | 140 | Affx-88940276 | chr28 | CM007962.1 | 11537736 | T | C | selecting a rainbow trout from said initial population based on the presence of the at least one late maturation allele in the nucleic acid samples; and
   mating said selected rainbow trout with a second rainbow trout to produce progeny rainbow trout having late onset of sexual maturation.

2. The method according to claim 1, wherein at least one rainbow trout within said mating pair is homozygous for the late maturation allele.

3. The method according to claim 1, wherein each rainbow trout within said mating pair is homozygous for the late maturation allele.

4. The method according to claim 1, the method further comprising
   obtaining a nucleic acid sample from at least two individual rainbow trout within said initial population;
   detecting the presence of at least one allele conferring late onset of sexual maturation ("late maturation allele") within the genome of said at least two rainbow trout;
   selecting a mating pair of rainbow trout from said initial population based on the presence of the at least one allele conferring late onset of sexual maturation ("late maturation allele") in the nucleic acid samples of both rainbow trout within said mating pair; and
   mating said selected mating pair of rainbow trout to produce progeny rainbow trout having late onset of sexual maturation.

5. The method according to claim 4, wherein at least one rainbow trout within said mating pair is homozygous for the late maturation allele.

6. The method according to claim 4, wherein each rainbow trout within said mating pair is homozygous for the late maturation allele.

7. A method for obtaining gametes from rainbow trout having late onset of sexual maturation, said method comprising providing an initial population of rainbow trout;
   obtaining a nucleic acid sample from at least one individual rainbow trout within said initial population;
   detecting in each of said nucleic acid samples the presence of at least one allele conferring late onset of sexual maturation ("late maturation allele") within the genome of said rainbow trout; wherein the at least one late maturation allele is an allele of at least one single nucleotide polymorphism (SNP), the at least one SNP being selected from the SNPs listed in the following table;

| SNP # | Seq ID NO: | Affymetrix ID | Chromosome | GenBank contig | Position in Genbank contig | Late maturation allele | Normal maturation allele |
|---|---|---|---|---|---|---|---|
| 134 | 134 | Affx-88927547 | chr28 | CM007962.1 | 11382381 | A | C |
| 135 | 135 | Affx-88946147 | chr28 | CM007962.1 | 11414120 | G | A |
| 137 | 137 | Affx-88953900 | chr28 | CM007962.1 | 11414399 | A | G |
| 138 | 138 | Affx-88947402 | chr28 | CM007962.1 | 11487704 | C | T |
| 140 | 140 | Affx-88940276 | chr28 | CM007962.1 | 11537736 | T | C | selecting a rainbow trout from said initial population based on the presence of the at least one late maturation allele in the nucleic acid samples; and
   isolating gametes from said selected trout.

8. The method according to claim 7, wherein said gametes are eggs.

9. The method according to claim 7, wherein said gametes are spermatozoa.

10. A method for obtaining rainbow trout having late onset of sexual maturation, said method comprising:
    providing an initial population of rainbow trout;
    obtaining a nucleic acid sample from at least one individual rainbow trout within said initial population;
    detecting in each of said nucleic acid samples the presence of at least one allele conferring late onset of sexual maturation ("late maturation allele") within the genome of said rainbow trout; wherein the at least one late maturation allele is an allele of at least one single nucleotide polymorphism (SNP), the at least one SNP being selected from the group consisting of the SNPs listed in the following table;

| SNP # | Seq ID NO: | Affymetrix ID | Chromosome | GenBank contig | Position in Genbank contig | Late maturation allele | Normal maturation allele |
|---|---|---|---|---|---|---|---|
| 134 | 134 | Affx-88927547 | chr28 | CM007962.1 | 11382381 | A | C |
| 135 | 135 | Affx-88946147 | chr28 | CM007962.1 | 11414120 | G | A |
| 137 | 137 | Affx-88953900 | chr28 | CM007962.1 | 11414399 | A | G |
| 138 | 138 | Affx-88947402 | chr28 | CM007962.1 | 11487704 | C | T |
| 140 | 140 | Affx-88940276 | chr28 | CM007962.1 | 11537736 | T | C | selecting a rainbow trout from said initial population based on the presence of the at least one late maturation allele in the nucleic acid samples;

isolating gametes from said selected trout; and utilizing said isolated gametes to produce progeny rainbow trout comprising late onset of sexual maturation.

11. The method according to claim 10, wherein said gametes are eggs.

12. The method according to claim 10, wherein said gametes are spermatozoa.

13. The method of claim 7, further comprising producing progeny rainbow trout comprising late onset of sexual maturation from the isolated gametes.

* * * * *

SEQUENCE LISTING

<160> NUMBER OF SEQ ID NOS: 330

<210> SEQ ID NO 1
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is T or C

<400> SEQUENCE: 1
agtatatgat gattcaatga gatacagtac nttacactttt attgcccatt tccatgaaaa      60
t                                                                       61

<210> SEQ ID NO 2
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is A or C

<400> SEQUENCE: 2
tcagtccata agtaatgcaa agatcaaagt nattctacag aaaccgattg ggcagactaa      60
c                                                                       61

<210> SEQ ID NO 3
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is G or A

<400> SEQUENCE: 3
agtacaaaca gagatgtgtt atgttagaca nctgaagtga accgctacac ctgcttggtg      60
c                                                                       61

<210> SEQ ID NO 4
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is A or G

<400> SEQUENCE: 4
gagtgcagtg gatagagaca gctcctcagt ncataaaggc ccacctgtcc tgggggaaga      60
t                                                                       61

```
<210> SEQ ID NO 5
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is A or G

<400> SEQUENCE: 5
tactataatc ggggacagtg acatgcatcg ncccacaaag tttttaagac tgcagttatg    60
t                                                                   61

<210> SEQ ID NO 6
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is C or T

<400> SEQUENCE: 6
ggaaccagtc actgtctcac tacattttca ngtggcagtt ttgtcttcca ccgtgcaagc    60
c                                                                   61

<210> SEQ ID NO 7
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is C or T

<400> SEQUENCE: 7
ttggttcttg caactctata gctctgggtc nttcccttac ctcggcacgg cagccagtca    60
g                                                                   61

<210> SEQ ID NO 8
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is A or C

<400> SEQUENCE: 8
ctgtataaag ttgttactgc aggtacaggc ngtgatgctg agactcttct gccaagacac    60
c                                                                   61

<210> SEQ ID NO 9
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is A or G

<400> SEQUENCE: 9
atcgtactga gcttgttgtc attgcaggca ntctcaactc tgtgcattac actgaagact    60
```

```
t                                                              61

<210> SEQ ID NO 10
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is C or T

<400> SEQUENCE: 10
agacagatca tcaaaagctt ttattctgat naagttcagt agtttgttta ggacactgaa    60
a                                                              61

<210> SEQ ID NO 11
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is G or A

<400> SEQUENCE: 11
tgacctgcag ctatgcacca taatctagca ngttcatttg aacacccttt gaaaaggtaa    60
t                                                              61

<210> SEQ ID NO 12
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is T or C

<400> SEQUENCE: 12
tctatactac ggtctattgc ctattttttaa ngtatcttta atttcgtatc ccagttatta    60
g                                                              61

<210> SEQ ID NO 13
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is A or G

<400> SEQUENCE: 13
ttaccatact aacttgtagg gctgagcaat ntattttgaa tacaggcaca gagccacata    60
c                                                              61

<210> SEQ ID NO 14
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is A or G

<400> SEQUENCE: 14
ctacactaaa atgcaatttg atctggacag nttgtctgtt atgctattgc agtgttatga    60
``` c                                                             61

<210> SEQ ID NO 15
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is G or T

<400> SEQUENCE: 15
cactacctga tgcagtccca gtttgtgatt nttatctgca gaaactcaaa tataaattcc     60
a                                                             61

<210> SEQ ID NO 16
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is A or C

<400> SEQUENCE: 16
gacgctgctg ttcctgctgc tgccaccaca nccatttcct ctcgtcatga gcaaaagcta     60
t                                                             61

<210> SEQ ID NO 17
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is C or T

<400> SEQUENCE: 17
aggtaccctg cactacattc ctagcgcgac nagaggatgg tatagaaaat gtaatggtat     60
a                                                             61

<210> SEQ ID NO 18
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is G or A

<400> SEQUENCE: 18
tctctgagtg agatcaagaa cggttcggtt ntctacgact gttggggcca cttcatagaa     60
c                                                             61

<210> SEQ ID NO 19
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is T or G

<400> SEQUENCE: 19

```
tgcagatatg aacagcttga gtaaaaagat natgttaccc actgaacatc aatgaacaaa    60
t                                                                    61
```

\<210\> SEQ ID NO 20
\<211\> LENGTH: 61
\<212\> TYPE: DNA
\<213\> ORGANISM: Oncorhynchus mykiss
\<220\> FEATURE:
\<221\> NAME/KEY: misc_feature
\<222\> LOCATION: (31)..(31)
\<223\> OTHER INFORMATION: wherein "n" is C or T

\<400\> SEQUENCE: 20

```
caaagggact tatcttctcc caaaagacaa ngggccgatc atttaacgaa tcttctcttg    60
a                                                                    61
```

\<210\> SEQ ID NO 21
\<211\> LENGTH: 61
\<212\> TYPE: DNA
\<213\> ORGANISM: Oncorhynchus mykiss
\<220\> FEATURE:
\<221\> NAME/KEY: misc_feature
\<222\> LOCATION: (31)..(31)
\<223\> OTHER INFORMATION: wherein "n" is A or G

\<400\> SEQUENCE: 21

```
ctgcgacatg ttttgagtta gcgtaatttc ntactaaaga ttggagaagt gtgcctaatt    60
a                                                                    61
```

\<210\> SEQ ID NO 22
\<211\> LENGTH: 61
\<212\> TYPE: DNA
\<213\> ORGANISM: Oncorhynchus mykiss
\<220\> FEATURE:
\<221\> NAME/KEY: misc_feature
\<222\> LOCATION: (31)..(31)
\<223\> OTHER INFORMATION: wherein "n" is A or G

\<400\> SEQUENCE: 22

```
ttcgccttca ccctgagtta ggacggctcc nagccccata tttgaggcgt ctacctgcac    60
a                                                                    61
```

\<210\> SEQ ID NO 23
\<211\> LENGTH: 61
\<212\> TYPE: DNA
\<213\> ORGANISM: Oncorhynchus mykiss
\<220\> FEATURE:
\<221\> NAME/KEY: misc_feature
\<222\> LOCATION: (31)..(31)
\<223\> OTHER INFORMATION: wherein "n" is A or G

\<400\> SEQUENCE: 23

```
aattgactaa caatattgtc taacaagtgc ngtataaata aatccatcct tctcatcctc    60
c                                                                    61
```

\<210\> SEQ ID NO 24
\<211\> LENGTH: 61
\<212\> TYPE: DNA
\<213\> ORGANISM: Oncorhynchus mykiss
\<220\> FEATURE:
\<221\> NAME/KEY: misc_feature
\<222\> LOCATION: (31)..(31)
\<223\> OTHER INFORMATION: wherein "n" is G or T

\<400\> SEQUENCE: 24

-continued

```
gtatggtttt gaagagtaca actgtgtgag ngtggattga acaaaatagt atcttaaaca    60
c                                                                    61

<210> SEQ ID NO 25
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is G or A

<400> SEQUENCE: 25
taaacagcag ttgaacgagc tgggcagcga ntcggccaag atcaaggcca tgggcatcac    60
c                                                                    61

<210> SEQ ID NO 26
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is G or A

<400> SEQUENCE: 26
gatgcgtccc tccaacacag tgcatctgct ngttttgtgt gaggaccaca gagccggcat    60
g                                                                    61

<210> SEQ ID NO 27
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is A or C

<400> SEQUENCE: 27
gtgcggcagg cggcagtggt ggacaacttc ntgtcccagc aagagaagaa gcagaaacac    60
c                                                                    61

<210> SEQ ID NO 28
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is A or G

<400> SEQUENCE: 28
gcctgcagat gttcctcacg tgatgtgatg nccttttaac tgggcgtcct ttgaatataa    60
g                                                                    61

<210> SEQ ID NO 29
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is C or A
```

```
<400> SEQUENCE: 29
acgtgccttt tgatggttat tactagaccg nttattgtac ctgccctatt gatcaaccgg      60
a                                                                     61

<210> SEQ ID NO 30
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is T or C

<400> SEQUENCE: 30
gacataggga cgtttccaca tgaagtgaat nggaaaagca tacacttaca tgactttcaa      60
t                                                                     61

<210> SEQ ID NO 31
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is C or A

<400> SEQUENCE: 31
atcagattct ccaaaaaggt ccaggggaaa nagtttgctg cttttgttgg atattttac       60 a                                                                     61

<210> SEQ ID NO 32
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is G or T

<400> SEQUENCE: 32
atgagtgata ttacagtttg tccttcagat naaacaattg aggagccaac tatgtgtaat      60
c                                                                     61

<210> SEQ ID NO 33
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is T or C

<400> SEQUENCE: 33
gcataaagtt gatacaattc acacaaagtc nttgtcgggg gactccaatc ctctgtgttt      60
c                                                                     61

<210> SEQ ID NO 34
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is A or G
```

-continued

```
<400> SEQUENCE: 34
acacactgca gagtaaacag caaacactga naaagctgca cccagactgg cattcacaca    60
c                                                                    61

<210> SEQ ID NO 35
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is T or C

<400> SEQUENCE: 35
tgctctgaga aggggttct gatttctgtc nacagggggc tccctcctgc ctatccaacg    60
a                                                                    61

<210> SEQ ID NO 36
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is G or A

<400> SEQUENCE: 36
ctgtagtatc tggaagccta ggcccagtag natagtgttc ttattcccta tggagcgcat    60
c                                                                    61

<210> SEQ ID NO 37
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is A or G

<400> SEQUENCE: 37
atgagatatg aattagacct aaaggcctca ncatgcttca gttttgctgg tgcctagctt    60
g                                                                    61

<210> SEQ ID NO 38
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is A or G

<400> SEQUENCE: 38
cttgagtatg tgtgttccat tagagtgtat ncagagtgtg tcgctcgcac agacagattg    60
g                                                                    61

<210> SEQ ID NO 39
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
```

<223> OTHER INFORMATION: wherein "n" is A or G

<400> SEQUENCE: 39
tgtgattcga ttttgtagct acaacaagcg ntggctcaaa accaacctac acattttcag    60
t                                                                    61

<210> SEQ ID NO 40
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is A or G

<400> SEQUENCE: 40
acaaatacaa cgggatggag tgctcgtctc ntcacataat gttccctggc agtgcttcgt    60
t                                                                    61

<210> SEQ ID NO 41
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is G or A

<400> SEQUENCE: 41
gttgaccttc ttgttggtgg tgaaatcgca ntctgtgcac tggtacttct tcttgaagat    60
g                                                                    61

<210> SEQ ID NO 42
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is T or C

<400> SEQUENCE: 42
gtcttaactg caaatgtgag cttaaatcgg ntttcagctc ccatgtatta cggtattcaa    60
a                                                                    61

<210> SEQ ID NO 43
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is T or G

<400> SEQUENCE: 43
gggaatggat tgtagcagtg aaggaggaga nttattggtt tagagctaca ccaaggagca    60
c                                                                    61

<210> SEQ ID NO 44
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is G or T

<400> SEQUENCE: 44
aacagtaaat agagcctgag atgactcaaa ngtctgatac atggaggcag actcctttcc    60
a                                                                    61

<210> SEQ ID NO 45
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is G or T

<400> SEQUENCE: 45
aagaactgtc tgaccggaac cactcacaca naaaacagag aggcccgaag agatactgtt    60
g                                                                    61

<210> SEQ ID NO 46
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is T or C

<400> SEQUENCE: 46
tcgtagcatg tctgtgttcc tggtgaagaa ncttccagcg ggagtgacgg tggagaacct    60
g                                                                    61

<210> SEQ ID NO 47
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is C or T

<400> SEQUENCE: 47
tcacaaaata tgtatacaag tgtaaccatg ntggttttgt ggtaatatgt catgtgtatc    60
t                                                                    61

<210> SEQ ID NO 48
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is C or A

<400> SEQUENCE: 48
cggtaaagcc aatgggagcg tccttaacct naatcagccg ggctacaatc accacaacct    60
c                                                                    61

<210> SEQ ID NO 49
<211> LENGTH: 61
<212> TYPE: DNA
<213> ORGANISM: Oncorhynchus mykiss
<220> FEATURE:

<221> NAME/KEY: misc_feature
<222> LOCATION: (31)..(31)
<223> OTHER INFORMATION: wherein "n" is G or A

<400> SEQUENCE: 49
atattagtaa tctcaagcca tattcataca nttttgttga ataggaaata cgtcatataa    60
t                                                                   61

<210> SEQ ID NO 50
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is T or C

<400> SEQUENCE: 50
gaatggacaa tgaagtggta ttcatttcta ngggatatt cacggttcta aaataatga    60
c                                                                   61

<210> SEQ ID NO 51
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is G or T

<400> SEQUENCE: 51
tctgtcaacg gtcttccaaa acagtatgac ngaatcaaca gcagggctga aactgactaa    60
c                                                                    61

<210> SEQ ID NO 52
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is G or A

<400> SEQUENCE: 52
aaagaaacac gtcacatttc taatgatcca ncaatcacac ttggaggtgt ccatatccca    60
c                                                                    61

<210> SEQ ID NO 53
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is C or T

<400> SEQUENCE: 53
tttcatggca ataaatagaa gttggagaac nctgagaatg ttggagaacc ctgagaatgc    60
t                                                                    61

<210> SEQ ID NO 54
<211> LENGTH: 61
<212> TYPE: DNA
<213> ORGANISM: Oncorhynchus mykiss

```
<220> FEATURE:
<221> NAME/KEY: misc_feature
<222> LOCATION: (31)..(31)
<223> OTHER INFORMATION: wherein "n" is C or T

<400> SEQUENCE: 54
aaagccatag ataggatata ggcctacctc ngacacagaa ctgactgagt gtcagtcaac    60
t                                                                    61

<210> SEQ ID NO 55
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is C or T

<400> SEQUENCE: 55
ctttaaagtc ccttgtccta catatagtct ntagcttgta aaaagcccac aatacagagt    60
t                                                                    61

<210> SEQ ID NO 56
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is T or G

<400> SEQUENCE: 56
attgcagtct ccattctggc tctgtatcct nttctcacgg aagccacggt gattttata     60 g                                                                    61

<210> SEQ ID NO 57
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is G or A

<400> SEQUENCE: 57
gcatggcttt ctgtggctat atttggggtt ntctcagtct ccaaaaatct ctctgaaata    60
a                                                                    61

<210> SEQ ID NO 58
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is T or C

<400> SEQUENCE: 58
catagtttat tgttgcggac aataacttgc nctcacatta aaactatagt ctctcttacg    60
t                                                                    61

<210> SEQ ID NO 59
<211> LENGTH: 61
<212> TYPE: DNA
```

<213> ORGANISM: Oncorhynchus mykiss
<220> FEATURE:
<221> NAME/KEY: misc_feature
<222> LOCATION: (31)..(31)
<223> OTHER INFORMATION: wherein "n" is T or C

<400> SEQUENCE: 59
cattttggat gcatctgaag tcatcagtcg ncgtatcaac aaagggcttt ttattgactg   60
t                                                                  61

<210> SEQ ID NO 60
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is C or A

<400> SEQUENCE: 60
aactcggtat tagggaagca agcaggacaa natgggtttg gatgcgggtg aactaacgtg   60
a                                                                  61

<210> SEQ ID NO 61
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is G or T

<400> SEQUENCE: 61
acaatgatta ccttcaaaaa ataatgaata nattatgttt ttgcatttgt aactgagctc   60
a                                                                  61

<210> SEQ ID NO 62
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is T or G

<400> SEQUENCE: 62
tctcattgac acccactgtg ctctgtaaat nacttgattg tttgaagtaa ggcatactag   60
g                                                                  61

<210> SEQ ID NO 63
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is A or G

<400> SEQUENCE: 63
gagagtggta atatcagcag cagaagcaac ncggtttcct gctgtcctta ctgtcgagag   60
a                                                                  61

<210> SEQ ID NO 64
<211> LENGTH: 61

<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is A or G

<400> SEQUENCE: 64
caccacaaac cctagacgta ttatgaatag nataaaattt agagtaggtc tcaaatttag    60
g                                                                   61

<210> SEQ ID NO 65
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is A or G

<400> SEQUENCE: 65
acaggtggtg gtaacagaat attcattaag nttgctactg gcttttcaac taattcttag    60
t                                                                   61

<210> SEQ ID NO 66
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is G or T

<400> SEQUENCE: 66
ggagcataga gcagatgatg agaaaggaga ngatgttctg attgaaccaa cccctttga    60
c                                                                   61

<210> SEQ ID NO 67
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is T or C

<400> SEQUENCE: 67
tttgctgcca atgtcatgat tgattcaatg nattcggtgc cagtttagag cttcgttact    60
c                                                                   61

<210> SEQ ID NO 68
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is G or A

<400> SEQUENCE: 68
atctcagggt tataaaggta gaaaggcact ntgggttcaa ttttggaaaa caaaaggaga    60
g                                                                   61

<210> SEQ ID NO 69

```
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is C or T

<400> SEQUENCE: 69
ttgttccaca tgcctggatg ccacacagca ntagattttc actgctgcag ataccggtat    60
g                                                                    61

<210> SEQ ID NO 70
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is C or A

<400> SEQUENCE: 70
gactgaattg aaatggtatt gaccccaaac ntgagaggga agcatcaata caaaaggcac    60
a                                                                    61

<210> SEQ ID NO 71
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is A or C

<400> SEQUENCE: 71
cgacacagct gccgttttgga ctgcagcctt naacagtttg acagttttttg gtgtttctcg    60 t                                                                    61

<210> SEQ ID NO 72
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is C or T

<400> SEQUENCE: 72
tgcggtgggt gtctttgtgg tgtttctggc ngtcctcttc ctcttcatca ataagaagct    60
g                                                                    61

<210> SEQ ID NO 73
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is G or A

<400> SEQUENCE: 73
ttgtgattaa gtagagggtc actctgagta naacagtgct tcattagact caagcctaaa    60
a                                                                    61
```

```
<210> SEQ ID NO 74
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is G or T

<400> SEQUENCE: 74
tggatcaacc atttgttcca aattccactt naatgatgta aaaggtgtcc gcctgcctgc    60
g                                                                   61

<210> SEQ ID NO 75
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is T or G

<400> SEQUENCE: 75
atgtagcatt atgtcagact ttcgtcaaaa ncagttcaaa aggaatgggt gcagtgaccc    60
t                                                                   61

<210> SEQ ID NO 76
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is A or C

<400> SEQUENCE: 76
gttccaatgg tacatttgag taaataactt ngtttttaca atattgttta tcatttagtc    60
t                                                                   61

<210> SEQ ID NO 77
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is T or G

<400> SEQUENCE: 77
agaaaacact gccagttggt taccaacccg ncccatgtcc agctcaaaaa tatgttttgt    60
c                                                                   61

<210> SEQ ID NO 78
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is T or C

<400> SEQUENCE: 78
tgttgtcatc ctcgtcagag ctgtggactt nctcctcaga gtgagcatca tccaatccat    60
g                                                                   61
```

```
<210> SEQ ID NO 79
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is G or A

<400> SEQUENCE: 79
catatactgt ttttataaac tcactgtgat ntccagcttc tgcagagcaa aaagctggtg      60
a                                                                    61

<210> SEQ ID NO 80
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is A or G

<400> SEQUENCE: 80
aaaccgtctt ttaagtgttg atgacatcag ngagagaatt cattaatgat cagaggtact      60
t                                                                    61

<210> SEQ ID NO 81
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is A or G

<400> SEQUENCE: 81
aagtcatttt ggctgtcctg acaagctttg ngttttaatt ttgaggatgc cttggaggac      60
t                                                                    61

<210> SEQ ID NO 82
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is G or T

<400> SEQUENCE: 82
ggaatgatat taaaggaatt gttgtgagtt ntaaatgtgt ttcttaatat gtgtatgtgt      60
c                                                                    61

<210> SEQ ID NO 83
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is A or T

<400> SEQUENCE: 83
cacctacgga tggtacacac aattatgaca nacttctcaa ctatcattac ctcagccgct      60
a                                                                    61
```

<210> SEQ ID NO 84
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is A or G

<400> SEQUENCE: 84
ctttctagca tagcgtcgcc cacctgcagc naagccgtca atatcctgt tcttcctcag    60 g                                                                  61

<210> SEQ ID NO 85
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is T or G

<400> SEQUENCE: 85
aaaagattaa ttgagaaata gccatggtat nctgatttat tactgacgta acggtctcct    60
c                                                                   61

<210> SEQ ID NO 86
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is A or G

<400> SEQUENCE: 86
taaggcgtag tggtgcacta atgggggaac ncgcactaca tcttggacca gagatagagg    60
g                                                                   61

<210> SEQ ID NO 87
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is C or T

<400> SEQUENCE: 87
aggtgtgact gactgactga agtgtaggtg ngagtgagta actgaataag aaggtactgt    60
a                                                                   61

<210> SEQ ID NO 88
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is G or T

<400> SEQUENCE: 88
ctgttgtgaa ggtaactcac acgtatgtat ntatgtagac aaaatactgt catgagttac    60

| | |
|---|---|
| a | 61 |

<210> SEQ ID NO 89
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: n is a, c, g, or t

<400> SEQUENCE: 89

| | |
|---|---|
| actaaaaaat acaacagaac atcttccttt ngattcttaa aaccaacaaa ctgggcttta | 60 |
| g | 61 |

<210> SEQ ID NO 90
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is A or G

<400> SEQUENCE: 90

| | |
|---|---|
| cacatgctac aatgagttac tctatgaacc naacacatta ctgtcaagta aattgtctcc | 60 |
| c | 61 |

<210> SEQ ID NO 91
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is T or C

<400> SEQUENCE: 91

| | |
|---|---|
| actggactat ttgacatgaa cctattacct nactctctct ctcccctgac ctccctacct | 60 |
| c | 61 |

<210> SEQ ID NO 92
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is T or C

<400> SEQUENCE: 92

| | |
|---|---|
| gtgtgtgcta tacgacgtcc tcagcgtagt naaggagaag aagtacatgg ccctggaccc | 60 |
| a | 61 |

<210> SEQ ID NO 93
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is C or A

<400> SEQUENCE: 93

| | |
|---|---|
| acaaatccac gttgatttga ctcgcacggc naggagtatg acgctgatag taagattatt | 60 | t                                                              61

<210> SEQ ID NO 94
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is T or C

<400> SEQUENCE: 94
aagacggtaa atcacatcaa gtttagatgt ngagtgtctg aatactgagg aagtatgtct    60
t                                                              61

<210> SEQ ID NO 95
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is A or G

<400> SEQUENCE: 95
gcatcgctgc aggtaaaatg agaaccttca ngttgttttt cattgggctc atcttcatca    60
t                                                              61

<210> SEQ ID NO 96
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is C or T

<400> SEQUENCE: 96
ccttcctcac tttctacttc gactatcgct ntctgtcaca cgctcgtgca cacagaatgc    60
a                                                              61

<210> SEQ ID NO 97
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is T or G

<400> SEQUENCE: 97
cattcaaata ggccaaaagt ttacatacac ntttttctct ttttgcaaag ctaatcgcta    60
a                                                              61

<210> SEQ ID NO 98
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is G or A

<400> SEQUENCE: 98

```
gcctagaata agcatagatg agatatcttc ntcgtctcat caaaacattt tggtattgtg    60
c                                                                    61
```

<210> SEQ ID NO 99
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is A or G

<400> SEQUENCE: 99

```
caggttgtct ttgttgagct tgatgagggc ngagtagagc tctgaggctc ggcccatgcc    60
c                                                                    61
```

<210> SEQ ID NO 100
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is G or A

<400> SEQUENCE: 100

```
ttgatgtagt ctattcctga aatacaaggg ngatgacaat ataaatcatg cagttatgtt    60
t                                                                    61
```

<210> SEQ ID NO 101
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is C or T

<400> SEQUENCE: 101

```
cagtacagac aagatttatc gatagcattt natgtatgta acaggagact gtttatattt    60
c                                                                    61
```

<210> SEQ ID NO 102
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is T or G

<400> SEQUENCE: 102

```
ctgtgctcga agctagcaat cactgataaa ncaaataaca agcttttcct gaaaaccttt    60
a                                                                    61
```

<210> SEQ ID NO 103
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: n is a, c, g, or t

<400> SEQUENCE: 103
cattaaacca ctgatgacaa caaatatgct natttcccca tgtctctgta atgtcatcct    60
c                                                                   61

<210> SEQ ID NO 104
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is G or A

<400> SEQUENCE: 104
aacatgcaag gctataactc cccagcagga nagagagggg cttttaccac tccatcaagt    60
c                                                                   61

<210> SEQ ID NO 105
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is C or T

<400> SEQUENCE: 105
aagtatgatt ccaaattgaa ctgcaggtga ngcaatgcaa ctcatttcaa gcctgcactc    60
a                                                                   61

<210> SEQ ID NO 106
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is G or A

<400> SEQUENCE: 106
gacagttgaa tttaacaggt gaacattaca nttgatattt tacattgcat catgtatgca    60
a                                                                   61

<210> SEQ ID NO 107
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is C or T

<400> SEQUENCE: 107
atatctatac tcctattagt gaaattggaa nattatctag gcctacctac aatcatggat    60
t                                                                   61

<210> SEQ ID NO 108
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is C or A -continued

<400> SEQUENCE: 108
aggcccaata cattctgaga tacagggtcc naaggtctaa actaatagt tcaaaactttt    60
c                                                                    61

<210> SEQ ID NO 109
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is C or T

<400> SEQUENCE: 109
ctcattattt cacttgaaag gttttttcccc ngtatcacct ttcagtgcac aatttaaagg    60
a                                                                    61

<210> SEQ ID NO 110
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is C or A

<400> SEQUENCE: 110
tgtatgtgtg tcttgaaagg tcaggagctt nacagaggga ctgacattca ctgagaccaa    60
c                                                                    61

<210> SEQ ID NO 111
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is C or T

<400> SEQUENCE: 111
ttcatttcaa caccaagcag cagatcagct nagaacataa acataaaaca ccacagtgac    60
c                                                                    61

<210> SEQ ID NO 112
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is C or T

<400> SEQUENCE: 112
catttgcaaa tgcacactag aaaatttgag nctggtctga cctagcccga gccctacccg    60
a                                                                    61

<210> SEQ ID NO 113
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is T or C

<400> SEQUENCE: 113
atagctacca ttttggcccc attacggaaa ngttaaggtt tatgatatct cctctagtaa    60
t                                                                   61

<210> SEQ ID NO 114
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is T or C

<400> SEQUENCE: 114
ggagaaagaa cttaaaaaga tcaagaacag naccaataat gctgggactc ccaccaaaac    60
a                                                                   61

<210> SEQ ID NO 115
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is A or G

<400> SEQUENCE: 115
ctgagactgt taaggaagag gaggtgaaaa nggaagaaaa gccccctacag ttgattaggg    60
g                                                                   61

<210> SEQ ID NO 116
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is G or A

<400> SEQUENCE: 116
tactcggtat tctctttaaa ctacttccct ntatcccctt ctggtgagct tgggacagaa    60
a                                                                   61

<210> SEQ ID NO 117
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is A or G

<400> SEQUENCE: 117
aaatcatcta aaaagcaaga tatgaaattg naaatgcatt cacatttcac agatcgtcgt    60
c                                                                   61

<210> SEQ ID NO 118
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)

<223> OTHER INFORMATION: wherein "n" is A or G

<400> SEQUENCE: 118
gttcatcaaa gctcgaattt tcctagtagc nagccgggac ttggaggtaa aactgcagtc    60
t    61

<210> SEQ ID NO 119
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is T or G

<400> SEQUENCE: 119
caattaacag aaactgagtc aattcaaaac nttagttaga gaaattgcac ataaaaacac    60
a    61

<210> SEQ ID NO 120
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is C or A

<400> SEQUENCE: 120
cctcaactct ctcccaacac aatctttttcc ncactttttc aaattggatt tattcccaag    60
t    61

<210> SEQ ID NO 121
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is A or C

<400> SEQUENCE: 121
caccaatact tggtcacctg gctgtagtgg ncaagaaaaa gcctgtttat cattgtgtct    60
t    61

<210> SEQ ID NO 122
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is C or A

<400> SEQUENCE: 122
gttgtccagc ccaaattaca gttttgtatt ntctgtgtga cgaaaagtat acaatttcga    60
t    61

<210> SEQ ID NO 123
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is G or A

<400> SEQUENCE: 123
ttctcagggt ccatcatggc gatctctgca ntgggtactc agtgggtcca gctgcatggt    60
g                                                                    61

<210> SEQ ID NO 124
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is T or G

<400> SEQUENCE: 124
catcaattcc cctgcaagac cacagaaagt natttgcctt gtattttgca aagaccaaac    60
t                                                                    61

<210> SEQ ID NO 125
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is G or T

<400> SEQUENCE: 125
ctgtttgtac tggagagcca tgtaatccta natcctgtac tatctatcct cttattgttt    60
a                                                                    61

<210> SEQ ID NO 126
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is G or A

<400> SEQUENCE: 126
ggaggtgttc tttacagggg acgaggagga ngagctgtct gagagaaagt cccagagaaa    60
t                                                                    61

<210> SEQ ID NO 127
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is A or G

<400> SEQUENCE: 127
gcccgaacgt cctgtcctct atccgcgtca nggtgttgaa ggacaaatcc aggtaagcaa    60
g                                                                    61

<210> SEQ ID NO 128
<211> LENGTH: 61
<212> TYPE: DNA
<213> ORGANISM: Oncorhynchus mykiss
<220> FEATURE:

<221> NAME/KEY: misc_feature
<222> LOCATION: (31)..(31)
<223> OTHER INFORMATION: wherein "n" is C or T

<400> SEQUENCE: 128
aggcgaatgg cagcgtcagt aaagttatgt ntctccctct caaagttcct cctctgctcg    60
t                                                                    61

<210> SEQ ID NO 129
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is C or T

<400> SEQUENCE: 129
gtctaatgaa cactgccgtg gattgtcatc ngagttgtct gttgagtcca cagtaacaca    60
a                                                                    61

<210> SEQ ID NO 130
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is G or T

<400> SEQUENCE: 130
atactctgct aaaattagaa ctgaccagtt natttttttt acatgataca tgataataat    60
g                                                                    61

<210> SEQ ID NO 131
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is T or C

<400> SEQUENCE: 131
gttgaatttg gtcatataag gaaatgtgcc ntactgcctt tcgaattttg tgaaacttaa    60
a                                                                    61

<210> SEQ ID NO 132
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is T or G

<400> SEQUENCE: 132
gatacagtct gcatttcaac aggctgcatt ntattgcacc acaccctgct gttatcagat    60
a                                                                    61

<210> SEQ ID NO 133
<211> LENGTH: 61
<212> TYPE: DNA
<213> ORGANISM: Oncorhynchus mykiss

```
<220> FEATURE:
<221> NAME/KEY: misc_feature
<222> LOCATION: (31)..(31)
<223> OTHER INFORMATION: wherein "n" is T or G

<400> SEQUENCE: 133
ggaaaatgta acaaccaaac aggacagcac ncggtctgtt gatgttacag gcagctcagc    60
t                                                                   61

<210> SEQ ID NO 134
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is A or C

<400> SEQUENCE: 134
ccatatttct tgttgttgt ttggaatagt ntcctactcg aaaaaatatg catttgtatt     60
t                                                                   61

<210> SEQ ID NO 135
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is G or A

<400> SEQUENCE: 135
gccagcgggt cggcacagcc tagtcatgcg ntcacaagcc attcagtctg gtcgcagtct    60
a                                                                   61

<210> SEQ ID NO 136
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is C or T

<400> SEQUENCE: 136
aacaaactaa tcatctctag tggagcgcac ncgcaccaca aggggggcct tatcgtcgac    60
c                                                                   61

<210> SEQ ID NO 137
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is A or G

<400> SEQUENCE: 137
aacactgccc tgcccaccac agaggacatc ncgctgttca cggatttaga ccagggcaac    60
a                                                                   61

<210> SEQ ID NO 138
<211> LENGTH: 61
<212> TYPE: DNA
```

```
<213> ORGANISM: Oncorhynchus mykiss
<220> FEATURE:
<221> NAME/KEY: misc_feature
<222> LOCATION: (31)..(31)
<223> OTHER INFORMATION: wherein "n" is C or T

<400> SEQUENCE: 138
aactttgtgt gcgttctatc cttgtttccc nectacagcc agcggtaaca tcccggccat    60
g                                                                    61

<210> SEQ ID NO 139
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is C or T

<400> SEQUENCE: 139
tcaactgaac agacagcaac tttccctcct ngttcatttc atcttcacct gcttcttctt    60
t                                                                    61

<210> SEQ ID NO 140
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is T or C

<400> SEQUENCE: 140
agtgtcgatg ccaaacccctt gaaataggt ngggaaagga atcctttcc ctctaaatat     60 c                                                                    61

<210> SEQ ID NO 141
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is G or T

<400> SEQUENCE: 141
actagtggag atgaagggga ctggtaatga naatacagtg acagtaggca gtgttgtaaa    60
t                                                                    61

<210> SEQ ID NO 142
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is A or G

<400> SEQUENCE: 142
tgtacttgtt ttattaaaac acaatgcaag ncttaaaacg aactgtactg tagatataac    60
c                                                                    61

<210> SEQ ID NO 143
<211> LENGTH: 61
```

<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is A or G

<400> SEQUENCE: 143
ccgggttctg aacgaatagg cctacataac nggacatgga ttacgatggg accgttacga    60
a                                                                   61

<210> SEQ ID NO 144
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is T or C

<400> SEQUENCE: 144
catctctttc ctccacaatg catacttggg nttatgcctt gggttggtgt atctgaagac    60
a                                                                   61

<210> SEQ ID NO 145
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is A or G

<400> SEQUENCE: 145
aatggccttt gcaacgtgtt cccagcacac nctcagctcg gggagctttc tgtggtcctc    60
c                                                                   61

<210> SEQ ID NO 146
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is T or C

<400> SEQUENCE: 146
tcattaatgt gtagtagcag ttatttagtt nataatagtg atacaacaat aatacttcat    60
t                                                                   61

<210> SEQ ID NO 147
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is A or G

<400> SEQUENCE: 147
catttcctcg tatcactagg agttcctaac ntaacagatg taagctagtg agctgtatgc    60
t                                                                   61

<210> SEQ ID NO 148

```
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is G or T

<400> SEQUENCE: 148
aaataggaca ccatacctgg ttgatttcgt ntcggttgtg tgaagtcaat gttgtaaatg    60
t                                                                   61

<210> SEQ ID NO 149
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is G or T

<400> SEQUENCE: 149
gagattctaa ttatatattt ttttagagat naattatttt ggaggtttat atactcacat    60
a                                                                   61

<210> SEQ ID NO 150
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is T or C

<400> SEQUENCE: 150
catgaatagt ggcaaaatgt ccttcaattt nggtagctag atcataaaat acatttgtac    60
t                                                                   61

<210> SEQ ID NO 151
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is C or T

<400> SEQUENCE: 151
tggtcaccag ctgcattaag tactgcagtg natctcctca gactgcacca gatatgttct    60
t                                                                   61

<210> SEQ ID NO 152
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is A or C

<400> SEQUENCE: 152
agtttattgg cgtaaacata atctagaagt nattttcata atatgcaaca attggcatgt    60
a                                                                   61
```

```
<210> SEQ ID NO 153
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is C or T

<400> SEQUENCE: 153
actcttgaga ttcggatcag cctagatgga ngattgaagc tccagtcgat gatgaatcaa    60
t                                                                   61

<210> SEQ ID NO 154
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is C or A

<400> SEQUENCE: 154
attttcccta aattttgaa gaaattgttt ntttagctcc taattataca cccaggtgta    60
g                                                                   61

<210> SEQ ID NO 155
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is A or C

<400> SEQUENCE: 155
gccgatggaa acaaggttat ggttagtgac natacacagc gtacccagtc taatccaaag    60
a                                                                   61

<210> SEQ ID NO 156
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is A or G

<400> SEQUENCE: 156
gaacggcctg aacaccatgg acctcaacac ngagttcact gtggctcgcc tggaagcaat    60
a                                                                   61

<210> SEQ ID NO 157
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is A or G

<400> SEQUENCE: 157
ctaaggagga aatggagctt gtcttgctaa ngtcaatggt gatgtcaatg tctccctctc    60
a                                                                   61
```

<210> SEQ ID NO 158
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is G or T

<400> SEQUENCE: 158
gatcttgtac gctgtctgtg ggctccctga naataattg taagaagcct actgatgcca      60
t                                                                     61

<210> SEQ ID NO 159
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is C or T

<400> SEQUENCE: 159
tctgcgtcat tccatccctg ccatcacact nctgctacac tgcattctgc gtgtggtgta      60
t                                                                     61

<210> SEQ ID NO 160
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is C or T

<400> SEQUENCE: 160
aaaaactgcg tgtttatcaa attagaaatt nacaaccata aagttttgcg ttgacaaaaa      60
a                                                                     61

<210> SEQ ID NO 161
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is C or T

<400> SEQUENCE: 161
ctttgagctg gatccagtca agaagaaggc naaagagagg atggtgaagt ccaccagcag      60
c                                                                     61

<210> SEQ ID NO 162
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is C or T

<400> SEQUENCE: 162
aaagctgctt ccagctgatg gtgtagtcta nggacaggtt cgttacccat ccacatctct      60
c                                                                     61

```
<210> SEQ ID NO 163
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is T or G

<400> SEQUENCE: 163
agaataaatg caatcttaat gtgaatttat ntatgtttag aaactgctta ctaataggta    60
a                                                                    61

<210> SEQ ID NO 164
<211> LENGTH: 61
<212> TYPE: DNA
<213> ORGANISM: Oncorhynchus mykiss
<220> FEATURE:
<221> NAME/KEY: misc_feature
<222> LOCATION: (31)..(31)
<223> OTHER INFORMATION: wherein "n" is T or C

<400> SEQUENCE: 164
ctgaatcaaa tgctctcact tgccagactt ngaggttgac agtgcagcaa tgacaaatac    60
a                                                                    61

<210> SEQ ID NO 165
<211> LENGTH: 61
<212> TYPE: DNA
<213> ORGANISM: Oncorhynchus mykiss

<400> SEQUENCE: 165
agtatatgat gattcaatga gatacagtac tttacacttt attgcccatt tccatgaaaa    60
t                                                                    61

<210> SEQ ID NO 166
<211> LENGTH: 61
<212> TYPE: DNA
<213> ORGANISM: Oncorhynchus mykiss

<400> SEQUENCE: 166
tcagtccata agtaatgcaa agatcaaagt aattctacag aaaccgattg ggcagactaa    60
c                                                                    61

<210> SEQ ID NO 167
<211> LENGTH: 61
<212> TYPE: DNA
<213> ORGANISM: Oncorhynchus mykiss

<400> SEQUENCE: 167
agtacaaaca gagatgtgtt atgttagaca gctgaagtga accgctacac ctgcttggtg    60
c                                                                    61

<210> SEQ ID NO 168
<211> LENGTH: 61
<212> TYPE: DNA
<213> ORGANISM: Oncorhynchus mykiss

<400> SEQUENCE: 168
gagtgcagtg gatagagaca gctcctcagt acataaaggc ccacctgtcc tgggggaaga    60
```

-continued

| | |
|---|---|
| t | 61 |

<210> SEQ ID NO 169
<211> LENGTH: 61
<212> TYPE: DNA
<213> ORGANISM: Oncorhynchus mykiss

<400> SEQUENCE: 169

| | |
|---|---|
| tactataatc ggggacagtg acatgcatcg acccacaaag tttttaagac tgcagttatg | 60 |
| t | 61 |

<210> SEQ ID NO 170
<211> LENGTH: 61
<212> TYPE: DNA
<213> ORGANISM: Oncorhynchus mykiss

<400> SEQUENCE: 170

| | |
|---|---|
| ggaaccagtc actgtctcac tacattttca cgtggcagtt ttgtcttcca ccgtgcaagc | 60 |
| c | 61 |

<210> SEQ ID NO 171
<211> LENGTH: 61
<212> TYPE: DNA
<213> ORGANISM: Oncorhynchus mykiss

<400> SEQUENCE: 171

| | |
|---|---|
| ttggttcttg caactctata gctctgggtc cttcccttac ctcggcacgg cagccagtca | 60 |
| g | 61 |

<210> SEQ ID NO 172
<211> LENGTH: 61
<212> TYPE: DNA
<213> ORGANISM: Oncorhynchus mykiss

<400> SEQUENCE: 172

| | |
|---|---|
| ctgtataaag ttgttactgc aggtacaggc agtgatgctg agactcttct gccaagacac | 60 |
| c | 61 |

<210> SEQ ID NO 173
<211> LENGTH: 61
<212> TYPE: DNA
<213> ORGANISM: Oncorhynchus mykiss

<400> SEQUENCE: 173

| | |
|---|---|
| atcgtactga gcttgttgtc attgcaggca atctcaactc tgtgcattac actgaagact | 60 |
| t | 61 |

<210> SEQ ID NO 174
<211> LENGTH: 61
<212> TYPE: DNA
<213> ORGANISM: Oncorhynchus mykiss

<400> SEQUENCE: 174

| | |
|---|---|
| agacagatca tcaaaagctt ttattctgat caagttcagt agtttgttta ggacactgaa | 60 |
| a | 61 |

<210> SEQ ID NO 175
<211> LENGTH: 61
<212> TYPE: DNA
<213> ORGANISM: Oncorhynchus mykiss

```
<400> SEQUENCE: 175
tgacctgcag ctatgcacca taatctagca ggttcatttg aacacccttt gaaaaggtaa    60
t                                                                   61

<210> SEQ ID NO 176
<211> LENGTH: 61
<212> TYPE: DNA
<213> ORGANISM: Oncorhynchus mykiss

<400> SEQUENCE: 176
tctatactac ggtctattgc ctatttttaa tgtatcttta atttcgtatc ccagttatta    60
g                                                                   61

<210> SEQ ID NO 177
<211> LENGTH: 61
<212> TYPE: DNA
<213> ORGANISM: Oncorhynchus mykiss

<400> SEQUENCE: 177
ttaccatact aacttgtagg gctgagcaat atattttgaa tacaggcaca gagccacata    60
c                                                                   61

<210> SEQ ID NO 178
<211> LENGTH: 61
<212> TYPE: DNA
<213> ORGANISM: Oncorhynchus mykiss

<400> SEQUENCE: 178
ctacactaaa atgcaatttg atctggacag attgtctgtt atgctattgc agtgttatga    60
c                                                                   61

<210> SEQ ID NO 179
<211> LENGTH: 61
<212> TYPE: DNA
<213> ORGANISM: Oncorhynchus mykiss

<400> SEQUENCE: 179
cactacctga tgcagtccca gtttgtgatt gttatctgca gaaactcaaa tataaattcc    60
a                                                                   61

<210> SEQ ID NO 180
<211> LENGTH: 61
<212> TYPE: DNA
<213> ORGANISM: Oncorhynchus mykiss

<400> SEQUENCE: 180
gacgctgctg ttcctgctgc tgccaccaca accatttcct ctcgtcatga gcaaaagcta    60
t                                                                   61

<210> SEQ ID NO 181
<211> LENGTH: 61
<212> TYPE: DNA
<213> ORGANISM: Oncorhynchus mykiss

<400> SEQUENCE: 181
aggtaccctg cactacattc ctagcgcgac cagaggatgg tatagaaaat gtaatggtat    60
a                                                                   61
```

<210> SEQ ID NO 182
<211> LENGTH: 61
<212> TYPE: DNA
<213> ORGANISM: Oncorhynchus mykiss

<400> SEQUENCE: 182
tctctgagtg agatcaagaa cggttcggtt gtctacgact gttggggcca cttcatagaa    60
c                                                                   61

<210> SEQ ID NO 183
<211> LENGTH: 61
<212> TYPE: DNA
<213> ORGANISM: Oncorhynchus mykiss

<400> SEQUENCE: 183
tgcagatatg aacagcttga gtaaaaagat tatgttaccc actgaacatc aatgaacaaa    60
t                                                                   61

<210> SEQ ID NO 184
<211> LENGTH: 61
<212> TYPE: DNA
<213> ORGANISM: Oncorhynchus mykiss

<400> SEQUENCE: 184
caaagggact tatcttctcc caaaagacaa cgggccgatc atttaacgaa tcttctcttg    60
a                                                                   61

<210> SEQ ID NO 185
<211> LENGTH: 61
<212> TYPE: DNA
<213> ORGANISM: Oncorhynchus mykiss

<400> SEQUENCE: 185
ctgcgacatg ttttgagtta gcgtaatttc atactaaaga ttggagaagt gtgcctaatt    60
a                                                                   61

<210> SEQ ID NO 186
<211> LENGTH: 61
<212> TYPE: DNA
<213> ORGANISM: Oncorhynchus mykiss

<400> SEQUENCE: 186
ttcgccttca ccctgagtta ggacggctcc aagccccata tttgaggcgt ctacctgcac    60
a                                                                   61

<210> SEQ ID NO 187
<211> LENGTH: 61
<212> TYPE: DNA
<213> ORGANISM: Oncorhynchus mykiss

<400> SEQUENCE: 187
aattgactaa caatattgtc taacaagtgc agtataaata aatccatcct tctcatcctc    60
c                                                                   61

<210> SEQ ID NO 188
<211> LENGTH: 61
<212> TYPE: DNA
<213> ORGANISM: Oncorhynchus mykiss

<400> SEQUENCE: 188

```
gtatggtttt gaagagtaca actgtgtgag ggtggattga acaaaatagt atcttaaaca    60
c                                                                   61

<210> SEQ ID NO 189
<211> LENGTH: 61
<212> TYPE: DNA
<213> ORGANISM: Oncorhynchus mykiss

<400> SEQUENCE: 189
taaacagcag ttgaacgagc tgggcagcga gtcggccaag atcaaggcca tgggcatcac    60
c                                                                   61

<210> SEQ ID NO 190
<211> LENGTH: 61
<212> TYPE: DNA
<213> ORGANISM: Oncorhynchus mykiss

<400> SEQUENCE: 190
gatgcgtccc tccaacacag tgcatctgct ggttttgtgt gaggaccaca gagccggcat    60
g                                                                   61

<210> SEQ ID NO 191
<211> LENGTH: 61
<212> TYPE: DNA
<213> ORGANISM: Oncorhynchus mykiss

<400> SEQUENCE: 191
gtgcggcagg cggcagtggt ggacaacttc atgtcccagc aagagaagaa gcagaaacac    60
c                                                                   61

<210> SEQ ID NO 192
<211> LENGTH: 61
<212> TYPE: DNA
<213> ORGANISM: Oncorhynchus mykiss

<400> SEQUENCE: 192
gcctgcagat gttcctcacg tgatgtgatg accttttaac tgggcgtcct ttgaatataa    60
g                                                                   61

<210> SEQ ID NO 193
<211> LENGTH: 61
<212> TYPE: DNA
<213> ORGANISM: Oncorhynchus mykiss

<400> SEQUENCE: 193
acgtgccttt tgatggttat tactagaccg cttattgtac ctgccctatt gatcaaccgg    60
a                                                                   61

<210> SEQ ID NO 194
<211> LENGTH: 61
<212> TYPE: DNA
<213> ORGANISM: Oncorhynchus mykiss

<400> SEQUENCE: 194 gacatagggga cgtttccaca tgaagtgaat tggaaaagca tacacttaca tgactttcaa   60
t                                                                   61

<210> SEQ ID NO 195
```

-continued

<211> LENGTH: 61
<212> TYPE: DNA
<213> ORGANISM: Oncorhynchus mykiss

<400> SEQUENCE: 195
atcagattct ccaaaaaggt ccaggggaaa cagtttgctg cttttgttgg atattttac    60
a                                                                  61

<210> SEQ ID NO 196
<211> LENGTH: 61
<212> TYPE: DNA
<213> ORGANISM: Oncorhynchus mykiss

<400> SEQUENCE: 196
atgagtgata ttacagtttg tccttcagat gaaacaattg aggagccaac tatgtgtaat    60
c                                                                   61

<210> SEQ ID NO 197
<211> LENGTH: 61
<212> TYPE: DNA
<213> ORGANISM: Oncorhynchus mykiss

<400> SEQUENCE: 197
gcataaagtt gatacaattc acacaaagtc tttgtcgggg gactccaatc ctctgtgttt    60
c                                                                   61

<210> SEQ ID NO 198
<211> LENGTH: 61
<212> TYPE: DNA
<213> ORGANISM: Oncorhynchus mykiss

<400> SEQUENCE: 198
acacactgca gagtaaacag caaacactga aaaagctgca cccagactgg cattcacaca    60
c                                                                   61

<210> SEQ ID NO 199
<211> LENGTH: 61
<212> TYPE: DNA
<213> ORGANISM: Oncorhynchus mykiss

<400> SEQUENCE: 199
tgctctgaga aggggttct gatttctgtc tacagggggc tccctcctgc ctatccaacg     60
a                                                                   61

<210> SEQ ID NO 200
<211> LENGTH: 61
<212> TYPE: DNA
<213> ORGANISM: Oncorhynchus mykiss

<400> SEQUENCE: 200
ctgtagtatc tggaagccta ggcccagtag gatagtgttc ttattcccta tggagcgcat    60
c                                                                   61

<210> SEQ ID NO 201
<211> LENGTH: 61
<212> TYPE: DNA
<213> ORGANISM: Oncorhynchus mykiss

<400> SEQUENCE: 201
atgagatatg aattagacct aaaggcctca acatgcttca gttttgctgg tgcctagctt    60
g 61

<210> SEQ ID NO 202
<211> LENGTH: 61
<212> TYPE: DNA
<213> ORGANISM: Oncorhynchus mykiss

<400> SEQUENCE: 202
cttgagtatg tgtgttccat tagagtgtat acagagtgtg tcgctcgcac agacagattg    60
g                                                                    61

<210> SEQ ID NO 203
<211> LENGTH: 61
<212> TYPE: DNA
<213> ORGANISM: Oncorhynchus mykiss

<400> SEQUENCE: 203
tgtgattcga ttttgtagct acaacaagcg atggctcaaa accaacctac acattttcag    60
t                                                                    61

<210> SEQ ID NO 204
<211> LENGTH: 61
<212> TYPE: DNA
<213> ORGANISM: Oncorhynchus mykiss

<400> SEQUENCE: 204
acaaatacaa cgggatggag tgctcgtctc atcacataat gttccctggc agtgcttcgt    60
t                                                                    61

<210> SEQ ID NO 205
<211> LENGTH: 61
<212> TYPE: DNA
<213> ORGANISM: Oncorhynchus mykiss

<400> SEQUENCE: 205
gttgaccttc ttgttggtgg tgaaatcgca gtctgtgcac tggtacttct tcttgaagat    60
g                                                                    61

<210> SEQ ID NO 206
<211> LENGTH: 61
<212> TYPE: DNA
<213> ORGANISM: Oncorhynchus mykiss

<400> SEQUENCE: 206
gtcttaactg caaatgtgag cttaaatcgg ttttcagctc ccatgtatta cggtattcaa    60
a                                                                    61

<210> SEQ ID NO 207
<211> LENGTH: 61
<212> TYPE: DNA
<213> ORGANISM: Oncorhynchus mykiss

<400> SEQUENCE: 207
gggaatggat tgtagcagtg aaggaggaga tttattggtt tagagctaca ccaaggagca    60
c                                                                    61

<210> SEQ ID NO 208
<211> LENGTH: 61
<212> TYPE: DNA

<213> ORGANISM: Oncorhynchus mykiss

<400> SEQUENCE: 208
aacagtaaat agagcctgag atgactcaaa ggtctgatac atggaggcag actcctttcc      60
a                                                                    61

<210> SEQ ID NO 209
<211> LENGTH: 61
<212> TYPE: DNA
<213> ORGANISM: Oncorhynchus mykiss

<400> SEQUENCE: 209
aagaactgtc tgaccggaac cactcacaca gaaaacagag aggcccgaag agatactgtt      60
g                                                                    61

<210> SEQ ID NO 210
<211> LENGTH: 61
<212> TYPE: DNA
<213> ORGANISM: Oncorhynchus mykiss

<400> SEQUENCE: 210
tcgtagcatg tctgtgttcc tggtgaagaa tcttccagcg ggagtgacgg tggagaacct      60
g                                                                    61

<210> SEQ ID NO 211
<211> LENGTH: 61
<212> TYPE: DNA
<213> ORGANISM: Oncorhynchus mykiss

<400> SEQUENCE: 211
tcacaaaata tgtatacaag tgtaaccatg ctggttttgt ggtaatatgt catgtgtatc      60
t                                                                    61

<210> SEQ ID NO 212
<211> LENGTH: 61
<212> TYPE: DNA
<213> ORGANISM: Oncorhynchus mykiss

<400> SEQUENCE: 212
cggtaaagcc aatgggagcg tccttaacct caatcagccg ggctacaatc accacaacct      60
c                                                                    61

<210> SEQ ID NO 213
<211> LENGTH: 61
<212> TYPE: DNA
<213> ORGANISM: Oncorhynchus mykiss

<400> SEQUENCE: 213
atattagtaa tctcaagcca tattcataca gttttgttga ataggaaata cgtcatataa      60
t                                                                    61

<210> SEQ ID NO 214
<211> LENGTH: 61
<212> TYPE: DNA
<213> ORGANISM: Oncorhynchus mykiss

<400> SEQUENCE: 214
gaatggacaa tgaagtggta ttcatttcta tggggatatt cacggttcta aaaataatga      60
c                                                                    61

<210> SEQ ID NO 215
<211> LENGTH: 61
<212> TYPE: DNA
<213> ORGANISM: Oncorhynchus mykiss

<400> SEQUENCE: 215
tctgtcaacg gtcttccaaa acagtatgac ggaatcaaca gcagggctga aactgactaa    60
c                                                                    61

<210> SEQ ID NO 216
<211> LENGTH: 61
<212> TYPE: DNA
<213> ORGANISM: Oncorhynchus mykiss

<400> SEQUENCE: 216
aaagaaacac gtcacatttc taatgatcca gcaatcacac ttggaggtgt ccatatccca    60
c                                                                    61

<210> SEQ ID NO 217
<211> LENGTH: 61
<212> TYPE: DNA
<213> ORGANISM: Oncorhynchus mykiss

<400> SEQUENCE: 217
tttcatggca ataaatagaa gttggagaac cctgagaatg ttggagaacc ctgagaatgc    60
t                                                                    61

<210> SEQ ID NO 218
<211> LENGTH: 61
<212> TYPE: DNA
<213> ORGANISM: Oncorhynchus mykiss

<400> SEQUENCE: 218
aaagccatag ataggatata ggcctacctc cgacacagaa ctgactgagt gtcagtcaac    60
t                                                                    61

<210> SEQ ID NO 219
<211> LENGTH: 61
<212> TYPE: DNA
<213> ORGANISM: Oncorhynchus mykiss

<400> SEQUENCE: 219
ctttaaagtc ccttgtccta catatagtct ctagcttgta aaaagcccac aatacagagt    60
t                                                                    61

<210> SEQ ID NO 220
<211> LENGTH: 61
<212> TYPE: DNA
<213> ORGANISM: Oncorhynchus mykiss

<400> SEQUENCE: 220
attgcagtct ccattctggc tctgtatcct tttctcacgg aagccacggt gatttttata    60
g                                                                    61

<210> SEQ ID NO 221
<211> LENGTH: 61
<212> TYPE: DNA
<213> ORGANISM: Oncorhynchus mykiss

```
<400> SEQUENCE: 221
gcatggcttt ctgtggctat atttgggstt gtctcagtct ccaaaaatct ctctgaaata    60
a                                                                    61

<210> SEQ ID NO 222
<211> LENGTH: 61
<212> TYPE: DNA
<213> ORGANISM: Oncorhynchus mykiss

<400> SEQUENCE: 222
catagtttat tgttgcggac aataacttgc tctcacatta aaactatagt ctctcttacg    60
t                                                                    61

<210> SEQ ID NO 223
<211> LENGTH: 61
<212> TYPE: DNA
<213> ORGANISM: Oncorhynchus mykiss

<400> SEQUENCE: 223
cattttggat gcatctgaag tcatcagtcg tcgtatcaac aaagggcttt ttattgactg    60
t                                                                    61

<210> SEQ ID NO 224
<211> LENGTH: 61
<212> TYPE: DNA
<213> ORGANISM: Oncorhynchus mykiss

<400> SEQUENCE: 224
aactcggtat tagggaagca agcaggacaa catgggtttg gatgcgggtg aactaacgtg    60
a                                                                    61

<210> SEQ ID NO 225
<211> LENGTH: 61
<212> TYPE: DNA
<213> ORGANISM: Oncorhynchus mykiss

<400> SEQUENCE: 225
acaatgatta ccttcaaaaa ataatgaata gattatgttt ttgcatttgt aactgagctc    60
a                                                                    61

<210> SEQ ID NO 226
<211> LENGTH: 61
<212> TYPE: DNA
<213> ORGANISM: Oncorhynchus mykiss

<400> SEQUENCE: 226
tctcattgac acccactgtg ctctgtaaat tacttgattg tttgaagtaa ggcatactag    60
g                                                                    61

<210> SEQ ID NO 227
<211> LENGTH: 61
<212> TYPE: DNA
<213> ORGANISM: Oncorhynchus mykiss

<400> SEQUENCE: 227
gagagtggta atatcagcag cagaagcaac acggtttcct gctgtcctta ctgtcgagag    60
a                                                                    61
```

```
<210> SEQ ID NO 228
<211> LENGTH: 61
<212> TYPE: DNA
<213> ORGANISM: Oncorhynchus mykiss

<400> SEQUENCE: 228
caccacaaac cctagacgta ttatgaatag aataaaattt agagtaggtc tcaaatttag    60
g                                                                   61

<210> SEQ ID NO 229
<211> LENGTH: 61
<212> TYPE: DNA
<213> ORGANISM: Oncorhynchus mykiss

<400> SEQUENCE: 229
acaggtggtg gtaacagaat attcattaag attgctactg gcttttcaac taattcttag    60
t                                                                   61

<210> SEQ ID NO 230
<211> LENGTH: 61
<212> TYPE: DNA
<213> ORGANISM: Oncorhynchus mykiss

<400> SEQUENCE: 230
ggagcataga gcagatgatg agaaaggaga ggatgttctg attgaaccaa cccctttga     60
c                                                                   61

<210> SEQ ID NO 231
<211> LENGTH: 61
<212> TYPE: DNA
<213> ORGANISM: Oncorhynchus mykiss

<400> SEQUENCE: 231
tttgctgcca atgtcatgat tgattcaatg tattcggtgc cagtttagag cttcgttact    60
c                                                                   61

<210> SEQ ID NO 232
<211> LENGTH: 61
<212> TYPE: DNA
<213> ORGANISM: Oncorhynchus mykiss

<400> SEQUENCE: 232
atctcagggt tataaaggta gaaaggcact gtgggttcaa ttttggaaaa caaaaggaga    60
g                                                                   61

<210> SEQ ID NO 233
<211> LENGTH: 61
<212> TYPE: DNA
<213> ORGANISM: Oncorhynchus mykiss

<400> SEQUENCE: 233
ttgttccaca tgcctggatg ccacacagca ctagattttc actgctgcag ataccggtat    60
g                                                                   61

<210> SEQ ID NO 234
<211> LENGTH: 61
<212> TYPE: DNA
<213> ORGANISM: Oncorhynchus mykiss

<400> SEQUENCE: 234
```

```
gactgaattg aaatggtatt daccccaaac ctgagaggga agcatcaata caaaaggcac    60
a                                                                   61
```

<210> SEQ ID NO 235
<211> LENGTH: 61
<212> TYPE: DNA
<213> ORGANISM: Oncorhynchus mykiss

<400> SEQUENCE: 235

```
cgacacagct gccgtttgga ctgcagcctt aaacagtttg acagttttg gtgtttctcg    60
t                                                                   61
```

<210> SEQ ID NO 236
<211> LENGTH: 61
<212> TYPE: DNA
<213> ORGANISM: Oncorhynchus mykiss

<400> SEQUENCE: 236

```
tgcggtgggt gtctttgtgg tgtttctggc cgtcctcttc ctcttcatca ataagaagct    60
g                                                                   61
```

<210> SEQ ID NO 237
<211> LENGTH: 61
<212> TYPE: DNA
<213> ORGANISM: Oncorhynchus mykiss

<400> SEQUENCE: 237

```
ttgtgattaa gtagagggtc actctgagta gaacagtgct tcattagact caagcctaaa    60
a                                                                   61
```

<210> SEQ ID NO 238
<211> LENGTH: 61
<212> TYPE: DNA
<213> ORGANISM: Oncorhynchus mykiss

<400> SEQUENCE: 238

```
tggatcaacc atttgttcca aattccactt gaatgatgta aaaggtgtcc gcctgcctgc    60
g                                                                   61
```

<210> SEQ ID NO 239
<211> LENGTH: 61
<212> TYPE: DNA
<213> ORGANISM: Oncorhynchus mykiss

<400> SEQUENCE: 239

```
atgtagcatt atgtcagact ttcgtcaaaa tcagttcaaa aggaatgggt gcagtgaccc    60
t                                                                   61
```

<210> SEQ ID NO 240
<211> LENGTH: 61
<212> TYPE: DNA
<213> ORGANISM: Oncorhynchus mykiss

<400> SEQUENCE: 240

```
gttccaatgg tacatttgag taaataactt agttttaca atattgttta tcatttagtc    60
t                                                                   61
```

<210> SEQ ID NO 241
<211> LENGTH: 61

```
<212> TYPE: DNA
<213> ORGANISM: Oncorhynchus mykiss

<400> SEQUENCE: 241
agaaaacact gccagttggt taccaacccg tcccatgtcc agctcaaaaa tatgttttgt    60
c                                                                   61

<210> SEQ ID NO 242
<211> LENGTH: 61
<212> TYPE: DNA
<213> ORGANISM: Oncorhynchus mykiss

<400> SEQUENCE: 242
tgttgtcatc ctcgtcagag ctgtggactt tctcctcaga gtgagcatca tccaatccat    60
g                                                                   61

<210> SEQ ID NO 243
<211> LENGTH: 61
<212> TYPE: DNA
<213> ORGANISM: Oncorhynchus mykiss

<400> SEQUENCE: 243
catatactgt ttttataaac tcactgtgat gtccagcttc tgcagagcaa aaagctggtg    60
a                                                                   61

<210> SEQ ID NO 244
<211> LENGTH: 61
<212> TYPE: DNA
<213> ORGANISM: Oncorhynchus mykiss

<400> SEQUENCE: 244
aaaccgtctt ttaagtgttg atgacatcag agagagaatt cattaatgat cagaggtact    60
t                                                                   61

<210> SEQ ID NO 245
<211> LENGTH: 61
<212> TYPE: DNA
<213> ORGANISM: Oncorhynchus mykiss

<400> SEQUENCE: 245
aagtcatttt ggctgtcctg acaagctttg agttttaatt ttgaggatgc cttggaggac    60
t                                                                   61

<210> SEQ ID NO 246
<211> LENGTH: 61
<212> TYPE: DNA
<213> ORGANISM: Oncorhynchus mykiss

<400> SEQUENCE: 246
ggaatgatat taaaggaatt gttgtgagtt gtaaatgtgt ttcttaatat gtgtatgtgt    60
c                                                                   61

<210> SEQ ID NO 247
<211> LENGTH: 61
<212> TYPE: DNA
<213> ORGANISM: Oncorhynchus mykiss

<400> SEQUENCE: 247
cacctacgga tggtacacac aattatgaca aacttctcaa ctatcattac ctcagccgct    60
```

```
a                                                              61

<210> SEQ ID NO 248
<211> LENGTH: 61
<212> TYPE: DNA
<213> ORGANISM: Oncorhynchus mykiss

<400> SEQUENCE: 248
ctttctagca tagcgtcgcc cacctgcagc aaagccgtca aatatcctgt tcttcctcag    60
g                                                              61

<210> SEQ ID NO 249
<211> LENGTH: 61
<212> TYPE: DNA
<213> ORGANISM: Oncorhynchus mykiss

<400> SEQUENCE: 249
aaaagattaa ttgagaaata gccatggtat tctgatttat tactgacgta acggtctcct    60
c                                                              61

<210> SEQ ID NO 250
<211> LENGTH: 61
<212> TYPE: DNA
<213> ORGANISM: Oncorhynchus mykiss

<400> SEQUENCE: 250
taaggcgtag tggtgcacta atgggggaac acgcactaca tcttggacca gagatagagg    60
g                                                              61

<210> SEQ ID NO 251
<211> LENGTH: 61
<212> TYPE: DNA
<213> ORGANISM: Oncorhynchus mykiss

<400> SEQUENCE: 251
aggtgtgact gactgactga agtgtaggtg cgagtgagta actgaataag aaggtactgt    60
a                                                              61

<210> SEQ ID NO 252
<211> LENGTH: 61
<212> TYPE: DNA
<213> ORGANISM: Oncorhynchus mykiss

<400> SEQUENCE: 252
ctgttgtgaa ggtaactcac acgtatgtat gtatgtagac aaaatactgt catgagttac    60
a                                                              61

<210> SEQ ID NO 253
<211> LENGTH: 61
<212> TYPE: DNA
<213> ORGANISM: Oncorhynchus mykiss

<400> SEQUENCE: 253
actaaaaaat acaacagaac atcttccttt agattcttaa aaccaacaaa ctgggcttta    60
g                                                              61

<210> SEQ ID NO 254
<211> LENGTH: 61
<212> TYPE: DNA
<213> ORGANISM: Oncorhynchus mykiss
```

```
<400> SEQUENCE: 254
cacatgctac aatgagttac tctatgaacc aaacacatta ctgtcaagta aattgtctcc      60
c                                                                     61

<210> SEQ ID NO 255
<211> LENGTH: 61
<212> TYPE: DNA
<213> ORGANISM: Oncorhynchus mykiss

<400> SEQUENCE: 255
actggactat ttgacatgaa cctattacct tactctctct ctccctgac ctccctacct      60 c                                                                     61

<210> SEQ ID NO 256
<211> LENGTH: 61
<212> TYPE: DNA
<213> ORGANISM: Oncorhynchus mykiss

<400> SEQUENCE: 256
gtgtgtgcta tacgacgtcc tcagcgtagt taaggagaag aagtacatgg ccctggaccc      60
a                                                                     61

<210> SEQ ID NO 257
<211> LENGTH: 61
<212> TYPE: DNA
<213> ORGANISM: Oncorhynchus mykiss

<400> SEQUENCE: 257
acaaatccac gttgatttga ctcgcacggc caggagtatg acgctgatag taagattatt      60
t                                                                     61

<210> SEQ ID NO 258
<211> LENGTH: 61
<212> TYPE: DNA
<213> ORGANISM: Oncorhynchus mykiss

<400> SEQUENCE: 258
aagacggtaa atcacatcaa gtttagatgt tgagtgtctg aatactgagg aagtatgtct      60
t                                                                     61

<210> SEQ ID NO 259
<211> LENGTH: 61
<212> TYPE: DNA
<213> ORGANISM: Oncorhynchus mykiss

<400> SEQUENCE: 259
gcatcgctgc aggtaaaatg agaaccttca agttgttttt cattgggctc atcttcatca      60
t                                                                     61

<210> SEQ ID NO 260
<211> LENGTH: 61
<212> TYPE: DNA
<213> ORGANISM: Oncorhynchus mykiss

<400> SEQUENCE: 260
ccttcctcac tttctacttc gactatcgct ctctgtcaca cgctcgtgca cacagaatgc      60
a                                                                     61
```

```
<210> SEQ ID NO 261
<211> LENGTH: 61
<212> TYPE: DNA
<213> ORGANISM: Oncorhynchus mykiss

<400> SEQUENCE: 261
cattcaaata ggccaaaagt ttacatacac ttttttctct ttttgcaaag ctaatcgcta      60
a                                                                     61

<210> SEQ ID NO 262
<211> LENGTH: 61
<212> TYPE: DNA
<213> ORGANISM: Oncorhynchus mykiss

<400> SEQUENCE: 262
gcctagaata agcatagatg agatatcttc gtcgtctcat caaaacattt tggtattgtg      60
c                                                                     61

<210> SEQ ID NO 263
<211> LENGTH: 61
<212> TYPE: DNA
<213> ORGANISM: Oncorhynchus mykiss

<400> SEQUENCE: 263
caggttgtct tgttgagct tgatgagggc agagtagagc tctgaggctc ggcccatgcc       60
c                                                                     61

<210> SEQ ID NO 264
<211> LENGTH: 61
<212> TYPE: DNA
<213> ORGANISM: Oncorhynchus mykiss

<400> SEQUENCE: 264
ttgatgtagt ctattcctga aatacaaggg ggatgacaat ataaatcatg cagttatgtt      60
t                                                                     61

<210> SEQ ID NO 265
<211> LENGTH: 61
<212> TYPE: DNA
<213> ORGANISM: Oncorhynchus mykiss

<400> SEQUENCE: 265
cagtacagac aagatttatc gatagcattt catgtatgta acaggagact gtttatattt      60
c                                                                     61

<210> SEQ ID NO 266
<211> LENGTH: 61
<212> TYPE: DNA
<213> ORGANISM: Oncorhynchus mykiss

<400> SEQUENCE: 266
ctgtgctcga agctagcaat cactgataaa tcaaataaca agctttttct gaaaaccttt      60
a                                                                     61

<210> SEQ ID NO 267
<211> LENGTH: 61
<212> TYPE: DNA
<213> ORGANISM: Oncorhynchus mykiss

<400> SEQUENCE: 267
```

```
cattaaacca ctgatgacaa caaatatgct aatttcccca tgtctctgta atgtcatcct    60
c                                                                   61
```

<210> SEQ ID NO 268
<211> LENGTH: 61
<212> TYPE: DNA
<213> ORGANISM: Oncorhynchus mykiss

<400> SEQUENCE: 268

```
aacatgcaag gctataactc cccagcagga gagagagggg cttttaccac tccatcaagt    60
c                                                                   61
```

<210> SEQ ID NO 269
<211> LENGTH: 61
<212> TYPE: DNA
<213> ORGANISM: Oncorhynchus mykiss

<400> SEQUENCE: 269

```
aagtatgatt ccaaattgaa ctgcaggtga cgcaatgcaa ctcatttcaa gcctgcactc    60
a                                                                   61
```

<210> SEQ ID NO 270
<211> LENGTH: 61
<212> TYPE: DNA
<213> ORGANISM: Oncorhynchus mykiss

<400> SEQUENCE: 270

```
gacagttgaa tttaacaggt gaacattaca gttgatattt tacattgcat catgtatgca    60
a                                                                   61
```

<210> SEQ ID NO 271
<211> LENGTH: 61
<212> TYPE: DNA
<213> ORGANISM: Oncorhynchus mykiss

<400> SEQUENCE: 271

```
atatctatac tcctattagt gaaattggaa cattatctag gcctacctac aatcatggat    60
t                                                                   61
```

<210> SEQ ID NO 272
<211> LENGTH: 61
<212> TYPE: DNA
<213> ORGANISM: Oncorhynchus mykiss

<400> SEQUENCE: 272

```
aggcccaata cattctgaga tacagggtcc caaggtctaa aactaatagt tcaaaacttt    60
c                                                                   61
```

<210> SEQ ID NO 273
<211> LENGTH: 61
<212> TYPE: DNA
<213> ORGANISM: Oncorhynchus mykiss

<400> SEQUENCE: 273

```
ctcattattt cacttgaaag gttttttcccc cgtatcacct ttcagtgcac aatttaaagg    60
a                                                                   61
```

<210> SEQ ID NO 274

```
<211> LENGTH: 61
<212> TYPE: DNA
<213> ORGANISM: Oncorhynchus mykiss

<400> SEQUENCE: 274
tgtatgtgtg tcttgaaagg tcaggagctt cacagaggga ctgacattca ctgagaccaa    60
c                                                                    61

<210> SEQ ID NO 275
<211> LENGTH: 61
<212> TYPE: DNA
<213> ORGANISM: Oncorhynchus mykiss

<400> SEQUENCE: 275
ttcatttcaa caccaagcag cagatcagct cagaacataa acataaaaca ccacagtgac    60
c                                                                    61

<210> SEQ ID NO 276
<211> LENGTH: 61
<212> TYPE: DNA
<213> ORGANISM: Oncorhynchus mykiss

<400> SEQUENCE: 276
catttgcaaa tgcacactag aaaatttgag cctggtctga cctagcccga gccctacccg    60
a                                                                    61

<210> SEQ ID NO 277
<211> LENGTH: 61
<212> TYPE: DNA
<213> ORGANISM: Oncorhynchus mykiss

<400> SEQUENCE: 277
atagctacca ttttggcccc attacggaaa tgttaaggtt tatgatatct cctctagtaa    60
t                                                                    61

<210> SEQ ID NO 278
<211> LENGTH: 61
<212> TYPE: DNA
<213> ORGANISM: Oncorhynchus mykiss

<400> SEQUENCE: 278
ggagaaagaa cttaaaaaga tcaagaacag taccaataat gctgggactc ccaccaaaac    60
a                                                                    61

<210> SEQ ID NO 279
<211> LENGTH: 61
<212> TYPE: DNA
<213> ORGANISM: Oncorhynchus mykiss

<400> SEQUENCE: 279
ctgagactgt taaggaagag gaggtgaaaa aggaagaaaa gccccctacag ttgattaggg    60
g                                                                    61

<210> SEQ ID NO 280
<211> LENGTH: 61
<212> TYPE: DNA
<213> ORGANISM: Oncorhynchus mykiss

<400> SEQUENCE: 280
tactcggtat tctctttaaa ctacttccct gtatcccctt ctggtgagct tgggacagaa    60
``` a 61

<210> SEQ ID NO 281
<211> LENGTH: 61
<212> TYPE: DNA
<213> ORGANISM: Oncorhynchus mykiss

<400> SEQUENCE: 281
aaatcatcta aaaagcaaga tatgaaattg aaaatgcatt cacatttcac agatcgtcgt    60
c                                                                   61

<210> SEQ ID NO 282
<211> LENGTH: 61
<212> TYPE: DNA
<213> ORGANISM: Oncorhynchus mykiss

<400> SEQUENCE: 282
gttcatcaaa gctcgaattt tcctagtagc aagccgggac ttggaggtaa aactgcagtc    60
t                                                                   61

<210> SEQ ID NO 283
<211> LENGTH: 61
<212> TYPE: DNA
<213> ORGANISM: Oncorhynchus mykiss

<400> SEQUENCE: 283
caattaacag aaactgagtc aattcaaaac tttagttaga gaaattgcac ataaaaacac    60
a                                                                   61

<210> SEQ ID NO 284
<211> LENGTH: 61
<212> TYPE: DNA
<213> ORGANISM: Oncorhynchus mykiss

<400> SEQUENCE: 284
cctcaactct ctcccaacac aatcttttcc ccacttttc aaattggatt tattcccaag     60
t                                                                   61

<210> SEQ ID NO 285
<211> LENGTH: 61
<212> TYPE: DNA
<213> ORGANISM: Oncorhynchus mykiss

<400> SEQUENCE: 285
caccaatact tggtcacctg gctgtagtgg acaagaaaaa gcctgtttat cattgtgtct    60
t                                                                   61

<210> SEQ ID NO 286
<211> LENGTH: 61
<212> TYPE: DNA
<213> ORGANISM: Oncorhynchus mykiss

<400> SEQUENCE: 286
gttgtccagc ccaaattaca gttttgtatt ctctgtgtga cgaaaagtat acaatttcga    60
t                                                                   61

<210> SEQ ID NO 287
<211> LENGTH: 61
<212> TYPE: DNA

```
<213> ORGANISM: Oncorhynchus mykiss

<400> SEQUENCE: 287
ttctcagggt ccatcatggc gatctctgca gtgggtactc agtgggtcca gctgcatggt    60
g                                                                    61

<210> SEQ ID NO 288
<211> LENGTH: 61
<212> TYPE: DNA
<213> ORGANISM: Oncorhynchus mykiss

<400> SEQUENCE: 288
catcaattcc cctgcaagac cacagaaagt tatttgcctt gtattttgca aagaccaaac    60
t                                                                    61

<210> SEQ ID NO 289
<211> LENGTH: 61
<212> TYPE: DNA
<213> ORGANISM: Oncorhynchus mykiss

<400> SEQUENCE: 289
ctgtttgtac tggagagcca tgtaatccta gatcctgtac tatctatcct cttattgttt    60
a                                                                    61

<210> SEQ ID NO 290
<211> LENGTH: 61
<212> TYPE: DNA
<213> ORGANISM: Oncorhynchus mykiss

<400> SEQUENCE: 290
ggaggtgttc tttacagggg acgaggagga ggagctgtct gagagaaagt cccagagaaa    60
t                                                                    61

<210> SEQ ID NO 291
<211> LENGTH: 61
<212> TYPE: DNA
<213> ORGANISM: Oncorhynchus mykiss

<400> SEQUENCE: 291
gcccgaacgt cctgtcctct atccgcgtca aggtgttgaa ggacaaatcc aggtaagcaa    60
g                                                                    61

<210> SEQ ID NO 292
<211> LENGTH: 61
<212> TYPE: DNA
<213> ORGANISM: Oncorhynchus mykiss

<400> SEQUENCE: 292
aggcgaatgg cagcgtcagt aaagttatgt ctctccctct caaagttcct cctctgctcg    60
t                                                                    61

<210> SEQ ID NO 293
<211> LENGTH: 61
<212> TYPE: DNA
<213> ORGANISM: Oncorhynchus mykiss

<400> SEQUENCE: 293
gtctaatgaa cactgccgtg gattgtcatc cgagttgtct gttgagtcca cagtaacaca    60
a                                                                    61
```

<210> SEQ ID NO 294
<211> LENGTH: 61
<212> TYPE: DNA
<213> ORGANISM: Oncorhynchus mykiss

<400> SEQUENCE: 294
atactctgct aaaattagaa ctgaccagtt gatttttttt acatgataca tgataataat     60
g                                                                    61

<210> SEQ ID NO 295
<211> LENGTH: 61
<212> TYPE: DNA
<213> ORGANISM: Oncorhynchus mykiss

<400> SEQUENCE: 295
gttgaatttg gtcatataag gaaatgtgcc ttactgcctt tcgaattttg tgaaacttaa     60
a                                                                    61

<210> SEQ ID NO 296
<211> LENGTH: 61
<212> TYPE: DNA
<213> ORGANISM: Oncorhynchus mykiss

<400> SEQUENCE: 296
gatacagtct gcatttcaac aggctgcatt ttattgcacc acaccctgct gttatcagat     60
a                                                                    61

<210> SEQ ID NO 297
<211> LENGTH: 61
<212> TYPE: DNA
<213> ORGANISM: Oncorhynchus mykiss

<400> SEQUENCE: 297
ggaaaatgta acaaccaaac aggacagcac tcggtctgtt gatgttacag gcagctcagc     60
t                                                                    61

<210> SEQ ID NO 298
<211> LENGTH: 61
<212> TYPE: DNA
<213> ORGANISM: Oncorhynchus mykiss

<400> SEQUENCE: 298
ccatatttct tgttgttgt ttggaatagt atcctactcg aaaaaatatg catttgtatt      60
t                                                                    61

<210> SEQ ID NO 299
<211> LENGTH: 61
<212> TYPE: DNA
<213> ORGANISM: Oncorhynchus mykiss

<400> SEQUENCE: 299
gccagcgggt cggcacagcc tagtcatgcg gtcacaagcc attcagtctg gtcgcagtct     60
a                                                                    61

<210> SEQ ID NO 300
<211> LENGTH: 61
<212> TYPE: DNA
<213> ORGANISM: Oncorhynchus mykiss

```
<400> SEQUENCE: 300
aacaaactaa tcatctctag tggagcgcac ccgcaccaca agggggggcct tatcgtcgac    60 c                                                                    61

<210> SEQ ID NO 301
<211> LENGTH: 61
<212> TYPE: DNA
<213> ORGANISM: Oncorhynchus mykiss

<400> SEQUENCE: 301
aacactgccc tgcccaccac agaggacatc acgctgttca cggatttaga ccagggcaac    60
a                                                                    61

<210> SEQ ID NO 302
<211> LENGTH: 61
<212> TYPE: DNA
<213> ORGANISM: Oncorhynchus mykiss

<400> SEQUENCE: 302
aactttgtgt gcgttctatc cttgtttccc ccctacagcc agcggtaaca tcccggccat    60
g                                                                    61

<210> SEQ ID NO 303
<211> LENGTH: 61
<212> TYPE: DNA
<213> ORGANISM: Oncorhynchus mykiss

<400> SEQUENCE: 303
tcaactgaac agacagcaac tttccctcct cgttcatttc atcttcacct gcttcttctt    60
t                                                                    61

<210> SEQ ID NO 304
<211> LENGTH: 61
<212> TYPE: DNA
<213> ORGANISM: Oncorhynchus mykiss

<400> SEQUENCE: 304
agtgtcgatg ccaaacccctt gaaaataggt tgggaaagga aatcctttcc ctctaaatat    60
c                                                                    61

<210> SEQ ID NO 305
<211> LENGTH: 61
<212> TYPE: DNA
<213> ORGANISM: Oncorhynchus mykiss

<400> SEQUENCE: 305
actagtggag atgaagggga ctggtaatga gaatacagtg acagtaggca gtgttgtaaa    60
t                                                                    61

<210> SEQ ID NO 306
<211> LENGTH: 61
<212> TYPE: DNA
<213> ORGANISM: Oncorhynchus mykiss

<400> SEQUENCE: 306
tgtacttgtt ttattaaaac acaatgcaag acttaaaacg aactgtactg tagatataac    60
c                                                                    61
```

<210> SEQ ID NO 307
<211> LENGTH: 61
<212> TYPE: DNA
<213> ORGANISM: Oncorhynchus mykiss

<400> SEQUENCE: 307
ccgggttctg aacgaatagg cctacataac aggacatgga ttacgatggg accgttacga    60
a                                                                   61

<210> SEQ ID NO 308
<211> LENGTH: 61
<212> TYPE: DNA
<213> ORGANISM: Oncorhynchus mykiss

<400> SEQUENCE: 308
catctctttc ctccacaatg catacttggg tttatgcctt gggttggtgt atctgaagac    60
a                                                                   61

<210> SEQ ID NO 309
<211> LENGTH: 61
<212> TYPE: DNA
<213> ORGANISM: Oncorhynchus mykiss

<400> SEQUENCE: 309
aatggccttt gcaacgtgtt cccagcacac actcagctcg gggagctttc tgtggtcctc    60
c                                                                   61

<210> SEQ ID NO 310
<211> LENGTH: 61
<212> TYPE: DNA
<213> ORGANISM: Oncorhynchus mykiss

<400> SEQUENCE: 310
tcattaatgt gtagtagcag ttatttagtt tataatagtg atacaacaat aatacttcat    60
t                                                                   61

<210> SEQ ID NO 311
<211> LENGTH: 61
<212> TYPE: DNA
<213> ORGANISM: Oncorhynchus mykiss

<400> SEQUENCE: 311
catttcctcg tatcactagg agttcctaac ataacagatg taagctagtg agctgtatgc    60
t                                                                   61

<210> SEQ ID NO 312
<211> LENGTH: 61
<212> TYPE: DNA
<213> ORGANISM: Oncorhynchus mykiss

<400> SEQUENCE: 312
aaataggaca ccatacctgg ttgatttcgt gtcggttgtg tgaagtcaat gttgtaaatg    60
t                                                                   61

<210> SEQ ID NO 313
<211> LENGTH: 61
<212> TYPE: DNA
<213> ORGANISM: Oncorhynchus mykiss

<400> SEQUENCE: 313

```
gagattctaa ttatatattt ttttagagat gaattatttt ggaggtttat atactcacat    60
a                                                                    61
```

<210> SEQ ID NO 314
<211> LENGTH: 61
<212> TYPE: DNA
<213> ORGANISM: Oncorhynchus mykiss

<400> SEQUENCE: 314

```
catgaatagt ggcaaaatgt ccttcaattt tggtagctag atcataaaat acatttgtac    60
t                                                                    61
```

<210> SEQ ID NO 315
<211> LENGTH: 61
<212> TYPE: DNA
<213> ORGANISM: Oncorhynchus mykiss

<400> SEQUENCE: 315

```
tggtcaccag ctgcattaag tactgcagtg catctcctca gactgcacca gatatgttct    60
t                                                                    61
```

<210> SEQ ID NO 316
<211> LENGTH: 61
<212> TYPE: DNA
<213> ORGANISM: Oncorhynchus mykiss

<400> SEQUENCE: 316

```
agtttattgg cgtaaacata atctagaagt aattttcata atatgcaaca attggcatgt    60
a                                                                    61
```

<210> SEQ ID NO 317
<211> LENGTH: 61
<212> TYPE: DNA
<213> ORGANISM: Oncorhynchus mykiss

<400> SEQUENCE: 317

```
actcttgaga ttcggatcag cctagatgga cgattgaagc tccagtcgat gatgaatcaa    60
t                                                                    61
```

<210> SEQ ID NO 318
<211> LENGTH: 61
<212> TYPE: DNA
<213> ORGANISM: Oncorhynchus mykiss

<400> SEQUENCE: 318

```
attttcccta taattttgaa gaaattgttt ctttagctcc taattataca cccaggtgta    60
g                                                                    61
```

<210> SEQ ID NO 319
<211> LENGTH: 61
<212> TYPE: DNA
<213> ORGANISM: Oncorhynchus mykiss

<400> SEQUENCE: 319

```
gccgatggaa acaaggttat ggttagtgac aatacacagc gtacccagtc taatccaaag    60
a                                                                    61
```

<210> SEQ ID NO 320
<211> LENGTH: 61

```
<212> TYPE: DNA
<213> ORGANISM: Oncorhynchus mykiss

<400> SEQUENCE: 320
gaacggcctg aacaccatgg acctcaacac agagttcact gtggctcgcc tggaagcaat    60
a                                                                    61

<210> SEQ ID NO 321
<211> LENGTH: 61
<212> TYPE: DNA
<213> ORGANISM: Oncorhynchus mykiss

<400> SEQUENCE: 321
ctaaggagga aatggagctt gtcttgctaa agtcaatggt gatgtcaatg tctccctctc    60
a                                                                    61

<210> SEQ ID NO 322
<211> LENGTH: 61
<212> TYPE: DNA
<213> ORGANISM: Oncorhynchus mykiss

<400> SEQUENCE: 322
gatcttgtac gctgtctgtg ggctccctga gaaataattg taagaagcct actgatgcca    60
t                                                                    61

<210> SEQ ID NO 323
<211> LENGTH: 61
<212> TYPE: DNA
<213> ORGANISM: Oncorhynchus mykiss

<400> SEQUENCE: 323
tctgcgtcat tccatccctg ccatcacact cctgctacac tgcattctgc gtgtggtgta    60
t                                                                    61

<210> SEQ ID NO 324
<211> LENGTH: 61
<212> TYPE: DNA
<213> ORGANISM: Oncorhynchus mykiss

<400> SEQUENCE: 324
aaaaactgcg tgtttatcaa attagaaatt cacaaccata aagtttgcg ttgacaaaaa    60 a                                                                    61

<210> SEQ ID NO 325
<211> LENGTH: 61
<212> TYPE: DNA
```

<213> ORGANISM: Oncorhynchus mykiss

<400> SEQUENCE: 325
ctttgagctg atccagtca agaagaaggc caaagagagg atggtgaagt ccaccagcag    60
c                                                                   61

<210> SEQ ID NO 326
<211> LENGTH: 61
<212> TYPE: DNA
<213> ORGANISM: Oncorhynchus mykiss

<400> SEQUENCE: 326
aaagctgctt ccagctgatg gtgtagtcta cggacaggtt cgttacccat ccacatctct    60
c                                                                   61

<210> SEQ ID NO 327
<211> LENGTH: 61
<212> TYPE: DNA
<213> ORGANISM: Oncorhynchus mykiss

<400> SEQUENCE: 327
agaataaatg caatcttaat gtgaatttat ttatgtttag aaactgctta ctaataggta    60
a                                                                   61

<210> SEQ ID NO 328
<211> LENGTH: 61
<212> TYPE: DNA
<213> ORGANISM: Oncorhynchus mykiss

<400> SEQUENCE: 328
ctgaatcaaa tgctctcact tgccagactt tgaggttgac agtgcagcaa tgacaaatac    60
a                                                                   61

<210> SEQ ID NO 329
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: wherein "n" is C or T

<400> SEQUENCE: 329
ccgccagtgt cgatgccaaa cccttgaaaa taggtnggga aaggaaatcc tttccctcta    60
aatatctgtc g                                                        71

<210> SEQ ID NO 330
<211> LENGTH: 71
<212> TYPE: DNA
<213> ORGANISM: Oncorhynchus mykiss
<220> FEATURE:
<221> NAME/KEY: misc_feature
<222> LOCATION: (36)..(36)
<223> OTHER INFORMATION: wherein "n" is T or C

<400> SEQUENCE: 330
gctgtctata aatctcccctt tcctaaagga aagggntgga taaaagttcc caaaccgtag    60
ctgtgaccgc c                                                        71